(12) United States Patent
Branda et al.

(10) Patent No.: US 9,227,986 B2
(45) Date of Patent: Jan. 5, 2016

(54) DIARYLETHENE COMPOUNDS AND USES THEREOF

(71) Applicant: SWITCH MATERIALS, INC., Burnaby (CA)

(72) Inventors: Neil Robin Branda, North Vancouver (CA); Jeremy Graham Finden, North Vancouver (CA); Simon James Gauthier, Vancouver (CA); Ali Hayek, Burnaby (CA); Kyle Andrew Hope-Ross, Vancouver (CA); James Daniel Senior, Surrey (CA); Andreea Spantulescu, New Westminster (CA); Serguei Sviridov, Burnaby (CA)

(73) Assignee: Switch Materials, Inc., Burnaby, British Columbia (CA)

( * ) Notice: Subject to any disclaimer, the term of this patent is extended or adjusted under 35 U.S.C. 154(b) by 0 days.

(21) Appl. No.: 14/348,344

(22) PCT Filed: Sep. 28, 2012

(86) PCT No.: PCT/CA2012/000910
§ 371 (c)(1),
(2) Date: Mar. 28, 2014

(87) PCT Pub. No.: WO2013/044371
PCT Pub. Date: Apr. 4, 2013

(65) Prior Publication Data
US 2014/0256936 A1    Sep. 11, 2014

Related U.S. Application Data

(60) Provisional application No. 61/541,841, filed on Sep. 30, 2011, provisional application No. 61/675,460, filed on Jul. 25, 2012.

(51) Int. Cl.

| | |
|---|---|
| *C07D 307/93* | (2006.01) |
| *C07D 307/00* | (2006.01) |
| *C07D 513/14* | (2006.01) |
| *C07D 333/12* | (2006.01) |
| *C07D 493/04* | (2006.01) |
| *C07D 495/04* | (2006.01) |
| *C07D 277/22* | (2006.01) |

(Continued)

(52) U.S. Cl.
CPC ............ *C07D 513/14* (2013.01); *C07D 277/22* (2013.01); *C07D 307/79* (2013.01); *C07D 333/12* (2013.01); *C07D 333/18* (2013.01); *C07D 493/04* (2013.01); *C07D 493/22* (2013.01); *C07D 495/04* (2013.01); *C07D 513/04* (2013.01); *C09K 9/02* (2013.01); *G02B 1/04* (2013.01); *G02B 5/20* (2013.01); *G02B 5/223* (2013.01); *G02B 5/23* (2013.01); *C09K 2211/1007* (2013.01); *C09K 2211/1088* (2013.01); *C09K 2211/1092* (2013.01)

(58) Field of Classification Search
CPC .. C07D 307/77; C07D 307/80; C07D 493/04; C07D 307/79; C07D 333/54; C07D 333/56; C07D 409/12; C07D 495/04
USPC .................................. 549/456, 41, 51, 60, 469
See application file for complete search history.

(56) References Cited

U.S. PATENT DOCUMENTS

| 3,635,544 A | 1/1972 | Stamm et al. |
|---|---|---|
| 5,734,065 A | 3/1998 | Saika |
| 8,415,472 B2 | 4/2013 | Chung et al. |

FOREIGN PATENT DOCUMENTS

| CA | 2 494 920 | 2/2004 |
|---|---|---|
| CA | 2 764 751 | 12/2010 |

(Continued)

OTHER PUBLICATIONS

Boyer et al., "Two-Way Photoswitching Using One Type of Near-Infrared Light, Upconverting Nanoparticles, and Changing Only the Light Intensity", *J. Am. Chem. Soc.*, vol. 132, No. 44, pp. 15766-15772.

(Continued)

*Primary Examiner* — Andrew D Kosar
*Assistant Examiner* — Raymond Covington
(74) *Attorney, Agent, or Firm* — Merchant & Gould P.C.

(57) ABSTRACT

A compound according to Formula IA and IB, reversibly convertible under photochromic and electrochromic conditions between a ring-open isomer A and a ring-closed isomer B is provided. For substitutent groups, Z is N, O or S; each $R_1$ is independently selected from the group consisting of H, or halo; each $R_2$ is independently selected from the group consisting of H, halo, a polymer backbone, alkyl or aryl; or, when both $R_2$ together form —CH=CH— and form part of a polymer backbone; each $R_3$ is independently selected from the group consisting of H, halo, alkyl, alkoxy, thioalkyl or aryl; each $R_4$ is aryl; and each $R_5$ is independently selected from the group consisting of H, halo, alkyl, alkoxy, thioalkyl or aryl.

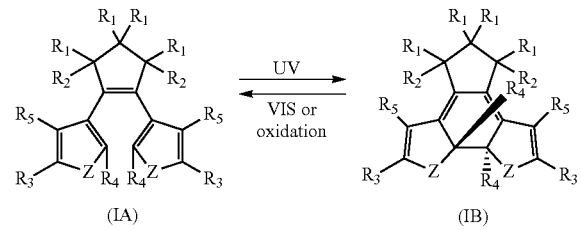

25 Claims, 8 Drawing Sheets

(51) Int. Cl.
| | |
|---|---|
| C07D 513/04 | (2006.01) |
| C07D 307/79 | (2006.01) |
| C09K 9/02 | (2006.01) |
| G02B 1/04 | (2006.01) |
| G02B 5/20 | (2006.01) |
| G02B 5/22 | (2006.01) |
| G02B 5/23 | (2006.01) |
| C07D 333/18 | (2006.01) |
| C07D 493/22 | (2006.01) |

(56) References Cited

FOREIGN PATENT DOCUMENTS

| | | |
|---|---|---|
| CN | 101851232 | 10/2010 |
| CN | 102079742 | 6/2011 |
| JP | 10-152679 | 6/1998 |
| JP | 2005-326503 | 11/2005 |
| WO | WO 02/06361 | 1/2002 |
| WO | WO 2004/015024 | 2/2004 |
| WO | WO 2006/125317 | 11/2006 |
| WO | WO 2007/059288 | 5/2007 |
| WO | WO 2010/142019 | 12/2010 |
| WO | WO 2012/079159 | 6/2012 |
| WO | WO 2012/079160 | 6/2012 |
| WO | WO 2012/128293 | 9/2012 |

OTHER PUBLICATIONS

Canadian Office Action from Canadian Application No. 2,832,149 mailed Dec. 13, 2013.

Gorodetsky et al., "Bidirectional Ring-Opening and Ring-Closing of Cationic 1,2-Dithienylcyclopentene Molecular Switches Triggered with Light or Electricity", *Adv. Funct. Mater.*, vol. 17, 2007, pp. 786-796.

Hiroto et al., "Synthetic protocol for diarylethenes through Suzuki-Miyaura coupling", *Chem. Commun.*, vol. 47, 2011, pp. 7149-7151.

Irie, M., "Photochromism of diarylethene molecules and crystals", *Proc. Jpn. Acad., Ser. B*, vol. 86, No. 5, 2010, pp. 472-483.

International Search Report and Writing Opinion from International Application No. PCT/CA2012/000910 mailed Jan. 25, 2013.

Krayushkin et al., "Photochromic dihetarylethenes 10.* Photochromic 1,2-bis[2-(benzothiazol-2-yl)-3-thienyl]- and 1,2-bis[2-(benzothiazol-2-yl)benzothiophen-3-yl]ethenes", *Russian Chemical Bulletin, International Edition*, vol. 50, No. 12, 2001, pp. 2420-2423.

Moriyama et al., "Electrochemical Cyclization/Cycloreversion Reactions of Diarylethenes", *Organic Letters*, vol. 7, No. 15, 2005, pp. 3315-3318.

Patel et al., "Theoretical Study of Photochromic Compounds. 1. Bond Length Alternation and Absorption Spectra for the Open and Closed Forms of 29 Diarylethene Derivatives", *J. Phys. Chem. A*, vol. 113, 2009, pp. 8409-8414.

Peters et al., "Regulating $\pi$-conjugated pathways using a photochromic 1,2-dithienylcyclopentene", *Chem Comm*, 2002, pp. 2274-2275.

Peters et al., "Electrochromism in Photochromic Dithienylcyclopentenes", *J. Am. Chem. Soc.*, vol. 125, 2003, pp. 3404-3405.

Peters et al., "Novel Photochromic Compounds Based on the 1-Thienyl-2-vinylcyclopentene Backbone", *Organic Letters*, vol. 5, No. 8, 2003, pp. 1183-1186.

Tanifuji et al., "Photochromic Oligothiophenes", *Chemistry Letters*, vol. 34, No. 12, 2005, pp. 1580-1581.

Yamaguchi et al., "Morphology change of diarylethene derivatives having benzofuran derivatives-Photoinduced crystallization", *Journal of Photochemistry and Photobiology A: Chemistry*, vol. 213, 2010, pp. 141-146.

Yamaguchi et al., "Photochromism of diarylethene derivatives bearing a benzo[*b*]silole unit", *Tetrahedron Letters*, vol. 52, 2011, pp. 5601-5604.

DIARYLETHENE COMPOUNDS AND USES THEREOF

This application is a National Stage Application of PCT/CA2012/000910, filed 28 Sep. 2012, which claims the benefit of U.S. Provisional Application No. 61/541,841 filed Sep. 30, 2011, and U.S. Provisional Application No. 61/675,460 filed Jul. 25, 2012, both of which are incorporated herein by reference in their entirety. To the extent appropriate, a claim of priority is made to each of the above disclosed applications.

FIELD OF THE INVENTION

The present invention relates to diarylethene compounds and uses thereof. More specifically, the compounds are reversibly convertible between ring-open and ring-closed isomers.

BACKGROUND OF THE INVENTION

Photochromic molecules are useful for a variety of research and commercial applications in fields ranging from sunglasses to memory storage devices. A myriad of configurations have been developed, seeking to obtain improvements in stability, control in switching, fatigue resistance, sensitivity and the like. Diarylethenes have found favour for several of these traits, and are the subject of continued investigation. A review by Irie (Proc. Jpn. Acad. Ser B 86:472-483, 2010) illustrates a range in stability, colour and the like of selected diarylethenes.

PCT Publication WO2004/015024 describes compounds that are both photochromic and electrochromic, and methods of making such compounds, and describes a mechanism of catalytic electrochromism. Briefly, a ring-closed form (isomer B) of a compound loses an electron under electrochemical conditions, forming a radical cation. A rapid ring-opening reaction occurs, providing the radical cation of isomer A, which oxidizes a neighbouring compound of isomer B, neutralizing the radical cation. This ring opening reaction may be initiated with a small charge, and perpetuates throughout the material, resulting in conversion of the ring-closed isomers to the ring-open isomers. PCT Publication WO2010/142019 describes variable transmittance optical filters comprising a material capable of transitioning between light and dark states in response to ultraviolet light and electric voltage, the material comprising a chromophore that has both electrochromic and photochromic properties.

Light transmission properties of such optical filters may be varied by selection of a photochromic-electrochromic diarylethene with greater or lesser light absorbance in the ring-open or ring-closed form. To provide for such variation, there is a need for molecules with improved photochromic, electrochromic or photochromic and electrochromic properties.

SUMMARY OF THE INVENTION

There is a need for photochromic and electrochromic compounds with photostationary states, or sensitivity index suitable for various applications. Such compounds may be useful as components of switchable, or dynamic, optical filters. The ability of a compound to absorb light in the visible spectrum may be illustrated by the photostationary state of the compound when exposed to full spectrum light. The problem of needing photochromic and electrochromic compounds that provide suitable light absorption in a visible-light absorbing state may be solved by synthesis of novel photochromic/electrochromic compounds demonstrating a suitable PSS, or a suitable sensitivity index.

The present disclosure relates to one or more compounds ("chromophores") reversibly convertible between isomers. Conversion between isomers may be light induced, or may occur under some oxidative conditions such as electrochemical conditions, or a combination thereof.

In one aspect, there is provided a 1,2-diaryl cyclopentene compound reversibly convertible between Formula 1A (ring-open isomer) and Formula 1B (ring-closed isomer) of Scheme 1:

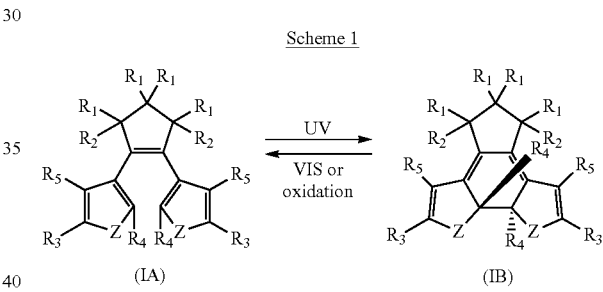

wherein

Z may be N, O or S;

Each $R_1$ may be independently selected from the group consisting of H, halo;

Each $R_2$ may be independently selected from the group consisting of H, halo, a polymer backbone, alkyl or aryl; or, when both $R_2$ together form —CH=CH— and form part of a polymer backbone;

Each $R_3$ may be independently selected from the group consisting of H, halo, $CO_2Y$, alkyl, alkoxy, carbonyl, thioalkyl, aryl,

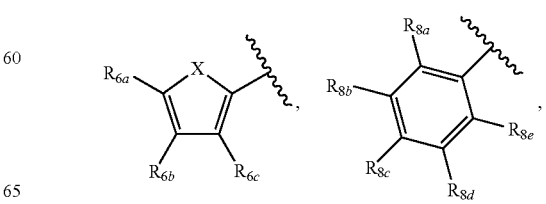

—CH=CH—;
and Y may be independently selected from the group comprising H, a metal, alkyl, aryl, —(O—CH$_2$CH$_2$)$_4$—H, or

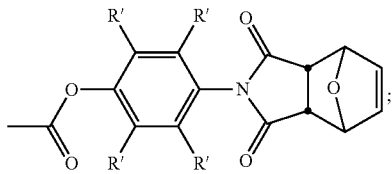

Each R$_4$ may be independently selected from the group consisting of aryl,

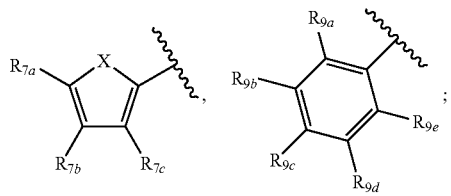

Each R$_5$ may be independently selected from the group consisting of H, halo, alkyl, alkoxy, —CH=CH—, thioalkyl or aryl; and;
Each X may independently be N, O or S:

R$_4$ may alternately be described as an "internal" group. R$_3$ may alternately be described as an "external" group.

Each of R$_{6a}$, R$_{6b}$, R$_{6c}$, R$_{7a}$, R$_{7b}$ and R$_{7c}$ may be independently selected from a group comprising one or more of H, halo, alkyl, alkoxy, carbonyl, siloxy, thioalkyl CO$_2$Y or aryl; and Y is as referenced herein, with the proviso that at least one of R$_{6a}$, R$_{6b}$, R$_{6c}$, and at least one of R$_{7a}$, R$_{7b}$ and R$_{7c}$ are not H. The R$_{6a}$ and R$_{7a}$ position may alternately be referred to as the "5 position"; the R$_{6b}$ and R$_{7b}$ position may alternately be referred to as the "4 position"; the R$_{6c}$ and R$_{7c}$ position may alternately be referred to as the "3 position" of the ring;

Each of R$_{8a}$, R$_{8b}$, R$_{8c}$, R$_{8d}$, R$_{8e}$, R$_{9a}$, R$_{9b}$, R$_{9c}$, R$_{9d}$ and R$_{9e}$ may be independently selected from the group consisting of H, halo, alkyl, alkoxy, thioalkyl, carbonyl, siloxy, aryl or CO$_2$Y, and Y is as referenced herein, with the proviso that at least one of R$_{8a}$, R$_{8b}$, R$_{8c}$, R$_{8d}$, or R$_{8e}$, and at least one of R$_{9a}$, R$_{9b}$, R$_{9c}$, R$_{9d}$ and R$_{9e}$ are not H The R$_{8c}$ and R$_{9c}$ positions may alternately be referred to as a 'para' position; the R$_{8b}$, R$_{8d}$, R$_{9b}$ and R$_{9d}$ positions may alternately be referred to as a 'meta' position; the R$_{8a}$, R$_{8e}$, R$_{9a}$ and R$_{9e}$ positions may alternately be referred to as an 'ortho' position.

In another aspect, R$_{6a}$ and R$_{6b}$, or R$_{6b}$ and R$_{6c}$ are each —CH=CH— and joined to form an unsaturated ring, In another aspect, R$_{7a}$ and R$_{7b}$, or R$_{7b}$ and R$_{7c}$ are each —CH=CH— and joined to form an unsaturated ring.

In another aspect, R$_{8a}$ and R$_{8b}$, or R$_{8b}$ and R$_{8c}$, or R$_{8c}$ and R$_{8d}$, or R$_{8d}$ and R$_{8e}$ are each —CH=CH— and joined to form an unsaturated ring, In another aspect, R$_{9a}$ and R$_{9b}$, or R$_{9b}$ and R$_{9c}$, or R$_{9c}$ and R$_{9d}$, or R$_{9d}$ and R$_{9e}$ are each —CH=CH— and joined to form an unsaturated ring.

In another aspect, R$_3$ is

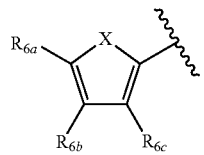

and R$_4$ is

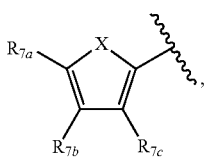

providing a compound reversibly convertible between Formula IIA (ring-open isomer) and Formula IIB (ring-closed isomer), and R$_{6a}$ and R$_{7a}$ are not methyl.

In another aspect, R$_3$ is

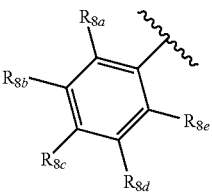

and R$_4$ is

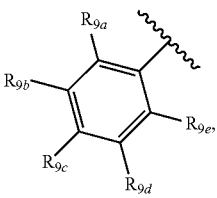

providing a compound reversibly convertible between Formula IIIA (ring-open isomer) and Formula IIIB (ring-closed isomer) and R$_{8c}$ and R$_{9c}$ are not all —O—CH$_3$, or all —C(CH$_3$)$_3$ In another aspect, R$_3$ is

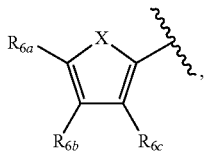

and $R_4$ is

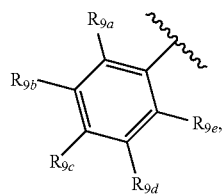

providing a compound reversibly convertible between Formula IVA (ring-open isomer) and Formula IVB (ring-closed isomer) and $R_{6a}$ is not methyl In another aspect, $R_3$ is

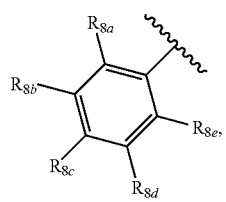

and $R_4$ is

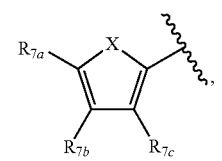

providing a compound reversibly convertible between Formula VA (ring-open isomer) and Formula VB (ring-closed isomer) and $R_{7a}$ is not methyl.

In another aspect, a first $R_3$ group is

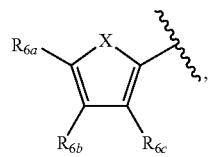

and a first $R_4$ group is

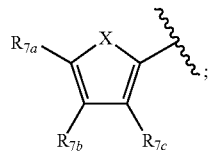

and a second $R_3$ group $R_3'$ is

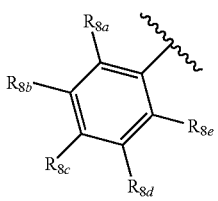

and a second $R_4$ ($R_4'$) group is

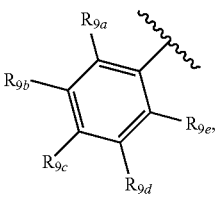

providing a compound reversibly convertible between Formula VIA (ring-open isomer) and Formula VIB (ring-closed isomer) of Scheme 2:

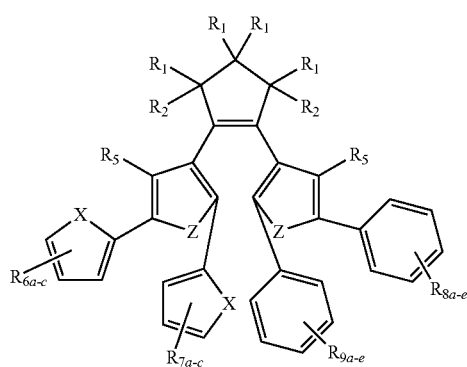

(VIA)

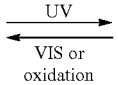

UV
⇌
VIS or oxidation

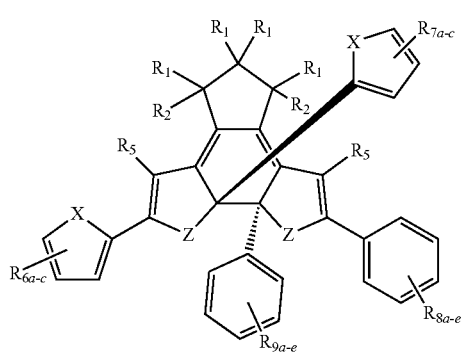

(VIB)

In another aspect, a first $R_3$ and a first $R_5$ are each —CH=CH— and joined to form an unsaturated ring, providing a group according to

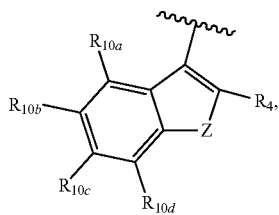

providing a compound reversibly convertible between Formula XA (ring-open isomer) and Formula XB (ring-closed isomer) of Scheme 3:

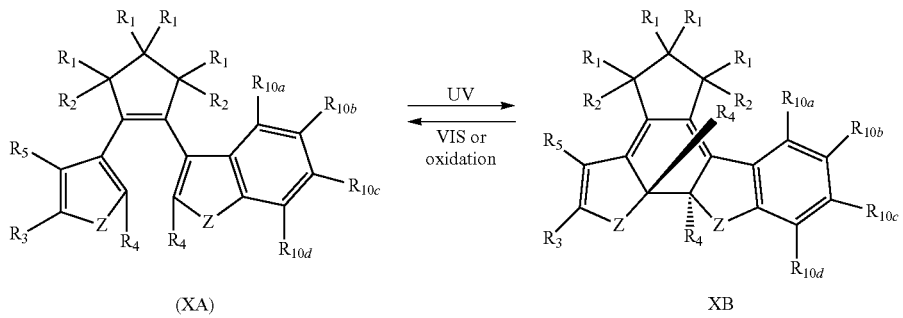

Where Z is N, O or S;

each $R_1$ is independently selected from the group consisting of H, or halo;

each $R_2$ is independently selected from the group consisting of H, halo, a polymer backbone, alkyl or aryl; or, when both $R_2$ together form —CH=CH— and form part of a polymer backbone;

$R_3$ is —CH$_2$=CH$_2$—,

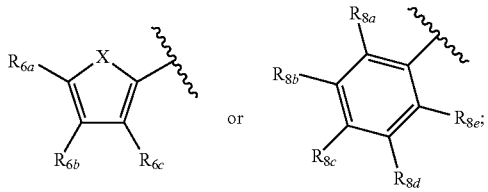

each $R_4$ is independently, aryl,

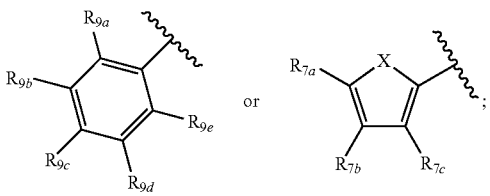

X is N, O or S;

$R_5$ is independently selected from a group consisting of H, alkyl, alkoxy, —CH=CH—;

each $R_{6a}$, $R_{6b}$, $R_{6c}$ is independently selected from the group consisting of H, halo, alkyl, alkoxy, siloxy, thioalkyl or aryl;

each $R_{7a}$, $R_{7b}$, $R_{7c}$ is independently selected from the group consisting of H, halo, alkyl, alkoxy, siloxy, thioalkyl or aryl;

each $R_{8a}$, $R_{8b}$, $R_{8c}$, $R_{8d}$, $R_{8e}$ is independently selected from the group consisting of H, halo, alkyl, alkoxy, siloxy, thioalkyl or aryl;

each $R_{10a}$, $R_{10b}$, $R_{10c}$, $R_{10d}$, is independently H, halo, alkyl, alkoxy, siloxy, thioalkyl or aryl, or any of $R_{10a}$ and $R_{10b}$, or $R_{10b}$ and $R_{10c}$, or $R_{10c}$ $R_{10d}$ are alkyl, or alkoxy, and joined to form a 5 or 6 or 7 membered ring.

In another aspect, $R_3$ is

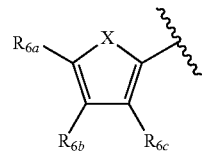

and $R_4$ is

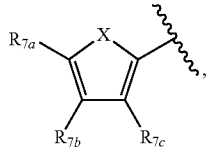

providing a compound reversibly convertible between Formula VIIIA (ring-open isomer) and Formula VIIIB (ring-closed isomer).

In another aspect, $R_3$ is

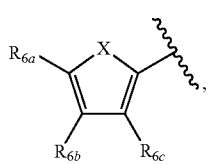

and $R_4$ is

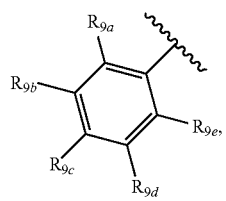

providing a compound reversibly convertible between Formula XIA (ring-open isomer) and Formula XIB (ring-closed isomer).

In another aspect, both $R_3$ and both $R_5$ are each —CH=CH— and joined to form an unsaturated ring, providing a compound reversibly convertible between Formula VIIA (ring-open isomer) and Formula VIIB (ring-closed isomer) of Scheme 4:

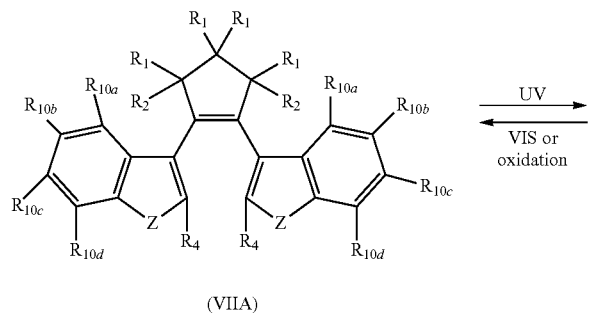

In another aspect, $R_{9c}$ may be an alkyl, alkoxy or siloxy group, selected from a group comprising an alkyl group comprising from one to 20 carbons. In another aspect, one or more of $R_{10a}$, $R_{10b}$, $R_{10c}$, $R_{10d}$ may be an alkoxy or siloxy group, comprising from one to ten oxygen atoms and from one to 20 carbons. In another aspect, an $R_{10b}$ and an $R_{10c}$ are each O, and joined with a —CH$_2$— to form a 5 membered ring.

In another aspect, the compounds each comprise ring-open, or open, isomers (Isomer A) and ring-closed, or closed, isomers (Isomer B). These compounds may be reversibly convertible between open and closed forms under photochemical, oxidative, or photochemical and oxidative conditions. Oxidative conditions may be electrochemical conditions.

In another aspect, the compounds may be convertible from the ring-open isomer A to the ring-closed isomer B under photochemical conditions, and from the ring-closed isomer B to the ring-open isomer A under electrochemical conditions.

In another aspect, the compounds may be convertible from the ring-open isomer A to the ring-closed isomer B under a first photochemical condition, and from the ring-closed isomer B to the ring-open isomer A under a second photochemical condition. The first photochemical condition may include light within the UV range.

In another aspect, one or more of the compounds may be included in a composition comprising one or more compounds, and one or more formulation components.

As used herein, photochromic and photochemical both refer to conversion from one isoform to another when exposed to light. As used herein, electrochromic and electrochemical both refer to conversion from one isoform to another when exposed to a voltage.

For visual clarity in some Formula and structures, abbreviated substituent groups may be used in this text;

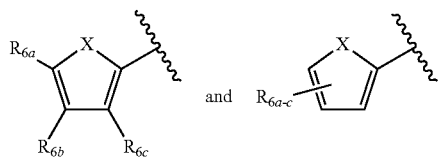

indicate the same substituents equivalent, with groups $R_{6a}$, $R_{6b}$, $R_{6c}$ as described herein:

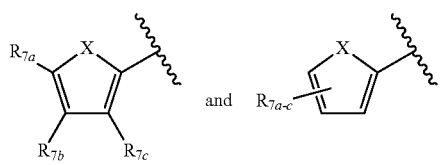

indicate the same substituents, with groups $R_{7a}$, $R_{7b}$ and $R_{7c}$ as described herein;

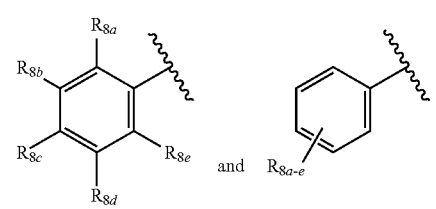

indicate the same substituents, with groups $R_{8a}$, $R_{8b}$, $R_{8c}$ $R_{8d}$, $R_{8e}$, as described herein;

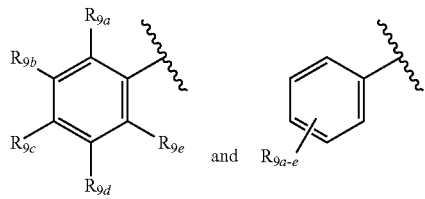

indicate the same substituents, with groups $R_{9a}$, $R_{9b}$, $R_{9c}$, $R_{9d}$ and $R_{9e}$ as described herein;

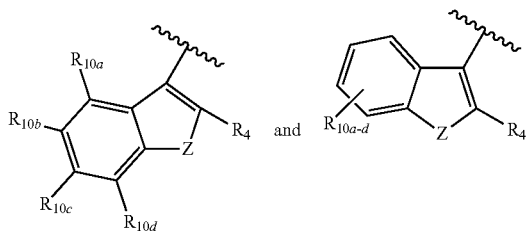

indicate the same substituents, with groups $R_{10a}$, $R_{10b}$, $R_{10c}$ and $R_{10d}$ as described herein.

For compounds comprising two $R_3$ or two $R_4$ groups, both $R_3$ or both $R_4$ groups may be the same or they may be different.

This summary does not necessarily describe all features. Other aspects, features and advantages will become apparent to those of ordinary skill in the art upon review of the following description of specific embodiments.

DESCRIPTION OF THE INVENTION

There is provided, in part, novel and/or improved compounds having both photochromic and electrochromic functionality ("chromophores", "hybrid compound", "P/E compounds"). Without wishing to be bound by theory, diarylethenes, such as dithienylethenes, having 'internal' aryl groups ($R_4$ as illustrated in Formula IA and IB) exhibit both photochromic and electrochromic functionality, and may be useful components of optical filters that vary in light transmissibility in response to stimuli. Some combinations of substituent groups may provide for compounds with improved or advantageous properties, including photostationary state, solubility, synthetic methods, sensitivity index, or the like.

There is further provided, in part, compounds that are reversibly convertible between a ring open isomer (Isomer A), and a ring-closed isomer (Isomer B). As used herein, a numeral or alpha-numeric reference (with suffix 'A') denotes the ring-open isomer of a compound, and a primed numeral or alpha-numeric reference (with suffix 'B') or a primed numeral or alpha-numeric reference denotes the ring-closed isomer of the same compound.

Compounds according to various embodiments may undergo catalytic electrochemical oxidation with application of a voltage and methods of switching, or operating, a switching material from a dark to a faded state may employ application of a catalytic amount of a voltage. A catalytic amount of a voltage may be positive or negative, and may be from about 0.1 to about 5 volts, or any amount or range therebetween.

A "switching material" is one that has both electrochromic and photochromic properties. A switching material may darken when exposed to ultraviolet (UV) light from a light source, and may lighten (fade, electrofade) when exposed to a voltage. In some embodiments, the switching material may fade upon exposure to selected wavelengths of visible (VIS) light ("photofade"), without sacrifice of the ability to be electrofaded when restored to a darkened state.

As used herein, light transmittance may be described with reference to "Visible light transmittance" (VLT) or $LT_A$ (luminous transmittance, illuminant A, 2% observer). Light transmittance may be expressed with reference to a change in light transmission and/or a particular type of light or wavelength of light transmitted.

Figure 1:
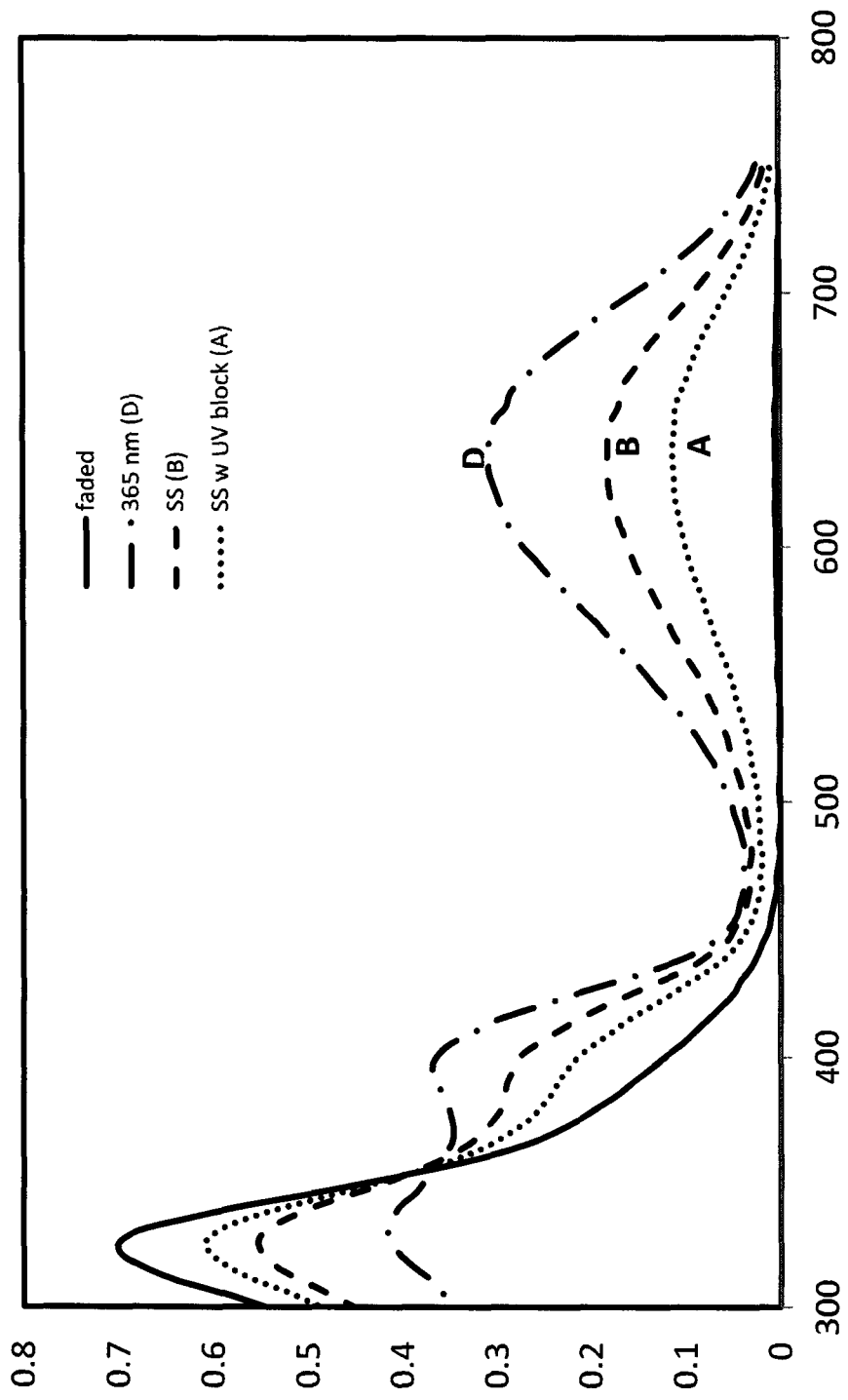
FIG. 1 shows the absorbance (Y axis) of S001 at various wavelengths of light (X axis, in nm) for two light sources—365 nm and solar simulator (SS) in the presence or absence of a UV blocking film. Solid line—absorbance plot of S001 in a faded state ("faded"-solid line); A-D absorbance plots with light source, +/−UV blocking film—A: Solar simulator with UV blocking film; B: Solar simulator without UV blocking film; D: 365 nm light source without UV blocking film.

As used herein, "photostationary state" (PSS) refers an equilibrium state of a compound or material where the rate of the ring closing (forward) reaction is equal to the rate of the ring-opening or fading (reverse) reaction, when irradiated with light in a given region of the spectrum; in other words, the ratio of ring-open isoform to ring-closed isoform is at an equilibrium. PSS may be expressed with reference to a light source, or with reference to a type of light—eg. QUV, Xenon-arc lamp, Q-SUN, natural or filtered sunlight, UV, VIS, IR, NIR, full spectrum, or the like, or with reference to a particular wavelength or range of wavelengths, or in the presence or absence of a filter. Some ring-open and ring-closed isomers may undergo isomerization from one to the other in response to different wavelengths of light—if a wavelength of light is used where only one of the isomers absorbs, irradiation results in complete isomerization to the other form. 254 nm, 313 nm or 365 nm light are commonly used in studies of UV-absorbing isomers, but this may not be representative of the PSS under other light conditions that include the visible spectrum such as natural or simulated sunlight ("full spectrum" light) and/or with filters that block a portion of the UV component of the light. For example, in a ring-closed (dark) state, the magnitude of the maximum absorbance in the visible range may change with the light source (FIG. 1)—the wavelength at this peak in the visible range may be referred to as lambda max, or λmax. Line D shows the absorption profile for a compound when exposed to a 365 nm light source. When full spectrum light from a solar simulator (Xenon arc lamp) is used as a light source (Line B), a balance is achieved between the ring closed (dark) state induced by the UV component, and ring-open (faded) state induced by the visible component of the light. Inclusion of a UV blocking layer in the light path (Line A) may reduce the UV component of the light, and the ring-opening reaction induced by the visible light component becomes more prominent. Different compounds may demonstrate different responsiveness to the composition of incident light. Depending on the use of a compound, one with greater or less sensitivity to light composition may be useful. This equilibrium state may be represented by an absorbance value at a particular wavelength (lambda max), and may include reference to a light source. Where desired, the ratio of ring-open and ring-closed isoforms at a PSS may be quantified by $^1$H NMR spectroscopy.

As used herein, contrast ratio is a ratio of the light transmittance of a material in the dark state and the light state. For example, a material may allow transmission of about 10% of the visible light (10% VLT) in a dark state, and about 60% of the visible light (60% VLT) in a faded state, providing a contrast ratio of 6:1. According to various embodiments of the invention, a material may have a contrast ratio of at least about 2 to about 20, or greater, or any amount or range therebetween, for example, about 2, 3, 4, 5, 6, 7, 8, 9, 10, 11, 12, 13, 14, 15, 16, 17, 18, 19 or 20. In some embodiments, a compound with a darker PSS (greater absorbance at lambda max) may provide a greater contrast ratio.

Photostability (resistance to light-induced degradation) may be measured by the amount of time it takes for the compound, or a material comprising the compound to degrade to a certain point under light exposure. The light exposure may be constant, or cyclic. The light transmittance or absorbance of the compound, or material comprising the compound may be determined at both a light state and dark state prior to testing, to determine a contrast ratio. During testing, the contrast ratio may be monitored (periodically or continually); the compound or material may be determined to have failed when the contrast ratio falls outside, or below, a selected range, or when the contrast ratio decreases to a percentage of the original contrast ratio. Photostability also, may be expressed with reference to a light source or with reference to a type of light.

As used herein "switching voltage" ("switching potential", "potential") refers to the electric potential required for a compound, or material, to achieve a faded state. Switching voltage may further refer to the relationship between voltage and time to switch. To assess the switching voltage of a material, the material may be first darkened by exposure to a light source, followed by passing an electric current through the material at a defined voltage or voltage range, and assessing the time until a clear state, or a desired increase in light transmissibility is achieved. Switching voltage may be expressed as a voltage or range of voltage (e.g. about 2.5 volts, about 2.2 volts, or below about 2 volts, or the like). In some embodiments of the invention, the compound or material has a switching potential of about 0.5 volts to about 5 volts, or from about 1 volt to about 2.5 volts, or any amount or range therebetween.

As used herein "switching time" refers to the time necessary for a material to transition from a dark state to a clear state, or from a clear state to a dark state, or to alter light transmittance by a defined amount.

"About" as used herein when referring to a measurable value such as an amount, a temporal duration, or the like, is meant to encompass variations of ±20% or ±10%, or ±5%, or ±1%, or ±0.1% or any amount therebetween from the specified value, as appropriate to perform the disclosed methods.

As used herein, "halogen" refers to F, Cl, Br or I. The term "halo" is generic, and refers to any halogen moiety, for example fluoro-chloro-, bromo- or iodo-, or the like.

As used herein, "metal" as used herein refers to a transition metal, or an alkali metal such as Li, Na, K, or the like; or a metalloid such as B or Si, or the like.

As used herein, "alkyl" refers to any linear or branched, non-aromatic monocyclic or polycyclic, substituted or unsubstituted alkyl group of 1 to 50 carbons, for example 2, 3, 4, 5, 6, 7, 8, 9, 10, 11, 12, 13, 14, 15, 16, 17, 18, 19, 20, 25, 30, 35, 40, or 45, or any amount therebetween. Examples of alkyl groups include methyl, ethyl, propyl, isopropyl, butyl, isobutyl, sec-butyl, tert-butyl, 1-pentyl, iso-pentyl, neo-pentyl, hexyl, cyclopropane, cyclobutane, cyclopentane, cyclohexane or the like. The alkyl group may have one or more saturated or unsaturated bonds. The alkyl group may contain only carbon and hydrogen atoms, or may further incorporate one or more heteroatoms such as Si, N, O or S as part of the alkyl group (a heteroalkyl group). Examples of cyclic heteroalkyl groups include aziridine, oxirane, thiirane, oxaziridine, dioxirane, azetidine, oxetane, thietane, diazetidine, dioxetane, dithietane, azirine, oxirene, thiirene, azete, oxete, thiete, dioxete, dithiete, pyrrolidine, oxolane, thiolane, borolane, silolane, dithiolane, dioxolane, oxazolidine, piperidine, oxane, thiane, piperazine, morpholine or the like. An alkyl group with an Si heteroatom may be described as a 'silyl' or 'silane' group.

As used herein, "alkoxy" refers to any —O—R group, where R (and R' for an ether, below) may independently be H, alkyl, siloxy or aryl. Examples of alkoxy groups include those with from 1 to 50 carbon or silicon atoms in a linear or branched chain, for example methoxy or ethoxy, or longer alkyl groups. Other alkoxy groups include ethers (—R—O—R'—), alcohol (—OH) or alkoxide (—R—O-metal) or the like. An alkyl group comprising an alkoxy substituent group may be referred to as an 'alkylalkoxy' group. An alkyl group comprising an Si heteroatom, and an alkoxy, or a siloxy group may be referred to as an alkylsiloxy, or silylsiloxy group.

As used herein, "carbonyl" refers to any group comprising RRC=O, where R may be any group. Examples of carbonyl groups include aldehyde (—COH), ketone (COR'), ester (COOR'), acyl (RR'C=O), carboxyl, thioester (COSR'), primary amide (CONH$_2$), secondary amide (CONHR'), tertiary amide (CONR'R") or the like.

As used herein, "siloxane" refers to an (R)$_2$—Si—O—, where R may independently be H, alkyl, aryl, thioether or alkoxy. A siloxane may be branched or linear, substituted or unsubstituted, or comprise alternating Si and O atoms.

As used herein, "thioether" refers to an —S—R group where R may independently be H, alkyl, aryl, alkoxy or the like.

R', R", R''' may be alkyl chains that contain between 1 and 50 non-hydrogen atoms such as C, N, O, S, Si, B or P that may be branched or unbranched, that may be acyclic or cyclic, and that may contain any permutation of heteroatomic substituents such as N, O, S, Si, B or halogen.

As used herein, "aryl" refers to a group or substituent derived from an aromatic ring compound where one or more hydrogen atoms are removed from the ring. An aryl group may alternately be referred to as an aromatic group. An aryl group may comprise a single atom species in the ring (e.g. all ring atoms may be carbon, such as in a phenyl ring—a 'carbocycle') or may comprise one or more heteroatoms in the ring—a "heteroaryl". An aryl group may be polycyclic. The carbocyclic, heterocyclic or polycyclic aryl group may comprise one or more substituent groups (a substituted aryl) or be unsubstituted (an unsubstituted aryl). A carbocyclic aryl group may be substituted or unsubstituted phenyl or the like. A carbocyclic aryl group may be polycyclic.

A heterocyclic aryl group may be substituted or unsubstituted pyrrole, furan, thiophene, imidazole, pyrazole, oxazole, isoxazole, thiazole, isothiazole, triazole, furazan, oxadiazole, thiadiazole, dithiazole, tetrazole, pyridine, pyran, thiopyran, diazine, oxazine, thiazine, dioxine, dithiine, triazine, tetrazine, or the like.

A polycyclic aryl group may be substituted or unsubstituted indole, isoindole, quinolone, isoquinoline, benzofuran, benzothiophene, acridine, dibenzothiophene, carbazole, dibenzofuran or the like.

As used herein, alkyl, heteroalkyl, alkoxy, alkylalkoxy or aryl groups may further comprise 1, 2, 3, 4, 5 or more substituent groups. Substituent groups may be independently selected from the groups comprising:
(i) hydrogen or halogen;
(ii) alkyl or alkoxy;
(iii) a derivative of group (ii) above in which one or more of the carbon atoms have been replaced with a heteroatom such as nitrogen, oxygen, sulfur, boron, silicon or phosphorous;
(iv) a derivative of groups (ii), (iii), or (ii) and (iii) above in which one or more of the hydrogen atoms have been replaced with a heteroatom such as nitrogen, oxygen, sulfur, fluorine, chlorine or bromine;
(v) a monocyclic or bicyclic cycloalkyl group containing from one to fifteen carbon atoms, or the like;
(vi) a derivative of group (v) above in which one or more of the carbon atoms have been replaced with a heteroatom such as nitrogen, oxygen, sulfur, boron, silicon or phosphorous;
(vi) a derivative of groups (v), (vi), or (v) and (vi) above in which one or more of the hydrogen atoms have been replaced with a heteroatom such as nitrogen, oxygen, sulfur, fluorine, chlorine or bromine;
(vii) an aryl group;

(viii) a derivative of group (vii) above in which one or more of the hydrogen atoms have been replaced with a heteroatom such as nitrogen, oxygen, sulfur, fluorine, chlorine or bromine;
(ix) a carbonyl group;
(x) a nitrogen-based group such as cyano (—CN), primary amine (NH$_2$), secondary amine (NHR'), tertiary amine (NR'R"), secondary amide (NHCOR'), tertiary amide (NR'COR"), secondary carbamate (NHCOOR'), tertiary carbamate (NR'COOR"), urea or N-substituted urea (NR'CONR"R'''), secondary sulfonamide (NHSO$_2$R'), tertiary sulfonamide (NR'SO$_2$R"), wherein groups R', R", R''', are defined supra;
(xi) an oxygen-based group e.g alcohol —OH, ether (OR'), primary carbamate (OCONH$_2$) secondary carbamate (OCONHR'), tertiary carbamate (OCONR'R"), wherein groups R', R", etc., are defined supra.
(xii) a sulfur-based group such as —SH, thioether (SR'), sulfoxide (SOR'), sulfone (SO$_2$R'), primary sulfonamide (SO$_2$NH$_2$), secondary sulfonamide (SO$_2$NHR'), tertiary sulfonamide (SO$_2$NR'R"), wherein groups R', R", R''' are defined supra.

In some aspects of the invention, $R_{6a}$, $R_{6b}$, $R_{6c}$, $R_{7a}$, $R_{7b}$, $R_{7c}$ $R_{8a}$, $R_{8b}$, $R_{8c}$, $R_{8d}$, $R_{8e}$, $R_{9a}$, $R_{9b}$, $R_{9c}$, $R_{9d}$, $R_{9e}$, $R_{10a}$, $R_{10b}$, $R_{10c}$, $R_{10d}$ may independently comprise an electron-withdrawing group (EWG), electron-donating group (EDG) or bulky group. It should be understood that the term "electron-accepting group" can be used synonymously herein with "electron acceptor" and "electron-withdrawing group". In particular, an "electron-withdrawing group" ("EWG") or an "electron-accepting group" or an "electron-acceptor" refers to a functional group that draws electrons to itself more than a hydrogen atom would if it occupied the same position in a molecule. Examples of EWG include halo, electron-poor heteroaryl groups, electron-poor substituted aryl groups, —NO$_2$, —$^+$NR$_3$, —$^+$NH$_3$, —SO$_3$H, —CN, CF$_3$, aldehyde, ester, carboxylic acid, carbonyl, carbonyl chloride, amide or the like. It should further be understood that the term "electron-donating group" can be used synonymously herein with "electron donor". In particular, an "electron-donating group" or an "electron-donor" refers to a functional group that donates electrons to a neighboring atom more than a hydrogen atom would if it occupied the same position in a molecule. Examples of EDG include —OH, OR, NH$_2$, NHR, NR$_2$, electron-rich heteroaryl groups, electron-rich substituted aryl groups, —O—, amine, alcohol, ether, carbamate, or the like.

A substituent group may comprise a siloxy or silyl component—for example silane, siloxy, alkylsiloxy, silanesiloxy, alkoxysilane, Formula XI, Formula XII, or the like—the substituent group may comprise:

Formula XI

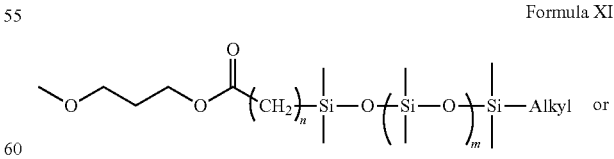

or

Formula XII

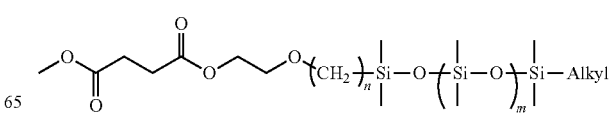

wherein n and m are independently any integer from 0 to 20, or any range therebetween, or 0, 1, 2, 3, 4, 5, 6, 7, 8, 9, 10, 11, 12, 13, 14, 15, 16, 17, 18, 19 or 20.

A "bulky" group may be an alkyl, aryl, alkoxy, silane, siloxy, alkylsiloxy, silanesiloxy, alkoxysilane, or a substituted alkyl, aryl, alkoxy, silane, siloxy, alkylsiloxy, silanesiloxy, alkoxysilane, the bulky substituent group comprising at least two atoms selected from the group comprising C, N, O, Si or S. In some embodiments, a bulky substituent group is a substituted or unsubstituted ethyl, propyl, butyl, tert-butyl or pentyl group, or a substituted or unsubstituted alkoxy group. In some embodiments, a bulky substituent group is a substituted or unsubstituted formula XI or formula XII. In some embodiments, a bulky substituent group is an alkyl-substituted thiophene, or an alkyl-substituted phenyl, or an alkyl substituted benzothiophene or an alkyl substituted benzofuran.

Inclusion of a bulky substituent group may increase the, photostationary state, solubility, photostability or durability of a compound. As an illustrative example, and without wishing to be bound by theory, some positions of an internal or external thiophenyl ring may polymerize when subjected to oxidation conditions by application of a voltage. Inclusion of a bulky group at $R_{6a}$ or $R_{7a}$ (5-position), or $R_{6b}$ or $R_{7b}$ (4-position) of a thiophenyl ring may improve the durability of the compound when subjected to multiple cycles of electrooxidation. In some embodiments, a small (e.g. 1 or 2 carbon containing moieties such as methyl or ethyl) group in both 4 and 5 positions, or a larger bulky group (e.g. 3, 4, 5 or 6 carbon-containing moieties such as propyl, butyl (primary, secondary or tertiary), pentyl or hexyl in the 5 position may provide improved durability of the compound.

Compounds according to various embodiments of the invention may include one or more of the following:

Each $R_1$ and $R_2$ may be independently selected from a group comprising H or F.

$R_3$ and $R_4$ may each be independently selected from a group comprising one or more than one of thiophenyl, substituted thiophenyl, benzyl, substituted benzyl,

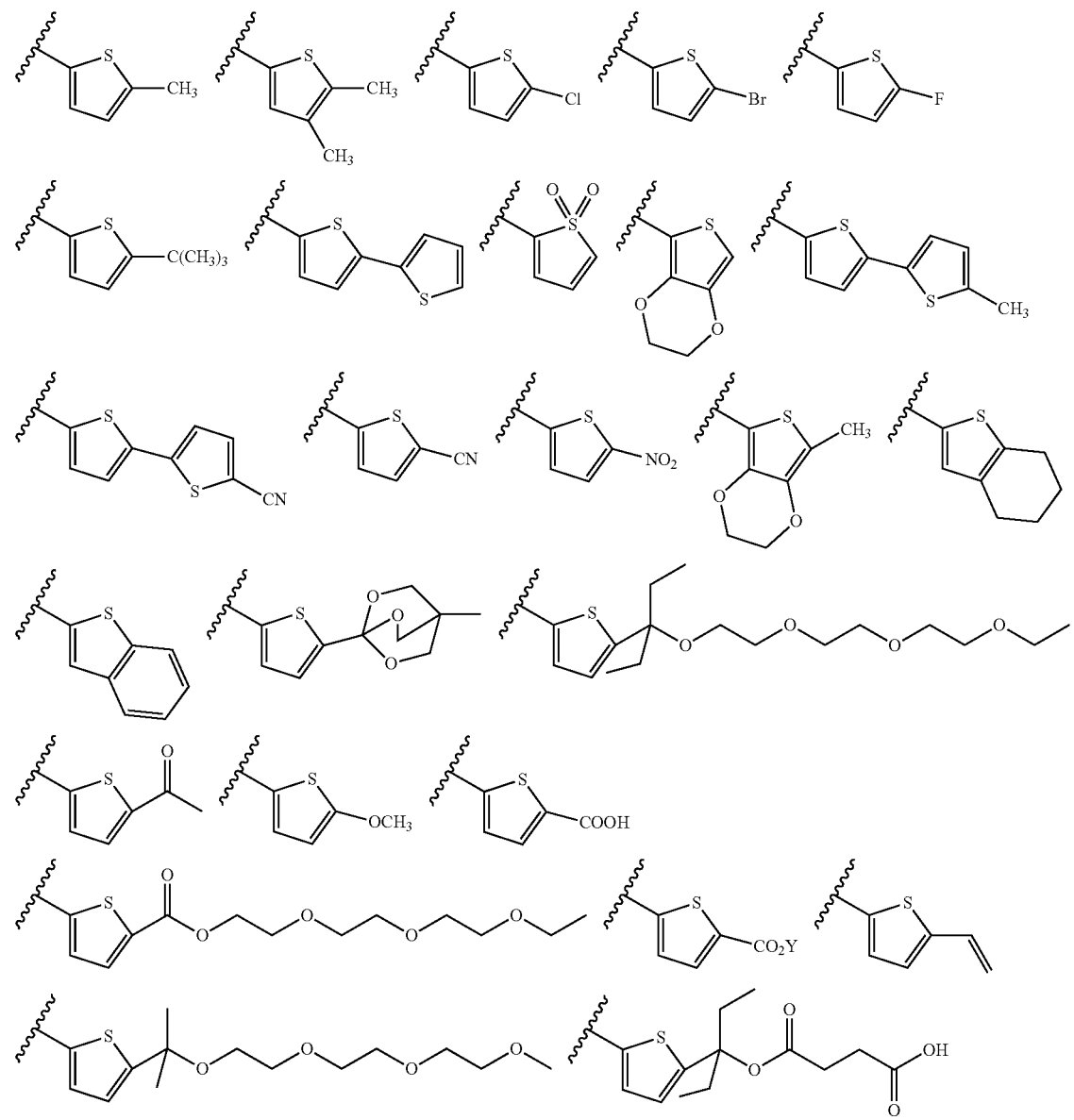

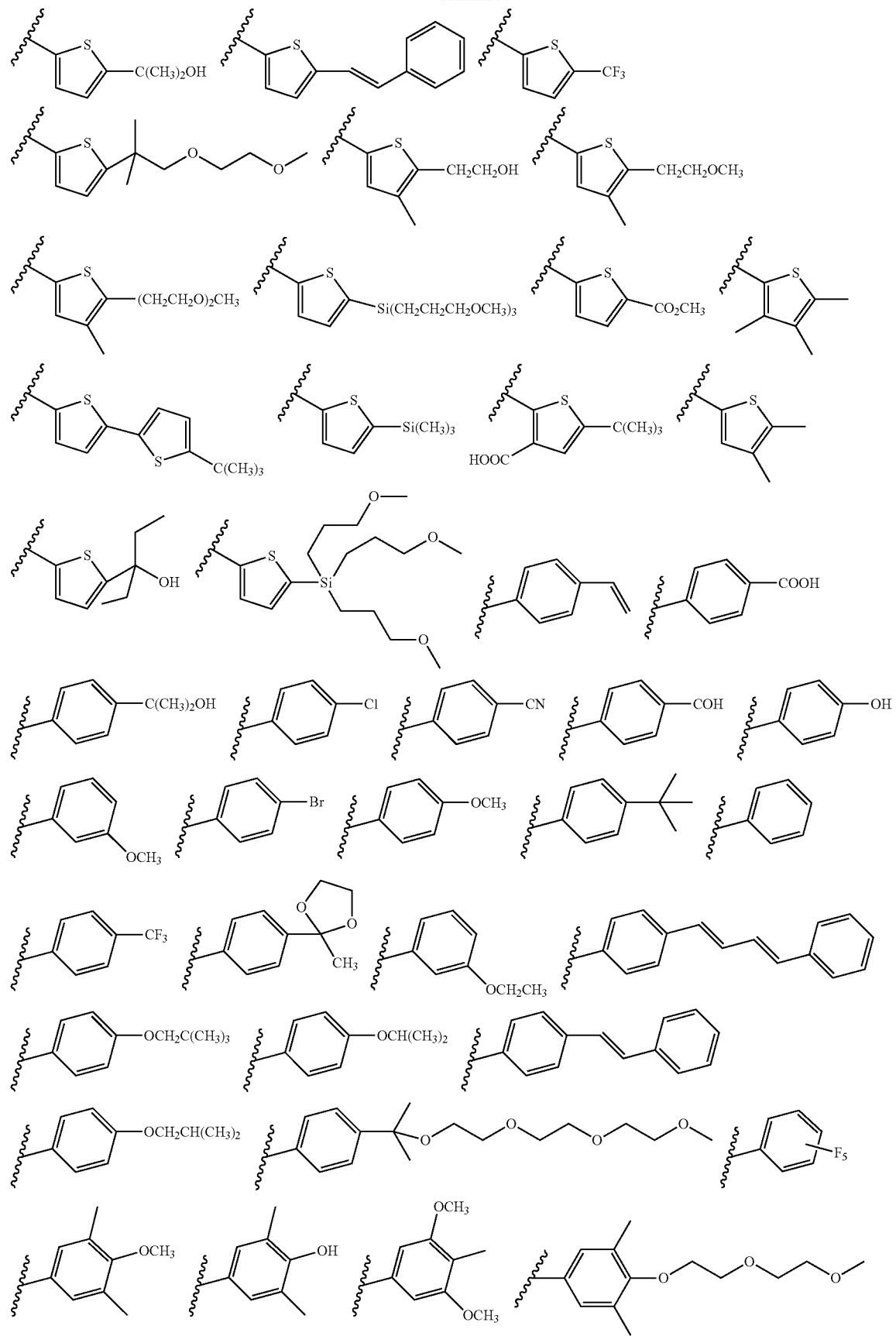

-continued

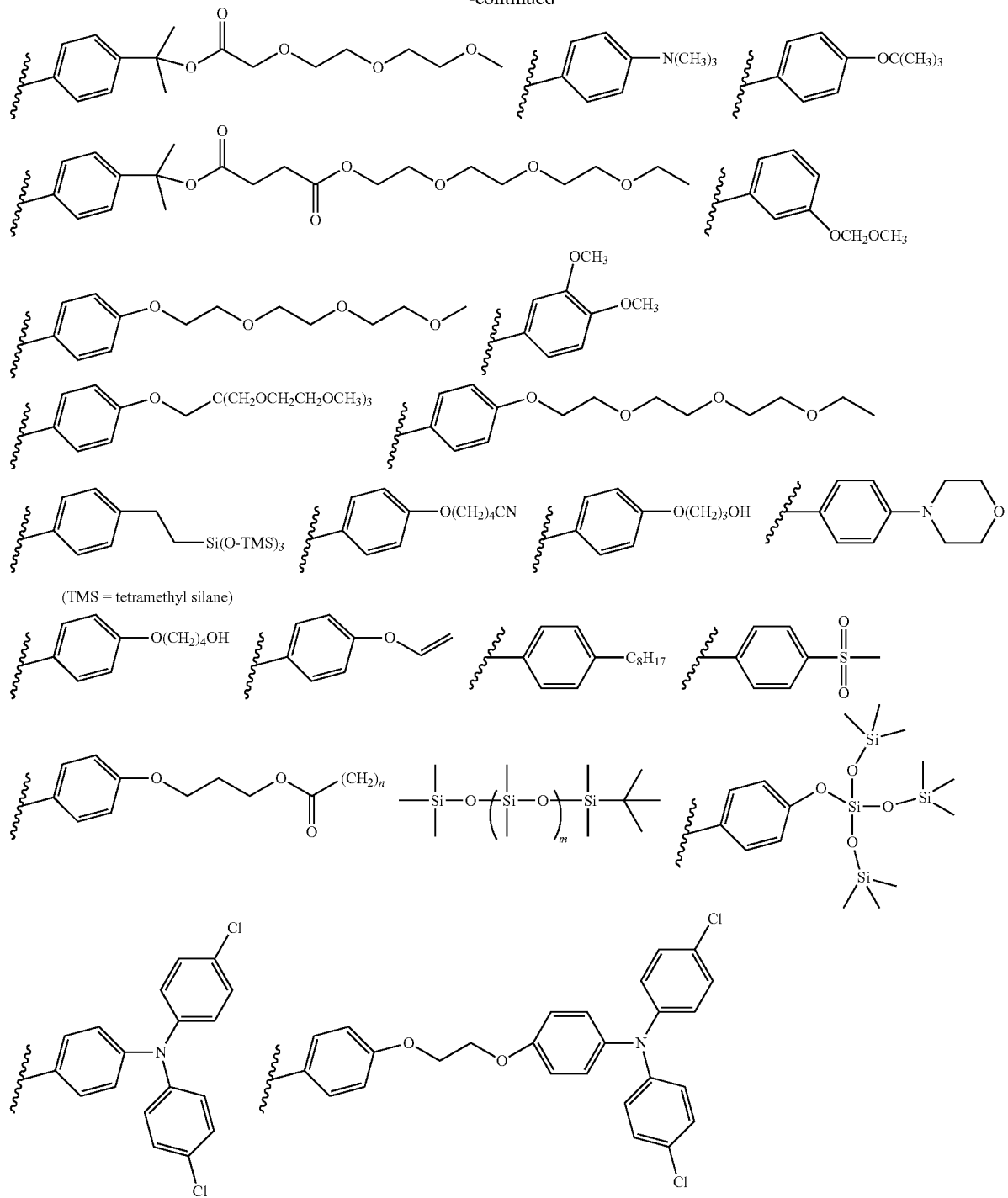

In some embodiments, the group from which $R_3$ may be selected may further comprise one or more of H, Cl, Br, F, $CF_3$, methyl, ethyl, propyl, butyl, tert-butyl, —$CH_2$—$CH_2$—, —CH═CH—, —$OCH_3$, $CO_2H$, $COCH_3$, $CO_2Y$, $C(CH_3)_2OH$, $Si(CH_2)_3OCH_3$, $Si(CH_3)_3$, $Si((CH_2)_3)$ $CH_3)_3CH_2CH_2OCH_3$, $CH_2CH_2OH$, Each $R_5$ may be independently selected from a group comprising: H, methyl, ethyl, propyl, butyl, tert-butyl, thiophenyl, substituted thiophenyl, benzyl, substituted benzyl, —CH═CH—, —CH═CH—, —$OCH_3$, $CO_2H$.

$R_3$ and $R_5$ may each be —CH═CH— and fused to form a ring, or $R_3$ and $R_5$ may each be —$CH_2$—$CH_2$— and fused to form a ring;

Substituent groups of a substituted thiophene or substituted benzyl group may include —CN, methyl, ethyl, propyl, butyl, tert-butyl;

$R_{6a}$ and $R_{6b}$, or $R_{6b}$ and $R_{6c}$, or $R_{7a}$ and $R_{7b}$, or $R_{7b}$ and $R_{7c}$ may each be a) —CH═CH— and fused to form a ring; or b) —$CH_2$—$CH_2$— and fused to form a ring; or c) —O—$CH_2$— and fused to form a ring;

One or more than one of: $R_{6a}$, $R_{6b}$, $R_{6c}$; and/or $R_{7a}$, $R_{7b}$, $R_{7c}$; and/or $R_{8a}$, $R_{8b}$, $R_{8c}$, $R_{8d}$, $R_{8e}$; and/or $R_{9a}$, $R_{9b}$, $R_{9c}$, $R_{9d}$, $R_{9e}$; and/or $R_{10a}$, $R_{10b}$, $R_{10c}$, $R_{10d}$ may each independently be selected from a group comprising one or more of: H, Cl, Br, F, —$CF_3$, —CN, —$NO_2$, methyl, ethyl, propyl, iso-propyl, butyl, sec-butyl, iso-butyl, tert-butyl, saturated or unsaturated alkyl that is linear or branched with 5-12 carbons, —$Si(R_{11})_3$, thiophene, substituted thiophene, benzyl, substituted benzyl, —$CH_2$—$CH_2$—, —CH=CH—, —CH=$CH_2$, —$OCH_3$, —COH, —OH, —$CO_2H$, —$COCH_3$, —$CO_2Y$, —$C(CH_3)_2OH$, —$Si(CH_3)_3$, —$CH_2CH_2OCH_3$, —$CH_2CH_2OH$, —$N(CH_3)_2$, —$CO_2CH_3$, —$OCH_2OCH_3$, —$SO_2CH_3$, —$OCH_2C(CH_3)_3$, —$OCH_2CH(CH_3)_2$, —$OC(CH_3)_3$, —OCH=$CH_2$, —$O(CH_2)_4CN$, —$O(CH_2)_4OH$, —$O(CH_2)_3OH$, —$C(CH_3)_2OH$, —$OCH_2)_2OCH_3$,

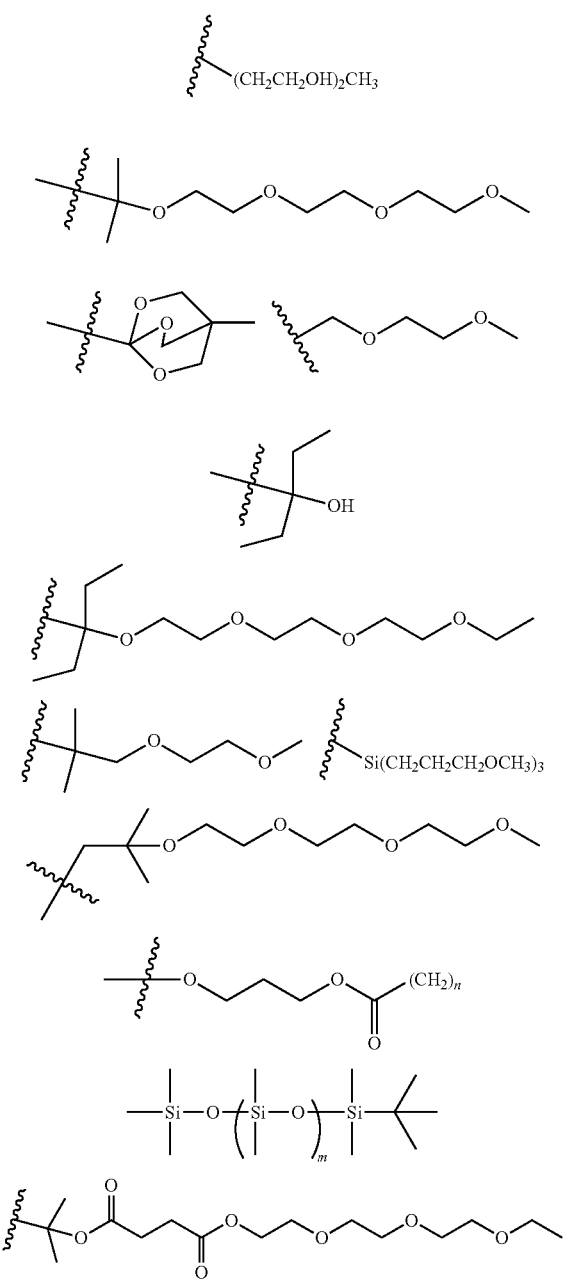

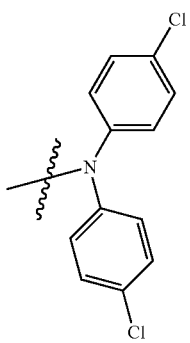

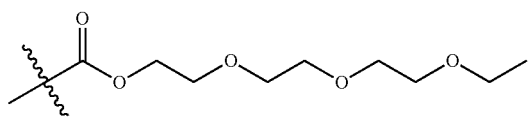

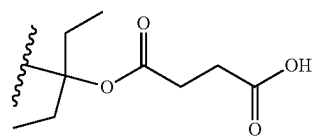

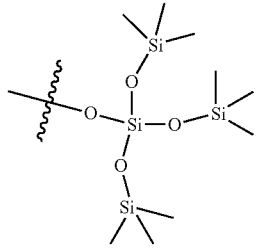

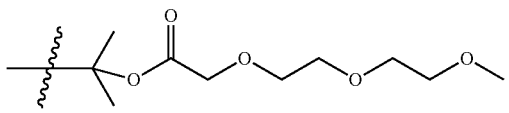

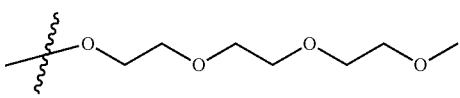

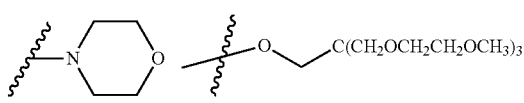

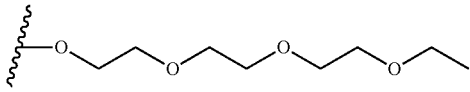

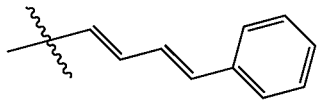

In some embodiments, each $R_{11}$ of —$Si(R_{11})_3$ may be independently selected from the group comprising R or —O—R, and wherein R is linear or branched, non-aromatic monocyclic or polycyclic, substituted or unsubstituted alkyl group of 1 to 20 carbons. In some embodiments, each R may be a heteroalkyl group comprising one or more of O, S, N or Si, or each R may be a saturated or unsaturated alkyl that is linear or branched with 1-12 carbons, or each R may be a substituted or unsubstituted methyl, ethyl, propyl, iso-propyl, butyl, sec-butyl, iso-butyl, tert-butyl, pentyl or hexyl.

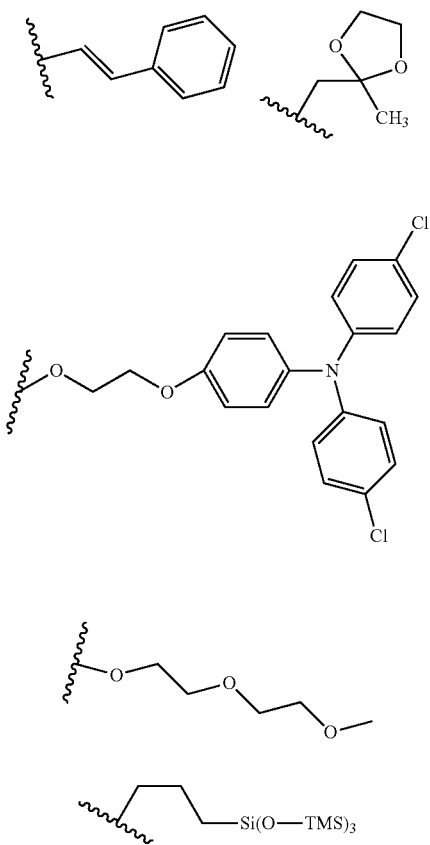

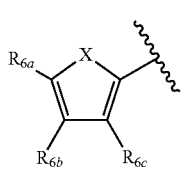

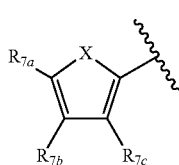

Exemplary compounds according to Formulae IA and IB include: S039, S053, S073, U130, U136, U142.

Exemplary compounds according to Formulae IIA and IIB (compounds according to Formula IA/IB where $R_3$ is

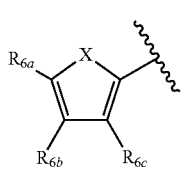

and $R_4$ is

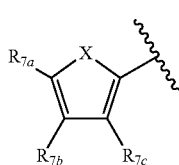

include one or more of: S001, S003, S007, S011, S012, S013, S019, S020, S024, S026, S027, S034, S036, S037, S038, S040, S047, S048, S106, S119, S124, S128, S135, S138, S143, S148, S149, S154, S158, S170, U008, U009, U010, U018, U021, U022, U023, U025, U028, U029, U030, U041, U100, U102, U117, U120, U125, U126, U127, U129, U131, U132, U133, U134, U156, U159, U160, U165, S170.

Exemplary compounds according to Formulae IIIA and IIIB (compounds according to Formula IA/IB where $R_3$ is

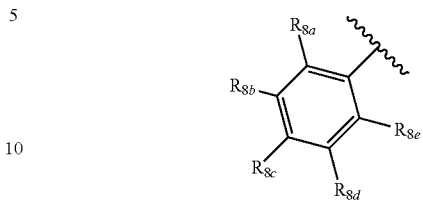

and $R_4$ is

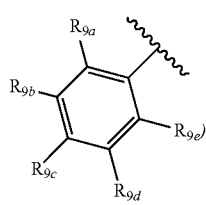

include one or more of: S002, S006, S016, S017, S042, S043, S044, S050, S054, S056, S057, S059, S060, S063, S064, S065, S066, S067, S068, S074, S084, S085, S086, S087, S088, S089, S090, S091, S092, S094, S095, S096, S097, S103, S116, U031, U051, U058, U061, U062, U069, U070, U071, U072, U076, U077, U078, U080, U081, U093, U099, U101.

Exemplary compounds according to Formulae IVA and IVB (compounds according to Formula IA/IB where $R_3$ is

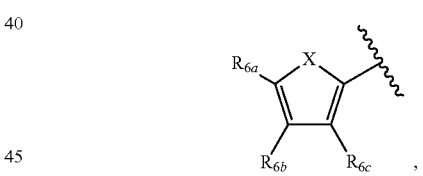

and $R_4$ is

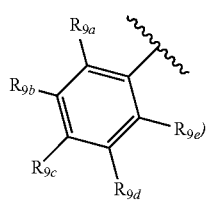

include one or more of: S052, S098, S104, S105, S108, S109, S110, S111, S112, S113, S115, S118, S139, S141, U107, U114, U122, U123.

Exemplary compounds according to Formulae VA and VB (compounds according to Formula IA/IB where $R_3$ is

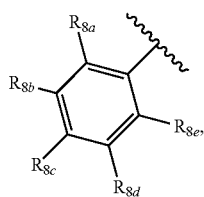

and $R_4$ is

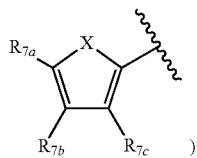

include: S049

Exemplary compounds according to Formulae VIA and VIB (compounds according to Formula IA/IB where a first $R_3$ is

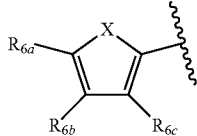

and a second $R_3$ is

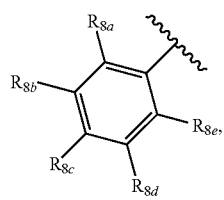

and a first $R_4$ is

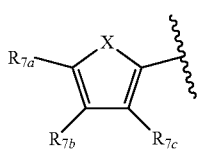

and a second $R_4$ is

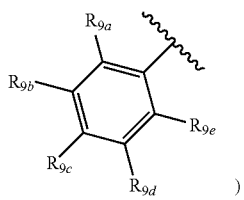

include one or more of: S004, S005.

Exemplary compounds according to Formula VIIA and VIIB include one or more of: S014, S015, S079, S083, S137, S140, S144, S157, U082, U121, U142, S144, U145, U146, U147, U150, S151, S152, U153, S155, U157, S161, S162, S163, S164.

Exemplary compounds according to Formulae VIIIA and VIIIB (compounds according to Formula VIIA/B where R4 is

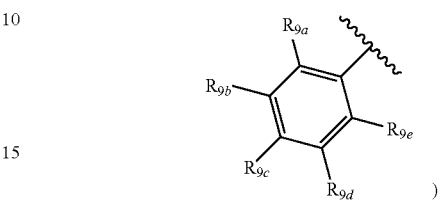

include one or more of S014, S015, S079, S083, S140, S157, U082, U121, S144, U142, U145, U146, U147, U150, S151, U153, S155, U157, S161, S162, S163, S164, S191 and S193.

Exemplary compounds according to Formulae IXA and IXB (compounds according to Formula VIIA/B where R4 is

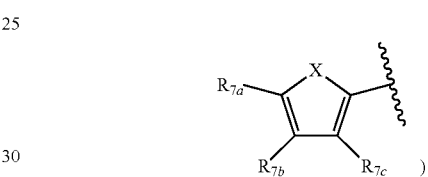

include one or more of S137, S144, S152.

Exemplary compounds according to Formulae XA and XB include one or more of S191 and S193.

Other exemplary compounds according to various embodiments of the invention include one or more of: S032, S035, S055, U045.

In some embodiments, compounds with an increased absorbance at a photostationary state (PSS) or a suitable, or increased contrast ratio, or an increased solubility may be an improvement. A compound with a greater absorbance in the visible range may be used in lesser quantities in a formulation or material to achieve a desired contrast ratio, whereas a compound with a lower absorbance at a PSS may need a higher concentration to achieve a desired contrast ratio. Absorbance at a PSS for selected compounds was measured at $2.0 \times 10^{-5}$ M in triglyme in the absence (full) or presence (+UV) of a UV blocking film with a UV cutoff wavelength of 370 nm (10% transmission at 370 nm), using simulated sunlight (QSUN solar simulator) as a light source, or a 365 nm light source; these PSS are reported in Tables 1.5. All of the compounds demonstrated electroswitching. "Switch" refers to the ability (yes or no) of the compound to be reversibly converted under photochromic and electrochromic conditions between a ring-open isomer and ring-closed isomer.

In addition to an electrochromic ring-opening isomerization, compounds according to various embodiments of the invention also exhibit a photochromic ring-opening isomerization when exposed to visible light. A sensitivity index (SI) is a ratio of the PSS under 365 nm light to the PSS under full spectrum light (without UV blocking film). SI is an indicator of the sensitivity of the compound to the composition of the incident light (a change in the ratio of UV and visible components)—photochemical ring-opening is induced by a portion of the visible light spectrum. An SI of about 1 indicates that the rate of photoconversion to the ring-closed state is about equal with both light sources, whereas as the SI increases it is indicative of a greater sensitivity to the composition of the light source.

Applications that may benefit from a higher rate of photoconversion to a ring-closed state may benefit from a compound having a higher PSS, while applications that may benefit from a low rate of photoconversion to a ring-closed state may benefit from a lower PSS. Applications that may benefit from a compound that is less responsive to the light composition may benefit from a compound having an SI closer to 1, whereas applications that may benefit from a compound that exhibits a higher sensitivity to the composition of light may benefit from a compound with a higher SI.

TABLE 1

Figure 5:
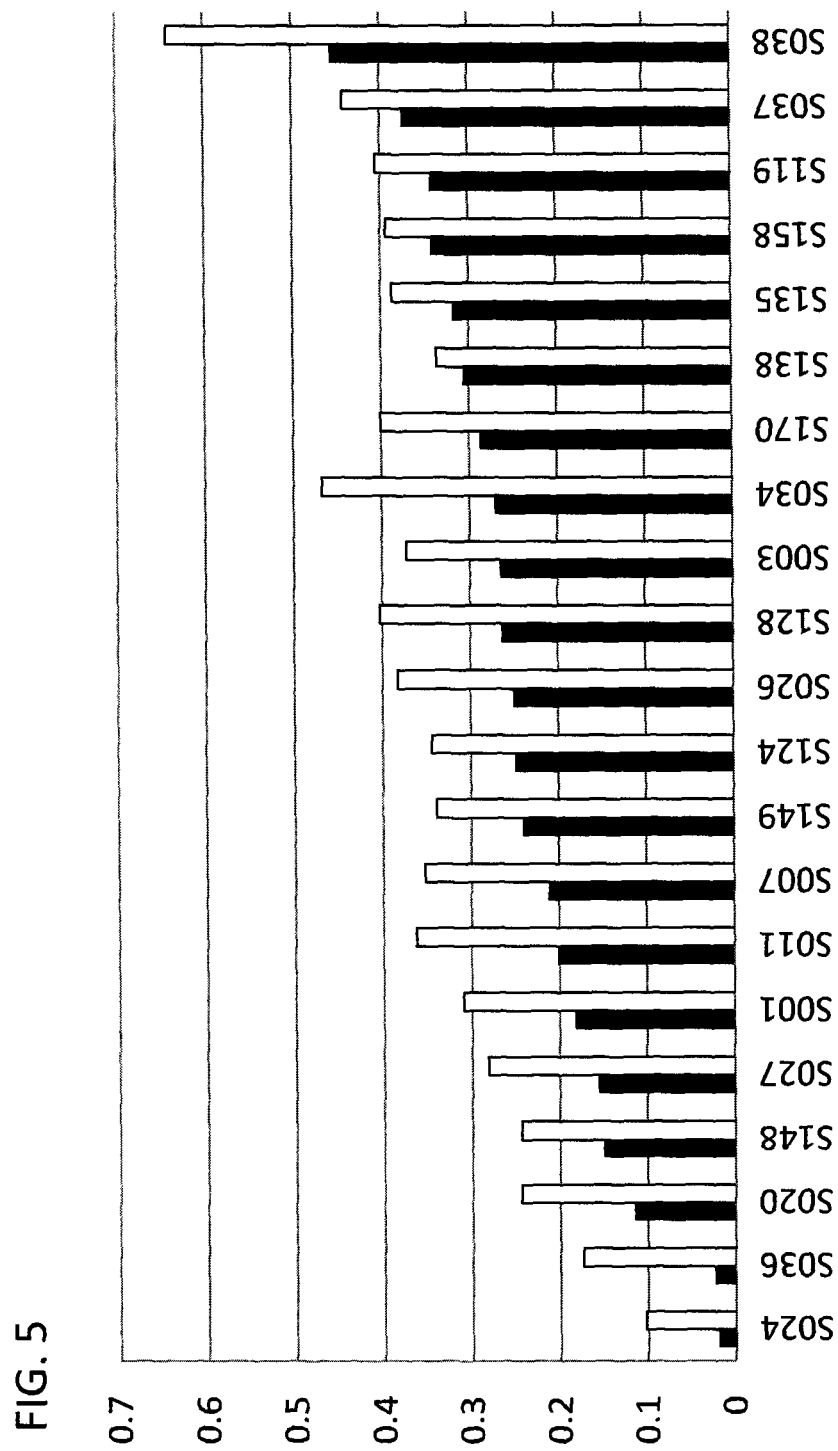
FIG. 5 provides a bar graph illustrating the PSS of selected compounds according to Formula IIA/IIB, in the ring-closed isoform (Formula IIB) when exposed to 365 nm light (open bar), or full spectrum light (QSUN solar simulator) (solid bar). X-axis—compound reference numbers; Y-axis—absorbance.

Absorbance at PSS for selected chromophores according to Formulae IIA and IIB. FIG. 5 provides a bar graph illustrating the PSS of Formula II compounds in the ring-closed isoform (Formula IIB) when exposed to 365 nm light (365 nm), or simulated sunlight.

| compound | $\lambda$ max | full | +UV | 365 nm | Switch | sensitivity index |
|---|---|---|---|---|---|---|
| S024 | 650 | 0.02 | 0.018 | 0.102 | Y | 5.10 |
| S036 | 665 | 0.024 | 0.016 | 0.174 | Y | 7.25 |
| S020 | 665 | 0.115 | 0.085 | 0.244 | Y | 2.12 |
| S148 | 650 | 0.15 | 0.092 | 0.244 | Y | 1.63 |
| S027 | 645 | 0.156 | 0.116 | 0.281 | Y | 1.80 |
| S001 | 640 | 0.182 | 0.113 | 0.309 | Y | 1.70 |
| S011 | 655 | 0.201 | 0.142 | 0.363 | Y | 1.81 |
| S007 | 650 | 0.212 | 0.154 | 0.353 | Y | 1.67 |
| S149 | 647 | 0.241 | 0.169 | 0.339 | Y | 1.41 |
| S124 | 649 | 0.249 | 0.225 | 0.344 | Y | 1.38 |
| S026 | 645 | 0.251 | 0.196 | 0.383 | Y | 1.53 |
| S128 | 648 | 0.264 | 0.224 | 0.403 | Y | 1.53 |
| S003 | 650 | 0.2655 | 0.2055 | 0.372 | Y | 1.40 |
| S034 | 690 | 0.271 | 0.246 | 0.468 | Y | 1.73 |
| S170 | 645 | 0.287 | 0.182 | 0.401 | Y | 1.40 |
| S138 | 650 | 0.306 | 0.262 | 0.337 | Y | 1.10 |
| S135 | 648 | 0.318 | 0.224 | 0.387 | Y | 1.22 |
| S158 | 650 | 0.342 | 0.291 | 0.394 | Y | 1.15 |
| S119 | 643 | 0.343 | 0.295 | 0.405 | Y | 1.18 |
| S037 | 680 | 0.375 | 0.355 | 0.442 | Y | 1.18 |
| S038 | 690 | 0.456 | 0.431 | 0.642 | Y | 1.41 |

TABLE 2

Figure 6:
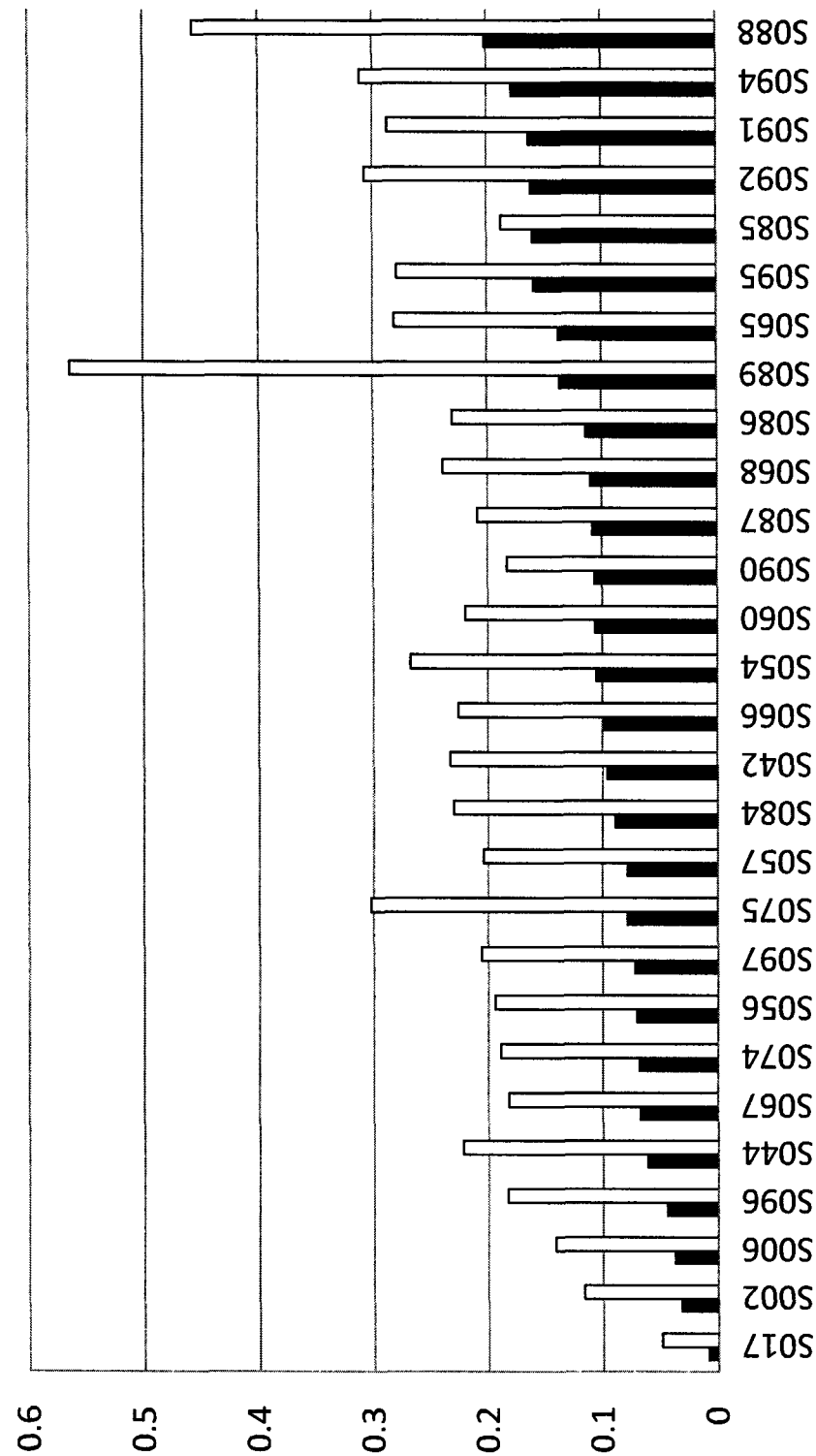
FIG. 6 provides a bar graph illustrating the PSS of selected compounds according to Formula IIIA/B, in the ring-closed isoform (Formula IIIB) when exposed to 365 nm light (open bar), or full spectrum light (solid bar). X-axis—compound reference numbers; Y-axis—absorbance.

Absorbance at PSS for selected chromophores according to Formulae IIIA and IIIB. FIG. 6 provides a bar graph illustrating the PSS of Formula III compounds in the ring-closed isoform (Formula IIIB) when exposed to 365 nm light (365 nm), or simulated sunlight.

| compound | $\lambda$ max | full | +UV | 365 nm | Switch | sensitivity index |
|---|---|---|---|---|---|---|
| S017 | 605 | 0.009 | 0.0025 | 0.049 | Y | 5.44 |
| S002 | 612 | 0.0325 | 0.0095 | 0.116 | Y | 3.57 |
| S006 | 610 | 0.038 | 0.013 | 0.141 | Y | 3.71 |
| S096 | 609 | 0.045 | 0.014 | 0.183 | Y | 4.07 |
| S044 | 605 | 0.062 | 0.027 | 0.222 | Y | 3.58 |
| S067 | 615 | 0.068 | 0.03 | 0.182 | Y | 2.68 |
| S074 | 620 | 0.069 | 0.024 | 0.189 | Y | 2.74 |
| S056 | 610 | 0.071 | 0.026 | 0.194 | Y | 2.73 |
| S097 | 611 | 0.073 | 0.029 | 0.206 | Y | 2.82 |
| S075 | 670 | 0.079 | 0.031 | 0.302 | Y | 3.82 |
| S057 | 610 | 0.079 | 0.033 | 0.204 | Y | 2.58 |
| S084 | 625 | 0.09 | 0.051 | 0.23 | Y | 2.56 |
| S042 | 612 | 0.097 | 0.04 | 0.233 | Y | 2.40 |
| S066 | 615 | 0.099 | 0.049 | 0.226 | Y | 2.28 |
| S054 | 630 | 0.106 | 0.056 | 0.268 | Y | 2.53 |
| S060 | 615 | 0.107 | 0.038 | 0.22 | Y | 2.06 |
| S090 | 624 | 0.107 | 0.058 | 0.183 | Y | 1.71 |
| S087 | 628 | 0.109 | 0.055 | 0.209 | Y | 1.92 |
| S068 | 615 | 0.111 | 0.051 | 0.239 | Y | 2.15 |
| S086 | 610 | 0.115 | 0.071 | 0.231 | Y | 2.01 |
| S089 | 656 | 0.137 | 0.126 | 0.564 | Y | 4.12 |
| S065 | 625 | 0.138 | 0.054 | 0.281 | Y | 2.04 |
| S095 | 625 | 0.16 | 0.086 | 0.279 | Y | 1.74 |
| S085 | 640 | 0.161 | 0.08 | 0.187 | Y | 1.16 |
| S092 | 627 | 0.162 | 0.093 | 0.307 | Y | 1.90 |
| S091 | 629 | 0.164 | 0.095 | 0.287 | Y | 1.75 |
| S094 | 625 | 0.179 | 0.103 | 0.311 | Y | 1.74 |
| S088 | 656 | 0.202 | 0.132 | 0.457 | Y | 2.26 |

TABLE 3

Figure 7:
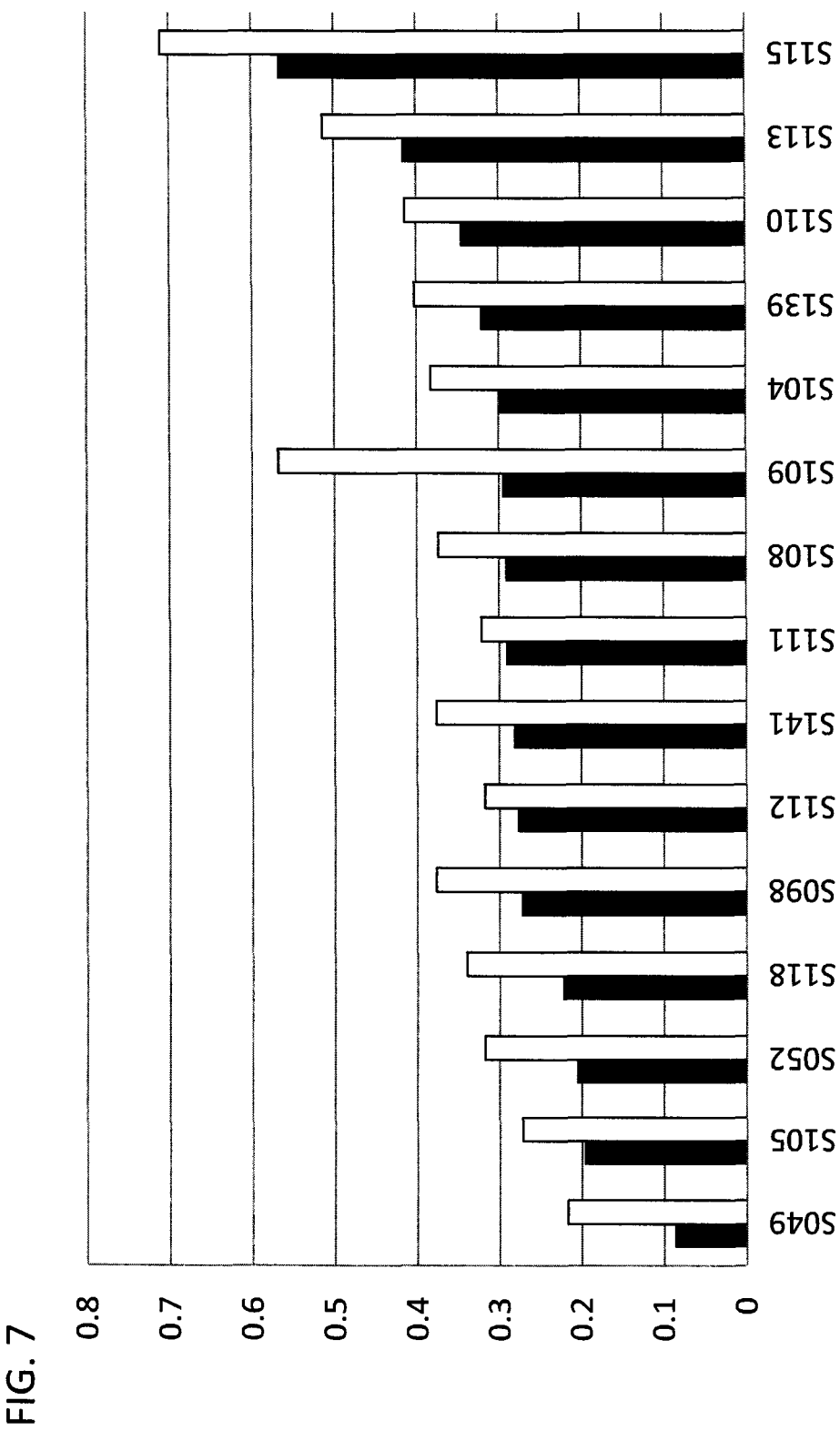
FIG. 7 provides a bar graph illustrating the PSS of selected compounds according to Formula IVA/B, in the ring-closed isoform (Formula IVB) when exposed to 365 nm light (open bar), or full spectrum light (solid bar). X-axis—compound reference numbers; Y-axis—absorbance.

Absorbance at PSS for selected chromophores according to Formula IVA and IVB. FIG. 7 provides a bar graph illustrating the PSS of Formula IV compounds in the ring-closed isoform (Formula IVB) when exposed to 365 nm light (365 nm), or simulated sunlight.

| compound | $\lambda$ max | full | +UV | 365 nm | Switch | sensitivity index |
|---|---|---|---|---|---|---|
| S049 | 625 | 0.087 | 0.044 | 0.217 | Y | 2.49 |
| S105 | 647 | 0.197 | 0.134 | 0.272 | Y | 1.38 |
| S052 | 630 | 0.206 | 0.116 | 0.318 | Y | 1.54 |
| S118 | 648 | 0.223 | 0.124 | 0.34 | Y | 1.52 |
| S098 | 645 | 0.273 | 0.182 | 0.377 | Y | 1.38 |
| S112 | 663 | 0.278 | 0.246 | 0.318 | Y | 1.14 |
| S141 | 643 | 0.282 | 0.183 | 0.377 | Y | 1.34 |
| S111 | 646 | 0.292 | 0.192 | 0.322 | Y | 1.10 |
| S108 | 645 | 0.292 | 0.215 | 0.374 | Y | 1.28 |
| S109 | 645 | 0.296 | 0.217 | 0.367 | Y | 1.24 |
| S104 | 645 | 0.299 | 0.203 | 0.383 | Y | 1.28 |
| S139 | 644 | 0.322 | 0.216 | 0.403 | Y | 1.25 |
| S110 | 653 | 0.346 | 0.221 | 0.414 | Y | 1.20 |
| S113 | 643 | 0.417 | 0.293 | 0.514 | Y | 1.23 |
| S115 | 644 | 0.567 | 0.401 | 0.71 | Y | 1.25 |

TABLE 4

Figure 8:
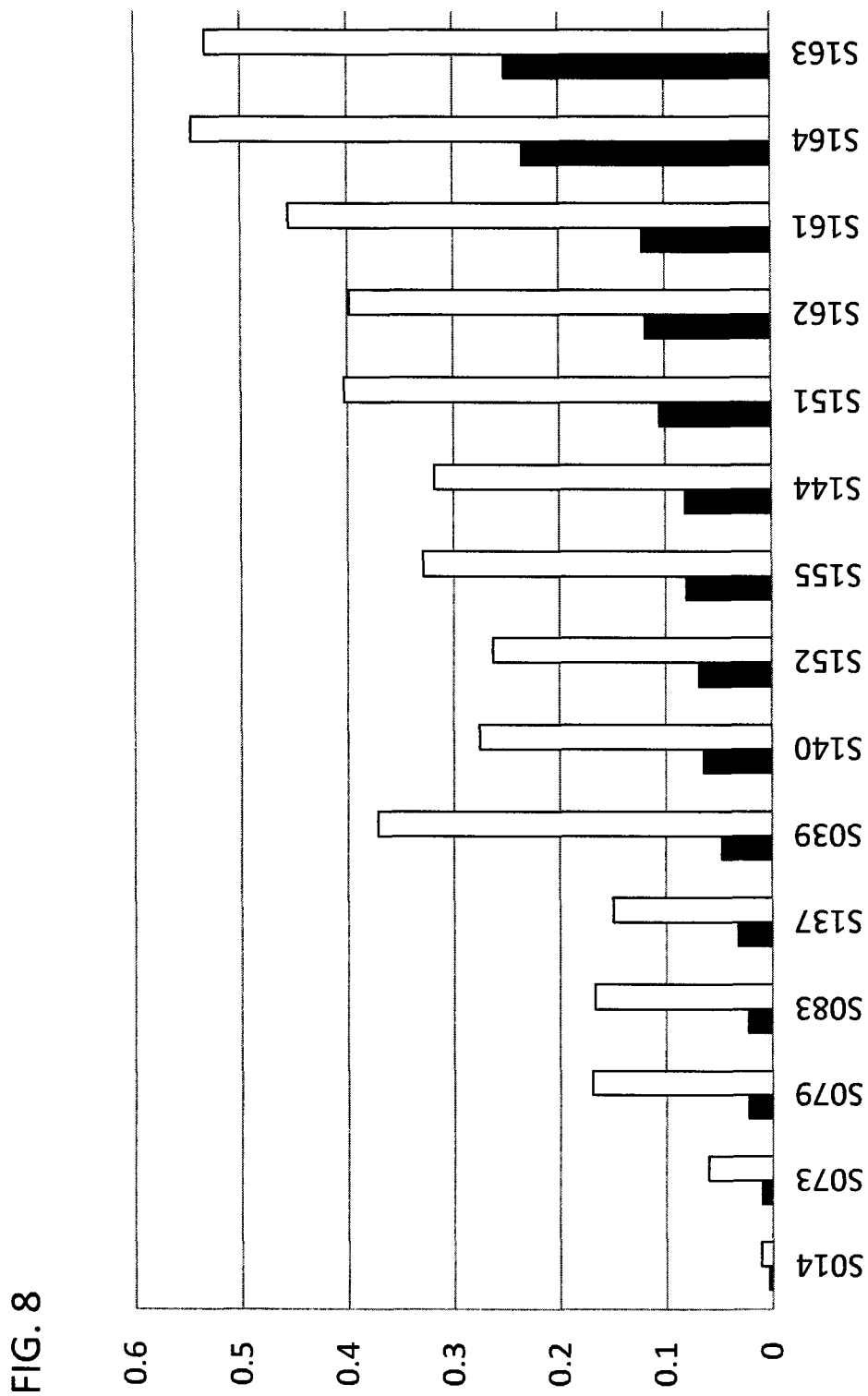
FIG. 8 provides a bar graph illustrating the PSS of selected compounds according to Formula VIIA/B, in the ring-closed isoform (Formula VIIB) when exposed to 365 nm light (open bar), or full spectrum light (solid bar). X-axis—compound reference numbers; Y-axis—absorbance.

Absorbance at PSS for selected chromophores according to Formula VIIA and VIIB. FIG. 8 provides a bar graph illustrating the PSS of Formula VII compounds in the ring-closed isoform (Formula VIIB) when exposed to 365 nm light (365 nm), or simulated sunlight.

| compound | $\lambda$ max | full | +UV | 365 nm | Switch | sensitivity index |
|---|---|---|---|---|---|---|
| S014 | 525 | 0.004 | 0.006 | 0.011 | Y | 2.75 |
| S073 | 550 | 0.0105 | 0.006 | 0.06 | Y | 5.71 |
| S079 | 490 | 0.023 | 0.008 | 0.17 | Y | 7.39 |
| S083 | 550 | 0.023 | 0.008 | 0.167 | Y | 7.26 |
| S137 | 497 | 0.033 | 0.016 | 0.15 | Y | 4.55 |
| S039 | 570 | 0.048 | 0.028 | 0.372 | Y | 7.75 |
| S140 | 516 | 0.065 | 0.032 | 0.276 | Y | 4.25 |
| S152 | 522 | 0.069 | 0.06 | 0.263 | Y | 3.81 |
| S155 | 516 | 0.081 | 0.045 | 0.329 | Y | 4.06 |
| S144 | 513 | 0.082 | 0.04 | 0.318 | Y | 3.88 |
| S151 | 514 | 0.106 | 0.056 | 0.403 | Y | 3.80 |
| S162 | 520 | 0.119 | 0.06 | 0.398 | Y | 3.34 |
| S161 | 511 | 0.122 | 0.06 | 0.455 | Y | 3.73 |
| S164 | 554 | 0.235 | 0.134 | 0.546 | Y | 2.32 |
| S163 | 588 | 0.252 | 0.116 | 0.533 | Y | 2.12 |

TABLE 5

Absorbance at PSS for selected chromophores.

| compound | λ max | full | +UV | 365 nm | Switch | sensitivity index |
|---|---|---|---|---|---|---|
| S032 | 600 | 0.032 | 0.008 | 0.594 | Y | 18.56 |
| S055 | 640 | 0.042 | 0.008 | 0.191 | Y | 4.55 |
| S035 | 540 | 0.05 | 0.016 | 0.416 | Y | 8.32 |
| S004 | 630 | 0.0325 | 0.02 | 0.139 | Y | 4.28 |
| S005 | 618 | 0.072 | 0.028 | 0.195 | Y | 2.71 |

Absorbance at a PSS, or the wavelength of maximum absorbance may vary with the substituent groups. Table 6 sets out some observations on the effect of various components, structures and substituent groups on PSS.

TABLE 6

PSS comparison of selected compounds. Relative impact of substituent groups on photostationary state is indicated with "✓" (increase) and "✗" (decrease); — No data; N/A: Not applicable.

| | | | Formula II | Formula III | Formula IV |
|---|---|---|---|---|---|
| Head | Perfluorocyclopentene | | ✓ | ✓ | — |
| | Thiazole derivative | | ✗ | ✓✗ | — |
| Core ring | Thiophene | | ✓✓ | ✓✓ | ✓✓ |
| | Thiazole | | — | ✓ | — |
| | Benzothiophene | | — | — | ✗ |
| | Benzofuran | | — | — | ✗ |
| Steric groups | All | | ✓✓ | ✓✓ | ✓✓ |
| | External | | ✓✓ | ✓✓ | ✓✓ |
| | Internal | | ✓ | ✓ | ✓ |
| EDG | All | | ✗ | ✓✓ | — |
| | External | | — | ✓✓ | — |
| | Internal | | — | ✓✗ | ✓✓ |
| EWG | All | | ✓✓ | ✗ | — |
| | External | | ✓✓ | ✗ | — |
| | Internal | | ✓✓ | ✗ | — |
| Peripheral rings | thiophene | R3 position | ✓✓✓ | N/A | ✓✓✓ |
| | | R4 position | ✓ | N/A | ✓ |
| | Phenyl | R3 positsion | N/A | ✗ | ✗ |
| | | R4 position | N/A | ✗ | ✓✗ |
| Extended π-conjugation | | | ✓✓✓ | ✓✗ | — |
| 4-Position core thiophene | | | — | ✗ | — |
| 4-Position peripheral thiophene | | | ✗ | — | — |
| Position of EDG | para | | — | ✓✓ | — |
| | meta | | — | ✗ | — |

The effect of different substituent groups on PSS may be considered. Compare compounds of the same, or different formula; for example:
- "head" structures of S032, S035, S055 and/or S075;
- core structure of S014, S032, S035, S079 and/or S083;
- peripheral rings—groups in the R3 and/or R4 position of 8001, S002, S003, S038, S049, S052, S088, S104, S108, S109, S138 and/or S158;
- substituent groups of S001, S007, S003, S042, S057, S110, and/or S068;
- electron withdrawing groups (EWG) and electron donating groups (EDG) of S002, S003, S020, S026, S034, S036, S037, S054, S074, S085, S086, S087, S096, S097, S098, S12, S118, and/or S119;
- extended conjugation of S034, S037, S038, S088, S089 and/or S110;
- position and species of substituent groups of S054, S091, S092, S094 and/or S095;
- substituent group size or length and composition of S098, S104, S105, S108, S109, S111, S113, S115, S138, S158, S170.

Other compounds described herein may be included in such comparisons of compounds and be instructive in selecting a compound according to various embodiments of the invention. Inclusion of some substituent groups may increase or decrease PSS or solubility or a combination thereof. For example, inclusion of "bulky", EWG or EDG substituent groups may improve absorbance at a PSS for some compounds in a family.

According to various embodiments of the invention, a compound according to Formula IIA/IIB, or IIIA/IIIB, or IVA/IVB, or VA/VB, or VIA/VIB, or VIIA/VIIB, or VIIIA/VIIIB, or XIA/XIB, or XA/XB may have an SI of about 1 to about 20, or any amount or range therebetween, for example, about 2, 3, 4, 5, 6, 7, 8, 9, 10, 11, 12, 13, 14, 15, 16, 17, 18, 19, or any amount or range therebetween; or about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8 or 3.9, or any amount or range therebetween.

According to various embodiments of the invention, a compound according to Formula IIA/IIB, or IIIA/IIIB, or IVA/IVb, or VA/VB, or VIA/VIB, or VIIA/VIIB, or VIIIA/VIIIB, or XIA/XIB, or XA/XB may have a PSS under 365 nm or full spectrum light (simulated sunlight) of about 0.05 to about 2 or any amount or range therebetween for example about 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0, or any amount or range therebetween. In some embodiments the compound may have a PSS under 365 nm or full spectrum light (simulated sunlight) of at least 0.05 to about 2 or any amount or range therebetween for example at least 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0, or any amount or range therebetween.

A compound with greater solubility allows for a formulation or material with a greater concentration of coloured molecule to be incorporated into a composition. This may allow for increasing the contrast ratio for a compound with a lesser absorbance at PSS. Inclusion of a solubilizing group in a compound according to various embodiments of the invention may increase solubility. Examples of solubilizing groups may include alkoxy or siloxy groups.

TABLE 7

Solubility for selected chromophores. Solubility = % wt soluble in indicated solvent.

| compound | Solvent | Solubility |
|---|---|---|
| S001 | triglyme | 5-6 |
| S002 | Triglyme | 1-1.5 |
| S003 | Triglyme | <3 |
| S006 | Triglyme | 3 |
| S011 | Triglyme | 3 |
| S017 | Triglyme | 1 |
| S020 | Triglyme | 3 |
| S032 | Triglyme | 1 |
| S039 | Triglyme | 2 |
| S042 | Triglyme | 0.5 |
| S044 | Triglyme | 1 |
| S049 | Triglyme | 2 |
| S052 | Triglyme | 1 |
| S054 | Triglyme | 5-6 |
| S057 | Triglyme | 1.5 |
| S060 | Triglyme | 1 |
| S066 | Triglyme | 2.5 |
| S068 | Triglyme | >20 |
| S075 | Triglyme | 1 |
| S079 | Triglyme | 8-11 |

TABLE 7-continued

Solubility for selected chromophores. Solubility = % wt soluble in indicated solvent.

| compound | Solvent | Solubility |
|---|---|---|
| S096 | Triglyme | 15 |
| S098 | Triglyme | 1.5 |
| S108 | Triglyme | >25 |
| S109 | Triglyme | >25 |
| S128 | Triglyme | >25 |
| S138 | Triglyme | >20 |
| S158 | Triglyme | >20 |

Compounds of the invention may be in a monomeric or polymeric form. In some embodiments, the polymeric form may be a homopolymer or heteropolymer; the polymeric form may be produced by a ring-opening methathesis polymerization (ROMP). Examples of ROMP conditions for polymer production with a photochromic moiety in a side chain or a main chain of the polymer are described for selected 1,2-bis(3-thienyl)cyclopentene molecules in PCT Publications WO 02/06361 and WO2004/015024, respectively.

In some embodiments, where compounds according to any of Formulae IA and IB, IIA and IIB, IIIA and IIIB, IVA and IVB, VA and VB, VIA and VIB, VIIA and VIIB, VIIIA and VIIIB, XIA and XIB or XA and XB, where both $R_2$ are —CH=CH— and joined to form a cyclic structure, a homopolymer or heteropolymer may be produced using the ROMP method and conditions described in PCT Publication WO2004/015024.

In some embodiments, for compounds according to Formulae IA and IB where $R_3$ is $CO_2Y$ and $R_4$ is aryl, a homopolymer or heteropolymer having photochromic and electrochromic properties maybe produced using the ROMP methods and conditions described in PCT Publication WO02/06361. In some embodiments, $R_1$ and $R_2$ may be F.

In some embodiments where compounds according to any of Formulae IIA and IIB, IVA and IVB, VIA and VIB, one of $R_{6a-c}$ is $CO_2Y$, and a homopolymer or heteropolymer having photochromic and electrochromic properties may be produced using the ROMP methods and conditions described in PCT Publication WO02/06361. In some embodiments, $R_1$ and $R_2$ may be F. S048 is an example of a compound of the invention that may be incorporated into a polymeric composition according to some embodiments of the invention.

In some embodiments where compounds according to any of Formulae IIIA and IIIB, VA and VB, VIA and VIB, one of $R_{8a-c}$ is $CO_2Y$, and a homopolymer or heteropolymer having photochromic and electrochromic properties may be produced using the ROMP methods and conditions described in PCT Publication WO02/06361. In some embodiments, $R_1$ and $R_2$ may be F.

In some embodiments where compounds according to any of Formulae VIIA and VIIB, VIIIA and VIIIB, XIA and XIB or XA and XB, one of $R_{10a-d}$ and/or one of $R_{6a-c}$ is $CO_2Y$, and a homopolymer or heteropolymer having photochromic and electrochromic properties maybe produced using the ROMP methods and conditions described in PCT Publication WO02/06361. In some embodiments, $R_1$ and $R_2$ may be F.

Formulation and Switching Materials

The invention also relates to compositions comprising one or more compounds, and one or more formulation components. The invention also relates to compositions comprising one or more formulation components, in the absence of a compound. Examples of formulation components include a solvent and optionally a supporting electrolyte and a gelling agent. A formulation may further comprise one or more of a polymer, a polymer, a monomer, an initiator, a catalyst, an electrolyte, a charge compensator, anti-oxidant, a rheology modifier, a colourant (dye, non-switching chromophore), a UV blocking agent, or the like. Those skilled in the art will recognize that a formulation component may perform one or more than one function. For example, compounds comprising polymeric compositions, and the polymeric composition included in a material may provide a single formulation component that provides both a switching function, as well as a structural or rheological function.

A switching material may have a VLT or $LT_A$ of at least about 50%, at least about 60%, at least about 70%, at least about 80% or at least about 90% when in a light state, or any amount or range therebetween, according to various aspects of the invention. Alternately, a switching material may have a VLT or $LT_A$ of less than about 50%, or less than about 40% or less than about 30% or less than about 20% or less than about 10% when in a dark state, or any amount or range therebetween, according to various aspects of the invention.

One or more compounds according to various embodiments of the invention may be present in a switching material in an amount (% weight) of about 0.05% to about 30%, or any amount or range therebetween, for example about 1, 2, 3, 4, 5, 6, 7, 8, 9, 10, 11, 12, 13, 14, 15, 16, 17, 18, 19, 20, 21, 22, 23, 24, 25, 26, 27, 28 or 29%.

Suitable solvents include those with one or more of the following characteristics: boiling point of about 150° C. or greater, vapour pressure of about 0.001 mmHg or less at 20° C., Yellowness Index (YI) of about 6 or less; a flash point of about 80° C. or greater, a melting point of about 40° C. or less. In some embodiments, the solvent does not have HCN or HCl degradation products, or does not have —NH, urea or ketone functional groups. Examples of solvents include, but are not limited to triglyme, tetraglyme, propylene carbonate, ethylene carbonate, water, butyrolactone, cyclopentanone or a combination thereof.

Further examples of solvents include ethylene glycol phenyl ether; diethylene glycol monobutyl ether; diethyl succinate; dimethylglutarate; N-methylpyrrolidone (NMP)ethyl myristate; mineral seal oil; diethylene glycol n-butyl ether acetate; Eastman C11 ketone; diisobutyl adipate; dihexyl azelate; diethyl maleate; diisooctyl azelate; triethylene glycol monobutyl ether (butoxytriglycol); diisooctyl dodecanedioate; 2-(2-ethylhexyloxy)ethanol; glyceryl triacetate; tetramethylene sulfoxide; dibutyl adipate; 3-dodecylheptamethyltrisiloxane; diethyl sebacate; dibutyl itaconate; 1,4-Butanediol; butyl sulfoxide; diethylene glycol; octyl octanoate; hexyl octanoate; diisodecyl adipate; diethylene glycol monoethyl ether acetate; 1,3/1,4-cyclohexanedimethanol (CHDM); 1-Decanol; 2-methylglutaronitrile; methyl palmitate; tri(propylene glycol)butyl ether, mixture of isomers (Dowanol™ TPnB); 1-Dodecanol; tetradecane; diethylene glycol hexyl ether; dioctyl ether; methyl stearate; hexyl hexanoate; butyl diglyme; triisopentylamine; Bis(2-ethylhexyl) sebacate; 1,5-dicyanopentane; diisobutyl fumarate; 2,2,4-trimethyl-1,3-pentanediol dibenzoate; poly(ethylene glycol)monolaurate; isooctyl tallate; poly(ethylene glycol)monooleate; hexaethyldisiloxane; poly(ethylene glycol)dioleate; triethylene glycol di-2-ethyl butyrate (TEG DEB); tributyrin (butanoic acid), 1,2,3-propanetriyl ester; tetramethylene sulfone (sulfolane); polyethylene glycol dimethyl ether m.w.~250 (PEG-DME 250); ethylene carbonate (EC); bis(2-ethylhexyl) adipate; tetraethylene glycol; hexadecamethylheptasiloxane; dioctyl terephthalate; Bis[2-(2-butoxyethoxy)ethyl]adipate (BBEEA); triethylene gylcol bis (2-ethylhexanoate) (TEG BEH); propylene carbonate (PC);

triethylene glycol monomethyl ether(methoxytriglycol); triethylene glycol monoethyl ether (ethoxytriglycol); tetraglyme; 18-Crown 6-Ether; 1,3-dimethylimidazolidinone (DMI); poly(ethylene glycol) bis(2-ethylhexanoate); 1,5-pentanediol; di(ethylene glycol)dibenzoate; 2-ethylhexyl-(s)-lactate; tripropylene glycol; dipropylene glycol; 2,2,4-trimethyl-1,3-pentanediol monoisobutyrate; tri(propylene glycol)methyl ether, mixture of isomers (Dowanol™ TPM); di(propylene glycol)dibenzoate; dipropylene glycol n-butyl ether; diethyl azelate; poly(propylene glycol)dibenzoate; propylene glycol phenyl ether; poly(ethylene glycol) dibenzoate; 2-ethyl-1,3-hexanediol; or the like.

One or more solvents may be present in a switching material in an amount from about 50% to about 95% (by weight), or any amount or range therebetween, for example 50, 60, 70, 80 or 90%, or any amount or range therebetween.

In some embodiments of the invention, one or more polymers may be included in the compositions. Examples of such polymers include polyvinylbutyral (PVB) B-90, PVB-B72, poly(methyl methacrylate) (PMMA), nitrile rubber (NBR), polyvinylpyrrolidone (PVP), polyvinylidene fluoride (PVDF), poly(dimethylsiloxane) (PDMS), poly(ethyl methacrylate) (PEMA), NBR, hydroxypropyl cellulose, PEG-DMA (poly(ethylene glycol)dimethacrylate), PHEMA (poly (2-hydroxyethyl methacrylate), Plexiglas™ G-UVT acrylic, polychloroprene, polybutadiene, PDMS-g-PEG (PEG-modified PDMS), PEO (polyethylene oxide), PEG-MEMA (PEG-methylether methacrylate), PPGMA (poly(propylene glycol), EGDMA (ethylene glycol dimethacrylate), PVDC (polyvinylidene chloride), PVC (polychlorovinyl), PVDC-PVC, cyclo olefin copolymer (COC) (APEL™), carboxymethyl cellulose (CMC), SOLEF™ 21520, SOLEF™ 21508, zein, polyisobytulene-600, poly(ethylene-co-methacrylic acid (EMAA, SURLYN™ 60), polyethylene-co-(ethylacrylate), ethylacrylate, poly(vinylidene chloride-co-vinyl chloride), polyisoprene, polybutene, poly(sodium 4-styrene sulfonate), HEMA (hydroxyethyl)methacrylate or combinations thereof, or copolymers thereof. The one or more polymers may be present in an amount from about 0.1% to about 10% (by weight) or any amount or range therebetween, for example 1, 2, 3, 4, 5, 6, 7, 8, or 9%, or any amount or range therebetween. In some embodiments the one or more polymers may function as a rheology modifier.

Supporting electrolytes are generally electrically conductive, and may comprise alkali metal salts, tetralkylammonium salts or the like. Examples of such salts include TBABF$_4$ (tetrabutylammonium tetrafluoroborate), TBAPF$_6$ (tetrabutylammonium hexafluorophosphate), tetrabutylammonium perchlorate, lithium bis(trifluoromethane sulfonimide), triflate, LiBOB (lithium bis(oxatlato)borate), LiClO$_4$ (lithium perchlorate) or the like. The one or more salts may be present in an amount from about 0.1% to about 10% (by weight) or any amount or range therebetween, for example 1, 2, 3, 4, 5, 6, 7, 8, or 9%.

In some embodiments of the invention, a charge compensator (charge-transfer complex or charge-transfer salt) may be included in one or more compositions. A charge compensator may be a cathodic material to aid in redox balance of an anodic chromophore. The charge compensator may be stable, or sufficiently stable in both reduced and oxidized forms. The charge compensator may be an organic semiconductor. Examples of charge compensators include Prussian Blue, ferrocenium tetrafluoroborate, ferrocenium hexafluorophosphate, tetracyanoquinodimethane, tetrafluoro-tetracyanoquinodimethane, 1,4-dicyanobenzene, 1,2,4,5-tetracyanobenaene, pyrene, tetracene, pentacene or the like. The one or more charge compensators may be present in an amount from about 0.1% to about 10% (by weight) or any amount or range therebetween, for example 1, 2, 3, 4, 5, 6, 7, 8, or 9%.

Inclusion of a colourant in a composition according to various embodiments of the invention may achieve a desired colour and/or adjust the visible light transmission of the composition. A variety of colourants are known in the art, and selection of a colourant to achieve a desired colour, hue or transmissibility is within the ability of a skilled worker. Examples of colourants include one or more chromophores as described herein, Prussian blue, or the like. One or more colourants may be present in an amount from about 0.01% to about 10% (by weight) or any amount or range therebetween, for example 1, 2, 3, 4, 5, 6, 7, 8, or 9%.

UV absorbers (compounds or compositions that absorb light and dissipate energy by thermal relaxation) may be included in a composition according to various embodiments of the invention. Examples of UV blocking agents include Biphenyl, 2-Hydroxybenzophenone, 2,2'-Dihydroxy-4,4'-dimethoxybenzophenone, 2,4-Dihydroxybenzophenone, 2-(2-Hydroxy-5-methylphenyl)benzotriazole, Ethyl 2-cyano-3,3-diphenylacrylate, 2-(2H-Benzotriazol-2-yl)-4,6-di-tert-pentylphenol, 2-(2H-Benzotriazol-2-yl)-4,6-bis(1-methyl-1-phenylethyl), Hostavin™ VSU (N1-(2-ethoxyphenyl)-N2-(2-ethylphenyl)-ethanediamide) and the like. One or more UV absorbers may be present in an amount from about 0.01% to about 10% (by weight) or any amount or range therebetween, for example 1, 2, 3, 4, 5, 6, 7, 8, or 9%.

UV stabilizers, such as HALS (hindered amine light scavengers may be included in a composition according to various embodiments of the invention. Examples of HALS include 2,2,6,6-tetramethyl-piperidine, 2,2,6,6-tetramethyl-4-piperidinol, 1,2,2,6,6-pentamethyl-4-piperidinol, 1,5,8,12-Tetrakis [4,6-bis(N-butyl-N-1,2,2,6,6-pentamethyl-4-piperidylamino)-1,3,5-triazin-2-yl]-1,5,8,12-tetraazododecane, Bis (2,2,6,6-tetramethyl-4-piperidyl)sebacate, Bis(1-octyloxyl-2,2,6,6-tetramethyl-4-piperidyl) sebacate, Chimassorb™944 (Poly[[6-[(1,1,3,3-tetramethylbutyl)amino]-s-triazine-2,4-diyl]-[(2,2,6,6-tetramethyl-4-piperidyl)imino]-hexamethylene-[(2,2,6,6-tetramethyl-4-piperidyl)imino]]), HS-508 (Bis (1,2,2,6,6-pentamethyl-4-piperidyl) sebacate; decanedioic acid bis(1,2,2,6,6-pentamethyl-4-piperidinyl) ester or the like. One or more UV stabilizers may be present in an amount from about 0.01% to about 10% (by weight) or any amount or range therebetween, for example 1, 2, 3, 4, 5, 6, 7, 8, or 9%.

Uses

Compounds, and compositions or switching materials according to various embodiments of the invention, may be useful in devices or applications where an optical filter is employed. The compounds or compositions may be used in films or coatings that may be applied to a surface such as glass, a lens or the like, and modify the light transmittance. Examples of such devices include opthalmic lenses, actinometers, molecular sensors, photochromic inks, paints or fibers, variable transmission filters, optical information storage systems, optoelectronic systems, reversible holographic systems, molecular switches such as those used in molecule-based Wires and circuitry or the like.

In some embodiments, the switching material may be disposed upon a first substrate, or "sandwiched' between a first substrate and a second substrate, the switching material capable of transitioning between a light state and a dark state based on application of light in the UV and/or VIS range, and application of an electric voltage. Switching material disposed upon a substrate, with or without a second substrate, may be generally referred to as an optical filter. The switching material may be a liquid, a gel, a solid, a semi-solid or a sol-gel, and may be formed in a layer with a thickness of about 0.1 micron (micrometer, μm) to about 100 microns, or any amount or range therebetween, for example from about 10 microns to about 50 microns, or from about 0.1 micron to about 10 microns, or from about 0.5 micron to about 5 microns, or any amount or range therebetween. In some embodiments, the layer of switching material is of uniform, or substantially uniform, thickness. In some embodiments, the layer of switching material is of non-uniform thickness.

The first and/or second substrates may be independently opaque or transparent, or substantially transparent. In some embodiments, when the switching material is disposed upon, or sandwiched between the substrate(s), it is optically clear (e.g. demonstrating a haze of less than about 5%, less than about 4%, less than about 3%, less than about 2% or less than about 1%. Haze may be measured using methods known in the art, for exampley use of an XL-211 Hazemeter from BYK-Gardner, according to manufacturer's instructions.

In some embodiments, the first and/or second substrates may block (absorb or reflect) selected ranges or wavelengths of light. In some embodiments the first and/or second substrates may be treated with, or have applied to them, a film or other material that blocks selected ranges or wavelengths of light. In some embodiments, the range or wavelength of light may be in the UV range. Examples of UV blocking films that may be applied include EnergyFilm™ (ArtScape) and EnerLogic™ (Solutia).

In some embodiments, the optical filter may be disposed upon a pane of glass, or other transparent material suitable for use as a window, or incorporation into an insulated glazing unit (IGU), or a storm window or secondary glazing. Methods of making IGU, windows or the like, and affixing an optical filter to glass or other suitable material are described in, for example, WO2010/142019 as are methods of configuring an electrical system and/or control system for operation (electrofading) of an IGU comprising an optical filter.

In some embodiments, for a compound according to Formula IIA and IIB, where $R_1$ and $R_2$ are F, Z is S and X is S, at least one of $R_6$ or $R_7$ is not H or not methyl, or not alkyl.

In some embodiments, for a compound according to Formula IIA and IIB, where $R_1$ and $R_2$ are F, Z is S and X is S, at least one of $R_7$ is not methyl.

In some embodiments, for a compound according to Formula IIIA and IIIB, where $R_1$ and $R_2$ are F and Z is S, at least one of $R_{8c}$ or $R_{9c}$ is not butyl, or not tert-butyl or not alkyl or not methoxy.

In some embodiments, for a compound according to Formula IIIA and IIIB, where $R_1$ and $R_2$ are F and Z is S, at least one of $R_9$ is Cl or both $R_8$ is Cl.

In some embodiments, for a compound according to Formula IIIA and IIIB, where $R_1$ and $R_2$ are F, and Z is S, $R_{9c}$ is not butyl, or not tert-butyl.

In some embodiments, for a compound according to Formula IA and IB, where $R_1$ and $R_2$ are F, Z is S and R4 is

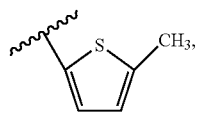 [SMILES: *c1ccc(C)s1]

$R_3$ is not

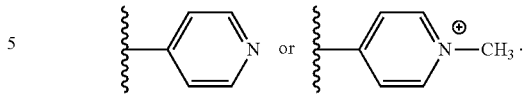

In some embodiments, for a compound according to Formula IA and IB, where $R_1$ and $R_2$ are F, Z is S and $R_3$ is

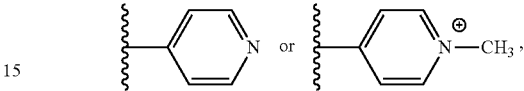

$R_4$ is not

CH3.

In some embodiments, for a compound according to Formula IA and IB, where $R_1$ and $R_2$ are F and Z is S, $R_3$ and $R_4$ are not In some embodiments, for a compound according to Formula VIIIA and VIIIB, where $R_1$ and $R_2$ are F and Z is O and all of $R_{10a}$, $R_{10b}$, $R_{10c}$ and $R_{10d}$ are H, $R_9$ in the para position (specifically $R_{9a}$) is not an alkyl chain according to $C_4H_9$, $C_8H_{17}$ or $C_{12}H_{25}$.

In some embodiments, the invention does not include one or more of S001, S002, S006 S042, S054, S068 or S079. In some embodiments, the invention does not include one or more of S003, S004, U008, S014 or S015, S033 or S075.

For all diarylethenes disclosed herein, where a ring-open isomer is illustrated, it is understood how the ring-closed isomer may be prepared from it; where a ring-closed isomer is illustrated, it is understood how the ring-open isomer may be prepared from it.

The present invention also provides for an embodiment comprising any combination of embodiments or aspects as referenced herein. Any embodiment or aspect referenced in this specification may be implemented or combined with respect to any other embodiment, aspect, method, composition or use of the invention, and vice versa. Exemplary embodiments of the invention are illustrated, in part, by the following non-limiting methods and examples:

General Methods

All solvents were dried prior to use; where necessary, solvents were degassed by bubbling with argon or nitrogen. Alternately, solvents were passed through a steel column containing activated alumina under nitrogen or argon using an MBRAUN solvent purification system. Solvents for NMR analysis (Cambridge Isotope Laboratories) were used as received. Column chromatography was performed using silica gel 60 (230-400 mesh) from Silicycle Inc. Octafluorocyclopentene was purchased from SynQuest and catalysts Pd(dppf)Cl$_2$ and Pd(PPh$_3$)$_4$ were purchased from Strem. All other synthetic precursors, solvents and reagents were purchased from Aldrich, Anachemia or Calcdon. $^1$H NMR characterizations were performed on a Bruker AMX 400 instrument working at 400.103 MHz. $^{13}$C NMR characterizations were performed on a Bruker AMX 400 instrument working at 100.610 MHz. Chemical shifts (δ) are reported in parts per million relative to tetramethylsilane (TMS) using the residual solvent peak as a reference standard. Coupling constants (J) are reported in Hertz. Standard lamps for visualizing TLC plates (Spectroline E-series, 470 µW/cm$^2$) were used to carry out the ring-closing reaction for a compound, using a 365 nm, a 313 nm or a 254 nm light source where appropriate. The compositions of all photostationary states were detected using $^1$H NMR spectroscopy. The ring-opening reactions were carried out using the light of a 150 W tungsten source that was passed through a 490 nm or a 434 nm cutoff filter to eliminate higher energy light.

Synthesis of Ring-Closed or Ring-Open Isomer of Compounds

Where a preparation of a ring-closed isomer is desired (as an isolated compound, e.g. for NMR studies, or some syntheses), the compound may be dissolved in CHCl$_2$ and placed in a quartz glass cell. The solution was irradiated at 365 nm for 10 minutes, or until no further change in absorbance is observed. Solvent was evaporated off under reduced pressure and the product purified using HPLC to afford the respective ring-closed isomer. Where a preparation of a ring-open isomer is desired (as an isolated compound, e.g. for NMR studies, or some syntheses), the compound may be dissolved in CHCl$_2$ and placed in a quartz glass cell as described. The solution may be irradiated with visible light comprising a wavelength of ~500 to 700 nm for 10 minutes, or until no further change in absorbance is observed. Solvent may be evaporated off under reduced pressure and the product purified using HPLC to afford the respective ring-open isomer.

Photostationary State (PSS)

UV/Vis spectra are obtained using an OceanOptics™ Spectrophotometer until absorption in the visible region of the spectrum stabilizes. A 2×10$^{-5}$M solution of compound in solvent is prepared, and photofaded using visible light until absorption in the visible region of the spectrum stabilizes. The sample is then irradiated with simulated sunlight (QSUN SS-150 Solar Simulator with xenon arc lamp) until the absorption spectrum stabilizes. To obtain PSS in the presence of a UV blocking film, a second sample is prepared and irradiated as described, with a UV blocking film inserted in the light path when irradiating.

Electrochemical Switching

A 1 mM solution of compound in solvent (triglyme, acetonitrile or dichloroethane) with 1% wt electrolyte (TBAPF$_6$ or TBAPF$_4$) was prepared, placed in a capillary device (50 micron wide chamber of two panes of glass with ITO-coated interior walls, separated by a circumferential bead of sealant; one of the two panes comprising two fill ports), and exposed to 365 nm UV light source until a PSS is reached. A voltage is applied to the capillary device (from 0 to about 2, or from 0 to about 2.5 volts), and the solution inspected visually for colorimetric change to a faded state, indicating the chromophore exhibits electrochemical switching.

General Synthetic Methods:

General Procedure for Bi-Functional Kumada Coupling (Protocol A):

A reaction flask was charged with magnesium turnings (2.4 eq.) and anhydrous diethyl ether and flushed with argon. A small amount of the bromothiophene was added to initiate the reaction, followed by the dropwise addition of balance of the bromothiophene (2 eq. total) as a solution in anhydrous diethyl ether at such a rate as to maintain a mild reflux. After the addition was complete, the reaction was refluxed for a further 30 minutes. The mixture was cooled to RT, and the liquid portion was transferred to an addition funnel and added dropwise to a solution of 2,3,5-tribromothiophene (1 eq.) and [1,1'-bis(diphenylphosphino)ferrocene]dichloropalladium (II) (Pd(dppf)Cl$_2$) (0.4 mol %) in anhydrous diethyl ether. The reaction mixture was stirred for 16 h at room temperature, then was poured over ice and quenched with 5% HCl. The organic portion was separated and the aqueous layer was extracted with diethyl ether. The combined organic extracts were washed with brine, dried over MgSO$_4$, filtered and solvent removed by rotary evaporation. Flash chromatography afforded the product, which was sonicated in methanol, filtered and dried to give an off-white powder.

General Procedure for Mono-Functional Kumada Coupling (Protocol B):

A reaction flask was charged with magnesium turnings (1.1 eq.) and anhydrous diethyl ether and flushed with argon. A small amount of the bromothiophene was added to initiate the reaction, followed by the dropwise addition of balance of the bromothiophene (1 eq. total) as a solution in anhydrous diethyl ether at such a rate as to maintain a mild reflux. After the addition was complete, the reaction was refluxed for a further 30 minutes. The mixture was cooled to RT, and the liquid portion was transferred to an addition funnel and added dropwise to a cooled (0° C.) solution of aryl bromide (1 eq.) and Pd(dppf)Cl$_2$ (0.5 mol %) in anhydrous diethyl ether. The reaction mixture was stirred for 1 h, then warmed to room temperature and stirred for 16 h. The reaction was quenched by pouring it over ice and the mixture was acidified with 5% HCl. The organic portion was separated and the aqueous layer was extracted with diethyl ether. The combined organic extracts were washed with brine, dried over MgSO$_4$, filtered and solvent removed by rotary evaporation. Flash chromatography afforded the product.

General Procedure for Bi-Functional Suzuki Coupling (Protocol C):

Sodium carbonate monohydrate (5 eq.) was dissolved in water and a solution of 2,3,5-tribromothiophene (1 eq.) and boronic acid (2.3 eq.) in THF was added. The reaction mixture was deoxygenated by bubbling argon through the solution for 60 minutes. Tetrakis(triphenylphosphine) palladium (0) (Pd(PPh$_3$)$_4$) (5 mol %) was added and the reaction mixture was heated to reflux for 18 hours. After cooling to RT, the organic and aqueous phases were separated and the aqueous phase was extracted with EtOAc. The combined organics were washed with water, dried over MgSO$_4$, filtered and solvent removed by rotary evaporation. Flash chromatography (hexanes) afforded the desired compound.

General Procedure for Mono-Functional Suzuki Coupling (Protocol D):

Sodium carbonate monohydrate (3 eq.) was dissolved in water and a solution of aryl bromide (1 eq.) and aryl boronic acid (1.1 eq.) in THF was added. The reaction mixture was deoxygenated by bubbling argon through the solution for 60 minutes. (Pd(PPh$_3$)$_4$) (2 mol %) was added and the reaction mixture was heated to reflux for 2-48 hours. After cooling to RT, the organic and aqueous phases were separated and the aqueous phase was extracted with EtOAc. The combined organics were washed with water, dried over MgSO$_4$, filtered and solvent removed by rotary evaporation. Flash chromatography afforded the desired compound.

General Procedure for Friedel-Crafts Alkylation (Protocol E):

Aluminum chloride (1.2-1.5 eq.) was added to a stirred solution of the aromatic compound (1.0 eq.) and either tert-butyl chloride or t-butyl bromide (1.5-4.0 eq.) in anhydrous DCM. The mixture was stirred for between 30 min and 60 h at room temperature, then poured into cold water, mixed well and separated. The aqueous portion was extracted with DCM and the combined organics were washed with water, dried over $MgSO_4$, filtered and solvent removed by rotary evaporation. Flash chromatography afforded the desired compound.

General Procedure for NBS Bromination (Protocol F):

The aryl compound (1 eq.) was dissolved in dichloromethane (DCM) (protocol F1), chloroform (protocol F2), tetrahydrofuran (THF) (protocol F3) or a mixture of DCM and THF (protocol F4). N-bromosuccinimide (1.1 eq.) was added and the mixture stirred at room temperature for 1-24 h. The reaction was quenched by pouring it into a 1 M NaOH solution, and the organic portion was separated. The aqueous portion was extracted with dichloromethane and the combined organics were washed with water, dried over $MgSO_4$, filtered and solvent removed by rotary evaporation. Sonication of the residue in methanol, followed by filtration and drying afforded the desired compound.

General Procedure for the Synthesis of Chromophores (Protocol G):

The aryl bromide (2.0 eq.) was dissolved in anhydrous diethyl ether and solution was cooled to between −25° C. and −50° C. n-Butyl lithium (2.5 M in hexanes, 2.2 eq.) was added and the reaction mixture was stirred for 15 min. Octafluorocyclopentene (1.0 eq.) was added neat, and the reaction mixture was allowed to stir and warm slowly to room temperature overnight, then was quenched by the addition of 10% HCl. The organic portion was separated and the aqueous portion was extracted with ether. The combined organic extracts were washed with brine, dried over $MgSO_4$, filtered and the solvent removed by rotary evaporation. The crude material was purified by column chromatography and the resulting material was sonicated in methanol, filtered and air dried to afford the desired compound.

General Procedure for the Synthesis of Chromophores (Ether): Protocol H.

The aryl bromide (2.0 eq.) was dissolved in anhydrous diethyl ether (protocol H1), anhydrous tetrahydrofuran (protocol H2) or a mixture of anhydrous diethyl ether and anhydrous tetrahydrofuran (protocol H3) and the solution was cooled to between −25° C. and −50° C. n-Butyl lithium (2.5 M in hexanes, 2.2 eq.) was added and the reaction mixture was stirred for 15 min. A solution of octafluorocyclopentene (1.0 eq.) in the reaction solvent was added over a period of 20-30 minutes. The reaction mixture was allowed to stir and warm slowly to room temperature overnight, and quenched by the addition of 10% HCl. The organic portion was separated and the aqueous portion was extracted with ether. The combined organic extracts were washed with brine, dried over $MgSO_4$, filtered and the solvent removed by rotary evaporation. The crude material was purified by column chromatography and the resulting material was sonicated in methanol, filtered and dried to afford the desired compound.

General Procedure for Olefin Preparation (Protocol I):

To a substituted phenol (1 eq.) solution in DMSO (3.1 molar) was added sodium hydroxide (2 eq.). The mixture was stirred until most of solids were dissolved (an increase in the temperature was noted). The reaction mixture was allowed to cool down to ~40° C. and 1,1,2-trichloroethene (1.08 eq.) was added dropwise over (the temperature of the reaction mixture was controlled to not pass the 60° C. at maximum). At the end of addition the reaction temperature reached 60° C., and then started to drop. The reaction was stirred and allowed to cool down for 1 h. The reaction mixture temperature was cooled to ~30° C. and was poured onto ice. The mixture was transferred to a separation funnel and washed with hexanes several times until extraction of the entire product was achieved. The organic layer was then dried over anhydrous magnesium sulfate and filtered through a plug of silica gel. Hexanes were removed to afford the pure product.

General Procedure for Benzofuran Cyclization (Protocol J):

Boronic acid (1.1 eq.), $Pd_2 dba_3$ (1.2 mol %), (oxybis(2,1-phenylene))bis(diphenylphosphine) (5 mol %), cesium fluoride (3 eq.) and cesium carbonate (3 eq.) were placed into a three-neck round bottom flask, sealed with a septum and purged with argon for 20-30 minutes. A solution of the olefin (1 eq.) in 1,4-dioxane (0.35 molar) was added. The solution was vigorously stirred and brought to reflux for 48 hours. The reaction was cooled down to room temperature and partitioned between water and ether. The layers were separated and the aqueous layer was extracted with ether once more. The combined organic layers were washed with brine, dried with anhydrous magnesium sulfate, filtered and concentrated. The pure product was obtained either after sonication in methanol or chromatography column.

General Synthetic Scheme for Compounds According to Formula XA/B (Scheme 5), according to Protocols K1, K2. Only the ring-open configuration is shown; Scheme 4 illustrates both Formula XA and XB. At least one of R3 and R3', or R4 and R4', or R5 and R5' are not identical.

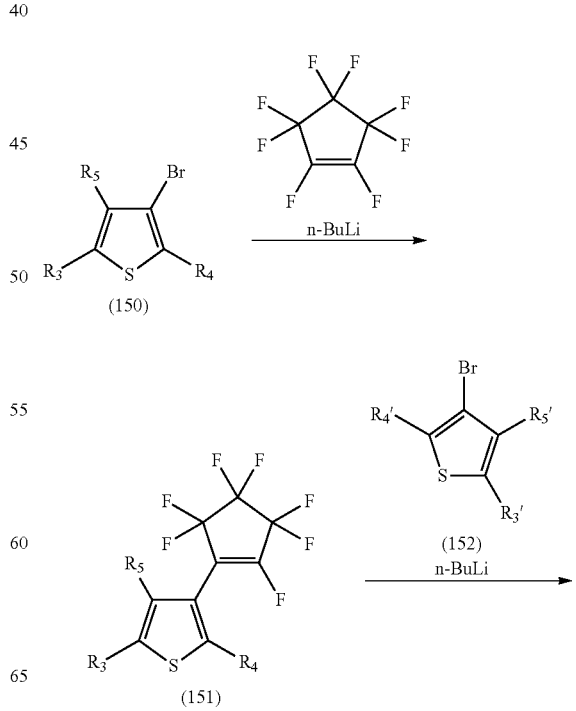

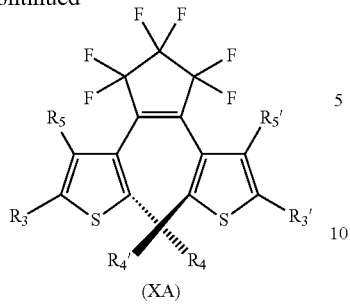

(XA)

General procedure for the synthesis of chromophores (Protocol K1, K2):

K1: A first aryl bromide (150) (1.0 eq.) was dissolved in anhydrous diethyl ether and solution was cooled to between −25° C. and −50° C. n-Butyl lithium (2.5 M in hexanes, 1.1 eq.) was added and the reaction mixture was stirred for 15 min. Octafluorocyclopentene (1.0 eq.) was added neat, and the reaction mixture was allowed to stir and warm slowly to room temperature overnight, then was quenched by the addition of 10% HCl. The organic portion was separated and the aqueous portion was extracted with ether. The combined organic extracts were washed with brine, dried over $MgSO_4$, filtered and the solvent removed by rotary evaporation. The crude material was purified by column chromatography and the resulting material was sonicated in methanol, filtered and air dried to afford intermediate (151).

K2: A Solution of a Second Aryl Bromide (152) (1.0 eq.) was dissolved in anhydrous diethyl ether and solution was cooled to between −25° C. and −50° C.; n-Butyl lithium (2.5 M in hexanes 1.1 eq) was added and the reaction mixture stirred for 10-15 minutes, and a solution of intermediate (151) (1.0 eq) in ether was added over 5 minutes. The reaction mixture was stirred for 15 minutes, quenched with addition of 10% HCl. The organic portion was separated and the aqueous portion was extracted with ether. The combined organic extracts were washed with brine, dried over $MgSO_4$, filtered and the solvent removed by rotary evaporation. The crude material was purified by column chromatography and the resulting material was sonicated in methanol, filtered and air dried to afford the desired compound.

Examples of compounds according to various embodiments of the invention are referenced and set out herein. For clarity, only ring-open isomers are illustrated—ring-closed isomers may be produced by methods and schemes described herein and will be readily apparent upon consideration of the present specification, and are included in the instant disclosure as if each were individually set out herein.

Example 1

Synthesis of S003

3',3'''-(perfluorocyclopent-1-ene-1,2-diyl)bis(5,5''-di-tert-butyl-2,2':5',2''-terthiophene)

(Scheme 11)

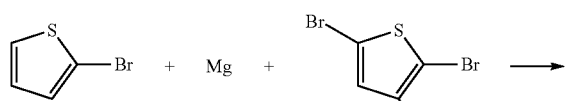

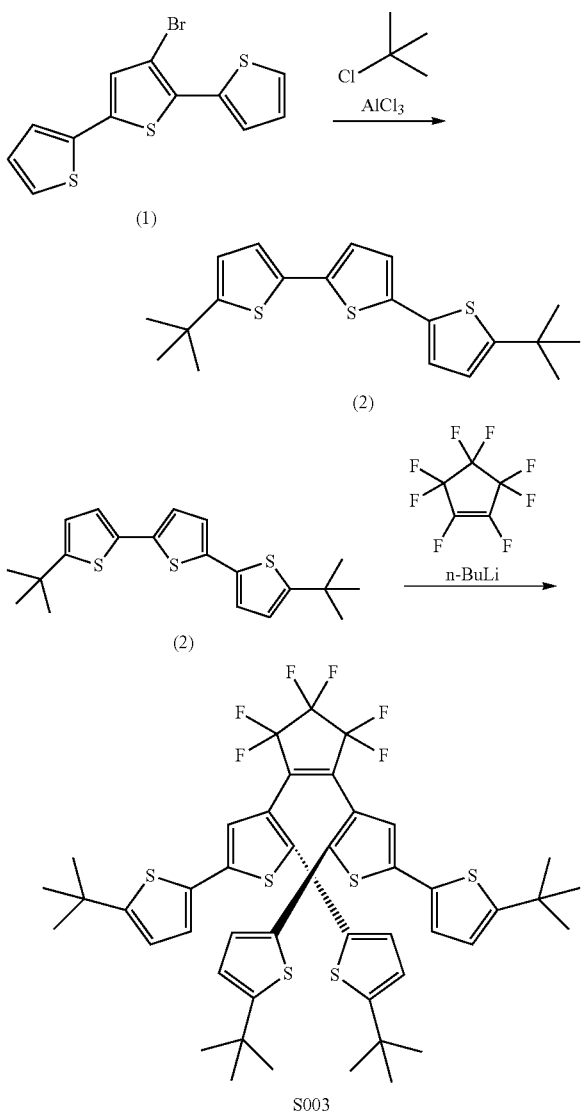

Synthesis of 3'-bromo-2,2':5',2''-terthiophene (1)

(1) was prepared on 83 mmol scale (83% yield) according to protocol A.

Synthesis of 3'-bromo-5,5''-di-tert-butyl-2,2':5',2''-terthiophene (2)

(2) was prepared on 38.8 mmol scale (97% yield) according to protocol E.

Synthesis of S003

Compound (2)

S003 was prepared on 7 mmol scale (37% yield) according to protocol G. $^1$H NMR (400 MHz, CDCl3) δ ppm 6.85 (d, J=3.7, 2H), 6.70 (d, J=3.7, 2H), 6.45 (q, J=3.7, 4H), 6.38 (s, 2H), 1.39 (s, 18H), 1.20 (s, 18H).

Example 2

Synthesis of S005

3'-(2-(2,5-diphenylthiophen-3-yl)-3,3,4,4,5,5-hexafluorocyclopent-1-en-1-yl)-2,2':5',2''-terthiophene

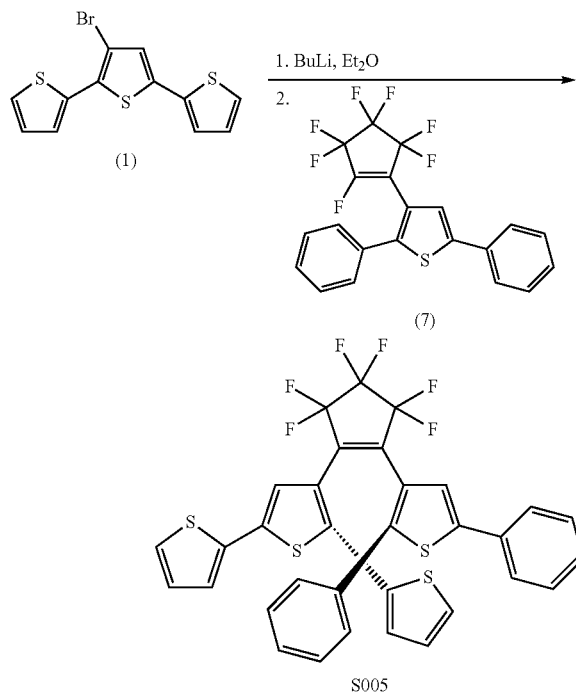

Synthesis of S005

A solution of Compound (1) (0.39 g, 1.19 mmol) in anhydrous ether (50 mL) at −20° C. was treated with n-BuLi (0.50 mL, 1.23 mmol, 2.5 M solution in hexanes) dropwise over 10 minutes, then was stirred for an additional 20 minutes before the addition of a solution of compound (7) (0.34 g, 0.79 mmol) in anhydrous ether (50 mL) via cannula. The reaction mixture stirred for 16 hours and during this time gradually warmed to 10° C. The reaction was quenched with the addition of 5% HCl (aq) (30 mL) and extracted with EtOAc (2×30 mL). The combined organic fractions were washed with brine (30 mL) dried over MgSO$_4$, filtered and concentrated onto silica gel. Purification by flash column chromatography (95:5 hexanes/chloroform) followed by sonication of the solid product in a mixture of ether and ethanol yielded 90 mg (17% yield) of S005. $^1$H NMR (600 MHz, CDCl$_3$) δ 7.45-7.43 (m, 2H), 7.39 (t, J=7.6, 2H), 7.32 (t, J=7.3, 1H), 7.25 (dd, J=4.7, 1.5, 1H), 7.17-7.12 (m, 3H), 7.09 (dd, J=5.1, 1.2, 1H), 7.03-7.00 (m, 4H), 6.78 (dd, J=5.1, 3.5, 1H), 6.70 (dd, J=3.5, 1.2, 1H), 6.57 (s, 1H), 6.07 (s, 1H).

Example 3

Synthesis of S006

5-(4-chlorophenyl)-3-(2-(2,5-diphenylthiophen-3-yl)-3,3,4,4,5,5-hexafluorocyclopent-1-en-1-yl)-2-phenylthiophene

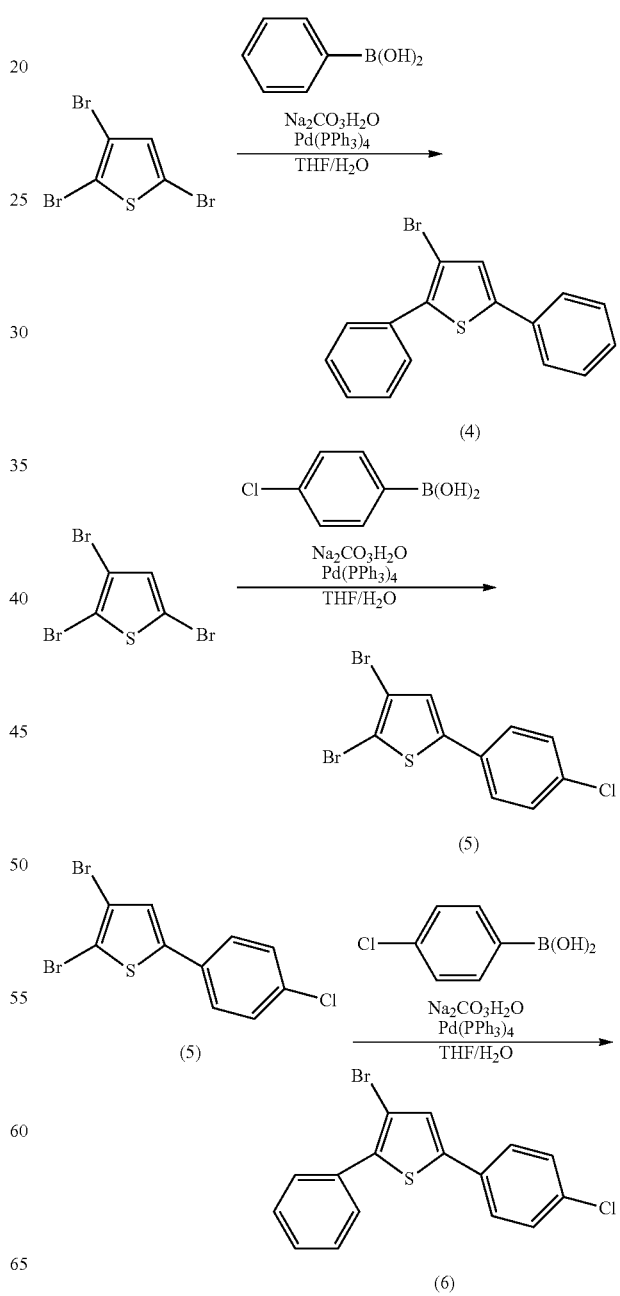

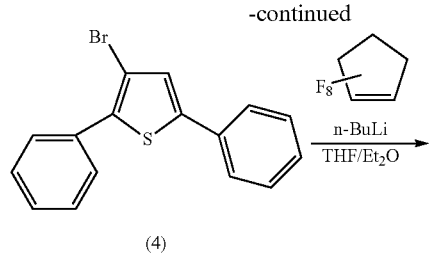

(4)

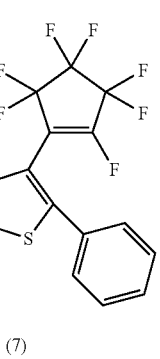

(7)

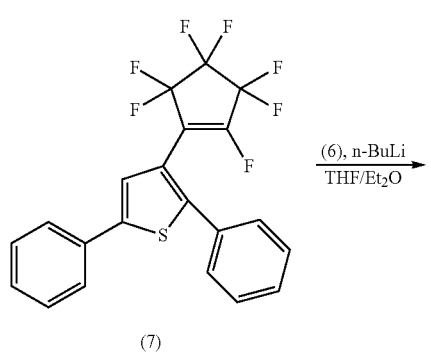

(7)

S006

Synthesis of 3-bromo-2,5-diphenylthiophene (4)

(4) was prepared on 67 mmol scale (77% yield) according to protocol C.

Synthesis of 2,3-dibromo-5-(4-chlorophenyl)thiophene (5)

(5) was prepared on 19.7 mmol scale (23% yield) according to protocol C.

Synthesis of 3-bromo-5-(4-chlorophenyl)-2-phenylthiophene (6)

(6) was prepared on 32.1 mmol scale (78% yield) according to protocol C.

Synthesis of 3-(perfluorocyclopent-1-en-1-yl)-2,5-diphenylthiophene (7)

In a flame-dried, 2 L, 3-neck, rbf fitted with an argon inlet and internal thermometer, 3-bromo-2,5-diphenylthiophene (21.0 g, 66.6 mmol) was dissolved in anhydrous THF (300 mL) and anhydrous ether (400 mL) was added. The solution was cooled to −43° C. (dry ice/acetone) and n-BuLi (2.5 M in hexanes, 32.0 mL, 80 mmol) was added dropwise over a period of 10 minutes. A yellow colour was observed. The temperature increased to −40° C. and the reaction mixture was stirred for 15 minutes. A white precipitate was observed. Octafluorocyclopentene (10.7 mL, 80 mmol) was added in one portion, and the temperature increased to −24° C. The temperature gradually decreased to −38° C. and the reaction mixture was stirred until the temperature reached −5° C. (3 hours). The reaction was quenched by the addition of 10% HCl (15 mL) and the mixture was poured into water (300 mL). The organic phase was separated and the aqueous phase extracted with EtOAc (150 mL). The combined organics were washed with water (2×500 mL), dried over $MgSO_4$, filtered and solvent removed by rotary evaporation. The resulting brown slurry was sonicated with MeOH (50 mL) and filtered to afford a yellow powder (2.30 g). The filtrate was redissolved in DCM and dry-loaded onto silica gel. Flash chromatography (hexanes) afforded (7) as a clear, colourless oil, 20.7 g (73%).

Synthesis of S006

In a flame dried, 1 L, 3-neck, rbf equipped with a stirbar and an argon inlet, (6) (10.67 g, 30.5 mmol) was dissolved in anhydrous THF (150 mL) and anhydrous diethyl ether (250 mL) was added. The reaction mixture was cooled to −40° C. and n-BuLi (2.5 M in hexanes, 15.3 mL) was added dropwise over a period of 10 minutes. The resulting yellow solution was allowed to stir for 10 minutes. A solution of (7) (13.07 g, 30.5 mmol) in anhydrous THF (100 mL) was added via cannula over a period of 5 minutes. The temperature of the reaction increased to −28° C. and slowly cooled back down to −40° C. The reaction was allowed to stir until the internal temperature reached −12° C. The reaction was quenched by the addition of 10% HCl (15 mL) and was poured into water (200 mL) and mixed well. The aqueous phase was separated and extracted with EtOAc (250 mL). The combined organics were washed with water (500 mL), dried over $MgSO_4$, filtered and solvent removed by rotary evaporation. Flash chromatography Silica gel, (hexanes to 2% EtOAc/hexanes) afforded a yellow, powdery solid, two fractions: F1: 5.57 g (26.9%) and F2: 6.08 g (29.3%). $^1$H NMR (400 MHz, $CDCl_3$) δ 7.38-7.28 (m, 9H), 7.10-7.07 (m, 6H), 7.02-6.97 (m, 4H), 6.28 (s, 1H), 6.25 (s, 1H).

Example 4

Synthesis of S007

3',3'''-(perfluorocyclopent-1-ene-1,2-diyl)bis(5,5''-dimethyl-2,2':5',2''-terthiophene)

(Scheme 14)

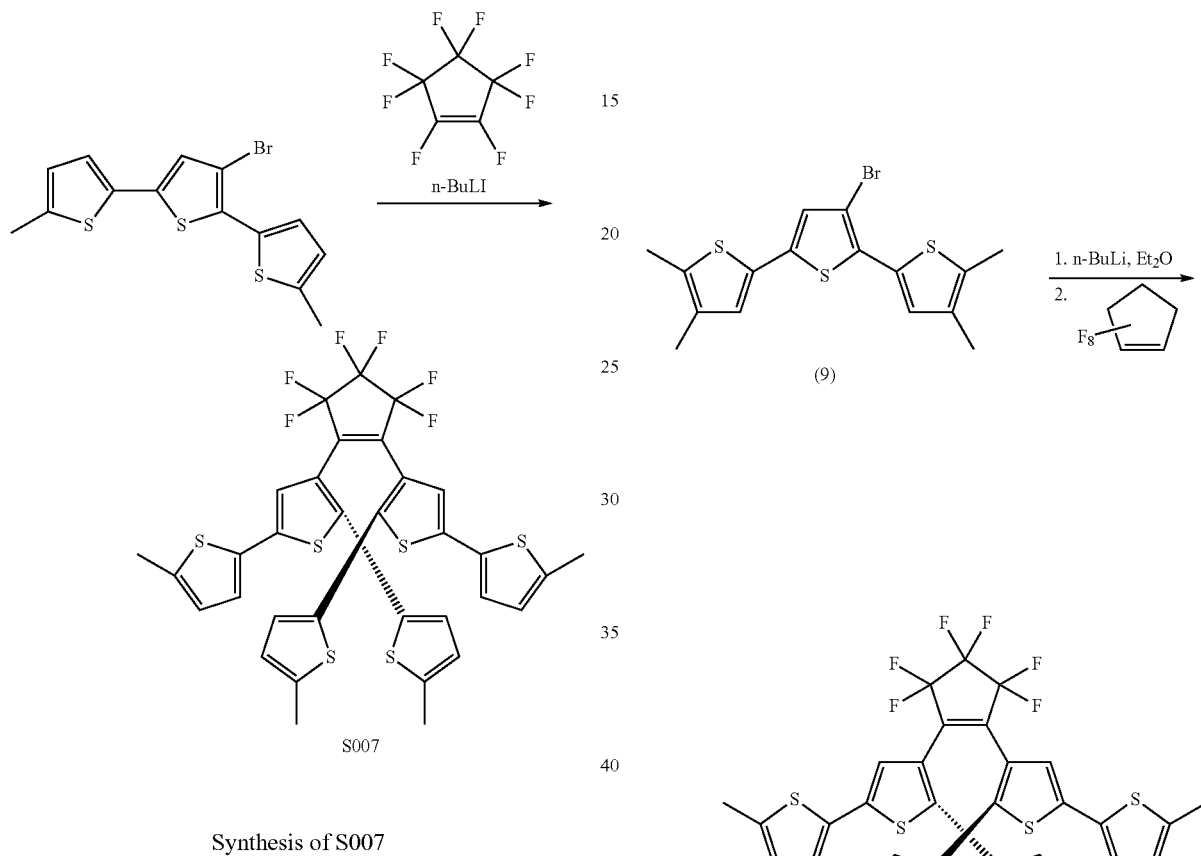

S007

Synthesis of S007

S007 was prepared on 3.6 mmol scale (51% yield) according to protocol G. $^1$H NMR (400 MHz, CDCl$_3$) δ 6.86 (d, J=3.5 Hz, 2H), 6.65 (dd, J=3.5, 1.1 Hz, 2H), 6.46 (dt, J=3.5, 2.3 Hz, 4H), 6.33 (s, 2H), 2.49 (d, J=0.7 Hz, 6H), 2.20 (d, J=0.7 Hz, 6H).

Example 5

Synthesis of S011

3',3'''-(perfluorocyclopent-1-ene-1,2-diyl)bis(4,4'',5,5''tetramethyl-2,2':5',2''-terthiophene (Scheme 15)

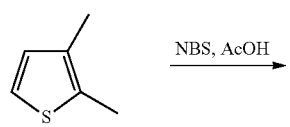

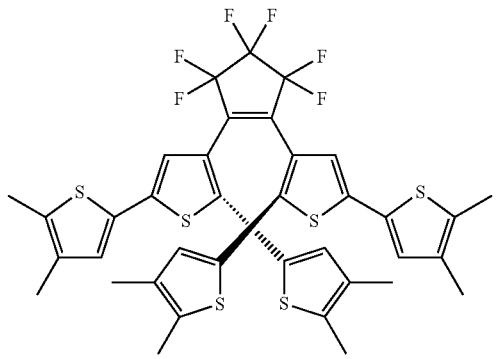

S011

Synthesis of 5-bromo-2,3-dimethylthiophene (8)

To a solution of 2,3-dimethylthiophene (21.68 g, 192 mmol) in glacial acetic acid (20 mL) was added N-bromosuccinimide (NBS) (34.39 g, 192 mg) over 5 minutes (the temperature increased to 50° C.). The reaction was complete (TLC: hexanes) after 10 minutes then poured over ice. Once cooled, the organics were extracted with DCM and the combined fractions were washed with 1M NaOH, water and brine. The resulting solution was dried with MgSO$_4$, concentrated under vacuum to yield a light orange oil. Flash chromatography afforded 8 (19.07 g, 52%). $^1$H NMR (600 MHz, CDCl$_3$) δ 6.72 (s, 1H), 2.27 (s, 3H), 2.09 (s, 3H).

Synthesis of 3'-bromo-4,4'',5,5''-tetramethyl-2,2':5',2''-terthiophene (9)

(9) was prepared on 3.9 mmol scale (30% yield) according to protocol A. $^1$H NMR (600 MHz, CDCl$_3$) δ 7.09 (s, 1H), 6.93 (s, 1H), 6.85 (s, 1H), 2.36 (s, 3H), 2.34 (s, 3H), 2.15 (s, 3H), 2.12 (s, 3H).

Synthesis of S011

S011 was prepared on 0.27 mmol scale (20% yield) according to protocol H2. $^1$H NMR (400 MHz, CDCl3) δ 6.74 (s, 2H), 6.34 (s, 4H), 2.34 (s, 6H), 2.11 (s, 6H), 2.08 (s, 6H), 1.85 (s, 6H).

Example 6

Synthesis of S012 methyl 4'-(2-([2,2':5',2''-terthiophen]-3'-yl)-3,3,4,4,5,5-hexafluorocyclopent-1-en-1-yl)-[2,2':5',2''-terthiophene]-5-carboxylate (Scheme 16)

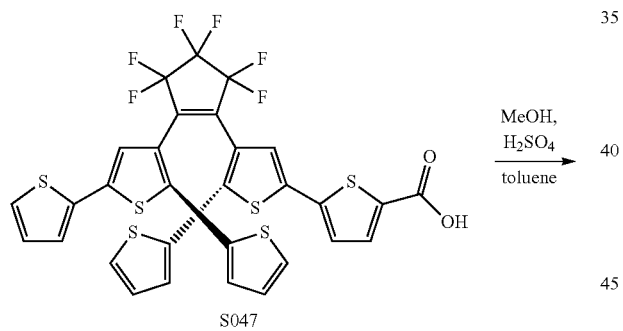

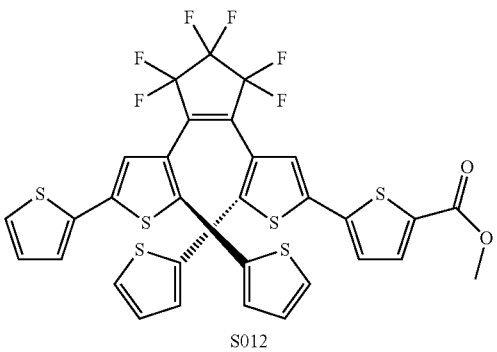

To a 100 mL round bottom flask was added S047 (32 mg, 0.055 mmol), toluene (20 mL), MeOH (5 mL) and concentrated H$_2$SO$_4$ (0.2 mL). The flask was fitted with a Dean Stark trap and the mixture was heated to reflux for 18 hours. After cooling the reaction mixture was diluted with water (20 mL) and extracted with DCM (2×20 mL). The combined organic fractions were washed with brine, dried with MgSO$_4$ and concentrated onto silica gel. The crude product was purified by flash column chromatography (9:1 hexanes/EtOAc) to yield 19 mg of S012. $^1$H NMR (600 MHz, CDCl$_3$) δ 7.70 (d, J=3.9, 1H), 7.28-7.25 (m, 1H), 7.18 (dd, J=5.1, 1.2, 1H), 7.16 (dd, J=5.1, 1.2, 1H), 7.07 (dd, J=3.6, 1.1, 1H), 7.05-7.01 (m, 2H), 6.84-6.81 (m, 2H), 6.73 (dd, J=3.6, 1.2, 1H), 6.71 (dd, J=3.5, 1.2, 1H), 6.46 (s, 1H), 6.37 (s, 1H), 3.92 (s, 3H).

Example 7

Synthesis of S013

2-(2-(2-ethoxyethoxy)ethoxy)ethyl 4'-(2-([2,2':5',2''-terthiophen]-3'-yl)-3,3,4,4,5,5-hexafluorocyclopent-1-en-1-yl)-[2,2':5',2''-terthiophene]-5-carboxylate (Scheme 17)

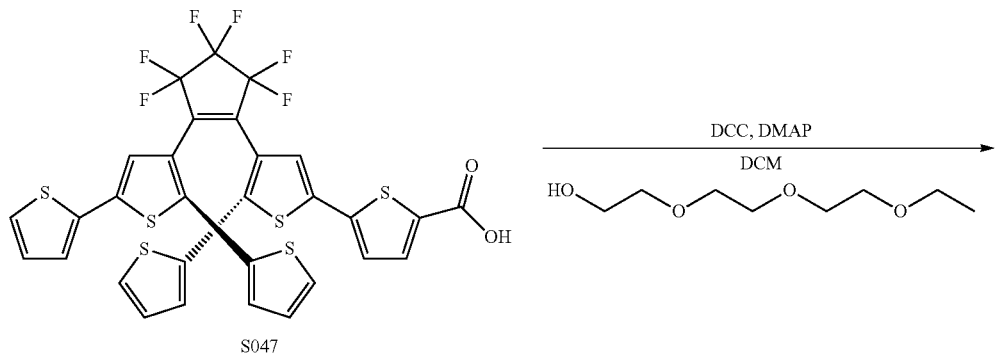

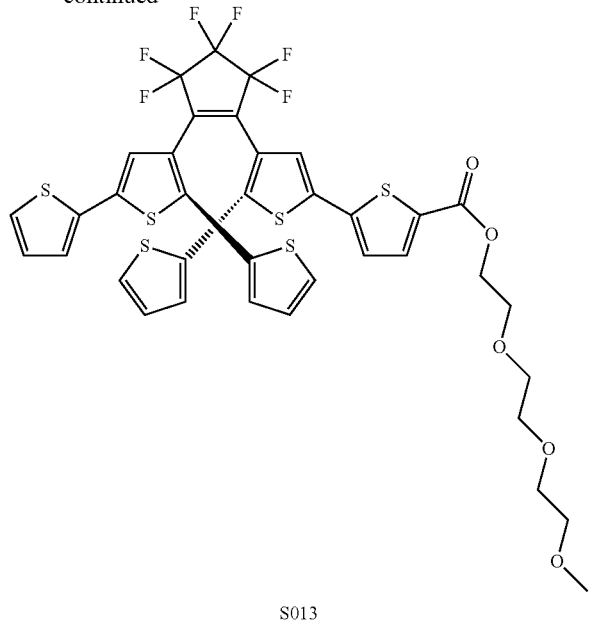

S013

To a 50 mL round bottom flask was added S047 (28 mg, 0.039 mmol), triethylene glycol monoethyl ether (50 mg, 0.08 mmol), DCC (17 mg, 0.08 mmol), DMAP (10 mg, 0.08 mmol) and DCM (15 mL). The reaction mixture stirred under Ar for 42 hours. The reaction mixture was then filtered by gravity, diluted with water (10 mL) and extracted with DCM (2×10 mL). The combined organic fraction were washed with brine (10 mL), dried over $MgSO_4$ and concentrated onto silica gel. The crude product was purified by flash column chromatography to yield 13 mg of S013. $^1$H NMR (600 MHz, $CD_2Cl_2$) δ 7.72 (d, J=3.9, 1H), 7.30 (dd, J=5.1, 1.2, 1H), 7.22 (dd, J=5.1, 1.2, 1H), 7.20 (dd, J=5.1, 1.3, 1H), 7.11 (dd, J=3.6, 1.2, 1H), 7.08 (d, J=3.9, 1H), 7.06-7.03 (m, 1H), 6.85-6.81 (m, 2H), 6.77-6.74 (m, 1H), 6.74-6.71 (m, 1H), 6.52 (s, 1H), 6.41 (s, 1H), 4.47-4.42 (m, 2H), 3.83-3.78 (m, 2H), 3.70-3.66 (m, 2H), 3.65-3.62 (m, 2H), 3.62-3.58 (m, 2H), 3.56-3.52 (m, 2H), 3.48 (q, J=7.0, 2H), 1.17 (t, J=7.0, 3H).

Example 8

Synthesis of S014

3,3'-(perfluorocyclopent-1-ene-1,2-diyl)bis(2-phenylbenzo[b]thiophene)

(Scheme 18)

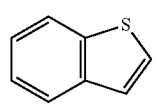 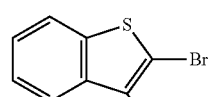

(10)

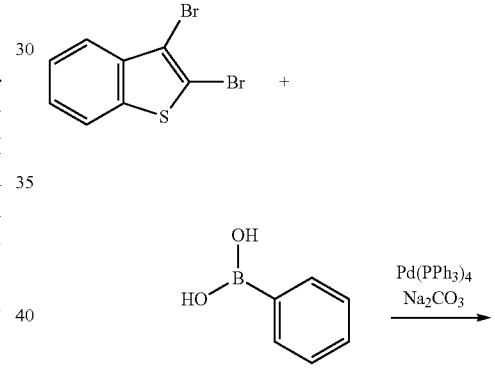

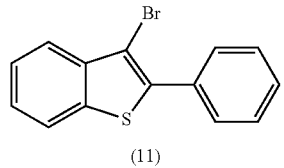

(11)

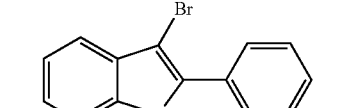

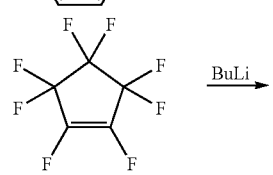

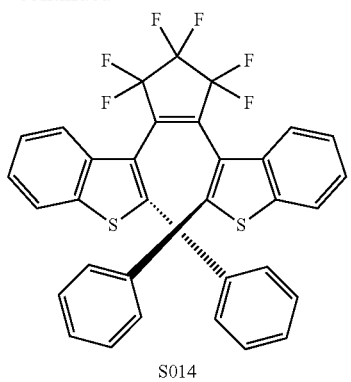

S014

Synthesis of 2,3-dibromobenzo[b]thiophene (10)

A solution of 18 g (134 mmol) of benzo[b]thiophene in 200 mL of chloroform was stirred and to this mixture was added 42.9 g (13.7 mL, 268 mmol) of bromine in 100 mL of chloroform dropwise at RT over 1.5 h. After stirring for 18 h, solid $NaHCO_3$ was added to neutralize the hydrobromic acid. The organic layer was washed with water and $Na_2S_2O_8$ and dried ($MgSO_4$). On evaporation of the solvent solid was obtained which was crystallized from methanol to give 38.8 g (99%) of 2,3-dibromobenzo[b]thiophene.

Synthesis of 3-bromo-2-phenylbenzo[b]thiophene (11)

(11) was prepared on 31 mmol scale (77% yield) yield according to protocol D.

Synthesis of S014

S014 was prepared on 0.72 mmol scale (15% yield according to protocol H2. $^1$H NMR (600 MHz, $CD_2Cl_2$) δ 7.65 (d, J=8.0 Hz, 1H), 7.23-7.17 (m, 1H), 7.04-6.96 (m, 2H), 6.91-6.83 (m, 4H), 6.81 (d, J=8.2 Hz, 1H).

Example 9

Synthesis of S017

4,4'-(perfluorocyclopent-1-ene-1,2-diyl)bis(3-methyl-2,5-diphenylthiophene)

(Scheme 19)

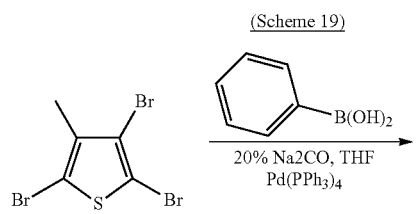

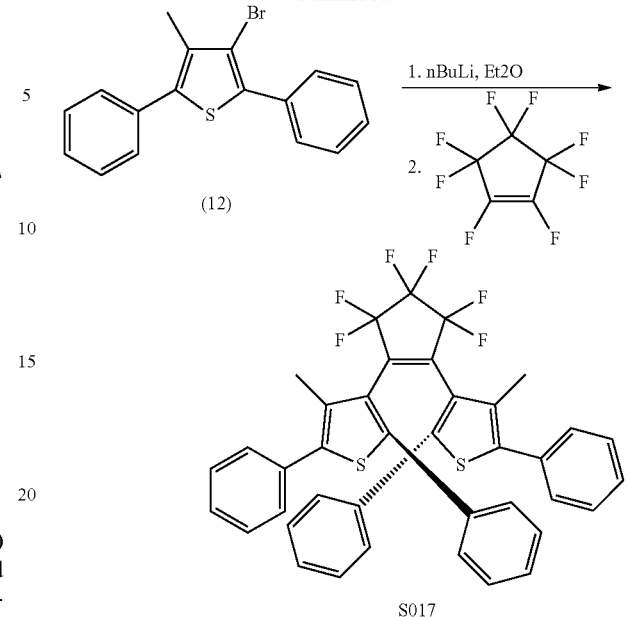

S017

Synthesis of 3-bromo-4-methyl-2,5-diphenylthiophene (12)

(12) was prepared on 8.1 mmol scale (68% yield) according to protocol C. $^1$H NMR (600 MHz, $CDCl_3$) δ 7.71-7.68 (m, 2H), 7.50-7.43 (m, 6H), 7.41-7.36 (m, 2H), 2.36 (s, 3H).

Synthesis of S017

S017 was prepared on 0.25 mmol scale (17% yield) according to protocol G. $^1$H NMR (600 MHz, $CDCl_3$) δ 7.47-7.41 (m, 4H), 7.39-7.34 (m, 6H), 7.19-7.15 (m, 2H), 7.15-7.10 (m, 4H), 7.10-7.06 (m, 4H), 1.14 (s, 3H), 1.13 (s, 3H).

Example 10

Synthesis of S019

3',3''''-(perfluorocyclopent-1-ene-1,2-diyl)bis(5,5''-dibromo-2,2':5',2''-terthiophene)

(Scheme 20)

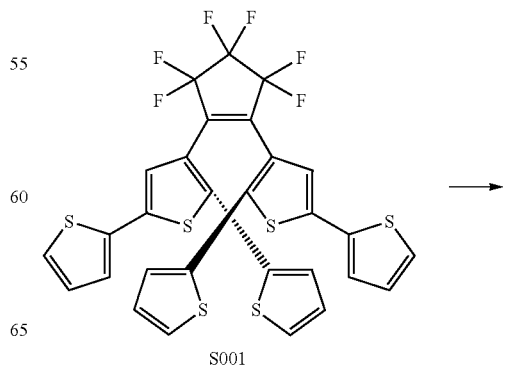

S001

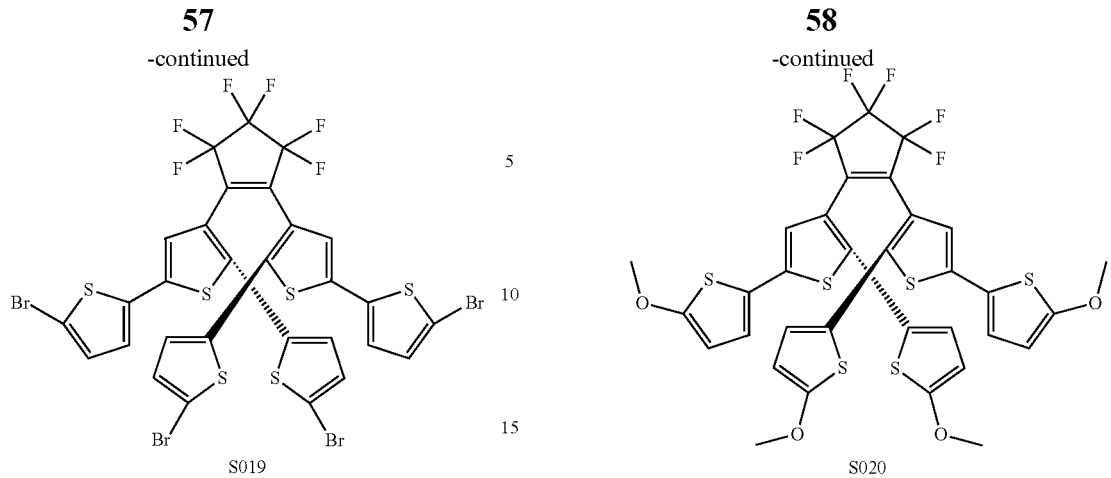

S019

Synthesis of S019

To a solution of S001 (2.0 g, 3 mmol) (U.S. Pat. No. 7,777,055) in DCM (50 mL) and acetic acid (50 mL) was added a solution of bromine (0.61 mL, 12 mmol) in acetic acid (30 mL) drop-wise over 30 minutes (reaction progress monitored by TLC-hexanes/DCM 9:1). The reaction was stirred for 16 hours then filtered. Traces of acetic acid were removed under high vacuum. The resulting yellow solid was triturated with cold diethyl ether, filtered and dried, yielding S019 (2.24 g, 76%) as a bright yellow solid. $^1$H NMR (600 MHz, CDCl$_3$) δ 6.99 (d, J=3.9 Hz, 2H), 6.89 (d, J=3.8 Hz, 2H), 6.78 (d, J=3.8 Hz, 2H), 6.44 (s, 2H), 6.42 (d, J=3.8 Hz, 2H).

Example 11

Synthesis of S020

3',3'''-(perfluorocyclopent-1-ene-1,2-diyl)bis(5,5''-dimethoxy-2,2':5',2''-terthiophene)

Synthesis of 3'-bromo-5,5''-dimethoxy-2,2':5',2''-terthiophene (13)

A mixture of 2-methoxythiophene (5.00 g, 43 mmol), potassium acetate (2.58 g, 26.3 mmol), tetrabutylammonium bromide (2.82 g, 8.76 mmol), palladium(II)acetate (0.10 g, 0.87 mmol), and 2,3,5-tribromothiophene (1.26 g, 3.93 mmol) in DMF (100 mL) was heated to 80° C. for two hours. Once the reaction was complete (TLC: 10% EtOAc in hexanes), it was cooled and the organics were extracted with DCM. Combined fractions were washed with 1 M NaOH, water, then brine. The resulting solution was dried with MgSO$_4$, concentrated under vacuum to afford a dark oil. Flash chromatography afforded 13 (0.88 g, 69%) as a yellow solid. $^1$H NMR (600 MHz, CDCl$_3$) δ 7.02 (d, J=4.0 Hz, 1H), 6.85 (s, 1H), 6.79 (d, J=4.0 Hz, 1H), 6.18 (d, J=4.0 Hz, 1H), 6.12 (d, J=4.0 Hz, 1H), 3.93 (s, 3H), 3.91 (s, 3H).

Synthesis of S020

S020 was prepared on 1.88 mmol scale (38% yield) according to protocol H2. $^1$H NMR (600 MHz, CDCl3) δ 6.71 (d, J=3.9 Hz, 2H), 6.38 (s, 2H), 6.31 (d, J=3.9 Hz, 2H), 6.12 (d, J=3.9 Hz, 2H), 5.90 (d, J=3.9 Hz, 2H), 3.91 (s, 6H), 3.68 (s, 6H). $^{13}$C NMR (151 MHz, CDCl$_3$) δ 167.92, 166.14, 137.41, 135.73, 124.53, 124.28, 122.93, 122.35, 121.93, 119.04, 104.61, 104.51, 60.55, 60.04, 29.92.

Example 12

Synthesis of S024

3',3'''-(perfluorocyclopent-1-ene-1,2 diyl)bis(([2,2':5',2''-terthiophene]-5,5''-dicarboxylic acid)

(Scheme 22)

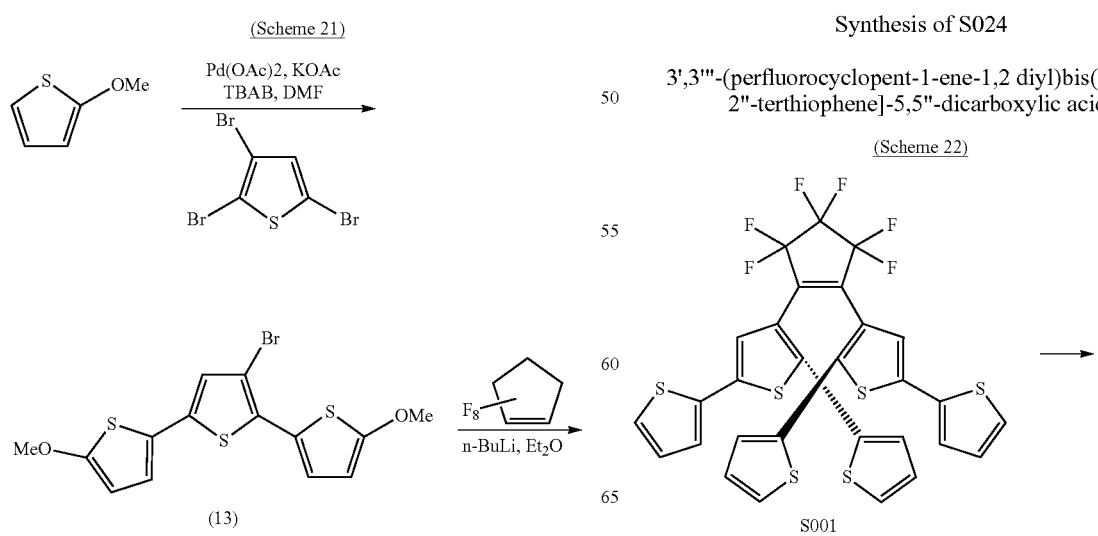

-continued

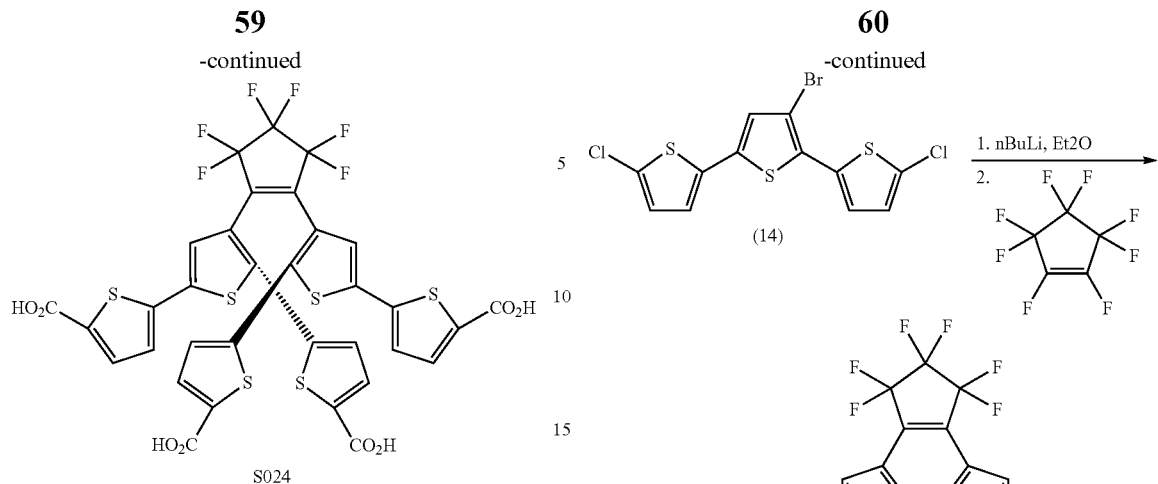

S024

In a flame-dried 250 mL rbf, diisopropylamine (3.0 mL, 21.7 mmol) was added to anhydrous THF (30 mL), and cooled to 0° C. n-BuLi (2.5 M in hexanes, 7.9 mL, 19.7 mmol) was added dropwise over a period of 5 minutes. The reaction mixture was allowed to stir at 0° C. for 30 minutes and then added dropwise to a solution of S001 (3.00 g, 4.49 mmol) in anhydrous THF (30 mL) at 0° C. Upon addition, an immediate red colour was observed, and over time a brown precipitate formed. The brown slurry was allowed to stir at 0° C. for 90 minutes, then was cooled to −78° and quenched by bubbling $CO_2$ through the solution for 2 hours. The cooling bath was removed and the reaction mixture allowed to slowly warm to RT while bubbling was continued overnight. The reaction was quenched by the addition of methanol (20 mL), and the mixture was poured into water (200 mL) and extracted with a mixture of THF/EtOAc (1:1, 2×100 mL). The combined organics were washed with water (200 mL), dried over $MgSO_4$, filtered and solvent removed by rotary evaporation to afford a yellow/green, flaky solid, 3.17 g (84%). $^1$H NMR (400 MHz, DMSO) δ 7.65 (d, J=3.9 Hz, 2H), 7.45 (d, J=3.9 Hz, 2H), 7.36 (d, J=3.9 Hz, 2H), 6.86 (d, J=3.8 Hz, 2H), 6.70 (s, 2H).

Example 13

Synthesis of S026

3',3'''-(perfluorocyclopent-1-ene-1,2-diyl)bis(5,5''-dichloro-2,2':5',2''-terthiophene)

(Scheme 23)

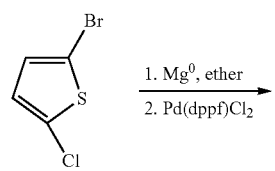

Synthesis of 3'-bromo-5,5''-dichloro-2,2':5'2''-terthiophene (14)

(14) was prepared on 9.2 mmol scale (54% yield) according to protocol A. $^1$H NMR (600 MHz, $CDCl_3$) δ 7.15 (d, J=4.0, 1H), 6.99 (s, 1H), 6.94 (d, J=3.9, 1H), 6.90 (d, J=4.0, 1H), 6.86 (d, J=3.9, 1H).

Synthesis of S026

S026 was prepared on 0.074 mmol scale (6% yield) according to protocol G. $^1$H NMR (600 MHz, $CDCl_3$) δ 6.89 (d, J=3.9, 2H), 6.86 (d, J=3.9, 2H), 6.65 (d, J=3.8, 2H), 6.47-6.44 (m, 4H).

Example 14

Synthesis of S027

3',3'''-(perfluorocyclopent-1-ene-1,2-diyl)bis(5-methyl-2,2':5',2''-terthiophene)

(Scheme 24)

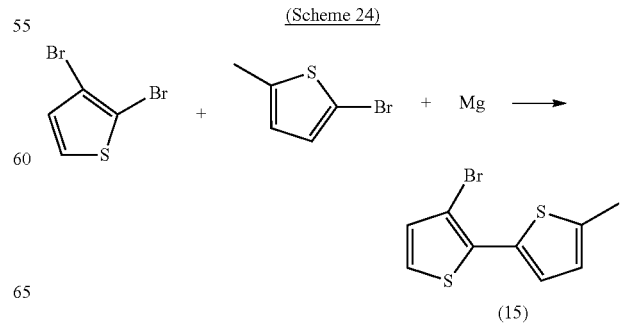

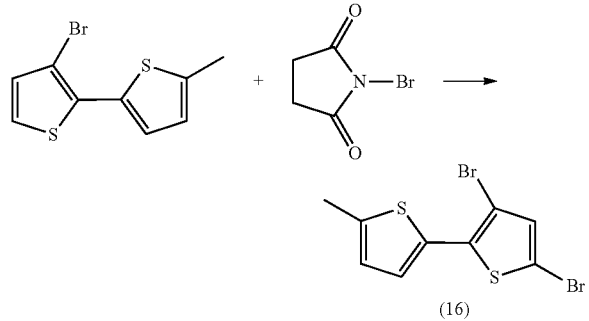

(16)

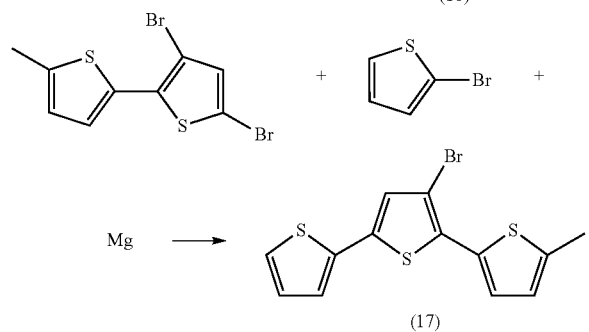

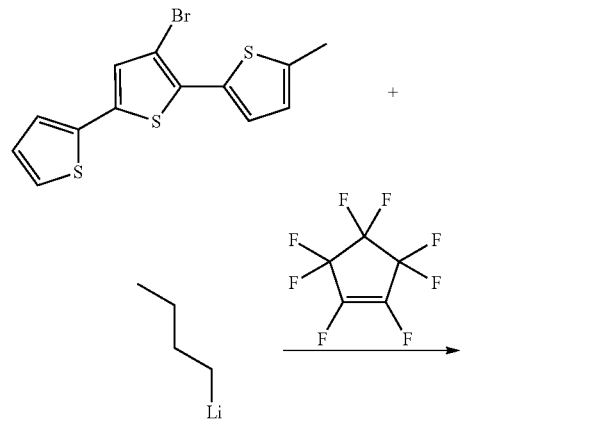

S027

Synthesis of 3-bromo-5'-methyl-2,2'-bithiophene (15)

(15) was prepared on 98 mmol scale (94% yield) according to protocol B. $^1$H NMR (CDCl$_3$, 600 MHz) δ 7.22 (d, J=3 Hz, 1H), 7.16 (d, J=5 Hz, 1H), 7.00 (d, J=5 Hz, 1H), 6.75 (d, J=3 Hz, 1H). 2.52 (s, 3H).

Synthesis of 3,5-dibromo-5'-methyl-2,2'-bithiophene (16)

N-Bromosuccinimide (15.55 g, 87 mmol) was added portionwise to stirred solution of 3-bromo-5'-methyl-2,2'-bithiophene (20.56 g, 79 mmol) in glacial acetic acid (200 mL) containing acetic anhydride (25 mL) at RT. The mixture was stirred and monitored by TLC. After completion (1.5 h) the reaction was diluted with water (200 mL) and the oily phase was taken into ether and separated. The aqueous phase was extracted with ether. The combined organic phases were washed with 1 M NaOH solution followed by water. Removal of the solvent left a solidifying oil, which was sonicated in methanol yielding after filtration and drying 3,5-dibromo-5'-methyl-2,2'-bithiophene as off-white solid (single spot on TLC). Yield: 20.6 g (77%). $^1$H NMR (600 MHz, CD$_2$Cl$_2$) ppm 7.13 (d, J=3.6 Hz, 1H), 6.97 (s, 1H), 6.74-6.72 (m, 1H), 2.48-2.47 (m, 3H)

Synthesis of 3'-bromo-5-methyl-2,2':5',2"-terthiophene (17)

(17) was prepared on 36 mmol scale (91% yield) according to protocol B.

Synthesis of S027

S027 was prepared on 3.76 mmol scale (8% yield) according to protocol G. $^1$H NMR (600 MHz, CDCl$_3$) δ ppm 7.30-7.28 (m, 2H), 7.18 (dd, J=5.1, 1.1 Hz, 2H), 7.10 (dd, J=3.6, 1.1 Hz, 2H), 7.05 (dd, J=5.1, 3.6 Hz, 2H), 6.85 (dd, J=5.1, 3.6 Hz, 2H), 6.74 (dd, J=3.6, 1.1 Hz, 2H), 6.40 (s, 2H).

Example 15

Synthesis of S032

2,2',2",5,5"-pentaphenyl-4,4':5',4"-terthiazole

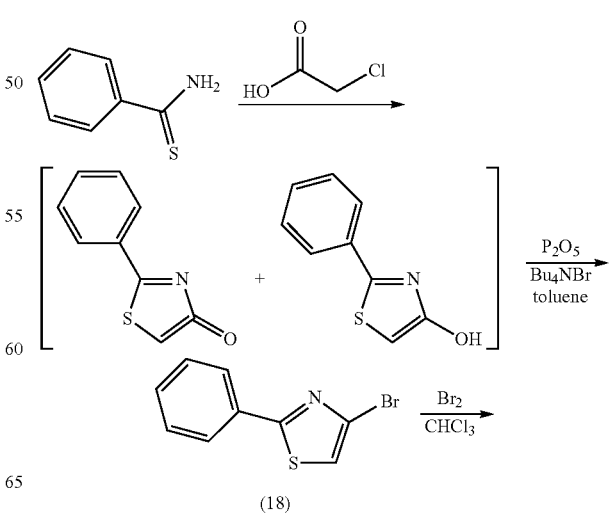

(Scheme 25)

(18)

-continued

(19)

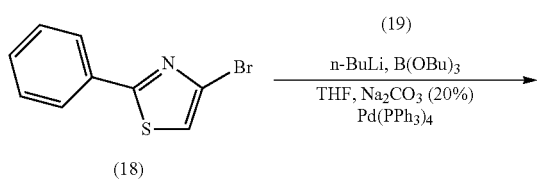

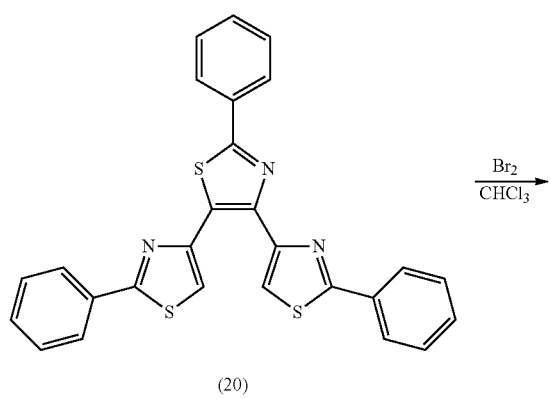

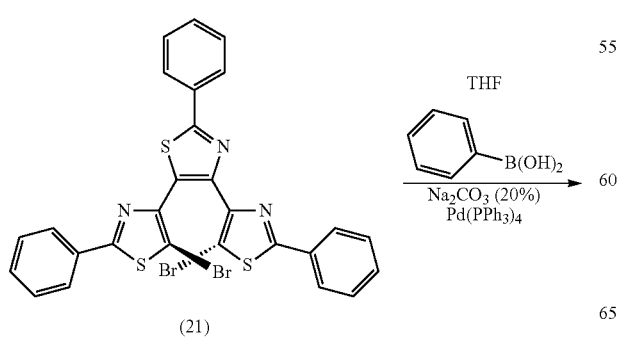

-continued

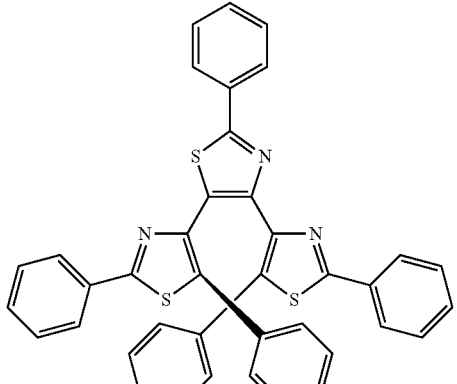

S032

Synthesis of 5-bromo-2-phenylthiazole (18)

Chloroacetic acid (43.7 g, 463 mmol) was ground in a mortar and pestle and added to thiobenzamide (63.5 g, 463 mmol) in a 1 L beaker. The two solids were stirred manually and heated to 100° C. in an oil bath. At a bath temperature of about 75° C., the mixture melted and an exothermic reaction ensued. The internal reaction temperature reached 115° C. The mixture was rigorously stirred at this temperature for 10 minutes. During this time the melt turned black and a gas was evolved (steam and HCL perhaps). The mixture was then cooled to room temperature and acetone (100 mL) was added. The viscous melt was carefully stirred up in acetone to produce a yellow suspension that was filtered and re-suspended in $H_2O$ (500 mL). The suspension was extracted with $Et_2O$ (4×400 mL). The ether fractions were combined and washed with brine, dried over $MgSO_4$ and concentrated to give a pale yellow solid (36.0 g). The crude product (35.9 g, 202.6 mmol) was used as-is, and transferred to a 1 L rbf; to this was added $Bu_4NBr$ (78.17 g, 242.5 mmol) followed by $P_2O_5$ (69.0 g, 486.24 g) and toluene (500 mL). The mixture was heated at 100° C. for 18 hours and cooled to room temperature. The top layer was decanted off and fresh toluene (300 mL) was added and the mixture again heated to 100° C. for 5 hours. The mixture was cooled, to room temperature and the top layer decanted. Another 300 mL of toluene was added to the mixture, heated at 100° C. in an oil bath for 20 hours. After cooling to room temperature, the top layer was decanted off. The combined toluene layers were vacuum-filtered to remove precipitates and the filtrate washed with brine (4×200 mL). The organic layer was dried over $MgSO_4$, filtered and concentrated onto Silica gel and purified by column (1:1 hexanes/$CHCl_3$). Two sets of fractions were collected (24.5 g and 3.0 g), both are the product but the later fraction had a strong yellow brown colouration. $^1H$ NMR (600 MHz, $CDCl_3$) δ 7.95-7.90 (m, 2H), 7.47-7.42 (m, 3H), 7.21 (s, 1H).

Synthesis of 4,5-dibromo-2-phenylthiazole (19)

Compound 18 (5.0 g, 21 mmol) was dissolved in $CHCl_3$ (250 mL). $Br_2$ (16.7 g, 105 mmol) was dissolved in $CHCl_3$ (50 mL) and added to the solution of 18 via addition funnel over 10 minutes. The reaction mixture stirred at room temperature for 5.5 hours; then was transferred to a 1 L separatory funnel and washed with $Na_2S_2O_3$ (3×100 mL) followed by brine (2×150 mL). The organic fractions were dried over $MgSO_4$ and concentrated. The crude product was purified by column (2:1 hexanes/CHCl$_3$). $^1$H NMR (600 MHz, CDCl$_3$) δ 7.85 (d, J=7.3, 2H), 7.50-7.40 (m, 3H).

Synthesis of 2,2',2"-triphenyl-4,4':5',4"-terthiazole (20)

Compound 23 (2.0 g, 8.33 mmol) was weighed into a 250 mL rbf and dissolved in ether (100 mL). The thiazole was fully soluble at room temperature but precipitated out at −78° C. The mixture was warmed back to room temperature to re-dissolve Compound 2 and then cooled to −25° C. n-BuLi (3.5 mL, 8.75 mmol, 2.5 M solution in hexanes) was added dropwise over 15 minutes and allowed to stir for an additional 30 minutes. The lithiation was determined to be complete by TLC (1:1 hexane/CHCl$_3$). The reaction was cooled to −50° C. and B(OBu)$_3$ was added all in one portion. The solid precipitate dissolved within 5-10 minutes (monitored by TLC—only a baseline spot was observed). The reaction mixture was concentrated and re-dissolved in THF (50 mL). Compound 19 (1.3 g, 4.2 mmol) was dissolved into the mixture, 20% Na$_2$CO$_3$ (aq) (50 mL) was added and the mixture de-oxygenated by bubbling Ar through for 30 minutes. Pd(PPh$_3$)$_4$ (0.30 g, 0.25 mmol) was added and the mixture refluxed for 16 hours (overnight). After cooling to room temperature the layers were separated and the aqueous fraction extracted with EtOAc (2×50 mL). The combined organic fractions were washed with brine, dried over MgSO$_4$, and concentrated onto Silica gel. The crude product (210 mg) was purified by column (1:1 hexanes/CHCl$_3$). The photochromic product was used immediately in the next step without characterization.

Synthesis of 5,5"-dibromo-2,2',2"-triphenyl-4,4':5', 4"-terthiazole (21)

Compound 4 (220 mg, 0.46 mmol) was dissolved in CHCl$_3$ (100 mL). Br$_2$ (0.3 g, 1.9 mmol) was dissolved in CHCl$_3$ (20 mL) and added to the reaction mixture dropwise over 30 minutes. The bromine colour did not immediately dissipate when added to the starting material solution. The reaction mixture stirred at room temperature for 15 hours, and washed with of 5% Na$_2$S$_2$O$_3$ (aq) (50 mL), followed by brine (50 mL) and dried over MgSO$_4$, filtered and concentrated. The crude mixture (260 mg) was used in the next step without further purification or characterization.

Synthesis of S032

Phenyl boronic acid (0.18 g, 1.5 mmol) was added to a 250 mL rbf containing of 20% Na$_2$CO$_3$ (50 g) and 50 mL THF. The mixture was de-oxygenated by bubbling Ar through for 30 minutes. The deoxygenated mixture was transferred via cannula to a second 250 mL rbf containing Compound 4 (0.29 g, 0.46 mmol). Pd(PPh$_3$)$_4$ (20 mg) was added, and refluxed under Ar gas for 6 hours. After cooling to room temperature, the layers were separated and the aqueous extracted with EtOAc (2×30 mL). The combined organic fractions were washed with brine, dried over MgSO$_4$ and concentrated. The crude product (160 mg) was purified by column (9:1 hexanes EtOAc) followed by trituration from methanol. $^1$H NMR (600 MHz, CDCl$_3$) δ 8.02-7.95 (m, 2H), 7.82-7.75 (m, 4H), 7.47-7.36 (m, 9H), 7.15-7.09 (m, 8H), 7.08-7.03 (m, 1H), 7.02-6.98 (m, 1H).

Example 16

Synthesis of S034

3',3""-(perfluorocyclopent-1-ene-1,2 diyl)bis(5,5'"-dimethyl-2,2':5',2":5",2'"-quaterthiophene)

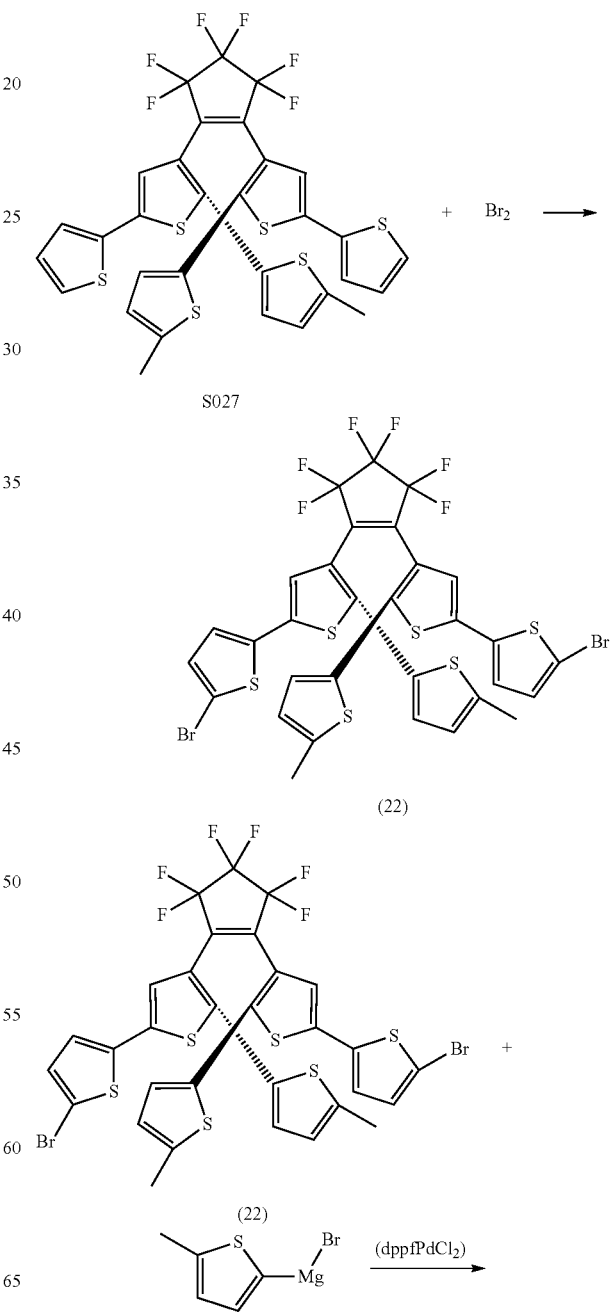

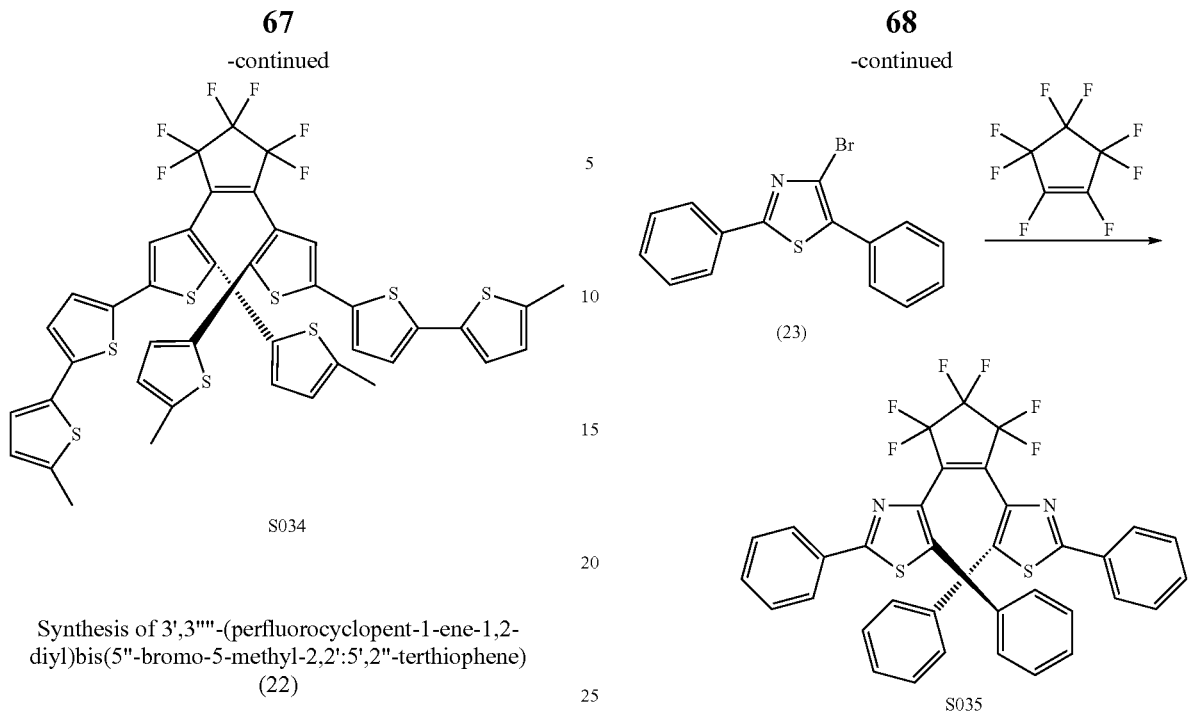

S034

Synthesis of 3',3''''-(perfluorocyclopent-1-ene-1,2-diyl)bis(5''-bromo-5-methyl-2,2':5',2''-terthiophene) (22)

To a solution of S027 (1.9 g; 2.76 mmol) in the mixture of acetic acid (20 mL) and DCM (20 mL) was added at stirring bromine (0.93 g; 5.8 mmol) as a solution in acetic acid (7.5 mL). The mixture was stirred at RT for 1 h then poured into 1 M NaOH solution and extracted with DCM. Organic phase was washed with 1 M NaOH and water, separated and concentrated under vacuum. Flash chromatography (hexanes/DCM 9:1) afforded 22 (2.3 g, 98% yield).

Synthesis of S034

S034 was prepared on 0.35 mmol scale (55% yield) according to protocol C. $^1$H NMR (600 MHz, CDCl$_3$) δ 6.97 (d, J=3.8 Hz, 2H), 6.82 (d, J=4.0 Hz, 2H), 6.50-6.48 (m, 4H), 6.36 (s, 2H), 2.25-2.23 (m, 6H).

Example 17

Synthesis of S035

4,4'-(perfluorocyclopent-1-ene-1,2-diyl)bis(2,5-diphenylthiazole)

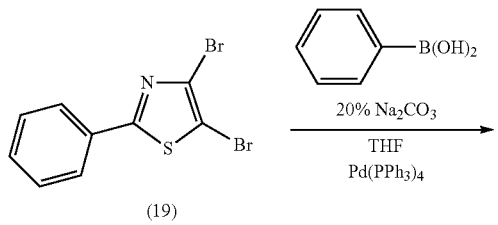

Synthesis of 4-bromo-2,5-diphenylthiazole (23)

(23) was prepared on 6.2 mmol scale (98% yield) according to protocol D. $^1$H NMR (600 MHz, CDCl$_3$) δ 7.99-7.93 (m, 2H), 7.73-7.68 (m, 2H), 7.50-7.40 (m, 6H).

Synthesis of S035

S035 was prepared on 0.26 mmol scale (17.6% yield) according to protocol G. $^1$H NMR (600 MHz, CDCl$_3$) δ 7.73-7.67 (m, 4H), 7.46-7.39 (m, 6H), 7.14-7.08 (m, 4H), 7.08-7.04 (m, 4H), 7.01-6.95 (m, 2H)

Example 18

Synthesis of S036

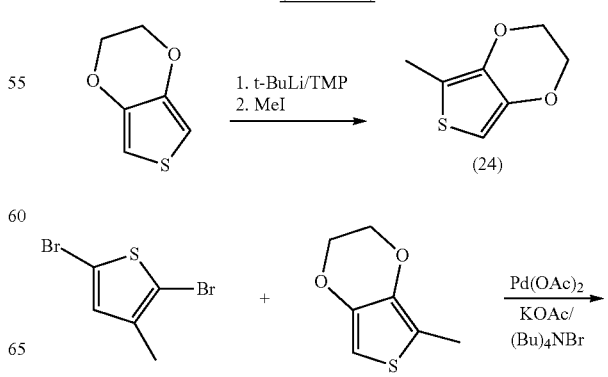

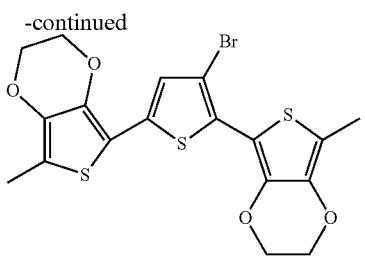

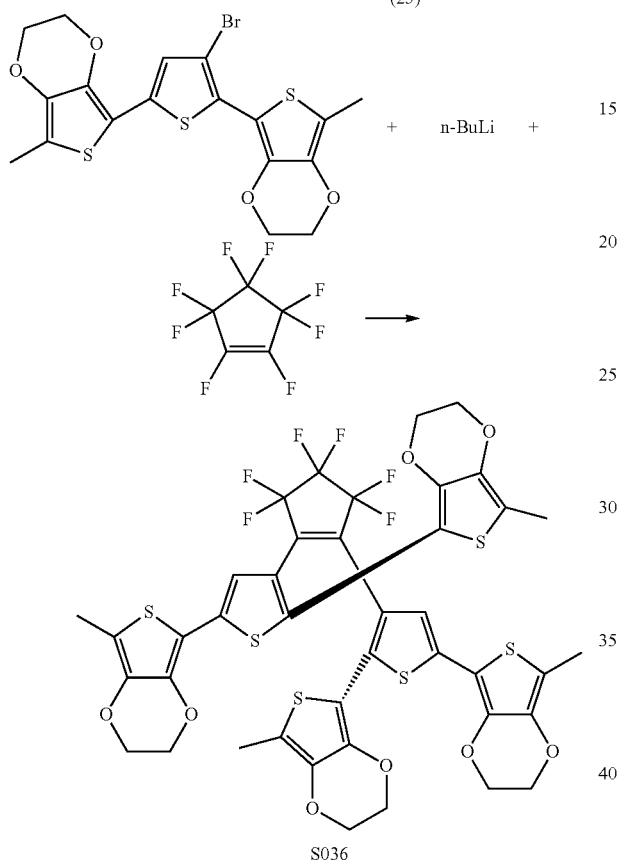

S036

Synthesis of 5-methyl-2,3-dihydrothieno[3,4-b][1,4]dioxine (24)

2,2,6,6-Tetramethylpiperidine (HTMP, 8.20 g, 58.0 mmol) was dissolved in dry THF (100 mL) in a septum sealed 250 mL rbf that had previously been flushed with argon. The mixture was cooled in a dry ice/acetone bath for 20 min; tert-BuLi (35.0 mL of a 1.7 M solution in pentane, 59.5 mmol) was added dropwise by syringe, and the reaction mixture was stirred for 45 min, forming a precipitate. 3,4-Ethylenedioxythiophene (EDOT) (7.82 g; 55 mmol) was added by syringe, and the mixture was stirred for 45 min to clarify. Iodomethane (12.5 g, 88.0 mmol) was added dropwise by syringe, and the mixture was stirred for 30 min, after which the cooling bath was removed and the mixture stirred overnight. HCl (2 M, 80 mL) was added to quench the reaction. The mixture was swamped with diethyl ether (120 mL) and washed with saturated sodium hydrogen carbonate solution (80 mL) and saturated NaCl solution (80 mL). The organic phase was dried over anhydrous MgSO$_4$, filtered through a plug of silica gel and evaporated providing 8.35 g (97% yield) of methylated product. The product was kept in ether/hexanes solution; to use in synthesis, 100 g of DMF was loaded into 500 mL rbf and the ether/hexane solution of (24) was added to the DMF and evaporated under vacuum. The DMF solution is clear and colourless and was used in the coupling reaction.

Synthesis of 5,5'-(3-bromothiophene-2,5-diyl)bis(5-methyl-2,3-dihydrothieno[3,4-b][1,4]dioxine (25)

To a stirred solution of 3,4-ethylenedioxy-5-methylthiophene (7.5 g, 48 mmol) in DMF (100 g) in argon flushed flask was added 2,3,5-tribromothiophene (7.3 g, 22.7 mmol), potassium acetate (8.9 g, 90 mmol), tetrabutylammonium bromide (14.7 g, 45.5 mmol), and palladium acetate (1.0 g, 4.55 mmol). The mixture was heated to 80° C. with stirring and the reaction was monitored by TLC. After 1.5 h the reaction was cooled and EtOAc (200 mL) and water (200 mL) were added. After separation, the organic layer was evaporated to dryness and the black tarry residue was loaded on silica gel. The product was isolated by flash chromatography using hexanes/EtOAc gradient (10 to 30% EtOAc) to give target product as an orange solid (4.23 g, 8.97 mmol, 39% yield). $^1$H NMR (600 MHz, CDCl$_3$) δ 7.01 (d, J=2.3 Hz, 1H), 4.33-4.29 (m, 4H), 4.23 (m, 4H), 2.27 (d, J=3.3 Hz, 3H), 2.25 (s, 3H).

Synthesis of S036

S036 was prepared on 1.73 mmol scale (42% yield) according to protocol H3. $^1$H NMR (600 MHz, CDCl$_3$) δ 6.69 (s, 2H), 4.33-4.28 (m, 4H), 4.25-4.21 (m, 4H), 4.16-4.09 (m, 8H), 2.25 (s, 6H), 1.89 (s, 6H).

Example 19

Synthesis of S037

4",4""'-(perfluorocyclopent-1-ene-1,2-diyl)bis(([2,2':5',2":5",2"'-quaterthiophene]-5-carbonitrile))

(Scheme 29)

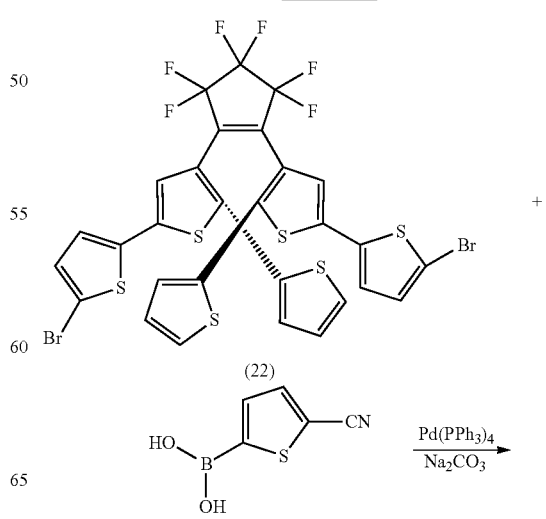

-continued
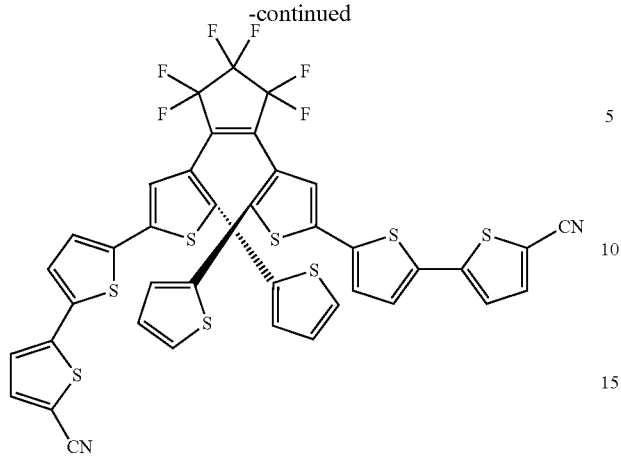
Synthesis of S037
S037 was prepared on 0.27 mmol scale (54% yield) according to protocol C. $^1$H NMR (600 MHz, CDCl$_3$) δ 7.56 (d, J=3.9 Hz, 2H), 7.22-7.18 (m, 4H), 7.16 (d, J=3.8 Hz, 2H), 7.02 (d, J=3.7 Hz, 2H), 6.87-6.84 (m, 2H), 6.74 (d, J=3.2 Hz, 2H), 6.40 (d, J=9.1 Hz, 2H).
Example 20
Synthesis of S038
(E)-4',4''''-(perfluorocyclopent-1-ene-1,2-diyl)bis(5-((E)-styryl)-2,2':5',2''-terthiophene)
(Scheme 30)
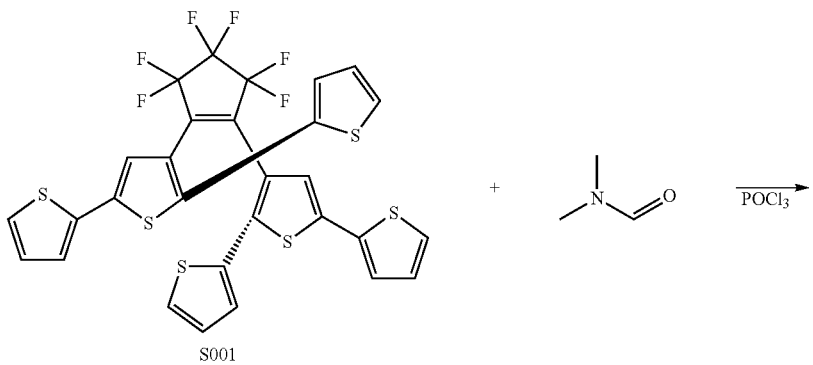
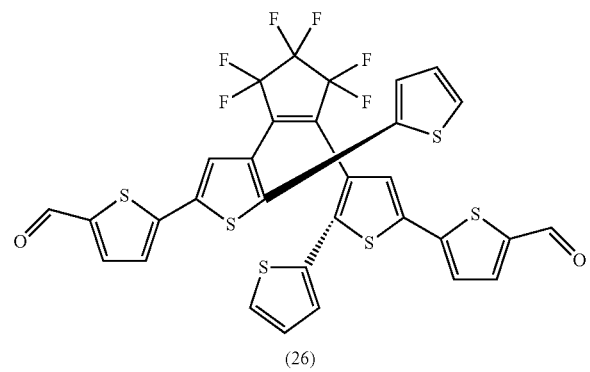
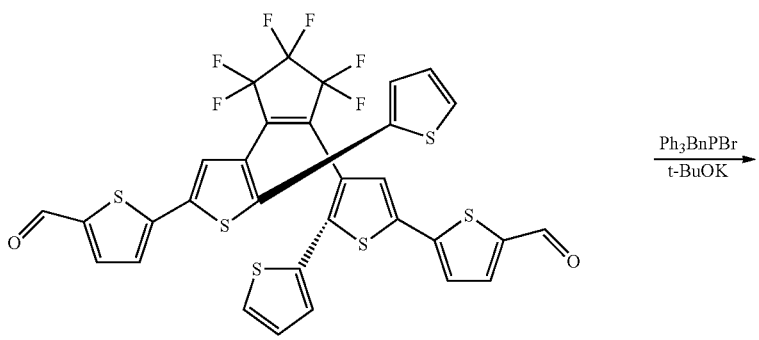

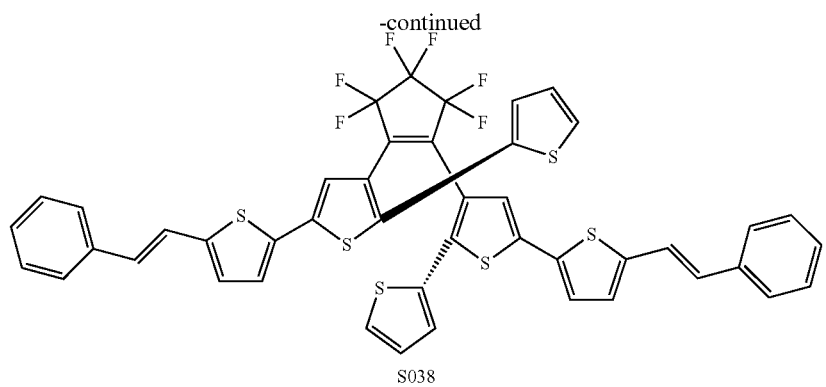

S038

Synthesis of 4',4""-(perfluorocyclopent-1-ene-1,2-diyl)bis(([2,2':5',2"-terthiophene]-5-carbaldehyde)) (26)

A solution of S001 (1.12 mmol, 0.75 g) and DMF (3.36 mmol, 0.25 g) in dry dichloroethane (10 mL) was purged with argon and cooled to 0° C. Phosphoryl chloride (2.47 mmol, 0.38 g) was slowly added and the reaction mixture was stirred for 1 h at 0° C. The temperature was raised to 20° C. for 16 h. Excess of DMF and POCl₃ (4 equiv.) was added and the reaction was continued for 6 days at RT. Yellow solid gradually precipitated and the spot of starting S001 was consumed (TLC). The mixture was poured into a potassium acetate solution (20 mL, 1 M) and vigorously stirred for 1 h at RT. The green mixture was extracted with DCM and the combined organic layers were dried over MgSO₄. The solvents were removed and two products were isolated by flash chromatography (hexanes) as yellow crystals. ¹H NMR (600 MHz, CDCl₃) δ ppm 9.90 (s, 2H), 7.68 (d, J=3.9, 2H), 7.20 (dt, J=5.0, 1.5, 2H), 7.14 (d, J=3.9, 2H), 6.85 (dd, J=5.1, 3.6, 2H), 6.75 (dd, J=5.1, 3.6, 1.2, 2H), 6.53 (s, 2H).

Synthesis of S038

A mixture of benzyltriphenylphosphonium bromide (0.72 g, 1.66 mmol) and 26 (0.40 g, 0.55 mmol) was dispersed in anhydrous THF (30 mL) and stirred at RT under argon atmosphere for 15 min. A solution of potassium tert-butoxide (0.25 g, 2.23 mmol) in anhydrous THF (8 mL) was added dropwise. The reaction mixture was stirred at RT for 45 min. Then water was added, followed by extraction with DCM (50 mL×3). The combined extracts were dried over anhydrous sodium sulfate. Solvents were removed by rotary evaporation, followed by column chromatography (Silica gel; hexanes/DCM (9:1)), to yield a yellow solid (0.245 g; 51% yield) of the target product. More of product (0.082 g) was isolated in a separate fraction. Overall yield 68%. Additional purification by means of crystallization was done using diethyl ether. Orange crystals were obtained after filtration and drying. ¹H NMR (600 MHz, CDCl₃) δ 7.49 (d, J=7.5 Hz, 4H), 7.38 (t, J=7.5 Hz, 4H), 7.28 (dd, J=12.3, 5.0 Hz, 2H), 7.20 (dd, J=10.0, 7.5 Hz, 4H), 7.00-6.91 (m, 6H), 6.86 (dd, J=5.0, 3.6 Hz, 2H), 6.73 (dd, J=3.6, 0.9 Hz, 2H), 6.39 (s, 2H).

Example 21

Synthesis of S039

3,3'-(perfluorocyclopent-1-ene-1,2-diyl)bis(4,4',5,5'-tetramethyl-2,2'-bithiophene)

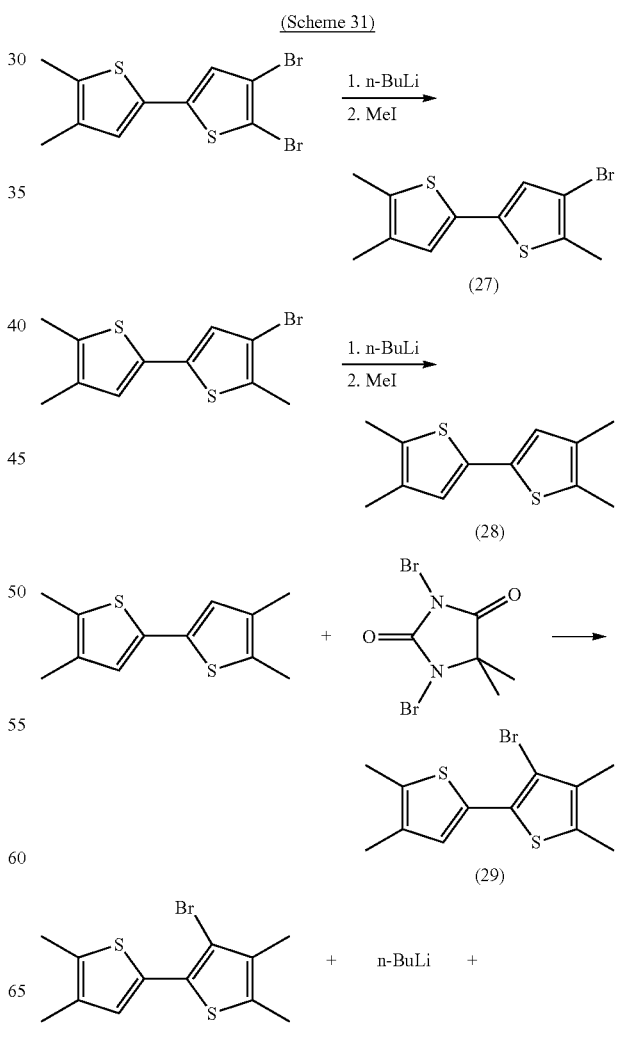

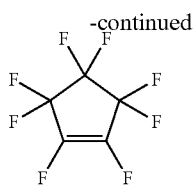

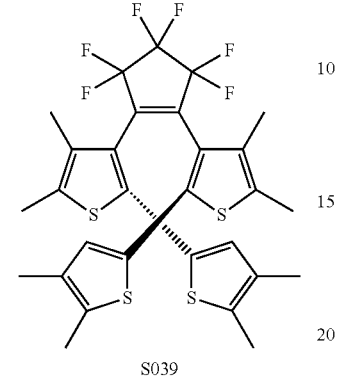

S039

Synthesis of 4-bromo-4',5,5'-trimethyl-2,2'-bithiophene (27)

n-BuLi (2.5M in hexane) (10 mL, 25 mmol) was added dropwise to a solution of 4,5-dibromo-4',5'-dimethyl-2,2'-bithiophene (3.37 g, 9.57 mmol) in 100 mL of THF at −78° C. After 90 minutes upon addition, excess iodomethane (3.6 g, 25 mmol) was added dropwise by syringe, and the mixture was stirred for 30 min, then warmed to RT and stirred for another 3 hours. Solvents were evaporated and the residue was poured into water. The mixture was extracted with hexanes, dried over $MgSO_4$, and the solvent was evaporated to give off-yellow solid (2.71 g, 9.43 mmol, 99% yield) of 4-bromo-4',5,5'-trimethyl-2,2'-bithiophene. $^1$H NMR (600 MHz, $CDCl_3$) δ 6.85 (s, 1H), 6.82-6.76 (m, 1H), 2.37 (s, 3H), 2.33 (s, 3H), 2.11 (s, 3H)

Synthesis of 4,4',5,5'-tetramethyl-2,2'-bithiophene (28)

n-BuLi (2.5M in hexane) (5 mL, 12.5 mmol) was added dropwise to a solution of 4-bromo-4',5,5'-trimethyl-2,2'-bithiophene (2.71 g, 9.43 mmol) in 100 mL of diethyl ether at −78° C. After 90 minutes upon addition, excess iodomethane (2 g, 14 mmol) was added by syringe, and the mixture was stirred for 30 min, then warmed to RT, and stirred overnight. Solvents were evaporated and the residue was poured into water. The mixture was extracted with hexanes, dried over $MgSO_4$, and the solvents were evaporated to give off-yellow solid (1.684 g, 7.57 mmol, 80% yield) of 4,4',5,5'-tetramethyl-2,2'-bithiophene. $^1$H NMR (600 MHz, $CDCl_3$) δ 6.77 (d, J=15.0 Hz, 2H), 2.31 (s, 6H), 2.10 (s, 6H)

Synthesis of 3-bromo-4,4',5,5'-tetramethyl-2,2'-bithiophene (29)

To a solution of 28 (3.618 g; 16.27 mmol) in chloroform (80.0 mL) was added N,N-dibromodimethylhydantoin (2.373 g; 8.30 mmol) in one portion at −10° C. The mixture was stirred for 0.5 h (TLC monitoring), poured into NaOH solution and extracted with DCM. Organic phase was separated, washed with water and dried over $MgSO_4$. The solvent was removed by rotary evaporation and trituration in methanol/DCM (10:1) afforded 29 (4.23 g, 86%) as a colourless solid.

Synthesis of S039

S039 was prepared on 0.26 mmol scale (4% yield) according to protocol G. $^1$H NMR (400 MHz, $CDCl_3$) δ 6.42 (s, 2H), 2.32 (s, 6H), 2.17 (s, 6H), 2.09 (s, 6H), 1.35 (d, J=4.1 Hz, 6H).

Example 22

Synthesis of S040

4',4''''-(perfluorocyclopent-1-ene-1,2-diyl)bis(([2,2':5',2''-terthiophene]-5-carboxylic acid))

(Scheme 32)

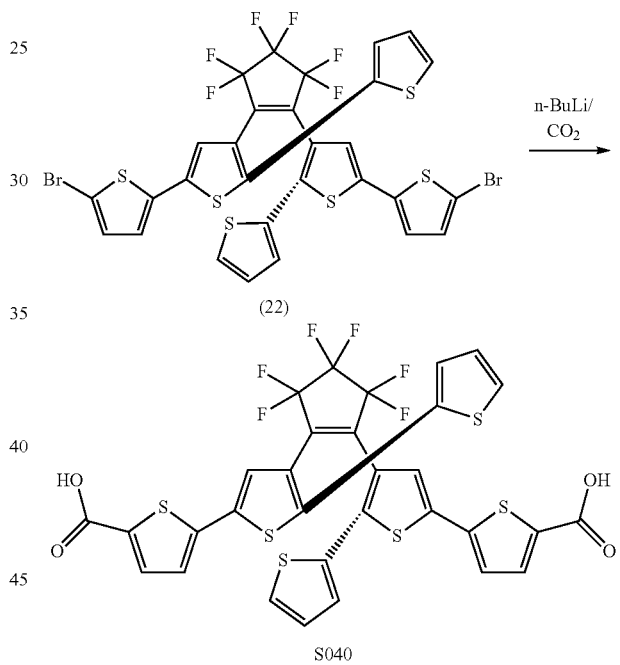

Synthesis of S040

A solution of 22 (0.6 mmol, 0.5 g) in dry ether (200 mL) was purged with argon and cooled to −75° C. Slowly, n-BuLi (1.27 mmol, 0.51 mL, 2.5M) was added and the reaction mixture was stirred for 1.5 h at −75° C. Carbon dioxide was bubbled through the suspension (TLC monitoring). The temperature was raised to 20° C. and the reaction was stirred overnight, concentrated, poured into NaOH solution (30 mL, 3 M) and was vigorously shaken. The ether phase was discarded and the aqueous suspension was acidified with concentrated HCl. The dark green solid was collected by filtration and dried in air to give crude di-acid. Flash chromatography with chloroform/ethanol (10%) followed by chloroform/ethanol (10%)/acetic acid (1%) provided pure S040 (1.7 g, 2.25 mmol, 73% yield. $^1$H NMR (600 MHz, DMSO) δ 13.30 (s, 2H), 7.68 (d, J=3.8 Hz, 2H), 7.55 (d, J=5.0 Hz, 2H), 7.33 (d, J=3.8 Hz, 2H), 6.94-6.85 (m, 2H), 6.81 (d, J=3.1 Hz, 2H), 6.57 (s, 2H).

(d, J=8.5 Hz, 4H), 7.30 (d, J=8.5 Hz, 4H), 7.05 (d, J=8.4 Hz, 4H), 6.92 (d, J=8.4 Hz, 4H), 6.13 (s, 2H), 1.34 (s, 18H), 0.91 (s, 18H).

Example 23

Synthesis of S042

Example 24

Synthesis of S043

3-(2-(2,5-diphenylthiophen-3-yl)-3,3,4,4,5,5-hexafluorocyclopent-1-en-1-yl)-2-phenyl-5-(4-vinylphenyl)thiophene

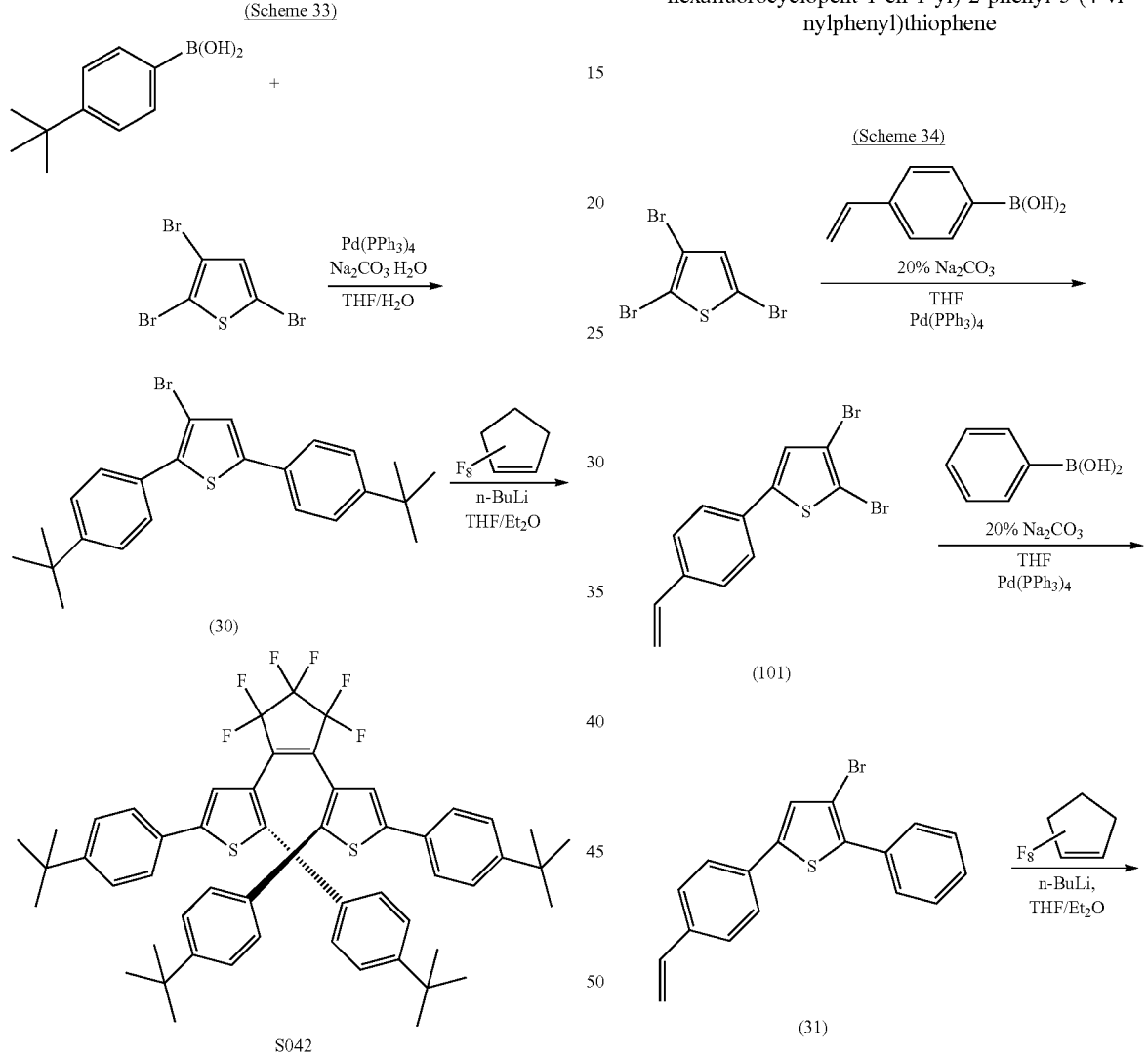

Synthesis of 3-bromo-2,5-bis(4-(tert-butyl)phenyl)thiophene (30)

(30) was prepared on 83 mmol scale (89% yield) according to protocol C.

Synthesis of S042

S042 was prepared on 6.16 mmol scale (15% yield) according to protocol H2. $^1$H NMR (400 MHz, CDCl$_3$) δ 7.37

-continued

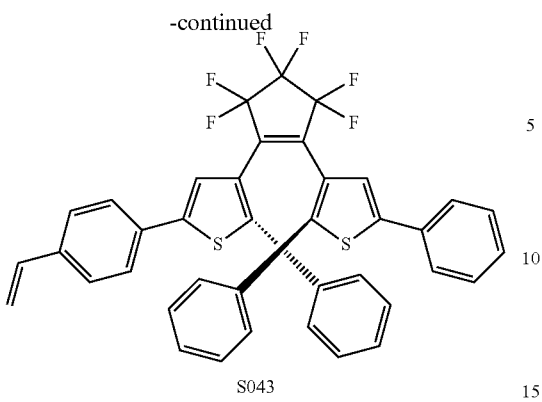

S043

Synthesis of 2,3-dibromo-5-(4-vinylphenyl)thiophene (101)

(101) was prepared on 19.4 mmol scale (57% yield) according to protocol D. $^1$H NMR (600 MHz, CDCl$_3$) δ 7.44 (d, J=8.5, 2H), 7.42 (d, J=8.5, 2H), 7.10 (s, 1H), 6.71 (dd, J=17.6, 10.9, 1H), 5.79 (d, J=17.6, 1H), 5.30 (d, J=10.9, 1H).

Synthesis of 3-bromo-2-phenyl-5-(4-vinylphenyl)thiophene (31)

(31) was prepared on 18.8 mmol scale (97%) yield according to protocol D. $^1$H NMR (600 MHz, CDCl$_3$) δ 7.70 (d, J=7.1, 2H), 7.55 (d, J=8.4, 2H), 7.47-7.42 (m, 4H), 7.39 (t, J=7.4, 1H), 7.27 (s, 1H), 6.73 (dd, J=17.6, 10.9, 1H), 5.80 (d, J=17.6, 1H), 5.30 (d, J=10.9, 1H).

Synthesis of 3-(perfluorocyclopent-1-en-1-yl)-2-phenyl-5-(4-vinylphenyl)thiophene (32)

Compound 31 (6.41 g, 18.8 mmol) was dissolved in 500 mL anhydrous Et$_2$O and cooled to −25° C. n-BuLi (2.5 M in hexane, 9.8 mL, 24.4 mmol) was added dropwise over 45 min. Lithiation was determined to be complete by TLC after the addition of approximately 7 mL. The lithiated species precipitated from solution. Octafluorocyclopentene (5.18 mL, 37.6 mmol) was added and the reaction mixture stirred at −70° C. for 1.5 hours before warming slowly to −20° C. over 30 min, to 0° C. for 30 minutes then to room temperature for 1 hour. The reaction mixture was quenched with water and extracted with EtOAc (3×100 mL). The combined organic fractions were washed with brine, dried over MgSO$_4$ and concentrated under vacuum. Purification by column chromatography afforded 32 (5.73 g, 67% yield). $^1$H NMR (600 MHz, CDCl$_3$) δ 7.59 (d, J=8.3, 2H), 7.46 (d, J=8.2, 2H), 7.45-7.35 (m, 6H), 6.74 (dd, J=17.6, 10.9, 1H), 5.81 (d, J=17.6, 1H), 5.31 (d, J=10.9, 1H).

Synthesis of S043

Compound 4 (1.61 g, 5.11 mmol) was dissolved in anhydrous Et$_2$O (100 mL) and cooled to −25° C. A solution of BuLi (2.2 mL, 5.44 mmol, 2.5 M in hexanes) was added dropwise over 30 minutes. Lithiation was monitored by TLC (hexanes) and determined to be complete after addition of 2.2 mL. Compound 32 (1.55 g, 3.40 mmol) was dissolved in anhydrous ether (50 mL) and added dropwise via cannula to the lithiated mixture at −40° C. The reaction mixture stirred for 16 hours while slowly warming to room temperature. The reaction mixture was quenched with water and extracted with EtOAc (3×50 mL). The combined organic fractions were washed with brine, dried over MgSO$_4$ and concentrated onto silica gel. Flash chromatography yielded S043 as a white solid (1.02 g, 45% yield). $^1$H NMR (400 MHz, CDCl$_3$) δ 7.44-7.28 (m, 9H), 7.12-7.06 (m, 6H), 7.03-6.98 (m, 3H), 6.74 (dd, J=17.6, 11.0, 1H), 6.28 (s, 2H), 5.81 (d, J=17.6, 1H), 5.31 (d, J=11.0, 1H).

Example 25

Synthesis of S044

3,3′-(perfluorocyclopent-1-ene-1,2-diyl)bis(2,5-bis(4-(trifluoromethyl)phenyl)thiophene)

(Scheme 35)

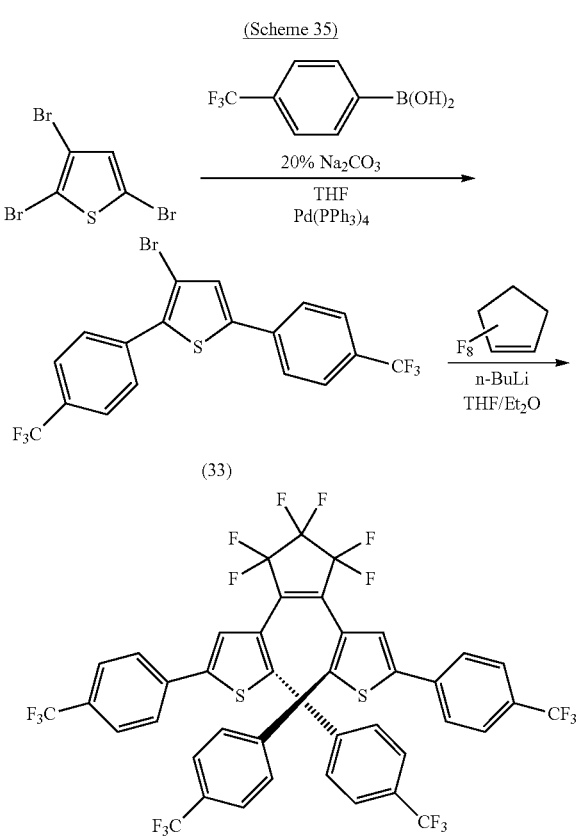

Synthesis of (33)

(33) was prepared on 10 mmol scale (32% yield) according to protocol C. $^1$H NMR (600 MHz, CDCl$_3$) δ 7.83 (d, J=8.1, 2H), 7.72 (d, J=8.2, 2H), 7.69 (d, J=8.8, 2H), 7.67 (d, J=8.8, 2H), 7.37 (s, 1H).

Synthesis of Compound S044

S044 was prepared according to protocol A. $^1$H NMR (400 MHz, CDCl$_3$) δ 7.65 (d, J=8.2, 4H), 7.44 (d, J=8.1, 4H), 7.38 (d, J=8.1, 4H), 7.14 (d, J=8.0, 4H), 6.39 (s, 2H).

Example 26

Synthesis of S047 and S048

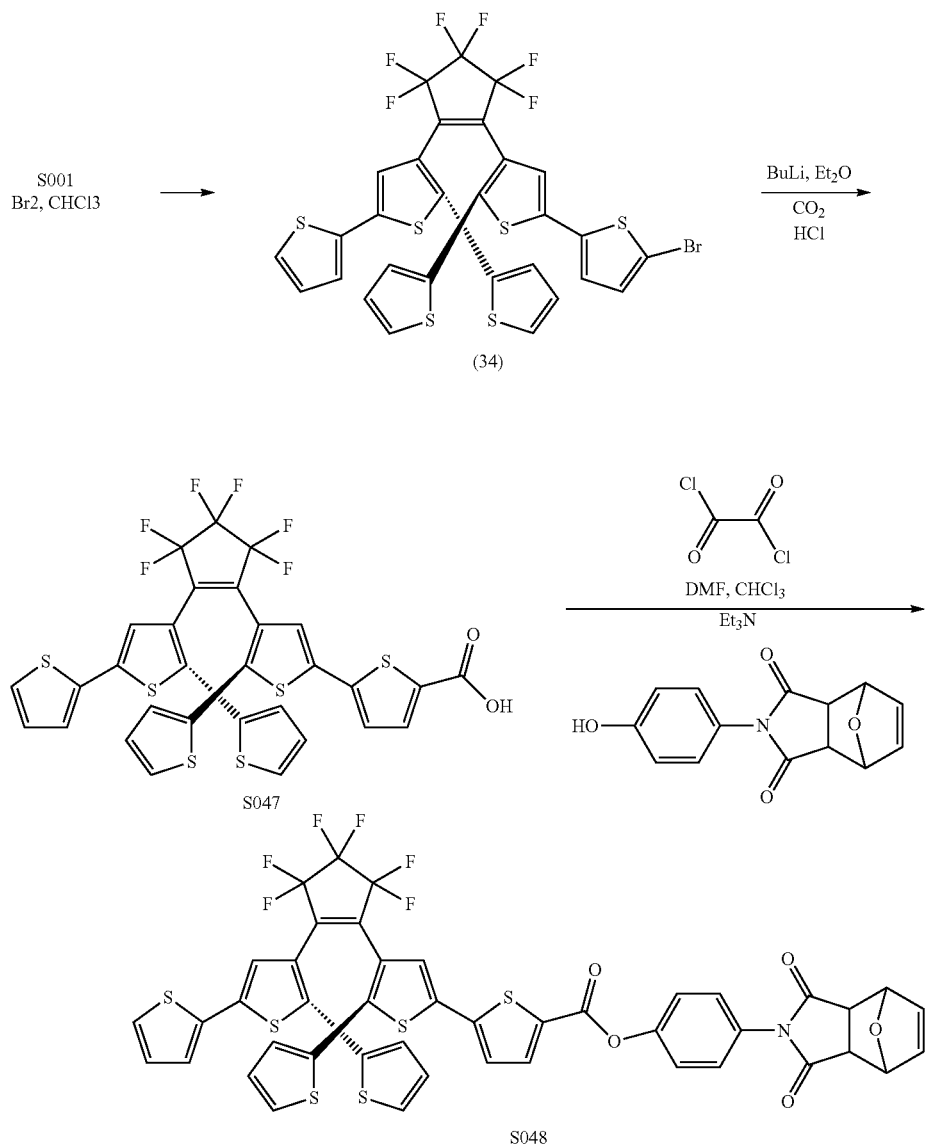

Synthesis of 3'-(2-([2,2':5',2"-terthiophen]-3'-yl)-3,3,4,4,5,5-hexafluorocyclopent-1-en-1-yl)-5"-bromo-2,2':5',2"-terthiophene (34)

S001 (7.00 g, 10.5 mmol) was dissolved in CHCl$_3$ (250 mL). Br$_2$ (1.67 g, 10.47 mmol) was dissolved in 100 mL CHCl$_3$ and added to the S001 solution dropwise over 3 hours. The reaction mixture was washed with water (100 mL) followed by brine (2×50 mL). The solution was dried over MgSO$_4$ and concentrated onto silica gel. Flash chromatography (95:5 hexanes/CHCl$_3$) afforded 34 (4.30 g, 55%). $^1$H NMR (600 MHz, CDCl$_3$) δ 7.27-7.25 (m, 1H), 7.19 (dd, J=5.1, 1.2, 1H), 7.16 (dd, J=5.1, 1.2, 1H), 7.07 (dd, J=3.6, 1.1, 1H), 7.02 (dd, J=5.1, 3.6, 1H), 6.98 (d, J=3.8, 1H), 6.85 (dd, J=5.1, 3.6, 1H), 6.84-6.80 (m, 2H), 6.72-6.70 (m, 2H), 6.37 (s, 1H), 6.30 (s, 1H).

Synthesis of S047

(4'-(2-([2,2':5',2"-terthiophen]-3'-yl)-3,3,4,4,5,5-hexafluorocyclopent-1-en-1-yl)-[2,2':5',2"-terthiophene]-5-carboxylic acid): Compound 34 (4.30 g, 5.75 mmol) was dissolved in anhydrous Et$_2$O (600 mL) and cooled to −78° C. BuLi (2.4 mL, 6.0 mmol, 2.5 M solution in hexanes) was added dropwise over 30 minutes. The lithiation was monitored by TLC (95:5 hexanes/CHCl$_3$) and determined to be incomplete so another 0.5 equivalents of n-BuLi was added. The mixture was left to stir for another 20 minutes and again monitored by TLC. A final 0.5 mL BuLi was added and the lithiation was determined to be complete. Carbon dioxide gas was passed through a bubbler containing H$_2$SO$_4$ followed by a plug of Drierite and then bubbled through the reaction mixture for 16 hours. The mixture was then quenched with 5% HCl (aq) and concentrated to remove Et$_2$O. The mixture was extracted with CHCl$_3$ (3×100 mL). The combined organic fractions were washed with brine, dried over MgSO$_4$ and concentrated to dryness under vacuum. Flash chromatography (CHCl$_3$) yielded 1.8 g of S047. $^1$H NMR (400 MHz, CDCl$_3$) δ 7.80 (d, J=4.0, 1H), 7.30-7.22 (m, 1H), 7.23-7.13 (m, 2H), 7.11-7.05 (m, 2H), 7.05-6.98 (m, 1H), 6.89-6.81 (m, 2H), 6.78-6.68 (m, 2H), 6.50 (s, 1H), 6.38 (s, 1H).

Synthesis of S048

(4-(1,3-dioxo-3a,4,7,7a-tetrahydro-1H-4,7-epoxyisoindol-2(3H)-yl)phenyl 4'-(2-([2,2':5',2''-terthiophen]-3'-yl)-3,3,4,4,5,5-hexafluorocyclopent-en-yl)-[2,2':5',2''-terthiophene]-5-carboxylate): Oxalyl chloride (0.83 mL, 9.84 mmol) was added to S047 (1.40 g, 1.97 mmol) in CHCl$_3$ (100 mL). The acid did not fully dissolve until acyl chloride began to form. To this mixture was added a single drop of DMF. The reaction flask was fitted with a bubbler to monitor the amount of gas evolved as the reaction proceeded. The reaction mixture stirred at room temperature for 3 hours. At this time the acyl chloride formation was determined to be complete by TLC (CHCl$_3$). The reaction mixture was then concentrated to dryness. The acyl chloride was then dissolved in anhydrous THF (120 mL). To this solution was added 6 mL Et$_3$N (purified by refluxing with Ac$_2$O followed by distillation and then a second distillation 12 days prior to use) A solution of the phenol (0.76 g, 2.96 mmol) in anhydrous THF (50 mL) was transferred into the acyl chloride solution over 30 minutes and stirred at room temperature for 20 hours. The mixture was then concentrated to dryness and redissolved in CHCl$_3$ (200 mL) and washed with 5% HCl, dried over MgSO$_4$ and evaporated to dryness. The crude product was purified by flash column chromatography (2% MeOH in CHCl$_3$, 2 successive columns) yielding 0.77 g of S048. $^1$H NMR (400 MHz, CDCl$_3$) δ 7.88 (d, J=4.0, 1H), 7.42-7.34 (m, 4H), 7.28-7.25 (m, 1H), 7.19 (dd, J=5.1, 1.1, 2H), 7.11 (d, J=3.9, 1H), 7.07 (dd, J=3.6, 1.2, 1H), 7.02 (dd, J=5.1, 3.6, 1H), 6.87-6.82 (m, 2H), 6.75 (dd, J=3.6, 1.2, 1H), 6.72 (dd, J=3.6, 1.2, 1H), 6.59 (s, 2H), 6.52 (s, 1H), 6.38 (s, 1H), 5.42 (s, 2H), 3.04 (s, 2H).

Example 27

Synthesis of S049

3,3''-(perfluorocyclopent-1-ene-1,2-diyl)bis(5-(4-(tert-butyl)phenyl)-2,2'-bithiophene)

(Scheme 37)

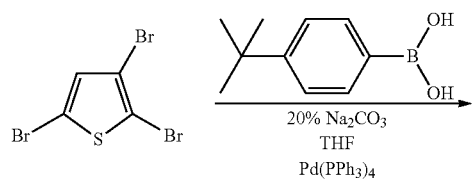

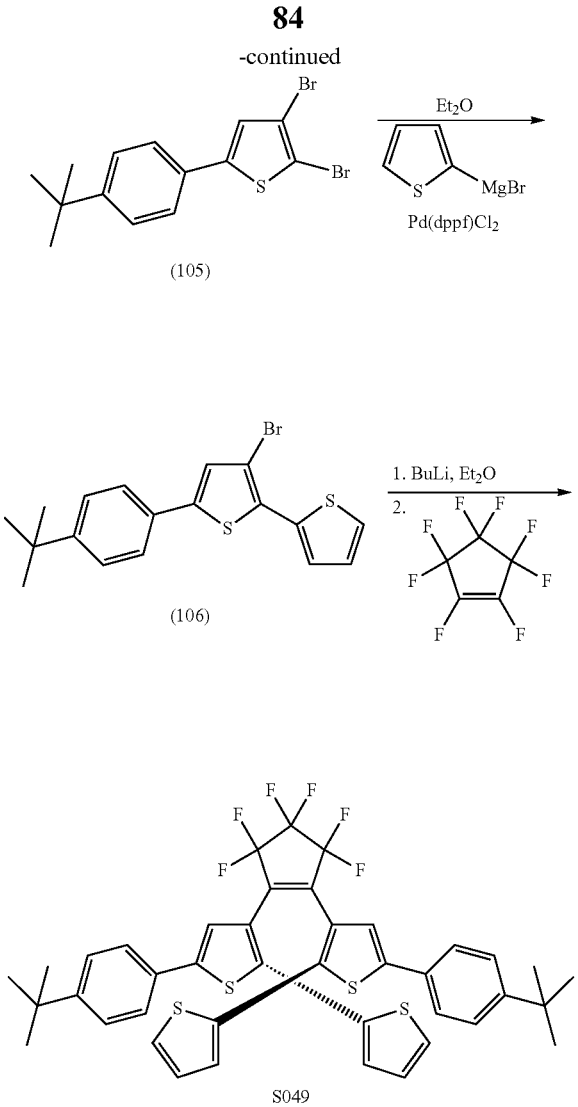

Synthesis of 2,3-dibromo-5-(4-(tert-butyl)phenyl)thiophene (105)

105 was prepared on 12.3 mmol scale (44% yield) according to protocol D. $^1$H NMR (600 MHz, CDCl$_3$) δ 7.45-7.39 (m, 4H), 7.07 (s, 1H), 1.34 (s, 9H).

Synthesis of 3-bromo-5-(4-(tert-butyl)phenyl)-2,2'-bithiophene (106)

(106) was prepared on 4.2 mmol scale (79%) yield according to protocol B. $^1$H NMR (400 MHz, CDCl$_3$) δ 7.54-7.40 (m, 5H), 7.36 (dd, J=5.1, 1.1, 1H), 7.20 (s, 1H), 7.10 (dd, J=5.1, 3.7, 1H), 1.36 (s, 9H).

Synthesis of S049

S049 was prepared on 0.36 mmol scale (17.3% yield) according to protocol G. $^1$H NMR (400 MHz, CDCl$_3$) δ 7.21 (dd, J=4.9, 1.4, 1H), 7.13 (d, J=8.4, 2H), 7.04-6.98 (m, 2H), 6.92 (d, J=8.4, 2H), 6.08 (s, 2H), 1.04 (s, 18H).

Example 28

Synthesis of S050

3,3'-(perfluorocyclopent-1-ene-1,2-diyl)bis(5-(4-bromophenyl)-2-phenylthiophene)

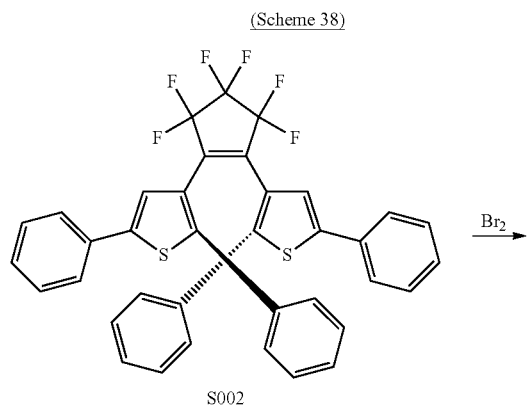

Synthesis of S050

S002 was prepared as described in U.S. Pat. No. 7,777,055. To the solution of S002 (0.306 g; 0.475 mmol) in a mixture of acetic acid (10.0 mL) and DCM (10.0 mL) was added bromine (0.05 mL; 0.973 mmol) as a solution in DCM (3 mL). Ammonium nitrate was added as a catalyst and the mixture was heated to reflux overnight. After cooling to RT, DCM was removed under vacuum. The remaining acetic acid solution was poured into water and extracted with DCM. The organic layer was separated, washed with sodium thiosulfate solution and water, and concentrated. Flash chromatography (hexanes) afforded S050 (0.36 g; 94%). $^1$H NMR (400 MHz, CDCl$_3$) δ 7.43 (d, J=8.4 Hz, 4H), 7.15 (d, J=8.4 Hz, 4H), 7.05-6.98 (m, 6H), 6.95-6.88 (m, 4H), 6.19 (s, 2H).

Example 29

Synthesis of S052

4,4''-(perfluorocyclopent-1-ene-1,2-diyl)bis(5-(4-(tert-butyl)phenyl)-2,2'-bithiophene)

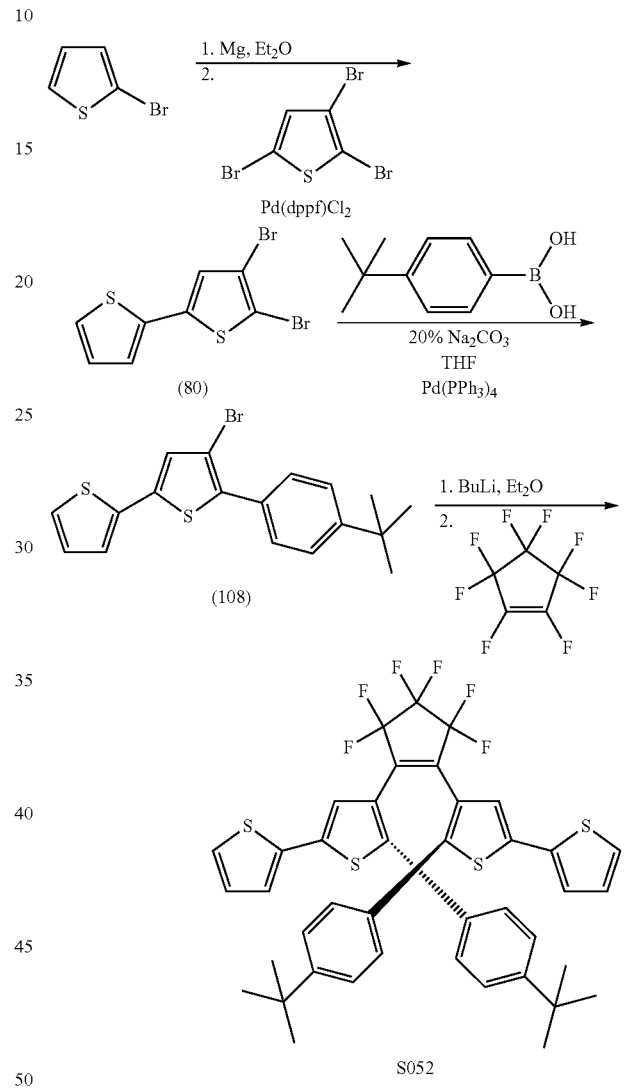

Synthesis of 4-bromo-5-(4-(tert-butyl)phenyl)-2,2'-bithiophene (108)

(108) was prepared on 5.5 mmol scale (100% yield) according to protocol D. $^1$H NMR (400 MHz, CDCl$_3$) δ 7.63 (d, J=8.6, 2H), 7.47 (d, J=8.6, 2H), 7.26 (dd, J=5.1, 1.1, 1H), 7.19 (dd, J=3.6, 1.1, 1H), 7.13 (s, 1H), 7.04 (dd, J=5.1, 3.6, 1H), 1.37 (s, 9H).

Synthesis of S052

S052 was prepared on 0.091 mmol scale (3.3% yield) according to protocol G. $^1$H NMR (400 MHz, CDCl$_3$) δ 7.40

(d, J=8.5, 4H), 7.35 (d, J=8.5, 4H), 7.11 (dd, J=5.1, 1.1, 2H), 6.80 (dd, J=5.1, 3.6, 2H), 6.72 (dd, J=3.6, 1.1, 2H), 6.50 (s, 2H), 1.36 (s, 18H).

Example 30

Synthesis of S053

4,4'-(perfluorocyclopent-1-ene-1,2-diyl)bis(5-methoxy-2,2'-bithiophene)

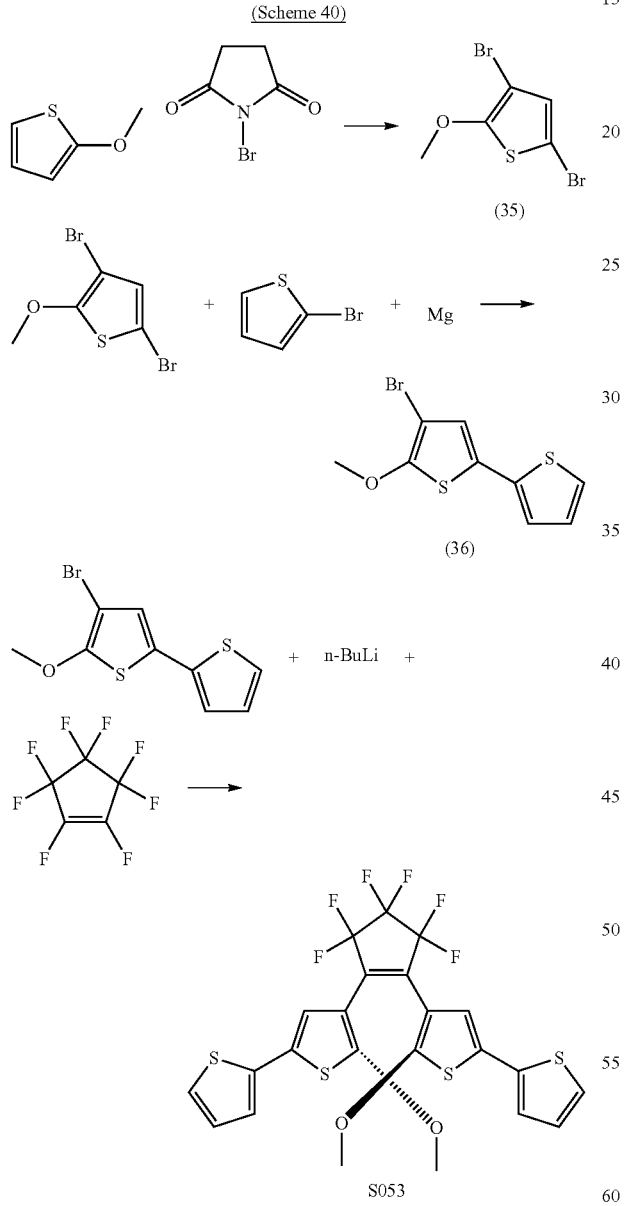

(Scheme 40)

S053

Synthesis of 3,5-dibromo-2-methoxythiophene (35)

(35) was prepared on 22.1 mmol scale (85% yield) according to protocol F1.

Synthesis of 4-bromo-5-methoxy-2,2'-bithiophene (36)

(36) was prepared on 13 mmol scale (59% yield) according to protocol B. $^1$H NMR (400 MHz, CDCl$_3$) d 7.16 (dd, J=5.1, 1.2 Hz, 1H), 7.02 (dd, J=3.6, 1.2 Hz, 1H), 6.97 (dd, J=5.1, 3.6 Hz, 1H), 6.82 (s, 1H), 3.97 (s, 3H).

Synthesis of S053

S053 was prepared on 0.56 mmol scale (15% yield) according to protocol G. $^1$H NMR (400 MHz, CDCl$_3$) δ 7.17 (dd, J=5.1, 1.1 Hz, 2H), 7.04 (dd, J=3.6, 1.1 Hz, 2H), 7.00-6.96 (m, J=4.8 Hz, 4H), 3.69 (s, 6H).

Example 31

Synthesis of S054

3,3'-(perfluorocyclopent-1-ene-1,2-diyl)bis(2,5-bis(4-methoxyphenyl)thiophene)

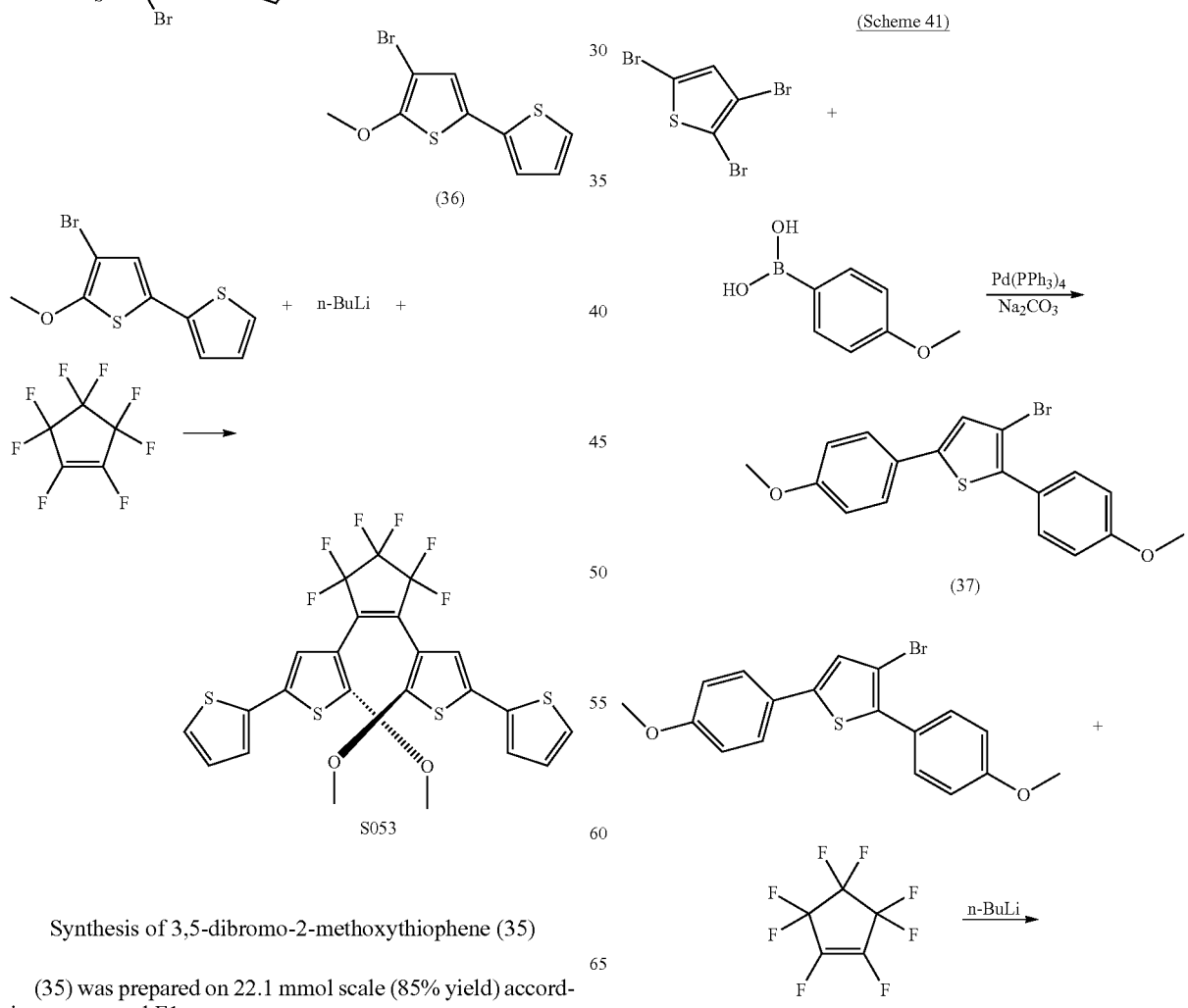

(Scheme 41)

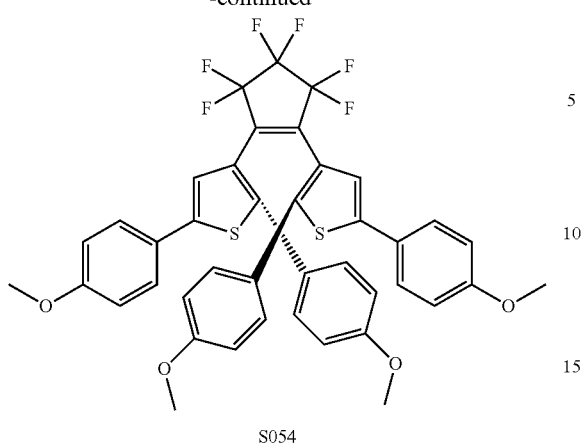

S054

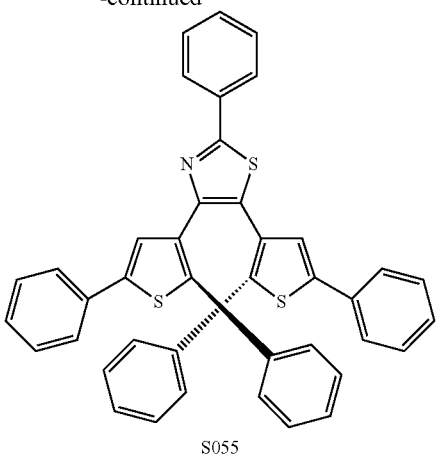

S055

Synthesis of 3-bromo-2,5-bis(4-methoxyphenyl)thiophene (37)

(37) was prepared on 13 mmol scale (65% yield) according to protocol C.

Synthesis of S054

S054 was prepared on 5.82 mmol scale (41% yield) according to protocol G. $^1$H NMR (400 MHz, CDCl$_3$) δ 7.32 (d, J=8.7 Hz, 4H), 6.91 (dd, J=8.7, 2.4 Hz, 9H), 6.60 (d, J=8.6 Hz, 4H), 6.25 (s, 2H), 3.85 (s, 6H), 3.41 (s, 6H).

Example 32

Synthesis of S055

4,5-bis(2,5-diphenylthiophen-3-yl)-2-phenylthiazole

Synthesis of S055

(4) (5.93 g, 18.8 mmol) was dissolved in Et$_2$O (100 mL) and cooled to −30° C. BuLi (8.8 mL, 22 mmol, 2.5 M in hexanes) was added dropwise over 30 minutes. After the reaction mixture stirred for an additional 30 minutes, B(OBu)$_3$ (5.6 mL, 20.7 mmol) was added and the reaction mixture was stirred for 1 hour while warming from −30° C. to 0° C. The cooling bath was then removed and the reaction mixture stirred for another hour. The reaction mixture was then concentrated to dryness and redissolved in THF (60 mL). To the reaction mixture was added 20% Na$_2$CO$_3$ (aq) (60 mL), compound (19) (2 g, 6.27 mmol) and the mixture was then deoxygenated by bubbling with argon 30 minutes. To this mixture was added Pd(PPh$_3$)$_4$ (0.2 g, 0.2 mmol) and the reaction mixture was heated to reflux for 16 hours. After cooling, the layers were separated and the aqueous layer was extracted with EtOAc (2×50 mL). The combined organic fractions were washed with brine (50 mL), dried over MgSO$_4$, filtered and concentrated onto silica gel. Flash chromatography (8:2 hexanes/chloroform followed by 1:1 hexanes/chloroform) afforded 3.86 g (98%). $^1$H NMR (400 MHz, CDCl$_3$) δ 8.04-7.98 (m, 2H), 7.51-7.43 (m, 5H), 7.43-7.34 (m, 6H), 7.33-7.27 (m, 2H), 7.11-6.98 (m, 10H), 6.80 (s, 1H), 6.47 (s, 1H).

Example 33

Synthesis of S056

3,3'-(perfluorocyclopent-1-ene-1,2-diyl)bis(2,5-bis(4-chlorophenyl)thiophene)

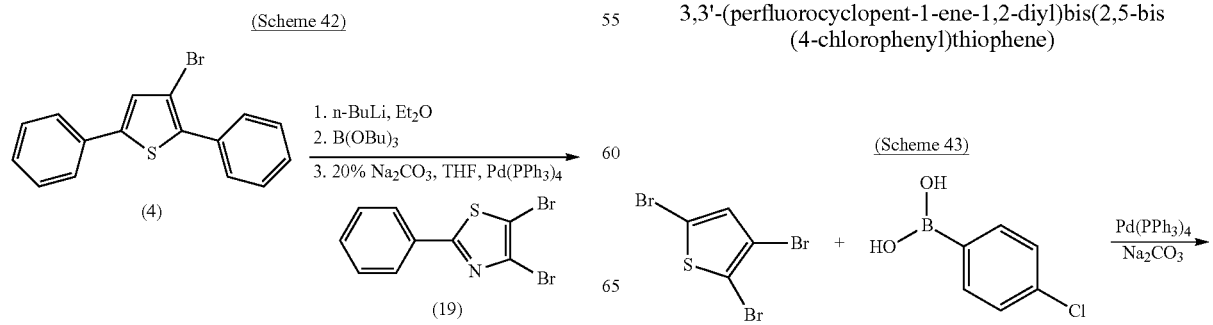

-continued

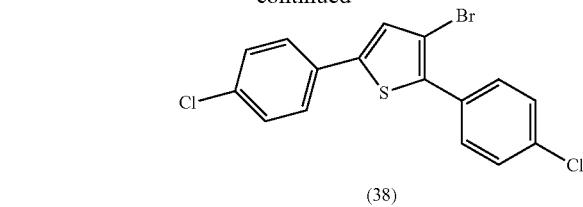

(38)

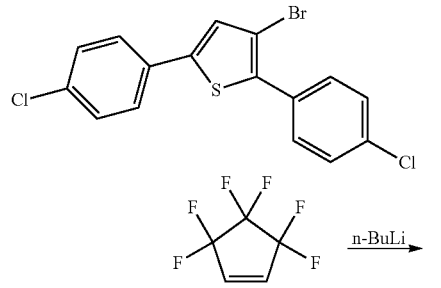

Synthesis of 3-bromo-2,5-bis(4-chlorophenyl)thiophene (38)

(38) was prepared on 13 mmol scale (34% yield) according to protocol C.

Synthesis of S056

S056 was prepared on 3.2 mmol scale (46% yield) according to protocol G. $^1$H NMR (400 MHz, CDCl$_3$) δ 7.43-7.31 (m, 9H), 7.15-7.04 (m, 4H), 6.92 (d, J=8.3 Hz, 4H), 6.37 (s, 2H).

Example 34

Synthesis of S057

3,3'-(perfluorocyclopent-1-ene-1,2-diyl)bis(2-(4-tert-butylphenyl)-5-phenylthiophene)

(Scheme 44)

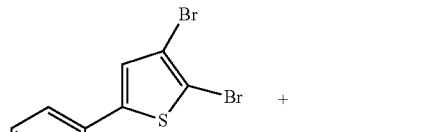

-continued

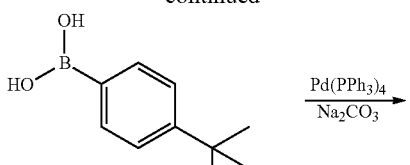

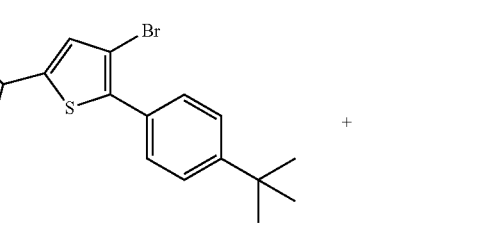

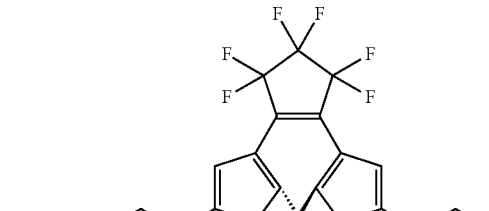

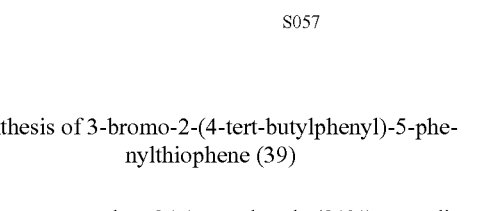

Synthesis of 3-bromo-2-(4-tert-butylphenyl)-5-phenylthiophene (39)

(39) was prepared on 24.1 mmol scale (81%) according to protocol D.

Synthesis of S057

S057 was prepared on 4.14 mmol scale (34% yield) according to protocol G. $^1$H NMR (400 MHz, CDCl$_3$) δ 7.29

(td, J=8.5, 4.5 Hz, 8H), 7.19 (dd, J=9.3, 4.3 Hz, 2H), 7.00 (d, J=8.3 Hz, 4H), 6.86 (d, J=8.3 Hz, 4H), 6.13 (s, 2H), 0.87 (s, 18H).

Example 35

Synthesis of S059

3-(2-(2,5-bis(4-tert-butylphenyl)thiophen-3-yl)-3,3,4,4,5,5-hexafluorocyclopent-1-enyl)-2-phenyl-5-(4-vinylphenyl)thiophene

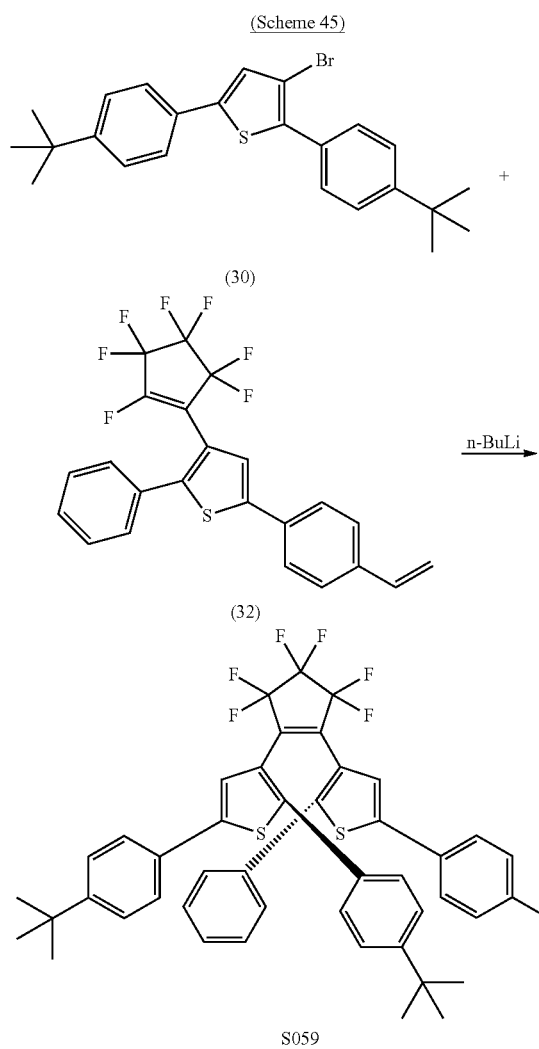

Synthesis of S059

Compound (30) (3.47 g; 8.11 mmol) was dissolved in anhydrous diethyl ether (250 mL) and cooled to −25° C. n-BuLi (3.6 mL; 8.9 mmol; 2.5 M in hexane) was added. The mixture was stirred for 10 min. Compound (32) (3.35 g; 7.37 mmol) was added as ether solution (50 mL) dropwise over 10 min. The reaction mixture was allowed to warm slowly overnight, and then quenched by addition of 10% aqueous HCl (50 mL). Organic layer was separated; aqueous phase was extracted with EtOAc (150 mL). Solvents were evaporated and the crude material was purified by column eluting with hexane. Collected product was sonicated in methanol and pale yellow powder was filtered and dried in air (3.464 g; 1.87 mmol; yield 60%). $^1$H NMR (400 MHz, CDCl$_3$) δ 7.43-7.36 (m, 5H), 7.47-7.29 (m, 8H), 7.34 (d, J=8.3 Hz, 2H), 7.30-7.26 (m, 2H), 7.12-7.10 (m, 2H), 7.11 (dd, J=6.2, 3.0 Hz, 5H), 7.09 (s, 2H), 7.01 (dd, J=6.5, 2.9 Hz, 2H), 7.01 (dd, J=6.5, 2.9 Hz, 2H), 6.92 (d, J=8.3 Hz, 2H), 6.92 (d, J=8.3 Hz, 2H), 6.72 (dd, J=17.6, 10.9 Hz, 1H), 6.25 (s, 1H), 6.21 (s, 1H), 5.77 (d, J=17.6 Hz, 1H), 5.28 (d, J=11.0 Hz, 1H), 1.36 (s, 9H), 0.97 (s, 9H).

Example 36

Synthesis of S060

3,3'-(perfluorocyclopent-1-ene-1,2-diyl)bis(2-(4-(tert-butyl)phenyl)-5-(4-chlorophenyl)thiophene

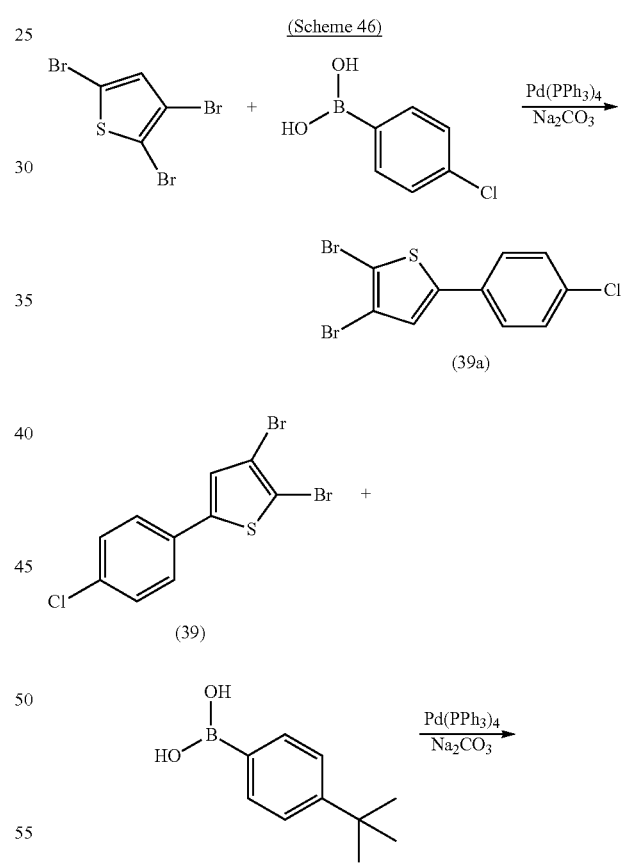

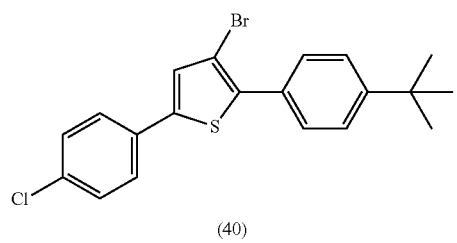

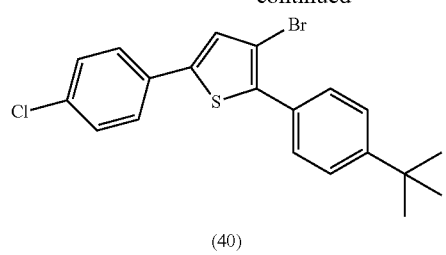

(40)

+

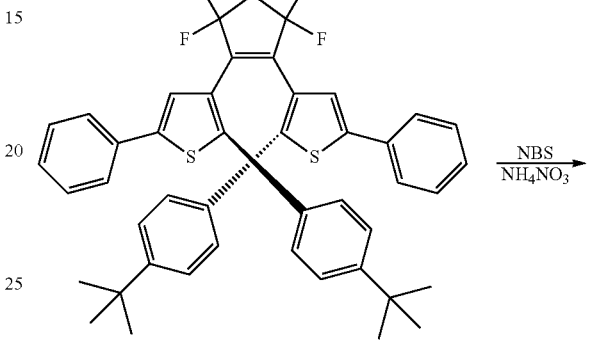

Synthesis of 2,3-dibromo-5-(4-chlorophenyl)thiophene (39a)

(39a) was prepared on 15 mmol scale (38% yield) according to protocol D.

Synthesis of 3-bromo-2-(4-tert-butylphenyl)-5-(4-chlorophenyl)thiophene (40)

(40) was prepared on 22.2 mmol scale (76% yield) according to protocol D.

Synthesis of S060

S060 was prepared on 3.75 mmol scale (34% yield) according to protocol G. $^1$H NMR (400 MHz, CDCl$_3$) δ 7.35-7.29 (m, 8H), 7.08 (d, J=8.3 Hz, 4H), 6.91 (d, J=8.3 Hz, 4H), 6.19 (s, 2H), 0.99 (s, 18H).

Example 37

Synthesis of S063

3,3'-(perfluorocyclopent-1-ene-1,2-diyl)bis(5-(4-bromophenyl)-2-(4-tert-butylphenyl)thiophene)

(Scheme 47)

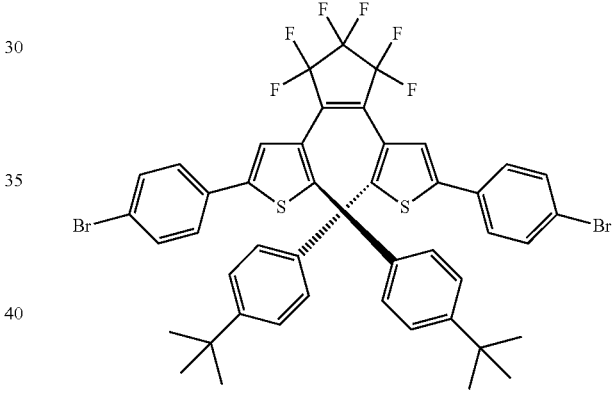

Synthesis of 2,3-dibromo-5-(4-chlorophenyl)thiophene (39a)

(39a) was prepared on 15 mmol scale (38% yield) according to protocol D.

Synthesis of 3-bromo-2-(4-tert-butylphenyl)-5-(4-chlorophenyl)thiophene (40)

(40) was prepared on 22.2 mmol scale (76% yield) according to protocol D.

Synthesis of S060

S060 was prepared on 3.75 mmol scale (34% yield) according to protocol G. $^1$H NMR (400 MHz, CDCl$_3$) δ 7.35-7.29 (m, 8H), 7.08 (d, J=8.3 Hz, 4H), 6.91 (d, J=8.3 Hz, 4H), 6.19 (s, 2H), 0.99 (s, 18H).

Example 38

Synthesis of S064

(1,1'-((4,4'-(perfluorocyclopent-1-ene-1,2-diyl)bis(5-(4-(tert-butyl)phenyl)thiophene-4,2-diyl))bis(4,1-phenylene))diethanone) and S065 ((1-(4-(5-(4-tert-butylphenyl)-4-(2-(2-(4-tert-butylphenyl)-5-phenylthiophen-3-yl)-3,3,4,4,5,5-hexafluorocyclopent-1-enyl)thiophen-2-yl)phenyl)ethanone))

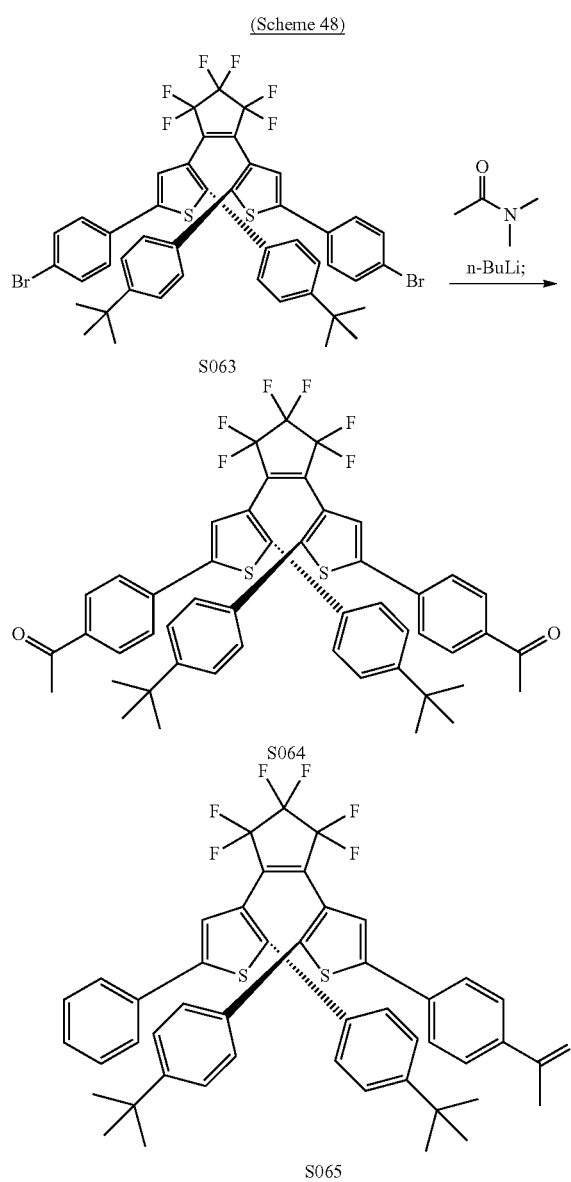

Synthesis of S064+S065

A solution of S063 (0.66 g, 0.72 mmol) in ether (20 mL) was cooled to −5° C. and a solution of n-BuLi in hexane (0.75 mL, 2.5 M, 1.9 mmol) was added dropwise. Reaction mixture was stirred for 15 min at 0 to −10° C. Anhydrous N,N-dimethylacetamide (1 mL) was added slowly as an ether solution (15 mL) at −5° C. and the mixture was stirred for 90 min and quenched with 10% HCl solution. Organic layer was separated, aqueous layer was extracted with EtOAc; organic fractions pooled and solvent evaporated. Flash chromatography (hexanes to 30% EtOAc/hexanes) gave S064 in 46% yield and S065 in 22% yield. S064: $^1$H NMR (600 MHz, CDCl$_3$) δ 7.95 (d, J=8.3 Hz, 4H), 7.46 (d, J=8.3 Hz, 4H), 7.08 (d, J=8.3 Hz, 4H), 6.94 (d, J=8.2 Hz, 4H), 6.34 (s, 2H), 2.62 (s, 6H), 0.95 (s, 18H). S065: $^1$H NMR (600 MHz, CDCl$_3$) δ 7.95 (d, J=8.3 Hz, 2H), 7.46 (d, J=8.3 Hz, 2H), 7.40-7.33 (m, 4H), 7.30-7.27 (m, 1H), 6.34 (s, 1H), 6.21 (s, 1H), 2.63 (s, 3H), 0.96 (s, 9H), 0.95 (s, 9H).

Example 39

Synthesis of S066

2,2'-((4,4'-(perfluorocyclopent-1-ene-1,2-diyl)bis(5-(4-(tert-butyl)phenyl)thiophene-4,2-diyl))bis(4,1-phenylene))bis(2-methyl-1,3-dioxolane)

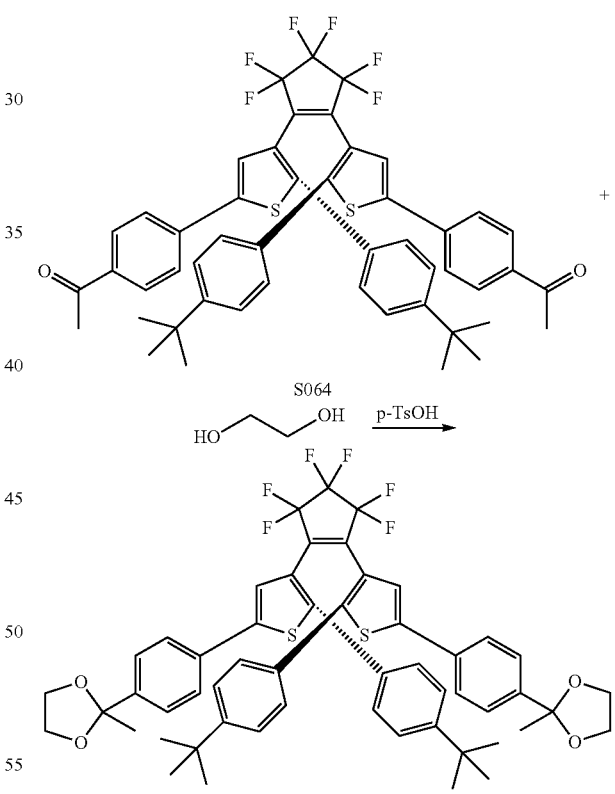

Synthesis of S066

A 50 mL flask was charged with 1 mg of p-toluenesulfonic acid monohydrate, 25 mL of benzene, 1 g (16 mmol) of ethylene glycol, and 0.2 g (0.238 mmol) of S064. The solution was brought to reflux with water collection in Dean-Stark apparatus. After 30 hours at reflux, the mixture was cooled to RT and poured into 80 mL of 10% aqueous NaOH. The benzene layer was washed with 25 mL of brine, dried over MgSO$_4$ for 10 minutes, and filtered. Removal of solvent and sonication of the residue in methanol provided a pale yellow solid, which was filtered off and dried under vacuum. Yield 0.22 g (0.237 mmol; 100%). $^1$H NMR (600 MHz, CD$_2$Cl$_2$) δ 7.51-7.45 (m, 4H), 7.40-7.36 (m, 4H), 7.08 (d, J=8.3 Hz, 4H), 6.94 (d, J=8.3 Hz, 4H), 6.22 (s, 2H), 4.06-4.00 (m, 4H), 3.80-3.72 (m, 4H), 1.63 (s, 6H), 0.90 (s, 18H).

Example 40

Synthesis of S067

2,2'-((4,4'-(perfluorocyclopent-1-ene-1,2-diyl)bis(5-(4-(tert-butyl)phenyl)thiophene-4,2-diyl))bis(4,1-phenylene))bis(propan-2-ol) (Scheme 50)

A solution of S064 (0.64 g, 0.76 mmol) in ether (100 mL) was cooled to –5° C. and a solution of MeLi in ether (12.5 mL, 1.6 M, 20 mmol) was added dropwise. Reaction mixture was stirred for 15 min at –5° C., then allowed to warm to RT, and stirred overnight. TLC indicates two spots. Another 8 equivalents of MeLi (12.5 mL) was added at RT along with 2-methyltetrahydrofuran (35 mL), and the mixture was continued to stir for 16 h and quenched with 10% HCl solution. The organic layer was separated and the aqueous was extracted with ethyl acetate. The solvent was removed by rotary evaporation and flash chromatography (hexanes to 40% EtOAc/hexanes) afforded S067 (1.44 g, 1.65 mmol) in 66% yield. 1H NMR (400 MHz, CDCl$_3$) δ 7.48 (d, J=8.4 Hz, 4H), 7.35 (d, J=8.4 Hz, 4H), 7.06 (d, J=8.4 Hz, 4H), 6.93 (d, J=8.3 Hz, 4H), 6.17 (s, 2H), 1.72 (s, 2H), 1.60 (s, 12H), 0.92 (s, 18H).

Example 41

Synthesis of S068

12,12'-((4,4'-(perfluorocyclopent-1-ene-1,2-diyl)bis(5-(4-(tert-butyl)phenyl)thiophene-4,2-diyl))bis(4,1-phenylene))bis(12-methyl-2,5,8,11-tetraoxatridecane)

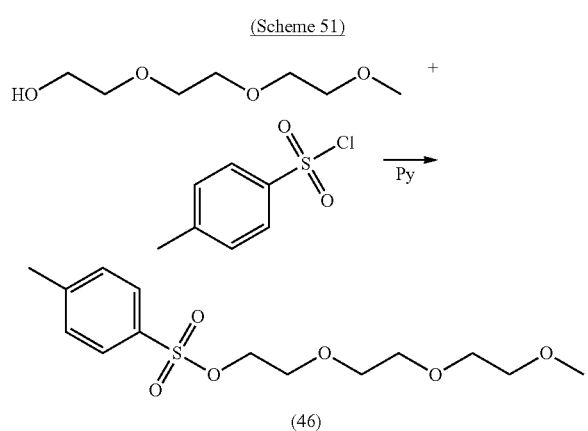

(Scheme 51)

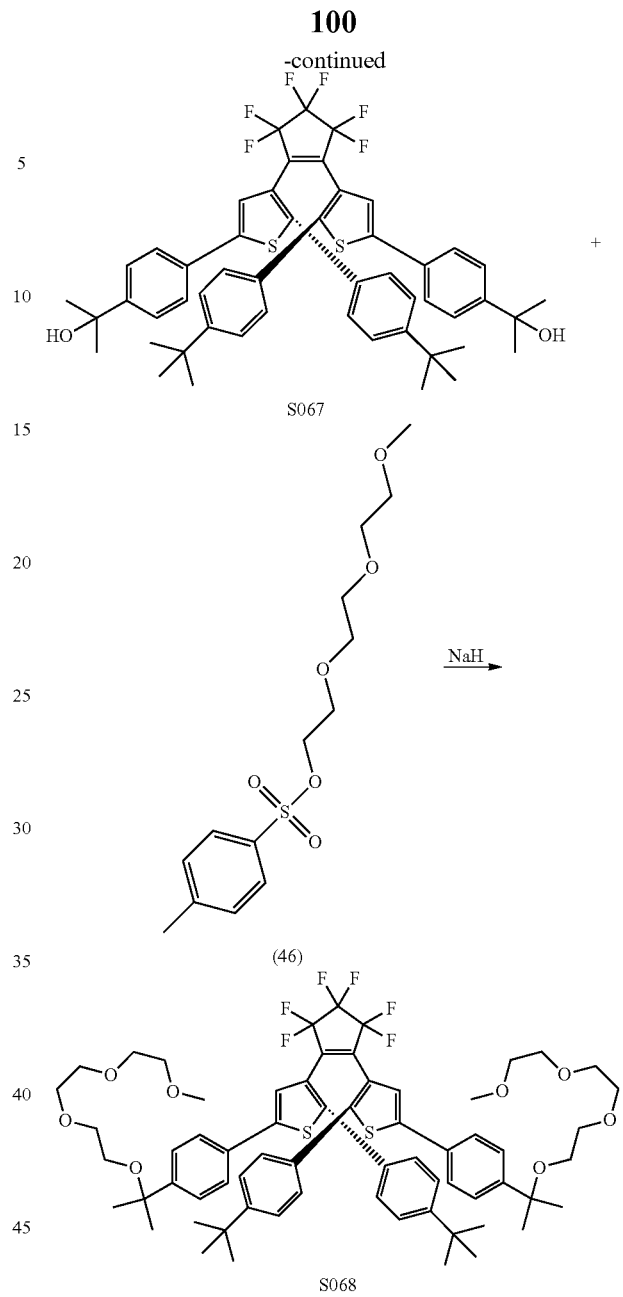

Synthesis of 2-(2-(2-methoxyethoxy)ethoxy)ethyl 4-methylbenzene sulfonate (46)

To a solution of p-toluenesulfonyl chloride (3.17 g, 19.3 mmol) in 20 mL of pyridine was added 2-(2-(2-methoxyethoxy)ethoxy)ethanol (4 g, 21 mmol), which was then stirred at 0° C. for 12 h and at RT for 2 h. To this suspension, water, hexanes, and ethyl acetate were added and separated. The organic layer was neutralized with dilute hydrochloric acid and separated again. The organic layer was dried over with magnesium sulfate and sodium bicarbonate, filtered, and concentrated under reduced pressure to give 4.87 g, 15.3 mmol (79%) of 2-(2-(2-methoxyethoxy)ethoxy)-ethyl 4-methylbenzene sulfonate as a colorless oil.

Synthesis of S068

Sodium hydride (0.24 g, 6 mmol, 60% dispersion in oil) was washed with hexanes (6 mL) and a solution of S067 (1.33 g, 1.52 mmol) in THF (25 mL) was added under argon. The reaction mixture was stirred for 1 h at RT. To the resulting suspension was added a solution of (46) (1.06 g, 3.35 mmol) in anhydrous DMF (12 mL) in one portion and the mixture was stirred for 48 h. The reaction was quenched by addition of brine (100 mL) and extracted with EtOAc (3×100 mL). The organic layer was washed with water (2×100 mL), dried over MgSO$_4$, filtered and evaporated to dryness. Flash chromatography (hexanes/EtOAc 1:1) afforded 1.24 g (1.06 mmol; 70%). $^1$H NMR (400 MHz, CDCl$_3$) δ 7.44 (d, J=8.4 Hz, 4H), 7.36 (d, J=8.4 Hz, 4H), 7.09 (d, J=8.4 Hz, 4H), 6.96 (d, J=8.3 Hz, 4H), 6.21 (s, 2H), 3.72-3.68 (m, 12H), 3.66 (t, J=5.3 Hz, 5H), 3.61-3.57 (m, 4H), 3.43-3.37 (m, 10H), 1.58 (s, 12H), 0.95 (s, 18H).

Example 42

Synthesis of S073

3,3'-(perfluorocyclopent-1-ene-1,2-diyl)bis(5,5'-di-tert-butyl-2,2'-bithiophene)

(Scheme 52)

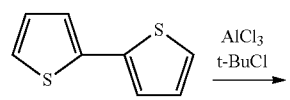

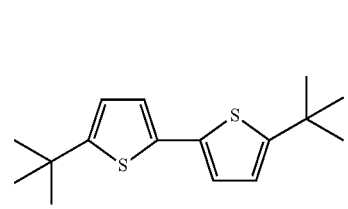

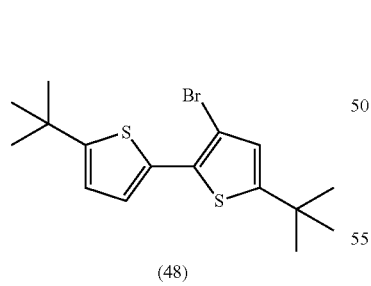

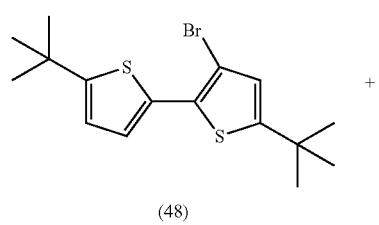

Synthesis of 5,5'-di-tert-butyl-2,2'-bithiophene (47)

(47) was prepared on 57 mmol scale (95% yield) according to protocol E.

Synthesis of 3-bromo-5,5'-di-tert-butyl-2,2'-bithiophene (48)

(48) was prepared on 37.7 mmol scale (66% yield) according to protocol F2.

Synthesis of S073

S073 was prepared on 0.49 mmol scale (6% yield) according to protocol G. $^1$H NMR (400 MHz, CDCl$_3$) δ 6.61-6.51 (m, 2H), 6.45-6.37 (m, 2H), 6.15-6.06 (m, 2H), 1.35 (d, J=12.5 Hz, 18H), 1.26 (s, 18H).

Example 43

Synthesis of S074

3,3'-(perfluorocyclopent-1-ene-1,2-diyl)bis(2,5-bis(4-cyanophenyl)thiophene)

(Scheme 53)

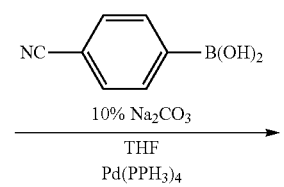

103
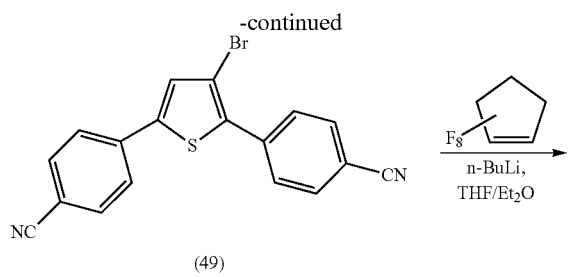
(49)
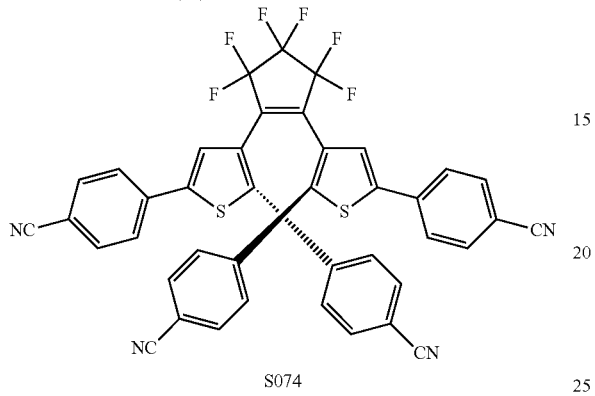
S074
104
Synthesis of 4,4'-(3-bromothiophene-2,5-diyl)dibenzonitrile (49)
(49) was prepared on 46 mmol scale (78% yield) according to protocol C.
Synthesis of S074
S074 was prepared on 0.29 mmol scale (13% yield) according to protocol H3. $^1$H NMR (400 MHz, DMSO) δ 7.92 (d, J=8.5 Hz, 4H), 7.78 (d, J=8.5 Hz, 4H), 7.59 (d, J=8.3 Hz, 4H), 7.22 (d, J=8.3 Hz, 4H), 6.83 (s, 2H).
Example 44
Synthesis of S079
1,2-bis(2-(4-n-octylphenyl)-1-benzofuran-3-yl)perfluorocyclopentene
(Scheme 54)
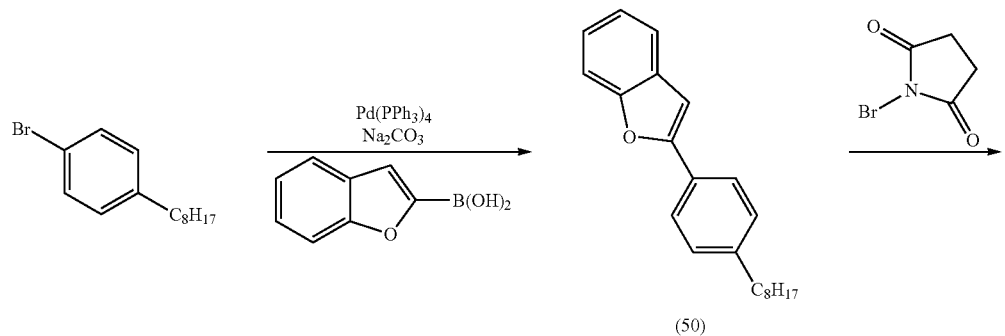
(50)
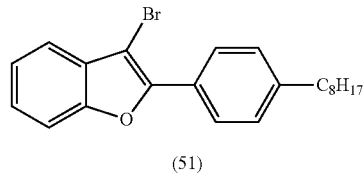
(51)
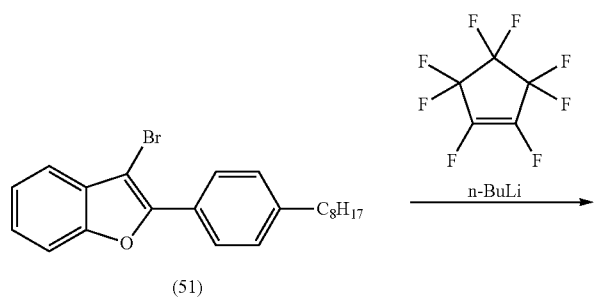
(51)

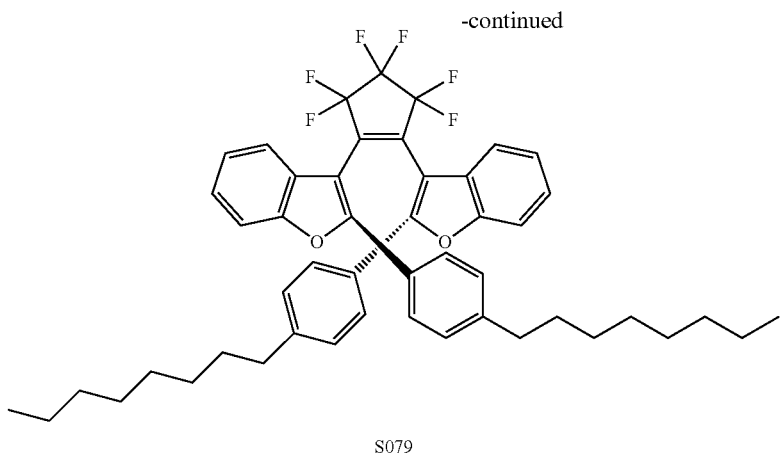

S079

Synthesis of 2-(4-n-octylphenyl)-1-benzofuran (50)

(50) was prepared on 20.4 mmol scale (66% yield) according to protocol D.

Synthesis of 3-bromo-2-(4-n-octylphenyl)-1-benzofuran (51)

(51) was prepared on 8.8 mmol scale (43% yield) according to protocol F3.

Synthesis of S079

S079 was prepared on 0.92 mmol scale (21% yield) according to protocol H3. $^1$H NMR (400 MHz, CDCl$_3$) δ 7.30-7.22 (m, 4H), 7.18-7.09 (m, 4H), 7.07-6.97 (m, 6H), 6.78 (d, J=8.0 Hz, 4H), 2.37-2.23 (m, 4H), 1.49-1.39 (m, 4H), 1.35-1.22 (m, 21H), 0.90 (t, J=6.8 Hz, 6H).

Example 45

Synthesis of S083

3,3'-(perfluorocyclopent-1-ene-1,2-diyl)bis(5-methoxy-2-(4-methoxyphenyl)-benzofuran (Scheme 55)

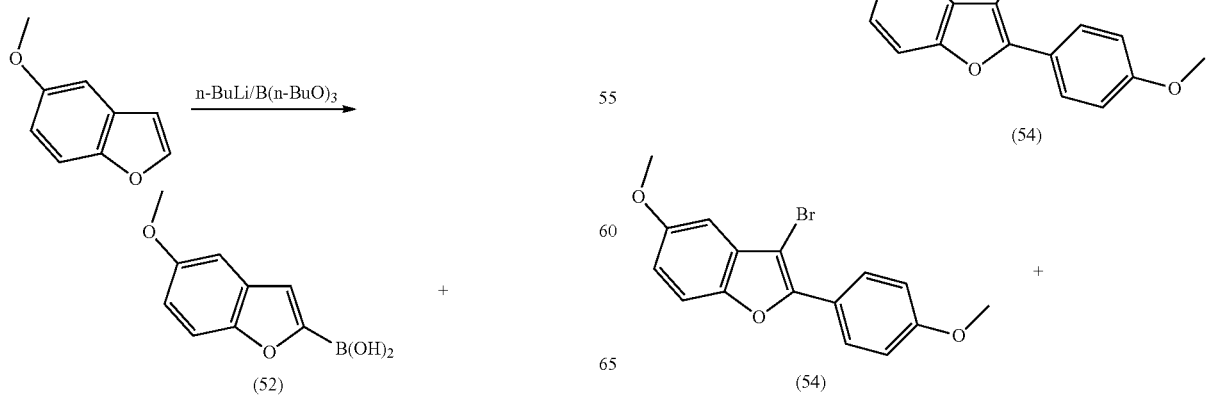

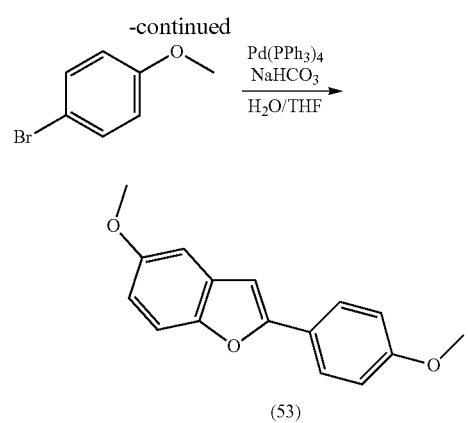

-continued

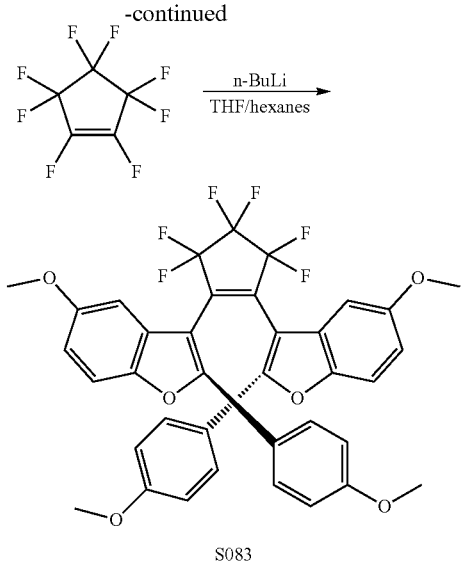

S083

Synthesis of 5-methoxybenzofuran-2-ylboronic acid (52)

5-Methoxybenzofuran (5.3 g, 35.8 mmol) was dissolved in anhydrous THF (120 mL) and cooled to −30° C. The solution was treated with n-BuLi (18 mL, 45 mmol, 2.5 M in hexanes) over 30 min, maintaining the internal temperature at −30° C. during the addition to give a yellow solution. After 1 h at −30° C., tributyl borate (12.2 mL, 45.1 mmol) was added over 10 min and the solution became pale yellow. The resulting solution was allowed to warm slowly to 14° C. over 12 h, then was quenched with 6 M HCl (50 mL) and extracted with EtOAc (150 mL). The organics were washed with water, then brine and dried over $MgSO_4$. After filtration, the organic solution was concentrated and the boronic acid precipitated by the addition of hexanes. The solid was filtered and washed with hexanes to give an off-white solid (3.95 g, 48%).

Synthesis of 5-methoxy-2-(4-methoxyphenyl)benzofuran (53)

(53) was prepared on 8.8 mmol scale (56% yield) according to protocol D.

Synthesis of 3-bromo-5-methoxy-2-(4-methoxyphenyl)benzofuran (54)

(54) was prepared on 9.6 mmol scale (83% yield) according to protocol F4.

Synthesis of S083

S083 was prepared on 1.1 mmol scale (22% yield) according to protocol H3 with the following exception: instead of using silica gel as the stationary phase in the flash chromatography step, basic alumina was used. $^1$H NMR (400 MHz, CDCl$_3$) δ 7.17 (d, J=8.9 Hz, 2H), 7.01-6.96 (m, 4H), 6.75 (dd, J=8.9, 2.6 Hz, 2H), 6.54 (s, 2H), 6.48 (d, J=8.7 Hz, 4H), 3.79 (d, J=4.6 Hz, 6H), 3.67 (s, 6H).

Example 46

Synthesis of S084

3,3'-(perfluorocyclopent-1-ene-1,2-diyl)bis(2,5-bis (4-hydroxyphenyl)thiophene) (Scheme 56)

To a solution of S054 (3.29 g, 4.3 mmol) in 150 mL of dichloromethane at 0° C. was added BBr$_3$ (1.0 M in DCM, 26 mL, 1.5 eq.). The resulting mixture was allowed to warm to RT and stirred for 12 h. Methanol was then added slowly to quench the reaction at 0° C. and the mixture was poured into water (300 mL) and extracted with EtOAc. Organic solvents were removed under vacuum. The residue was purified by sonication in chloroform and filtration. The grey solid was dried to give 2.81 g of S084. Yield 92%. $^1$H NMR (400 MHz, DMSO) δ 9.68 (s, 2H), 9.57 (s, 2H), 7.21 (d, J=8.3 Hz, 4H), 6.77 (dd, J=15.5, 8.3 Hz, 8H), 6.55 (d, J=8.3 Hz, 4H), 6.20 (s, 2H).

Example 47

Synthesis of S085, S086 and S087

(Schemes 57a, b, c)
Scheme 57a

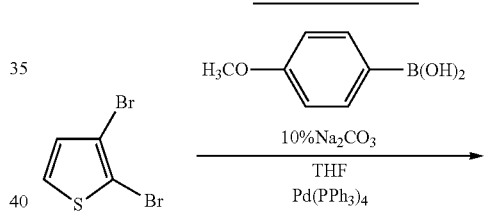

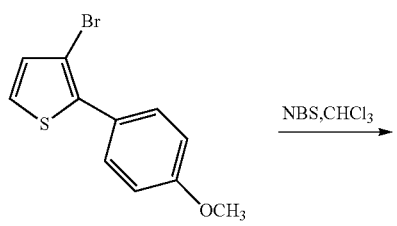

(55)

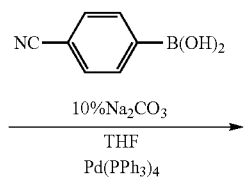

(56)

109

-continued

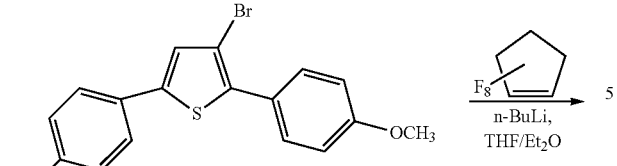

(57)

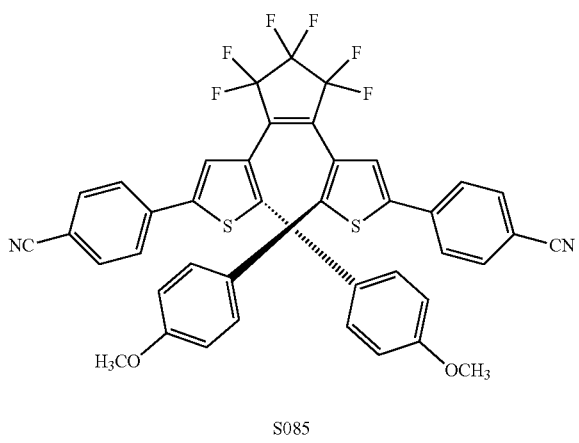

S085

Synthesis of 3-bromo-2-(4-methoxyphenyl)thiophene (55)

(55) was prepared on 85 mmol scale (82% yield) according to protocol D.

Synthesis of 3,5-dibromo-2-(4-methoxyphenyl)thiophene (56)

(56) was prepared on 59 mmol scale (70% yield) according to protocol F4.

Synthesis of 4-(4-bromo-5-(4-methoxyphenyl)thiophen-2-yl)benzonitrile (57)

(57) was prepared on 28.4 mmol scale (86% yield) according to protocol D.

Synthesis of S085

S085 was prepared according to protocol H3. $^1$H NMR (400 MHz, CDCl$_3$) δ 7.67 (d, J=8.5 Hz, 4H), 7.46 (d, J=8.5 Hz, 4H), 6.92 (d, J=8.7 Hz, 4H), 6.59 (d, J=6.8 Hz, 4H), 6.47 (s, 2H), 3.42 (s, 6H).

110

Preparation of S086

(4,4'-(3,3'-(perfluorocyclopent-1-ene-1,2-diyl)bis(5-(4-methoxyphenyl)thiophene-3,2-diyl))dibenzonitrile)

Scheme 57b

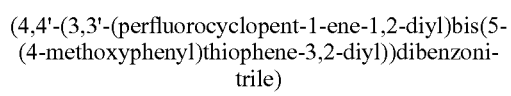

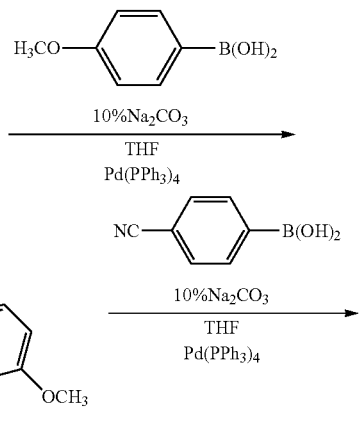

(59)

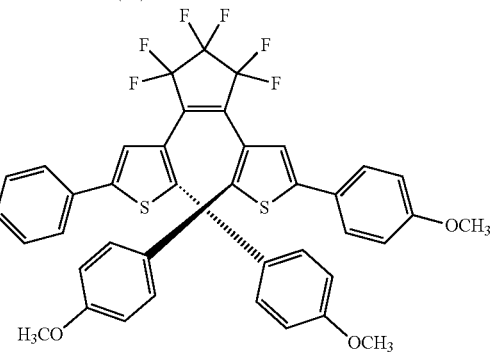

S086

Synthesis of 2,3-dibromo-5-(4-methoxyphenyl)thiophene (58)

(58) was prepared on 26.4 mmol scale (40% yield) according to protocol D.

Synthesis of 4-(3-bromo-5-(4-methoxyphenyl)thiophen-2-yl)benzonitrile (59)

(59) was prepared on 17 mmol scale (64% yield) according to protocol D.

Synthesis of S086

S086 was prepared on 0.39 mmol scale (9.7% yield) according to protocol H3. $^1$H NMR (400 MHz, CDCl$_3$) δ 7.38 (d, J=8.4 Hz, 4H), 7.30 (d, J=8.8 Hz, 4H), 7.09 (d, J=8.5 Hz, 4H), 6.99 (d, J=8.8 Hz, 4H), 6.23 (s, 2H), 3.87 (s, 6H).

Preparation of S087

(4-(3-(2-(5-(4-cyanophenyl)-2-(4-methoxyphenyl) thiophen-3-yl)-3,3,4,4,5,5-hexafluorocyclopent-1-en-1-yl)-5-(4-methoxyphenyl)thiophen-2-yl)benzonitrile): S087 is prepared in two steps using precursors prepared as per synthesis of S085 and S085.

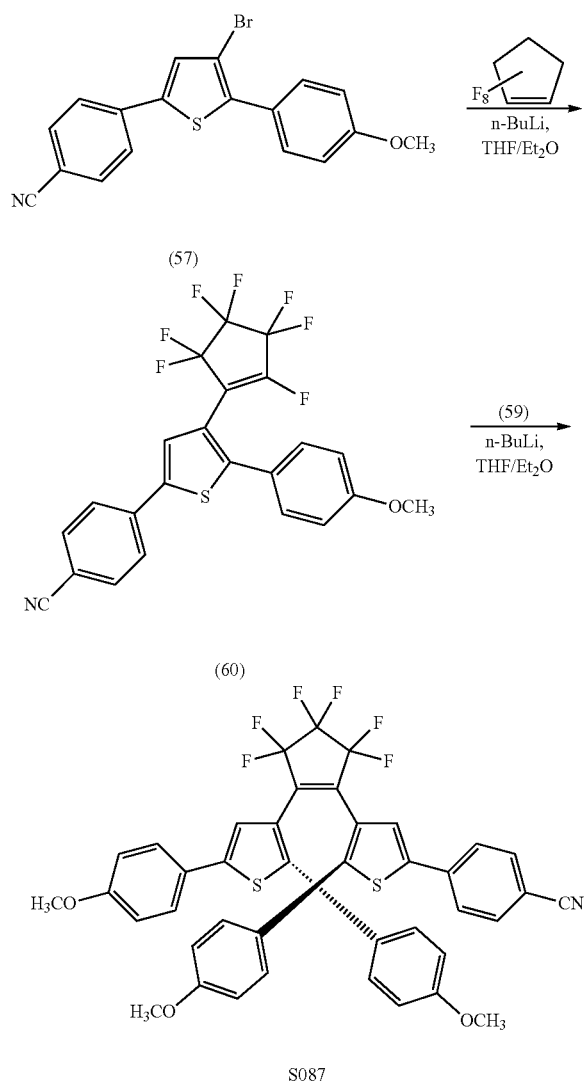

Synthesis of 4-(5-(4-methoxyphenyl)-4-(perfluorocyclopent-1-en-1-yl)thiophen-2-yl)benzonitrile (60)

To a solution of (57) (5.0 g, 13.50 mmol) in dry THF (300 mL) was slowly added n-BuLi hexane solution (2.0 M, 7.43 mL, 14.85 mmol) at −50° C. under an argon atmosphere. The solution was stirred for 15 minutes at −50° C. After the addition of octafluorocyclopentene (5.44 mL, 40.5 mmol), the reaction mixture was stirred for 2 h. The reaction was quenched by the addition of methanol and warmed to RT. The solvents were removed by rotary evaporation and flash chromatography (10% EtOAc in hexanes) afforded a dark yellow oil (4.0 g, 61.3%).

Synthesis of S087

To a solution of (59) (2.66 g, 7.20 mmol) in dry THF (190 mL) was slowly added n-BuLi hexane solution (2.0 M, 3.96 mL, 7.91 mmol) at −50° C. under an argon atmosphere. The solution was stirred for 15 minutes at −50° C., compound (60) (4.0 g in 50 mL of dry THF, 8.27 mmol) was added under argon, and the reaction mixture stirred for a further 2 h, and stopped by quenching it with methanol. THF and ether were then removed under vacuum. EtOAc and water were added to the reaction crude. The product was extracted with EtOAc and the organic layer was dried over MgSO$_4$ and concentrated under vacuum. The resulting brown solid was purified by column chromatography (Silica gel; 20% EtOAc in hexanes to provide a brown/yellowish solid 543 mg (10.0%). This solid was dissolved in DCM and purified again by column chromatography (aluminum oxide) and treated first with hexanes, followed by a gradual increase in polarity (3%, 6%, 10% and 20% of EtOAc in hexanes)—the product was collected at 20% EtOAc in hexanes. A final purification by preparative TLC using a mixture of 20% EtOAc in hexanes was performed. $^1$H NMR (400 MHz, CDCl$_3$) δ 7.73 (d, J=8.5 Hz, 2H), 7.46 (d, J=8.5 Hz, 2H), 7.36 (d, J=8.6 Hz, 2H), 7.34 (d, J=11.4 Hz, 2H), 7.10 (d, J=8.4 Hz, 2H), 6.92 (t, J=8.2 Hz, 4H), 6.63 (d, J=8.7 Hz, 2H), 6.42 (s, 1H), 6.30 (s, 1H), 3.86 (s, 3H), 3.42 (s, 3H).

Example 48

Synthesis of S088

(E)-3,3'-(perfluorocyclopent-1-ene-1,2-diyl)bis(2-(4-methoxyphenyl)-5-(4-((E)-styryl)phenyl)thiophene)

(Scheme 58)

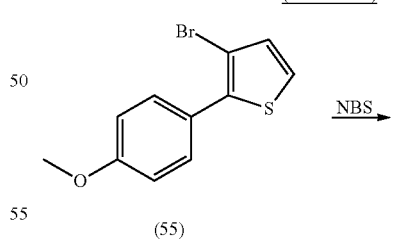

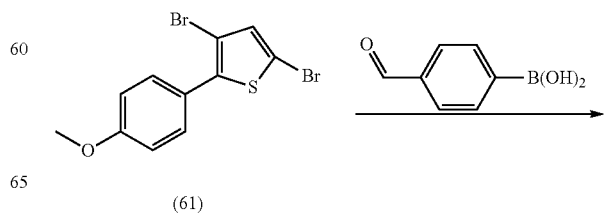

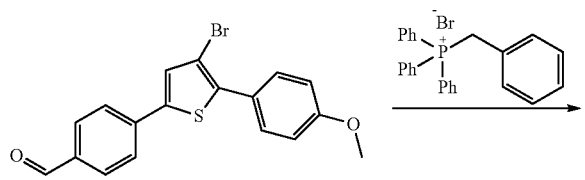

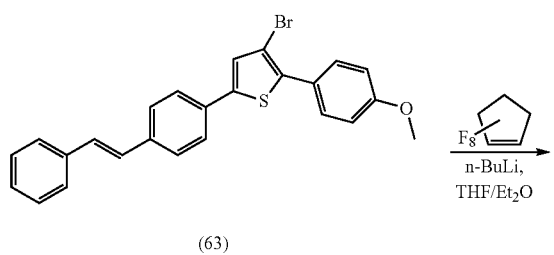

(63)

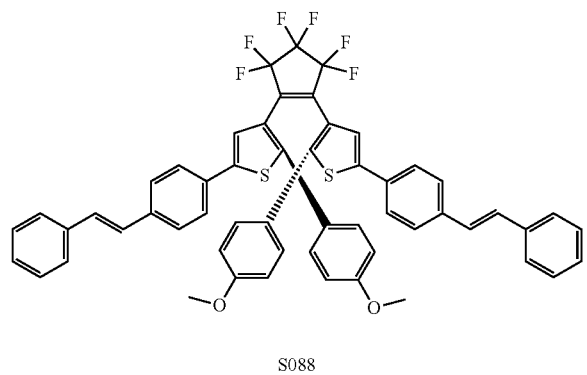

S088

Synthesis of
3,5-dibromo-2-(4-methoxyphenyl)thiophene (61)

(61) was prepared on 90.2 mmol scale (97% yield) according to protocol F4.

Synthesis of 4-(4-bromo-5-(4-methoxyphenyl)thiophen-2-yl)benzaldehyde (62): (62) was prepared on 67.2 mmol scale (74% yield) according to protocol D.

Synthesis of (E)-3-bromo-2-(4-methoxyphenyl)-5-(4-styrylphenyl)thiophene (63)

A mixture of benzyltriphenylphosphonium bromide (23.7 g, 54.7 mmol) and (62) (17 g, 45.5 mmol) was dispersed in chloroform (300 mL) and stirred at RT under argon atmosphere for 15 min. A solution of t-BuOK (10.3 g, 91 mmol) in anhydrous THF (80 mL) was added dropwise. The reaction mixture was stirred at RT for 3 h. Then water was added, followed by extraction with chloroform. The combined extracts were dried over anhydrous MgSO$_4$ and solvent evaporated to half of its initial volume by rotary evaporation; the resulting light yellow precipitation was filtered and dried (9.63 g; 47% yield).

Synthesis of S088

To a stirred THF suspension (350 mL) containing (63) (6.12 g, 13.7 mmol), 7.2 mL of 2.5 M n-BuLi hexane solution (17.8 mmol) was slowly added at −35° C., and the solution was stirred for 15 min. Octafluorocyclopentene (0.92 mL, 6.84 mmol) was added in one portion to the reaction mixture and stirred with gradual warming to 20° C. over 16 hours. The precipitation was filtered off and filtrate was evaporated under vacuum. The crude product was purified by column chromatography on silica gel (hexane/chloroform 20 to 50%) to give 0.92 g of S088 in 14.8% yield. $^1$H NMR (400 MHz, CD$_2$Cl$_2$) δ 7.64-7.51 (m, 8H), 7.47-7.34 (m, 8H), 7.29 (dt, J=11.4, 4.7 Hz, 2H), 7.18 (d, J=3.2 Hz, 4H), 6.99-6.91 (m, 4H), 6.65-6.58 (m, 4H), 6.43 (s, 2H), 3.38 (s, 6H).

Example 49

Synthesis of S089

3,3'-(perfluorocyclopent-1-ene-1,2-diyl)bis(2-(4-methoxyphenyl)-5-(4-((1E,3E)-4-phenylbuta-1,3-dien-1-yl)phenyl)thiophene)

(Scheme 59)

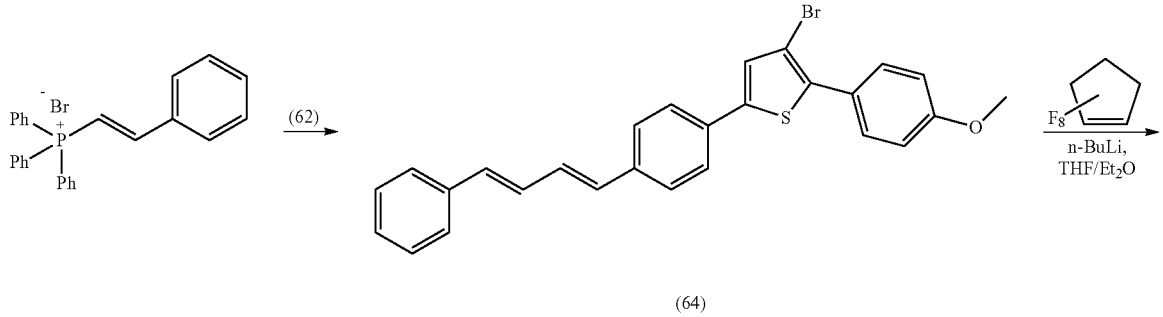

(64)

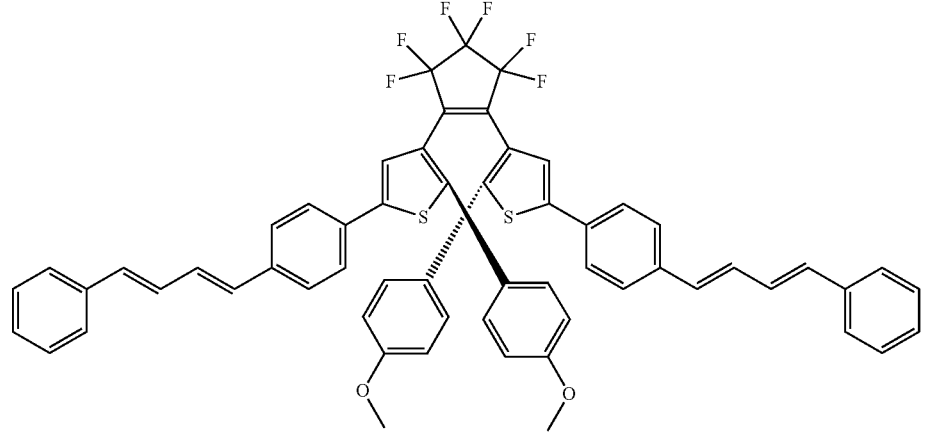

S089

Synthesis of 3-bromo-2-(4-methoxyphenyl)-5-(4-((1E,3E)-4-phenylbuta-1,3-dienyl)phenyl)thiophene (64)

10.83 g (23.6 mmol) of Cinnamyltriphenylphosphonium bromide was added to 2.70 g (24.10 mmol) of t-BuOK in 100 mL THF and the resulting solution was stirred at RT for 30 min. The reaction mixture was cooled to 0° C. and 8 g (21.4 mmol) of the aldehyde (62) was added in 35 mL THF. The solution was warmed to RT and stirred for 5 hrs. The solution was poured into 200 mL water. The precipitated product was separated by filtration to give 7.5 g (74% yield) of pure target molecule.

Synthesis of S089

To a stirred THF solution (400 mL) containing 3-bromo-2-(4-methoxyphenyl)-5-(4-((1E,3E)-4-phenylbuta-1,3-dienyl)phenyl)thiophene (7.47 g, 15.78 mmol), 8.2 mL of 2.5 M n-BuLi hexane solution (20.5 mmol) was slowly added at −30° C., and the solution was stirred for 15 min. Octafluorocyclopentene (1.1 mL, 7.9 mmol) was added in one portion to the reaction mixture and stirred with gradual warming to 20° C. over 12 hours. The reaction mixture was quenched by addition of 10% HCl solution and extracted with EtOAc. The organic phase was separated and the precipitation was filtered off. The filtrate was evaporated under vacuum. The crude product was purified by column chromatography on silica gel (hexane/chloroform 20 to 50% gradient) to give 1.14 g of S089 in 15% yield. $^1$H NMR (400 MHz, CD$_2$Cl$_2$) δ 7.56-7.48 (m, 8H), 7.46-7.36 (m, 8H), 7.29 (t, J=7.3 Hz, 2H), 7.13-7.02 (m, 4H), 6.98 (d, J=8.7 Hz, 4H), 6.83-6.71 (m, 4H), 6.64 (d, J=8.7 Hz, 4H), 6.45 (s, 2H), 3.41 (s, 6H).

Example 50

Synthesis of S090

4,4'-(((((4,4'-(perfluorocyclopent-1-ene-1,2-diyl)bis(5-(4-methoxyphenyl)thiophene-4,2-diyl))bis(4,1-phenylene))bis(oxy))bis(ethane-2,1-diyl))bis(oxy))bis(N,N-bis(4-chlorophenyl)aniline)

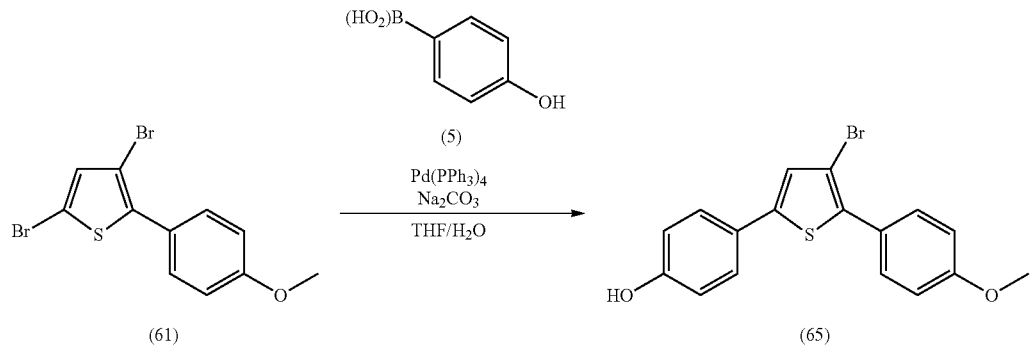

(Scheme 60)

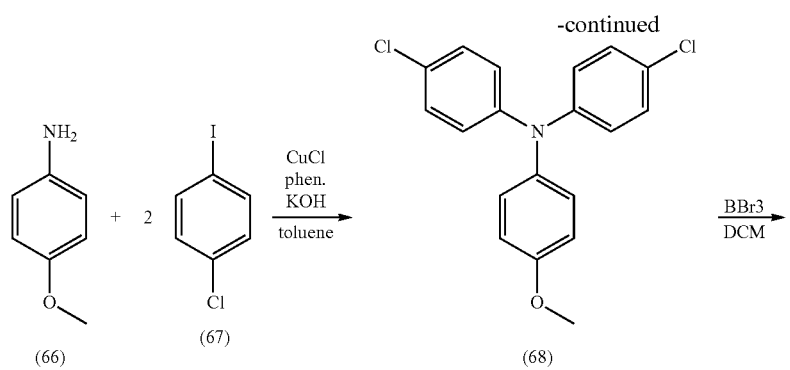
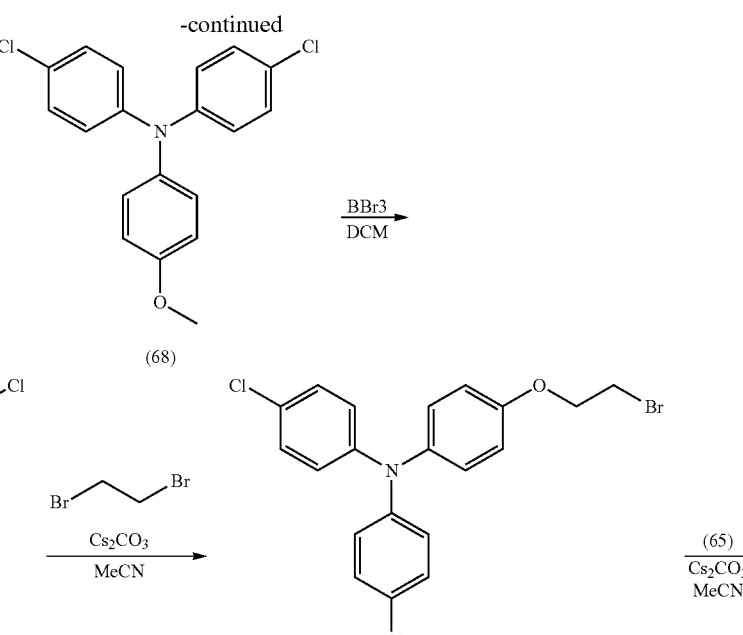
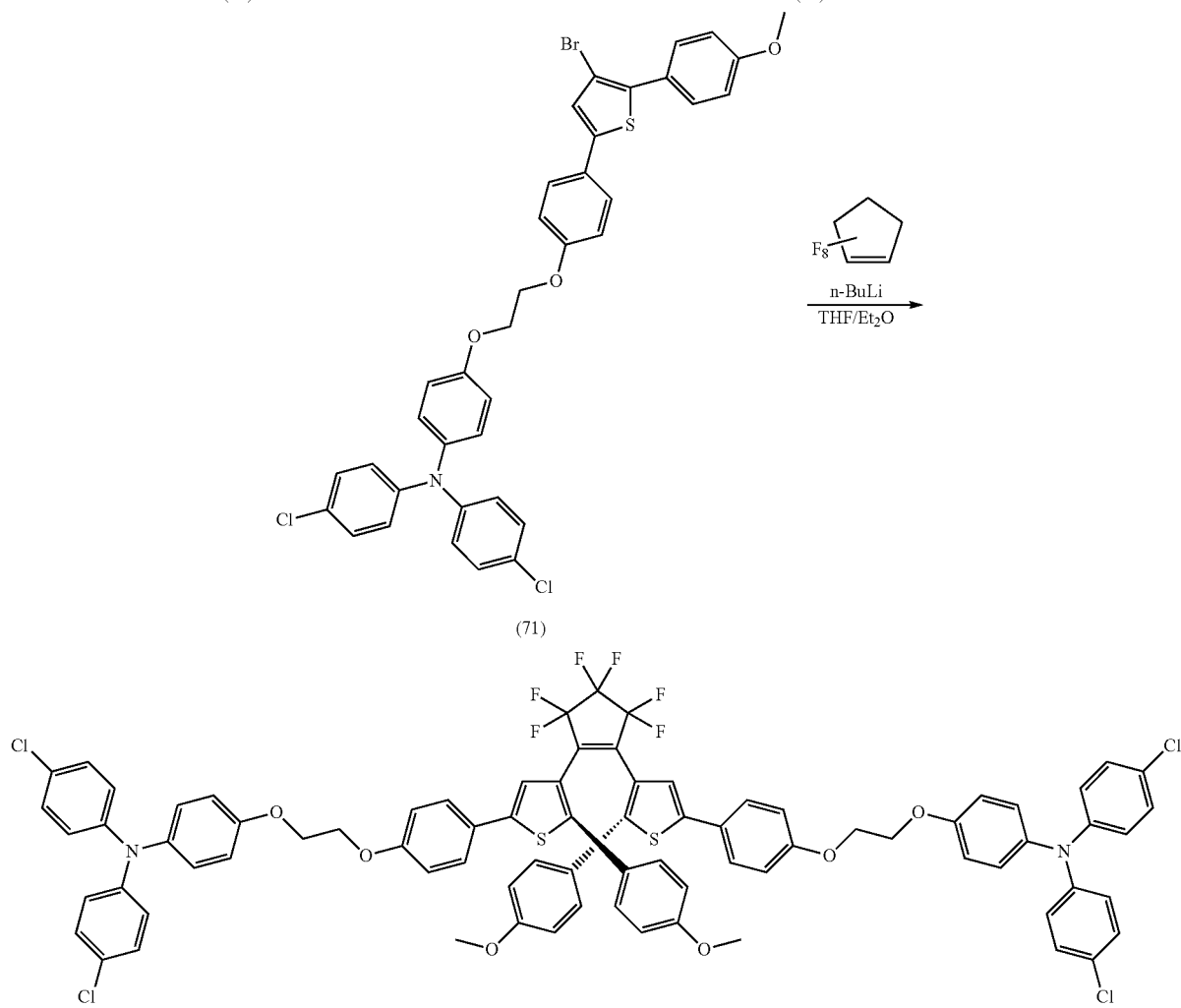

Synthesis of 4-(4-bromo-5-(4-methoxyphenyl)thiophen-2-yl)phenol (65)

(65) was prepared on 18.1 mmol scale (62% yield) according to protocol D Synthesis of 4-chloro-N-(4-chlorophenyl)-N-(4-methoxyphenyl)aniline (68): 4-methoxyaniline (66, 7.75 g, 62.9 mmol), 1-chloro-4-iodobenzene (67, 33 g, 138 mmol), phenanthroline (0.419 g, 2.33 mmol) and copper (I) chloride (0.23 g, 2.33 mmol) were added to a 250 mL rbf and toluene (60 mL) was added. Potassium hydroxide (27.5 g, 491 mmol) was added, and the reaction was heated to reflux for 18 h. A grey/purple solid was observed, but the reaction was incomplete, so a further 50 mL of toluene was added and the reaction reheated to reflux for a further 30 h. After cooling to RT, the mixture was poured into EtOAc (500 mL) and water (400 mL). The aqueous layer was separated and extracted with EtOAc (250 mL). The combined organic portions were washed with water (3×500 mL), dried over MgSO$_4$, filtered and solvent removed by rotary evaporation to afford a purple liquid. Flash chromatography (hexanes to 5% EtOAc/hexanes) afforded 68 as a clear, light yellow, viscous oil, 10.79 g (50%).

Synthesis of 4-(bis(4-chlorophenyl)amino)phenol (69)

4-chloro-N-(4-chlorophenyl)-N-(4-methoxyphenyl)aniline (68, 10.79 g, 31.3 mmol) was dissolved in anhydrous DCM (120 mL), and the BBr$_3$ (1.0 M, 38 mL, 37.6 mmol) was added slowly over a period of ~20 minutes. The reaction mixture was allowed to stir under an Argon atmosphere for 18 hours. The reaction mixture was slowly poured into water (500 mL) and stirred for 30 minutes. The purple organic layer was separated and the aqueous layer was extracted with DCM (100 mL). The combined organics were washed with water (500 mL), dried over MgSO$_4$, filtered and solvent removed by rotary evaporation. Flash chromatography (15% EtOAc/hexanes) afforded 69 as a clear, light green viscous oil, 9.41 g (91%).

Synthesis of 4-(2-bromoethoxy)-N,N-bis-(4-chlorophenyl)aniline (70)

To a 250 mL rbf was added cesium carbonate (4.93 g, 15.14 mmol) and anhydrous acetonitrile (50 mL). A solution of 4-(bis(4-chlorophenyl)amino)phenol (69, 2.5 g, 7.57 mmol) in acetonitrile (25 mL) was added, and an immediate light purple colour was observed. 1,2-dibromoethane (7.11 g, 37.9 mmol) was added and the reaction was heated to reflux for 5 days. After cooling to RT, the reaction mixture was poured into water (250 mL), mixed well and separated. The aqueous portion was extracted with EtOAc (2×100 mL) and the combined organics were washed with water (2×250 mL), dried over MgSO$_4$, filtered and solvent removed by rotary evaporation. Flash chromatography (2% EtOAc/hexanes) afforded 70 as a clear, colourless oil (1.42 g, 43%).

Synthesis of 4-(2-(4-(4-bromo-5-(4-methoxyphenyl)thiophen-2-yl)phenoxy)ethoxy)-N,N-bis(4-chlorophenyl)aniline (71)

4-(2-bromoethoxy)-N,N-bis-(4-chlorophenyl)aniline (70, 1.40 g, 3.20 mmol) and 4-(4-bromo-5-(4-methoxyphenyl)thiophen-2-yl)phenol (65, 1.16 g, 3.20 mmol) were dissolved in acetonitrile (40 mL) and the cesium carbonate (2.09 g, 6.41 mmol) was added. The reaction mixture was heated to reflux for 20 hours. After cooling to RT, the reaction mixture was poured into DCM (100 mL) and water (150 mL). The mixture was mixed well and the aqueous portion extracted with DCM (2×100 mL). The combined organics were washed with water (2×150 mL), dried over MgSO$_4$, filtered and solvent removed by rotary evaporation. The resulting off-white solid was sonicated in MeOH (100 mL), filtered and air dried to afford an off-white powder which still contained some minor impurities by TLC. This material was allowed to stir in refluxing EtOH (150 mL) for 15 minutes, cooled slightly, filtered and air dried to afford 71 as an off-white powder (1.60 g, 70%).

Synthesis of S090

S090 was prepared on 0.021 mmol scale (2% yield) according to protocol H3. $^1$H NMR (400 MHz, CDCl$_3$) δ 7.32 (d, J=8.7 Hz, 4H), 7.18 (d, J=8.9 Hz, 8H), 7.05 (d, J=8.9 Hz, 4H), 6.98-6.90 (m, 20H), 6.60 (d, J=8.7 Hz, 4H), 6.26 (s, 2H), 4.35 (m, 8H), 3.43 (s, 6H).

Example 51

Synthesis of S091, S092, S094 and S095

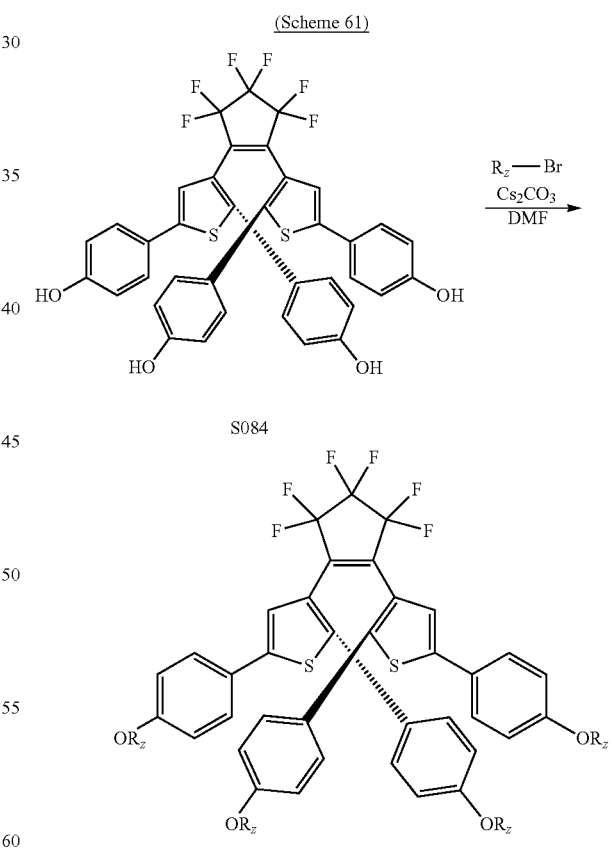

S091 Rz = Et
S092 Rz = iPr
S094 Rz = iPn
S095 Rz = Np

S084 (1 eq) and cesium carbonate (10 eq) were dissolved in anhydrous DMF (120 ml) and the alkylbromide (R$_z$—Br) added (20 eq) (Rz=ethyl for S091; isopropyl for S092; isopentyl for S094; or neopentyl for S095). The reaction mixture was heated to 90° C. and stirred for 18-36 hours. Completion was verified by TLC—if necessary a further 12-16 eq of the R—Br was added, with continued heating and stirring. After cooling to RT, the reaction mixture was poured into water and extracted with DCM (S091, S094) or EtOAc (S092, S095). Combined organics were washed with water, dried over MgSO$_4$, filtered and solvent removed by vacuum.

S091 (3,3'-(perfluorocyclopent-1-ene-1,2-diyl)bis(2,5-bis (4-ethoxyphenyl)thiophene)): Flash chromatography (10% EtOAc/hexanes) afforded a yellow solid, which was sonicated in MeOH (100 mL), filtered and air dried (1.58 g). A portion of this solid was purified by preparative TLC (25% DCM in hexanes) to afford 127 mg of S091. $^1$H NMR (400 MHz, CDCl$_3$) δ 7.30 (d, J=8.8 Hz, 4H), 6.89 (d, J=7.5 Hz, 8H), 6.57 (d, J=8.7 Hz, 4H), 6.24 (s, 2H), 4.07 (q, J=7.0 Hz, 4H), 3.51 (m, 4H), 1.45 (t, J=7.0 Hz, 6H), 1.27 (t, J=6.9 Hz, 6H).

S092 (3,3'-(perfluorocyclopent-1-ene-1,2-diyl)bis(2,5-bis (4-isopropoxyphenyl)thiophene)): Flash chromatography (10% EtOAc/hexanes) afforded a green/yellow solid which was sonicated in MeOH (30 mL), filtered and air dried to afford a yellow solid, 0.80 g. A portion of this solid was purified by preparative TLC (25% DCM in hexanes) to afford 145 mg of S092. $^1$H NMR (400 MHz, CDCl$_3$) δ 7.29 (d, J=8.7 Hz, 4H), 6.87 (d, J=8.7 Hz, 4H), 6.87 (d, J=8.7 Hz, 4H), 6.58 (d, J=8.7 Hz, 4H), 6.22 (s, 2H), 4.57 (sept, J=6.1 Hz, 2H), 4.11 (sept, J=6.0 Hz, 2H), 1.37 (d, J=6.1 Hz, 12H), 1.18 (d, J=6.0 Hz, 12H).

S094 (3,3'-(perfluorocyclopent-1-ene-1,2-diyl)bis(2,5-bis (4-(isopentyloxy)phenyl)thiophene)): The resulting dark green liquid was dried on the high vacuum pump to remove the residual DMF. To the dark green oil was added MeOH (50 mL) and after standing for 2 hours, a dark green material solidified. The solid was filtered off, ground in a mortar and pestle, washed with MeOH (50 mL), filtered and air-dried to afford a green powdery solid. A portion of this solid was purified by preparative TLC (25% DCM in hexanes) to afford 100 mg of S094. $^1$H NMR (400 MHz, CDCl$_3$) δ 7.30 (d, J=8.7 Hz, 4H), 6.90 (d, J=8.7 Hz, 4H), 6.87 (d, J=8.8 Hz, 4H), 6.58 (d, J=8.7 Hz, 4H), 6.24 (s, 2H), 4.00 (t, J=6.7 Hz, 4H), 3.48 (s, 4H), 1.86 (sept, J=6.7 Hz, 2H), 1.71 (m, 6H), 0.99 (d, J=6.6 Hz, 12H), 0.92 (d, J=6.6 Hz, 12H).

S095 (3,3'-(perfluorocyclopent-1-ene-1,2-diyl)bis(2,5-bis (4-(neopentyloxy)phenyl)thiophene)): A portion of this material was purified by preparative TLC (25% DCM in hexanes) to afford 60 mg of S095. $^1$H NMR (400 MHz, CDCl$_3$) δ 7.30 (d, J=8.7 Hz, 4H), 6.90 (d, J=8.6 Hz, 4H), 6.88 (d, J=8.7 Hz, 4H), 6.59 (d, J=8.7 Hz, 4H), 6.21 (s, 2H), 5.30 (s, 3H), 3.60 (s, 4H), 1.07 (s, 18H), 0.93 (s, 18H).

Example 52

Synthesis of S096

3,3'-(perfluorocyclopent-1-ene-1,2-diyl)bis(2,5-bis (3-methoxyphenyl)thiophene)

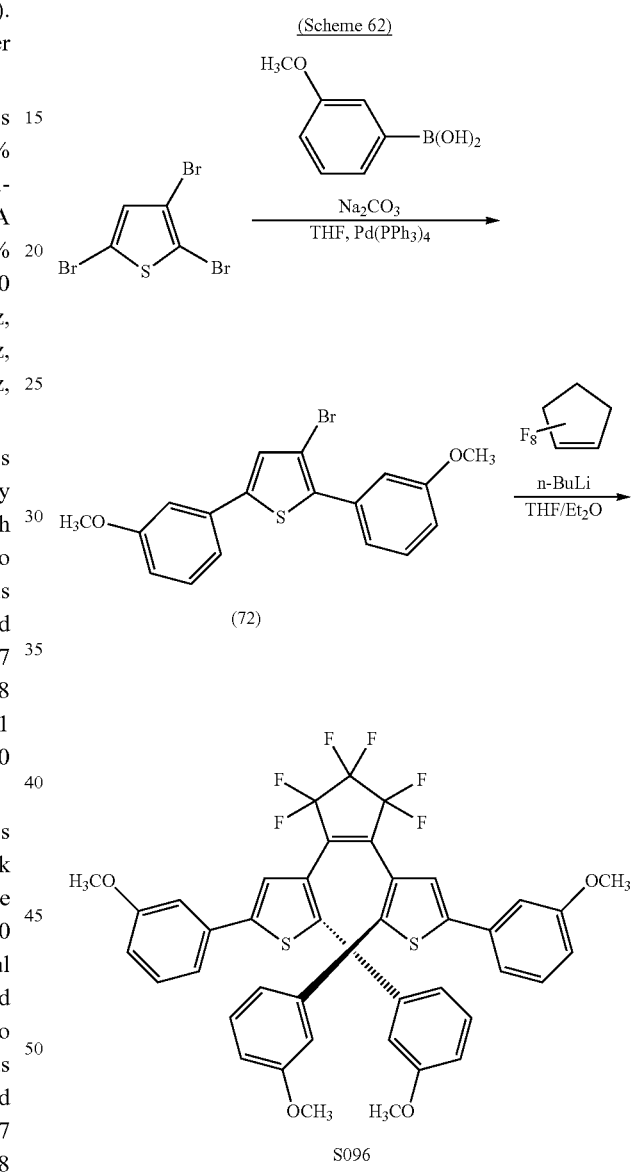

Synthesis of 3-bromo-2,5-bis(3-methoxyphenyl)thiophene (72)

(72) was prepared on 55 mmol scale (74%) according to protocol C.

Synthesis of S096: S096 was prepared on 3.53 mmol scale (53% yield) according to protocol H3. $^1$H NMR (400 MHz, CDCl$_3$) δ 7.29 (t, J=8.0 Hz, 2H), 7.05 (d, J=14.8 Hz, 2H), 7.01 (d, J=7.1 Hz, 2H), 6.95-6.91 (m, 2H), 6.85 (dd, J=8.2, 2.3 Hz, 2H), 6.60 (dd, J=8.4, 2.1 Hz, 4H), 6.53-6.49 (m, 2H), 6.37 (s, 2H), 3.88 (s, 6H), 3.47 (s, 6H).

Example 53

Synthesis of S097

3,3'-(perfluorocyclopent-1-ene-1,2-diyl)bis(2,5-bis(3,5-dimethoxyphenyl)thiophene)

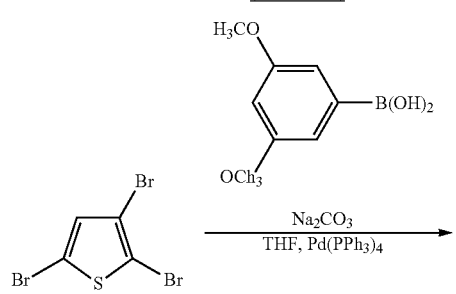

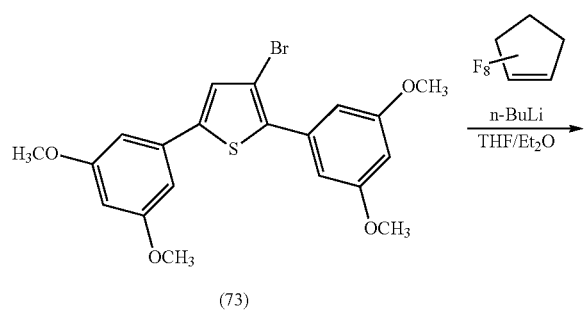

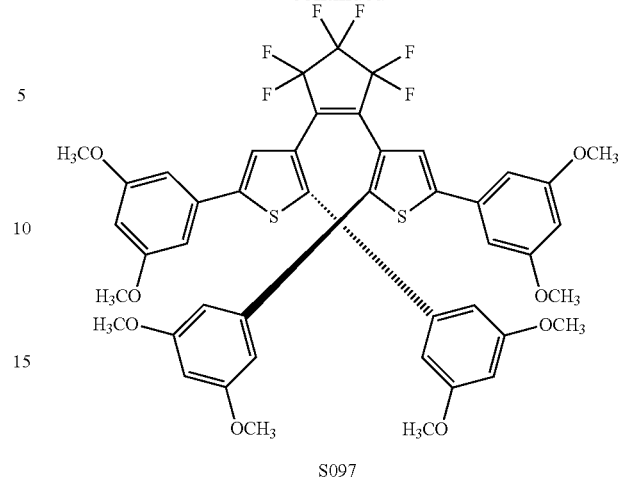

Synthesis of 3-bromo-2,5-bis(3,5-dimethoxyphenyl)thiophene (73)

(73) was prepared on 29 mmol scale (78%) yield according to protocol C.

Synthesis of S097

S097 was prepared on 3.96 mmol scale (69% yield) according to protocol H3. $^1$H NMR (400 MHz, CDCl$_3$) δ 6.58 (d, J=2.2 Hz, 4H), 6.45 (s, 2H), 6.42 (t, J=2.2 Hz, 2H), 6.14 (m, 6H), 3.87 (s, 12H), 3.51 (s, 12H).

Example 54

Synthesis of S098

4,4'-(perfluorocyclopent-1-ene-1,2-diyl)bis(5'tert-butyl-5-(4-methoxyphenyl)-2,2'-bithiophene)

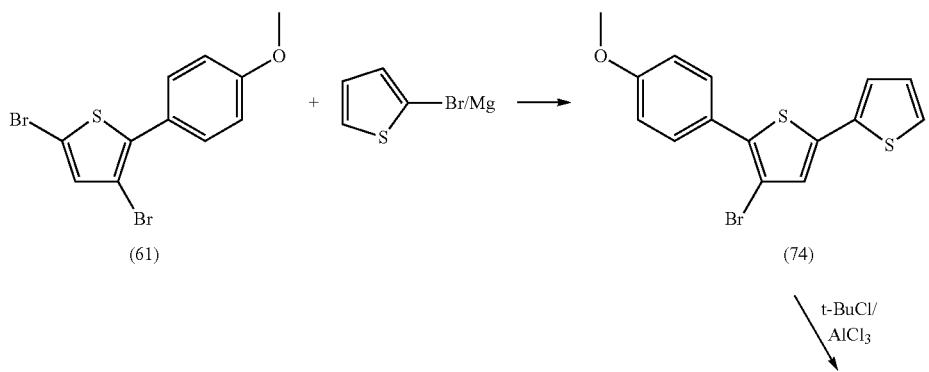

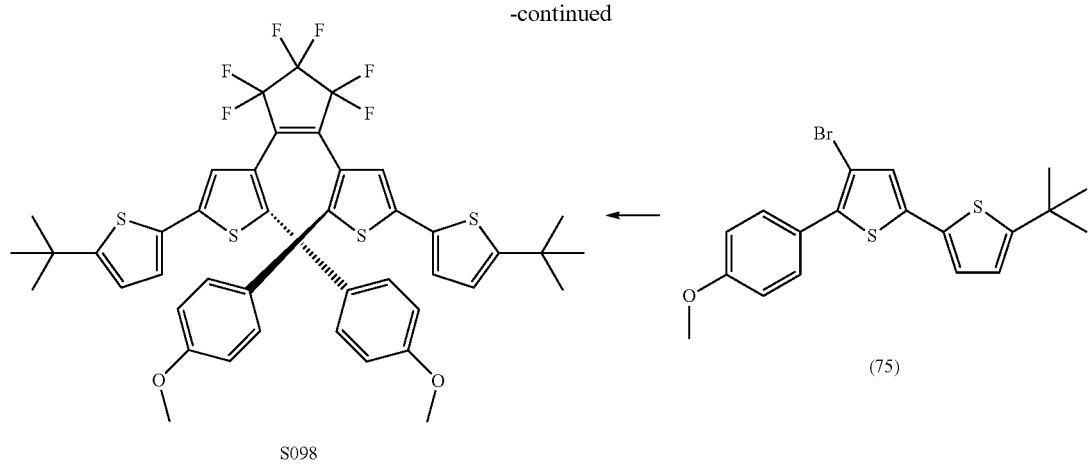

S098

Synthesis of 4-bromo-5-(4-methoxyphenyl)-2,2′-bithiophene (74)

(74) was prepared on 93.9 mmol scale (93% yield) according to protocol B.

Synthesis of 4-bromo-5′-tert-butyl-5-(4-methoxyphenyl)-2,2′-bithiophene (75): (75) was prepared according to protocol E.

Synthesis of S098

S098 was prepared on 15.5 mmol scale (35% yield) according to protocol H1. $^1$H NMR (400 MHz, CD$_2$Cl$_2$) δ 6.93-6.89 (m, 4H), 6.87 (d, J=3.7 Hz, 2H), 6.76 (d, J=3.7 Hz, 2H), 6.68-6.63 (m, 4H), 6.14 (s, 2H), 3.48 (s, 6H), 1.41 (s, 18H).

Example 55

Synthesis of S103 (3,3′-(perfluorocyclopent-1-ene-1,2-diyl)bis(5-(4-bromophenyl)-2-(4-methoxyphenyl)thiophene)) and S116 (4-(4-(2-(5-(4-bromophenyl)-2-(4-methoxyphenyl)thiophen-3-yl)-3,3,4,4,5,5-hexafluorocyclopent-1-en-1-yl)-5-(4-methoxyphenyl)thiophen-2-yl)-N,N-bis(4-chlorophenyl)aniline)

(Scheme 65)

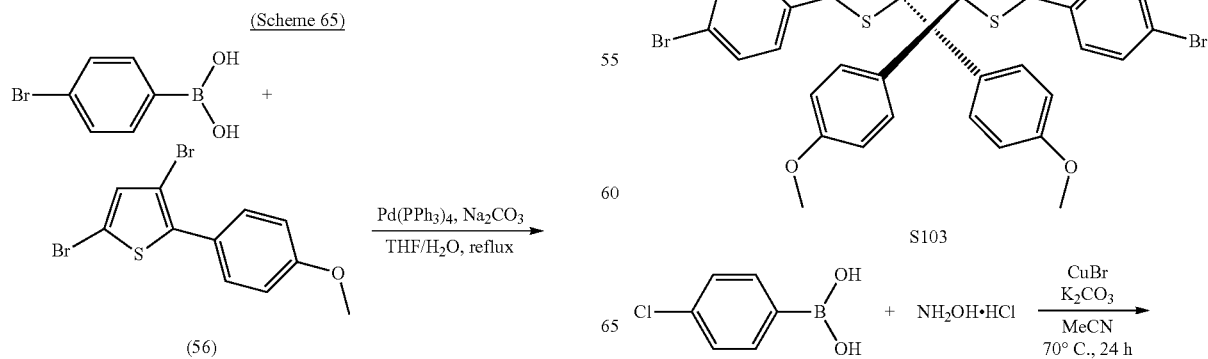

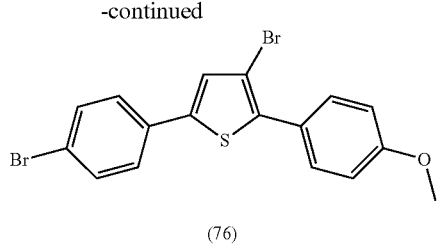

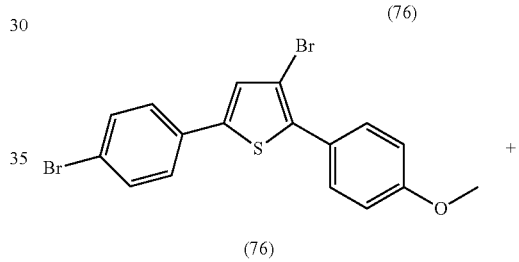

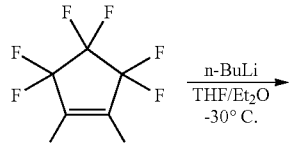

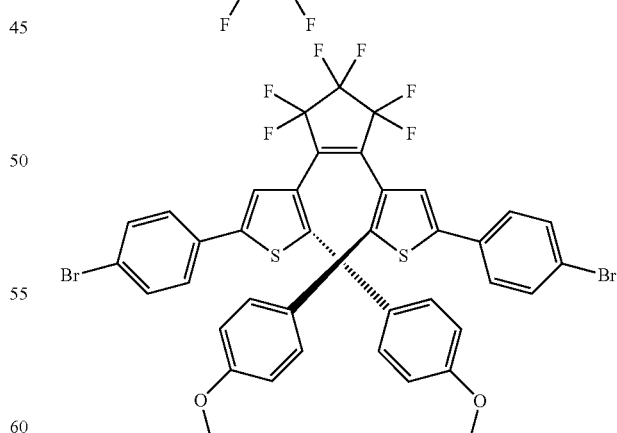

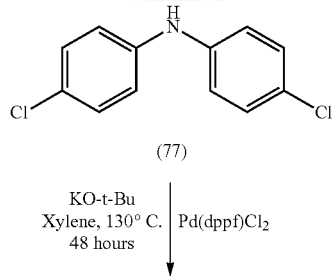

(77)

KO-t-Bu
Xylene, 130° C.  Pd(dppf)Cl₂
48 hours

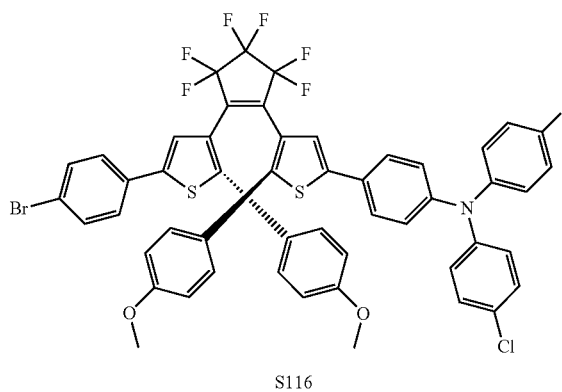

S116

Synthesis of 3-bromo-5-(4-bromophenyl)-2-(4-methoxyphenyl)thiophene (76)

(76) was prepared on 24.6 mmol scale (86% yield) according to protocol D.

Synthesis of S103

S103 was prepared on 0.58 mmol scale (4.7% yield) according to protocol H3. $^1$H NMR (400 MHz, CDCl₃) δ 7.50 (d, J=8.5 Hz, 4H), 7.26-7.22 (d, J=8.5 Hz, 4H), 6.90 (d, J=8.7 Hz, 4H), 6.59 (d, J=8.7 Hz, 4H), 6.35 (s, 2H), 3.42 (s, 6H).

Synthesis of bis(4-chlorophenyl)amine (77)

Under air, a 500-mL rbf was charged with (4-chlorophenyl)boronic acid (15.0 g, 96.0 mmol, 1 eq.), NH₂OH.HCl (8.0 g, 115 mmol, 1.2 eq.), CuBr (2.75 g, 19.18 mmol, 0.2 eq.), K₂CO₃ (19.89 g, 144.0 mmol, 1.5 eq.), and CH₃CN (320 mL). The reaction mixture was stirred at 70° C. for 24 h. The completion of the reaction was monitored by TLC. The solvent was evaporated under reduced pressure and the residue was purified by flash column chromatography on a silica gel using 10%-20% EtOAc in hexanes to give the product as brown oil that solidifies when dried under vacuum.

Synthesis of S116

In a one-neck 100-mL RBF containing S103 (350 mg, 0.406 mmol, 1 eq.), 213 mg of bis(4-chlorophenyl)amine (0.893 mmol, 2.2 eq.) were added followed by 100 mg of potassium tert-butoxide (0.893 mmol, 2.2 eq.). Xylene (20 mL) was then added and the mixture was deoxygenated for one hour using argon. Pd(dppf)Cl₂ (6.55 mg, 9.33 mol, 0.023 eq.) was then added to the reaction mixture and the RBF was connected to a condenser, where the reaction was heated to 130° C. for 48 hours. The heat was stopped and the reaction mixture was allowed to cool down to RT. The mixture was vacuum filtered through silica to remove the insoluble inorganics/catalyst and washed with DCM. The solvents (Xylene and DCM) were then removed under vacuum to provide a yellow oil. The crude was deposited on silica then purified by chromatography column using a mixture of 5% DCM in hexanes. The polarity of the solvent was then increased gradually (7.5%, 10%, 12.5%, 18.75% of DCM in hexanes) according to the progress of the purification. The product was isolated as yellow solid in 6.03% yield (~25 mg). $^1$H NMR (400 MHz, CDCl₃) δ 7.50 (d, J=8.5 Hz, 2H), 7.24 (s, 4H), 7.02 (d, J=8.6 Hz, 5H), 6.91 (dd, J=8.5, 7.0 Hz, 5H), 6.61 (dd, J=17.5, 8.7 Hz, 4H), 6.35 (s, 1H), 6.26 (s, 1H), 3.51 (s, 3H), 3.42 (s, 3H).

Example 56

Synthesis of S104 and S105

(Scheme 66)

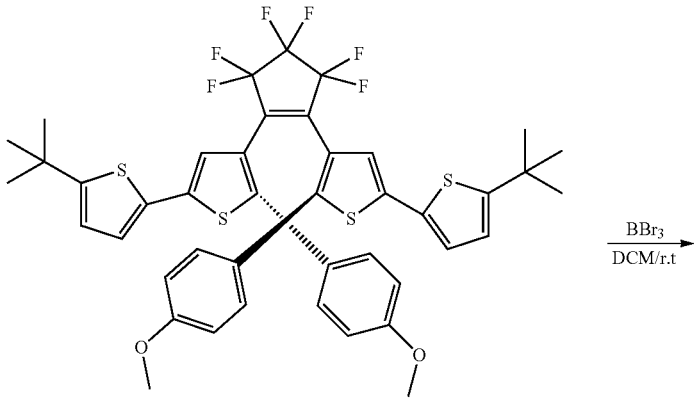

S098

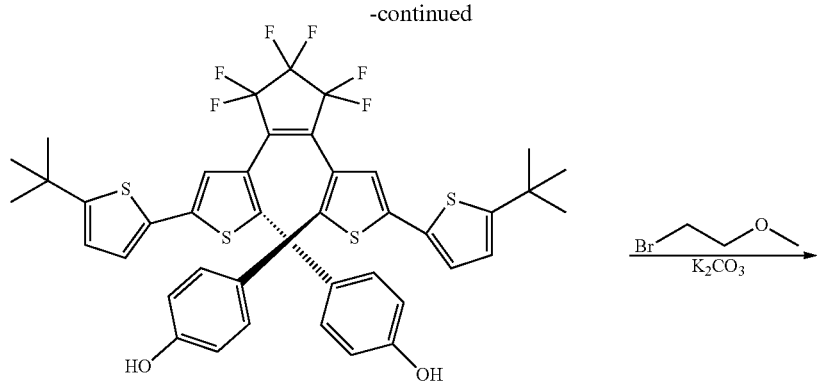

S105

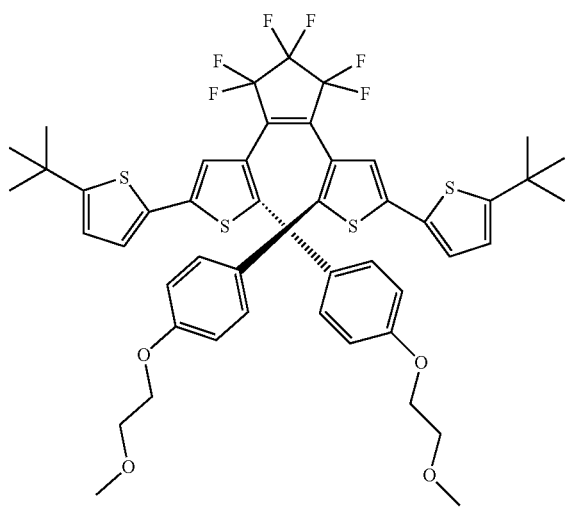

S104

Synthesis of S105 (4,4'-(4,4''-(perfluorocyclopent-1-ene-1,2-diyl)bis(5'-(tert-butyl)-[2,2'-bithiophene]-5,4-diyl))diphenol)

To a solution of S098 (1.36 g, 1.64 mmol) in 100 mL of CH$_2$Cl$_2$ at RT was added BBr$_3$ (1.0 M, 10 mL, 3 eq.). The resulting mixture was stirred for 12 h. MeOH was then added slowly to quench the reaction and the mixture was poured into water (300 mL) and extracted with EtOAc. Organic solvents were removed under vacuum. The residue was purified by flash chromatography (hexanes—5 to 20% EtOAc gradient). The yellow solid was obtained and dried in vacuum to give 0.97 g of S105. Yield 74%. $^1$H NMR (400 MHz, CDCl$_3$) δ 6.88-6.81 (m, 6H), 6.73 (d, J=3.7 Hz, 2H), 6.65-6.57 (m, 4H), 6.21-6.11 (m, 2H), 4.84-4.62 (m, 2H), 1.41 (d, J=6.1 Hz, 18H).

Synthesis of S104 (4,4''-(perfluorocyclopent-1-ene-1,2-diyl)bis(5'-(tert-butyl)-5-(4-(2-methoxyethoxy)phenyl)-2,2'-bithiophene))

To a solution of S105 (0.9 g, 1.12 mmol) in 100 mL of acetonitrile at RT was added potassium carbonate (1.56 g, 11.2 mmol). The resulting mixture was stirred for 0.5 h and 2-bromoethyl methyl ether (1.55 g, 11.2 mmol) was added. The reaction mixture was heated to reflux and stirred for 9 h. After completion, the mixture was poured into water (300 mL) and extracted with EtOAc. Organic solvents were removed under vacuum. The residue was purified by flash chromatography (hexanes—20% EtOAc). The yellow solid was obtained, sonicated in ether/methanol (10:1) and dried in vacuum to give 0.79 g (77%) of S104. $^1$H NMR (400 MHz, CDCl$_3$) δ 6.87 (d, J=8.7 Hz, 4H), 6.83 (d, J=3.6 Hz, 2H), 6.73-6.71 (m, 2H), 6.68 (t, J=7.7 Hz, 4H), 6.13 (s, 2H), 3.73 (d, J=4.4 Hz, 4H), 3.62 (dd, J=9.0, 4.3 Hz, 4H), 3.42 (d, J=7.2 Hz, 6H), 1.40 (d, J=4.7 Hz, 18H).

Example 57

Synthesis of S108

4,4''-(perfluorocyclopent-1-ene-1,2-diyl)bis(5'-(tert-butyl)-5-(4-(2-(2-(2-methoxyethoxy)ethoxy)ethoxy)phenyl)-2'',2'''-bithiophene (Scheme 67)

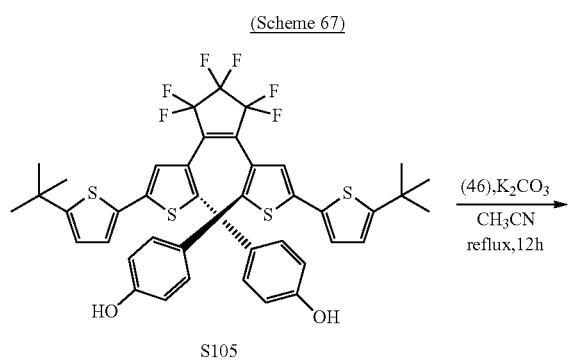

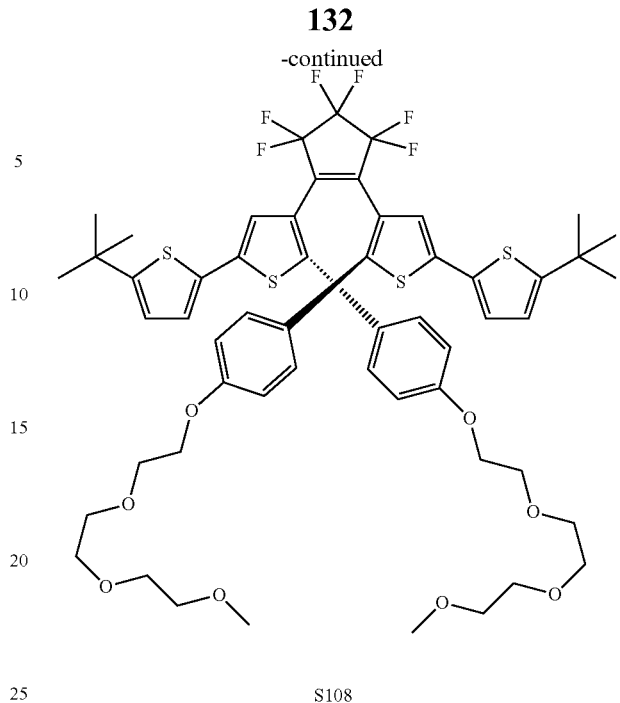

Synthesis of S108

Potassium carbonate (25 g, 180 mmol, 3 eq.) was added to a suspension of S105 (48.1 g, 60 mmol, 1 eq.) and 2-(2-(2-methoxyethoxy)ethoxy)ethyl 4-methylbenzenesulfonate (46) (38.2 g, 120 mmol, 2 eq.) in anhydrous acetonitrile (800 mL) under argon and the mixture was stirred overnight at reflux. The reaction was cooled and all solids were filtered off. The filtrate was concentrated and flash chromatography (CombiFlash, 20% EtOAC/hexanes to 60% EtOAc/hexanes) afforded S108 (44 g; 67%) as a thick dark blue oil. $^1$H NMR (500 MHz, CDCl$_3$) δ 6.86 (d, J=8.7 Hz, 4H), 6.82 (d, J=3.6 Hz, 2H), 6.71 (d, J=3.6 Hz, 2H), 6.67 (d, J=8.7 Hz, 4H), 6.12 (s, 2H), 3.72 (m, 12H), 3.64 (m, 8H), 3.55 (m, 4H), 3.38 (s, 6H), 1.40 (s, 18H).

Example 58

Synthesis of S106, S128 and S170

(Scheme 68)

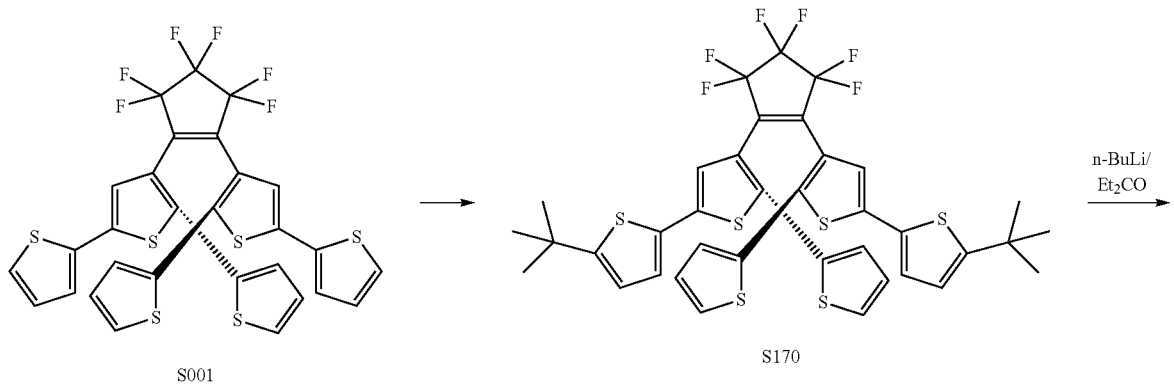

-continued

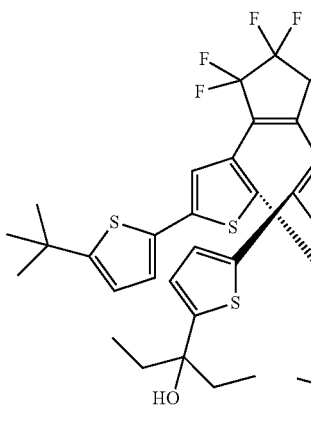

S106

+
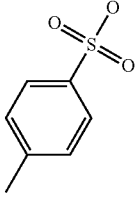

(103)

→ NaH

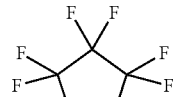

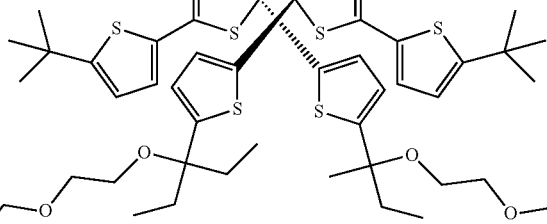

S128

Synthesis of S170

S170 4,4'-(perfluorocyclopent-1-ene-1,2-diyl)bis(5'-tert-butyl-5-(thiophenyl)-2,2'-bithiophene) was prepared on 17 mmol scale (78% yield) according to protocol E.

Synthesis of S106 (3,3'-(3',3''''-(perfluorocyclopent-1-ene-1,2-diyl)bis(5''-(tert-butyl)-[2,2':5',2''-terthiophene]-5,3'-diyl))bis(pentan-3-ol))

To a solution of S170 (6 g, 7.68 mmol) in THF (250 mL) at −35° C. was added n-BuLi (2.5 M in hexanes, 10 mL; 25 mmol). The mixture was stirred for 20 min. and the temperature reached −10° C. Di-ethyl ketone (2 g, 23 mmol) in THF (25 mL) was added to the reaction which was allowed to warm to RT and quenched with 10% HCl, extracted with ether/EtOAc. Organic solution was dried and evaporated. Column purification provided target di-alcohol (6.18 g, 6.48 mmol) in 84% yield as a slowly solidifying liquid. $^1$H NMR (400 MHz, CDCl$_3$) δ 6.90 (d, J=3.7 Hz, 2H), 6.76-6.72 (m, 2H), 6.60 (d, J=3.7 Hz, 2H), 6.56 (d, J=3.7 Hz, 2H), 6.44 (s, 2H), 1.72 (dd, J=14.1, 7.4 Hz, 4H), 1.62-1.55 (m, 4H+2H OH), 1.40 (s, 18H), 0.75 (t, J=7.4 Hz, 12H)

Synthesis of S128 (13,13'-(3',3''''-(perfluorocyclopent-1-ene-1,2-diyl)bis(5''-(tert-butyl)-[2,2':5',2''-terthiophene]-5,3'-diyl))bis(13-ethyl-3,6,9,12-tetraoxapentadecane)): NaH (0.1 g, 2.5 mmol, 60% dispersion in oil) was added to a solution of S106 (0.95 g, 0.997 mmol) in THF (50 mL) under argon. The reaction mixture was stirred for 0.25 h at RT. To resulting suspension was added a solution of (103) (0.73 g, 2.5 mmol) in anhydrous THF (10 mL) in one portion and the mixture was stirred for 1 h at RT and then refluxed for 2 h. Reaction was quenched by addition of saturated brine (100 mL) and extracted with ether. The organic layer was washed with water, dried over MgSO$_4$, filtered and evaporated to dryness. The residue was purified by column chromatography using a hexane/EtOAc gradient as the eluent to obtain S128 (0.446 g, 0.35 mmol; 35%) as thick dark green oil. $^1$H NMR (500 MHz, CDCl$_3$) δ 6.84 (t, J=4.3 Hz, 2H), 6.70 (d, J=3.6 Hz, 2H), 6.56 (d, J=3.6 Hz, 2H), 6.53-6.50 (m, 2H), 6.46 (s, 2H), 3.64 (dq, J=9.6, 3.7 Hz, 16H), 3.57 (qd, J=8.2, 3.4 Hz, 14H), 3.53-3.45 (m, 9H), 3.26 (dd, J=11.9, 6.8 Hz, 5H), 1.82-1.68 (m, 12H), 1.40 (d, J=5.9 Hz, 21H), 1.23-1.16 (m, 14H), 0.79-0.69 (m, 16H).

Example 59

Synthesis of S109

4,4''-(perfluorocyclopent-1-ene-1,2-diyl)bis(5'-(tert-butyl)-5-(4-(2-(2-(2-ethoxyethoxy)ethoxy)ethoxy)phenyl)-2,2'-bithiophene)

(Scheme 69)

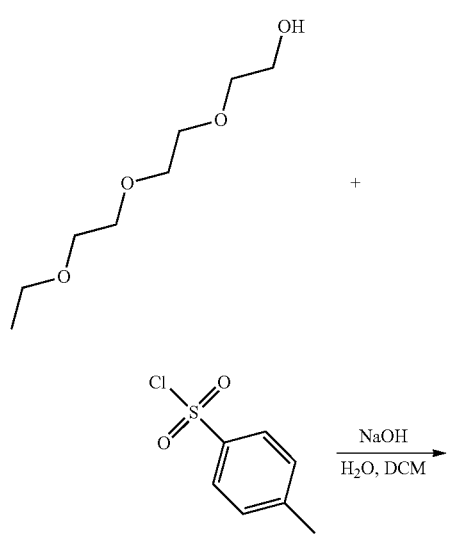

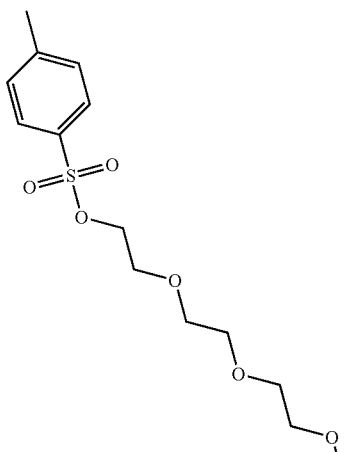

(103)

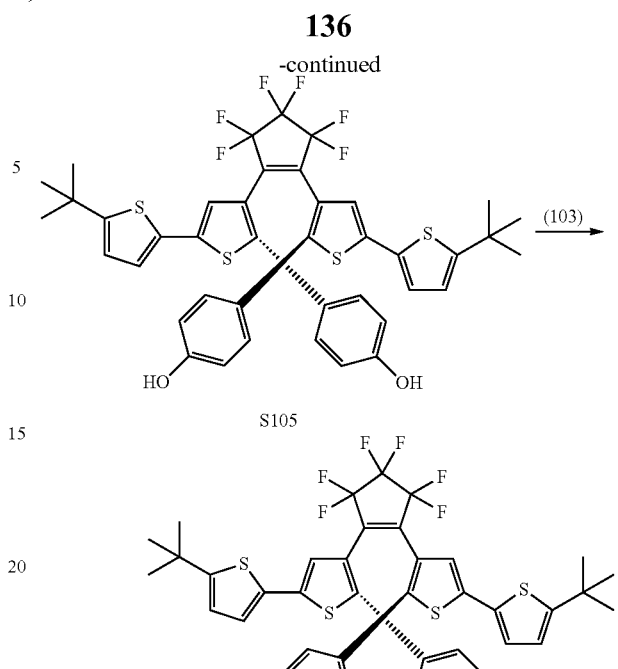

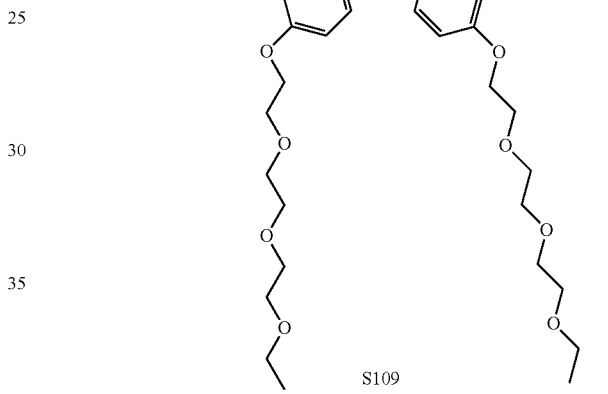

S109

Synthesis of 2-(2-(2-ethoxyethoxy)ethoxy)ethyl 4-methylbenzenesulfonate (103)

In a 3-neck, 2 L rbf, NaOH (135 g, 3.37 mol) was added slowly to water (1 L). After the addition was complete, the solution was cooled to room temperature and DCM (2 L) added, followed by triethylene glycol monoethyl ether (500 g, 2.81 mol). p-Toluenesulfonyl chloride (535 g, 2.81 mol) was added portion-wise over a period of 10 minutes, and the mixture refluxed for 2 hours. After cooling to room temperature, the reaction mixture was poured into water (2 L), mixed well and separated. The organic phase was washed with water (2×2 L), dried over MgSO$_4$, filtered and solvent removed by rotary evaporation. The resulting clear, colourless oil was stirred at room temperature with a 10% aqueous NaOH solution (1 L) to hydrolyze unreacted p-toluenesulfonyl chloride. After 18 hours, the material was poured into water (1 L), extracted with chloroform (500 mL) and separated. The organic portion was washed with water (2 L), 10% HCl (2 L) and water (2 L). The material was dried over anhydrous MgSO$_4$, filtered and solvent removed by rotavap to afford (103) as a clear, colourless oil (595 g, 64%).

Synthesis of S109

S105 (70.0 g, 80 mmol), potassium carbonate (44.2 g, 320 mmol) and potassium iodide (2.7 g, 16.0 mmol) in acetonitrile (1.2 L) was combined with (103) (55.8 g, 168 mmol) and the reaction heated to reflux for 16 hours. After cooling to RT, the material was filtered through a pad of celite, the filtrate washed with EtOAc (500 mL) and the combined organics were concentrated to dryness by rotary evaporation. The dried material was redissolved in DCM (500 mL) and dry-loaded onto silica gel, and purified by flash chromatography (Combiflash; 15% hexanes to 40% EtOAc/hexanes) to afford a dark green oil 70.0 g (78%). $^1$H NMR (500 MHz, CDCl$_3$) δ 6.86 (d, J=8.6 Hz, 4H), 6.82 (d, J=3.6 Hz, 2H), 6.71 (d, J=3.6 Hz, 2H), 6.67 (d, J=8.6 Hz, 4H), 6.12 (s, 2H), 3.77-3.64 (m, 20H), 3.61-3.57 (m, 4H), 3.52 (q, J=7.0 Hz, 4H), 1.40 (s, 18H), 1.21 (t, J=7.0 Hz, 6H)

Example 60

Synthesis of S110

2,2'-(4,4'-(perfluorocyclopent-1-ene-1,2-diyl)bis(5-(4-methoxyphenyl)thiophene-4,2-diyl))bis(benzo[b]thiophene)

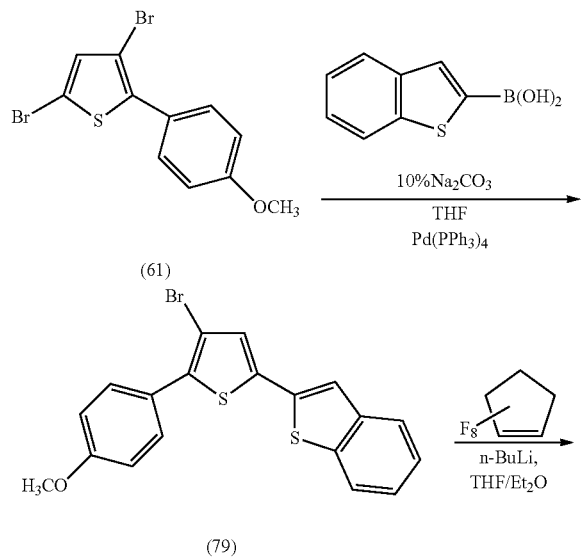

(Scheme 70)

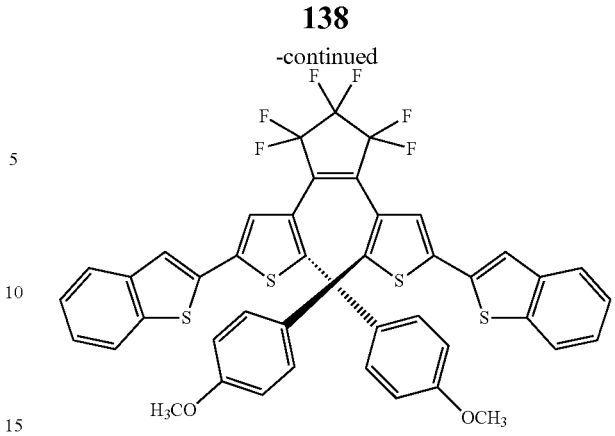

S110

Synthesis of 2-(4-bromo-5-(4-methoxyphenyl)thiophen-2-yl)benzo[b]thiophene (79): (79) was prepared from (61) on 24.2 mmol scale (56% yield) according to protocol D.

Synthesis of S110

S110 was prepared on 2.45 mmol scale (39% yield) according to protocol H3. $^1$H NMR (400 MHz, CDCl$_3$) δ 7.80 (d, J=7.7 Hz, 2H), 7.74 (d, J=7.1 Hz, 2H), 7.39-7.30 (m, 4H), 7.27 (s, 2H), 6.94 (d, J=8.7 Hz, 4H), 6.65 (d, J=8.7 Hz, 4H), 6.35 (s, 2H), 3.34 (s, 6H).

Example 61

Synthesis of 61

3,3'-(4,4'-(4,4'-(perfluorocyclopent-1-ene-1,2-diyl)bis(5'-tert-butyl-2,2'-bithiophene-5,4-diyl))bis(4,1-phenylene)bis(oxy))dipropan-1-ol (Scheme 71)

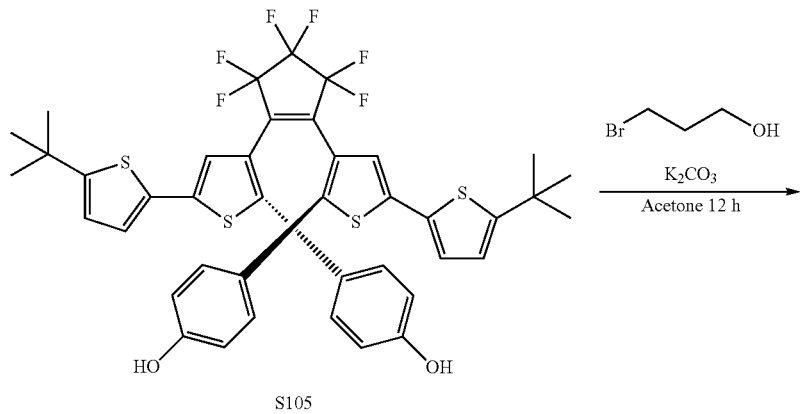

S105

-continued

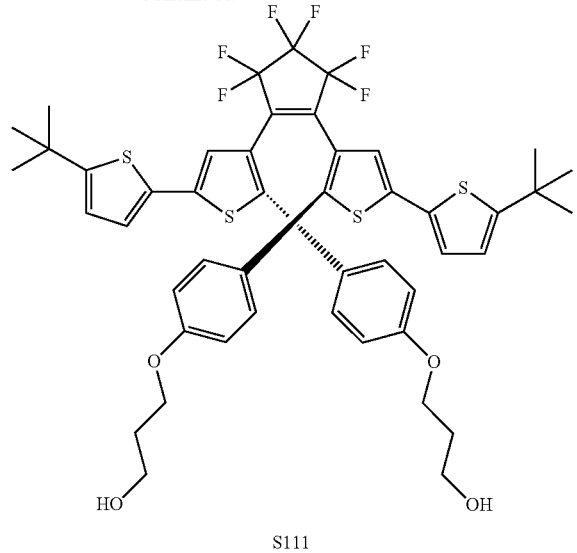

S111

To a solution of S105 (2 g, 2.5 mmol) in 100 mL of acetone at RT was added potassium carbonate (1.56 g, 11.2 mmol) and 18-crown-6 (6.6 g, 25 mmol). The resulting mixture was stirred for 0.5 h and 3-bromopropanol (1.4 g, 10 mmol) was added. The reaction mixture was heated to reflux and stirred for 9 h. After completion the mixture was poured into water (300 mL) and extracted with hexanes. Organic solvents were removed under vacuum. The residue was purified by flash chromatography (hexanes—40% EtOAc). Two dark green oils were obtained and dried in vacuum. The top one solidified by addition of small amount of chloroform and was sonicated in hexanes/ether mixture (5:1). The light yellow solid was then filtered and dried in air to give 1.46 g of S11. Yield 41%. $^1$H NMR (400 MHz, CDCl$_3$) δ 6.90-6.86 (m, 4H), 6.83 (d, J=3.6 Hz, 2H), 6.73 (d, J=3.6 Hz, 2H), 6.69-6.65 (m, 4H), 6.14 (s, 2H), 3.83-3.75 (m, 8H), 1.93 (p, J=5.9 Hz, 4H), 1.41 (s, 17H).

Example 62

Synthesis of S112

4,4'-((4,4''-(perfluorocyclopent-1-ene-1,2-diyl)bis(5'-(tert-butyl)-[2,2'-bithiophene]-5,4-diyl))bis(4,1-phenylene))dimorpholine (Scheme 72)

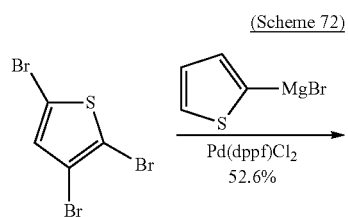

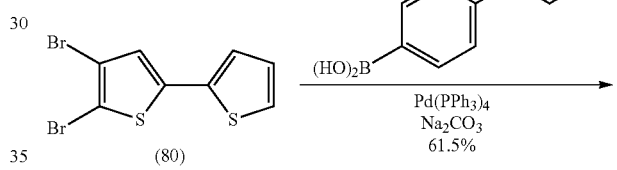

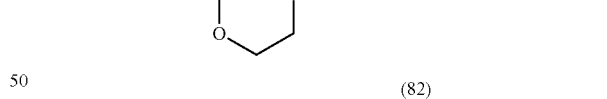

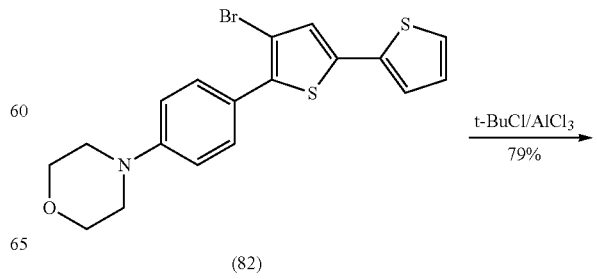

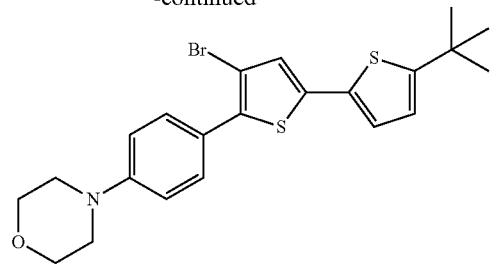

(83)

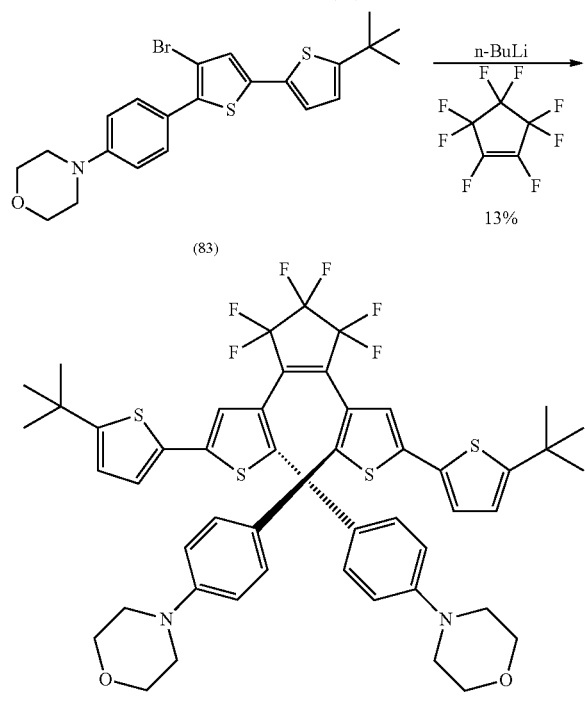

S112

Synthesis of 4,5-dibromo-2,2'-bithiophene (80)

(80) was prepared on 20.3 mmol scale (53% yield) according to protocol B. $^1$H NMR (400 MHz, CDCl$_3$) δ 7.27 (dd, J=5.5, 1.5 Hz, 1H), 7.13 (dd, J=3.6, 1.1 Hz, 1H), 7.02 (dd, J=5.1, 3.6 Hz, 1H), 6.97 (s, 1H).

Synthesis of 4-(4-(4-bromo-[2,2'-bithiophen]-5-yl)phenyl)morpholine (82)

(82) was prepared on 25.3 mmol scale (62% yield) according to protocol D. $^1$H NMR (400 MHz, CDCl$_3$) δ 7.60 (d, J=9.0 Hz, 2H), 7.25 (dd, J=5.1, 1.1 Hz, 1H), 7.17 (dd, J=3.6, 1.1 Hz, 1H), 7.10 (s, 1H), 7.03 (dd, J=5.1, 3.6 Hz, 1H), 6.95 (d, J=8.9 Hz, 2H), 3.93-3.85 (m, 4H), 3.27-3.20 (m, 4H).

Synthesis of 4-(4-(4-bromo-5'-(tert-butyl)-[2,2'-bithiophen]-5-yl)phenyl) morpholine (83)

(83) was prepared on 23 mmol scale (79% yield) according to protocol E. $^1$H NMR (400 MHz, CDCl$_3$) δ 7.59 (d, J=8.9 Hz, 2H), 7.02 (s, 1H), 6.97 (d, J=3.6 Hz, 1H), 6.94 (d, J=8.9 Hz, 2H), 6.74 (d, J=3.7 Hz, 1H), 3.90-3.85 (m, 4H), 3.25-3.21 (m, 4H), 1.40 (s, 9H).

Synthesis of S112

S112 was prepared on 1.38 mmol scale (13% yield) according to protocol G. $^1$H NMR (400 MHz, CDCl$_3$) δ 6.86 (d, J=8.7 Hz, 2H), 6.84 (d, J=3.6 Hz, 1H), 6.72 (d, J=3.6 Hz, 1H), 6.62 (d, J=8.7 Hz, 2H), 6.12 (s, 1H), 3.77-3.70 (m, 4H), 2.88-2.83 (m, 4H), 1.41 (s, 9H).

Example 63

Synthesis of S113 and S11

(Scheme 73)

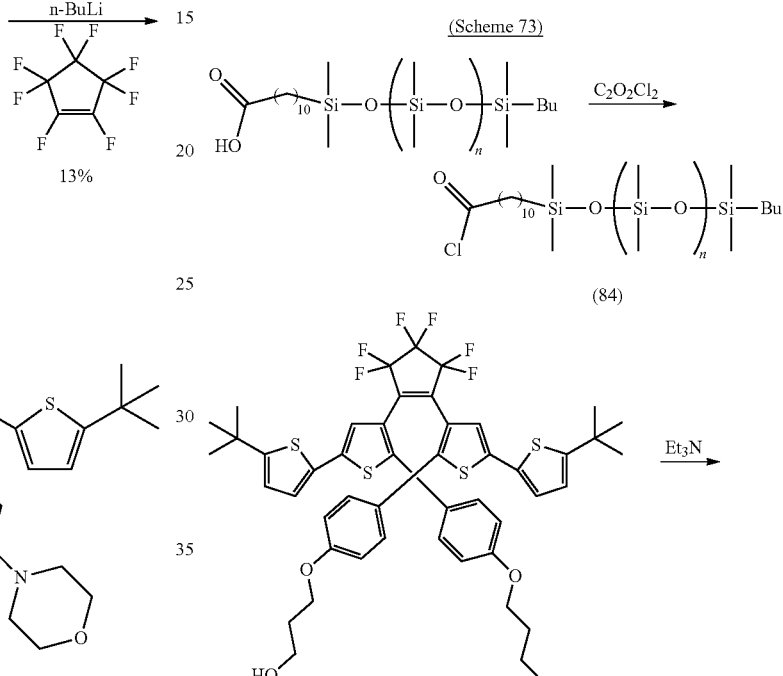

(84)

S111

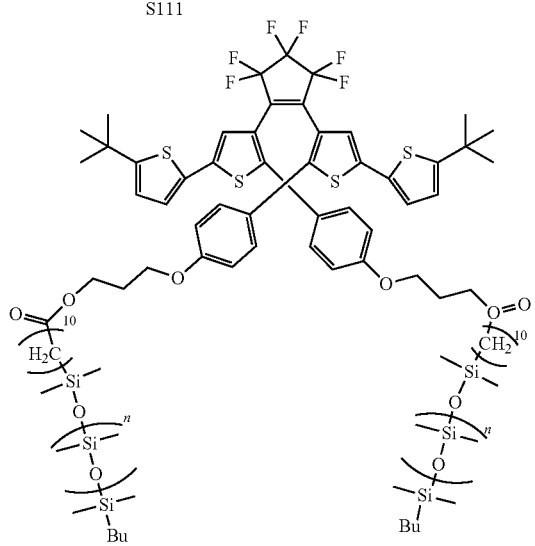

n = 3-5 for S113
n = 13-15 for S115

Synthesis of carboxylic acid chloride terminated poly(dimethylsiloxane) (84)

Carboxylic acid terminated poly(dimethylsiloxane) (15 g, ca. 10 mmol) was dissolved in dry DCM (100 mL) under nitrogen and a small drop of DMF was added. To the mixture was added oxalyl chloride (6 mL) in one portion. The mixture was stirred at RT for no more than 30 min. The solvent and excess reagent were removed under vacuum and residual traces of oxalyl chloride were removed with the aid of evaporation of 1,2-dichloroethane. The acid chloride product (84) was used immediately.

Syntheses of S113 and S115

S111 (4.1 g, 4.47 mmol) was dissolved in dry DCM (150 mL) followed by the addition of triethylamine (1.2 g, 1.6 mL, 11.7 mmol), under argon. Acid chloride end-functionalized PDMS (84) was then added dropwise in 1,2-dichloroethane (10 mmol) and the mixture was left to stir at RT overnight. The solvent was then removed under vacuum, the residue re-dissolved in diethyl ether-hexane (1:1) and the mixture filtered through a plug of silica gel. The solvent was removed and the remaining oily residue was purified by column chromatography (silica gel, hexanes:EtOAc 8:1) to give the pure PDMS conjugate as a viscous oil: fraction 1 (S115)-17 g; fraction 2 (S113)-1.4 g. S113: $^1$H NMR (400 MHz, CDCl$_3$) δ 6.90-6.85 (m, 4H), 6.82 (d, J=3.6 Hz, 2H), 6.72 (d, J=3.6 Hz, 2H), 6.68-6.62 (m, 4H), 6.13 (s, 2H), 4.20 (t, J=6.4 Hz, 4H), 3.71 (t, J=5.9 Hz, 4H), 2.30 (t, J=7.5 Hz, 4H), 2.04-1.94 (m, 5H), 1.68-1.51 (m, 10H), 1.40 (s, 18H), 1.31-1.19 (m, 30H), 0.91-0.84 (m, 7H), 0.07 (d, J=3.5 Hz, 25H).

Example 64

Synthesis of S118

(Scheme 74)

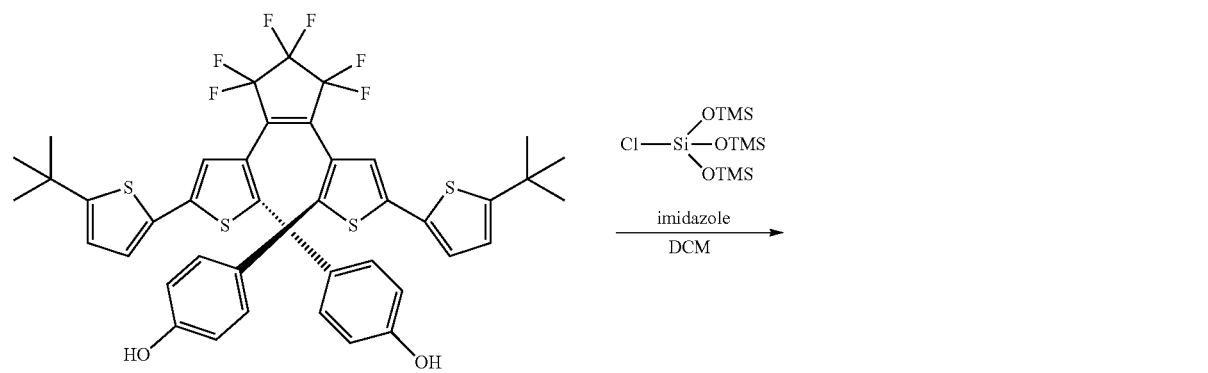

S105

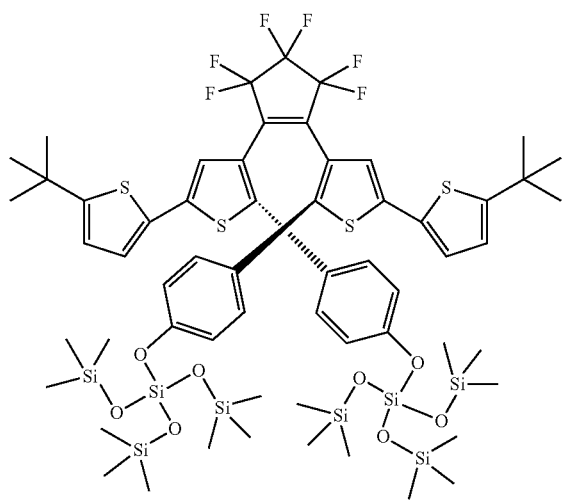

S118

Synthesis of S118

In a 100 mL rbf equipped with a stirbar, S105 (0.99 g, 1.24 mmol) and imidazole (0.37 g, 5.44 mmol) were dissolved in DCM (50 mL). Tris(OTMS)chlorosilane (1.7 mL) was added and an immediate white precipitate was observed. The reaction mixture was allowed to stir at RT for 10 minutes, then poured into water (200 mL), mixed well and separated. The aqueous phase was extracted with DCM (50 mL) and the combined organics were washed with water (250 mL), dried over $MgSO_4$, filtered and solvent removed by rotary evaporation. The resulting oil was sonicated in MeOH (50 mL) until a fine yellow powder precipitated, which was filtered and air-dried, 1.20 g (70%) $^1$H NMR (400 MHz, $CDCl_3$) δ 6.86-6.81 (m, 6H), 6.75-6.69 (m, 6H), 6.14 (s, 2H), 1.40 (s, 18H), 0.11 (s, 54H).

Example 65

Synthesis of S119 and S124

Bromination of S170

To the solution of S170 (1.06 g; 1.357 mmol) in the mixture of acetic acid (30.0 mL) and DCM (30.0 mL) was added at stirring bromine (0.434 g; 2.71 mmol) as a solution in DCM (20 mL). The mixture was stirred at RT for 20 min (TLC). DCM was evaporated The product which started to precipitate from acetic acid was poured into water and filtered off, washed with water and dried in air to give 1.26 g (1.34 mmol; 99% yield) of non-separable mixture of two compounds (85) and (86). The mixture was used in the next step.

Synthesis of S119+S124

To the solution of the mixture from bromination step (2.75 g, 2.93 mmol) in ether (150 mL) was added at stirring n-BuLi (2.58 mL; 6.45 mmol) as a solution in hexane at −74° C. The mixture was stirred for 20 min (TLC). Dry ice was rinsed with ether and added to the cold reaction which was allowed to warm to RT and quenched with 10% HCl, extracted with ether/EtOAc. Organic solution was dried and evaporated. Column purification provided target S119 (0.75 g, 0.86 mmol) in 46% yield. S124 was isolated in 35% yield (0.6 g, 0.66 mmol). S119: $^1$H NMR (400 MHz, DMSO) δ 13.17 (s,

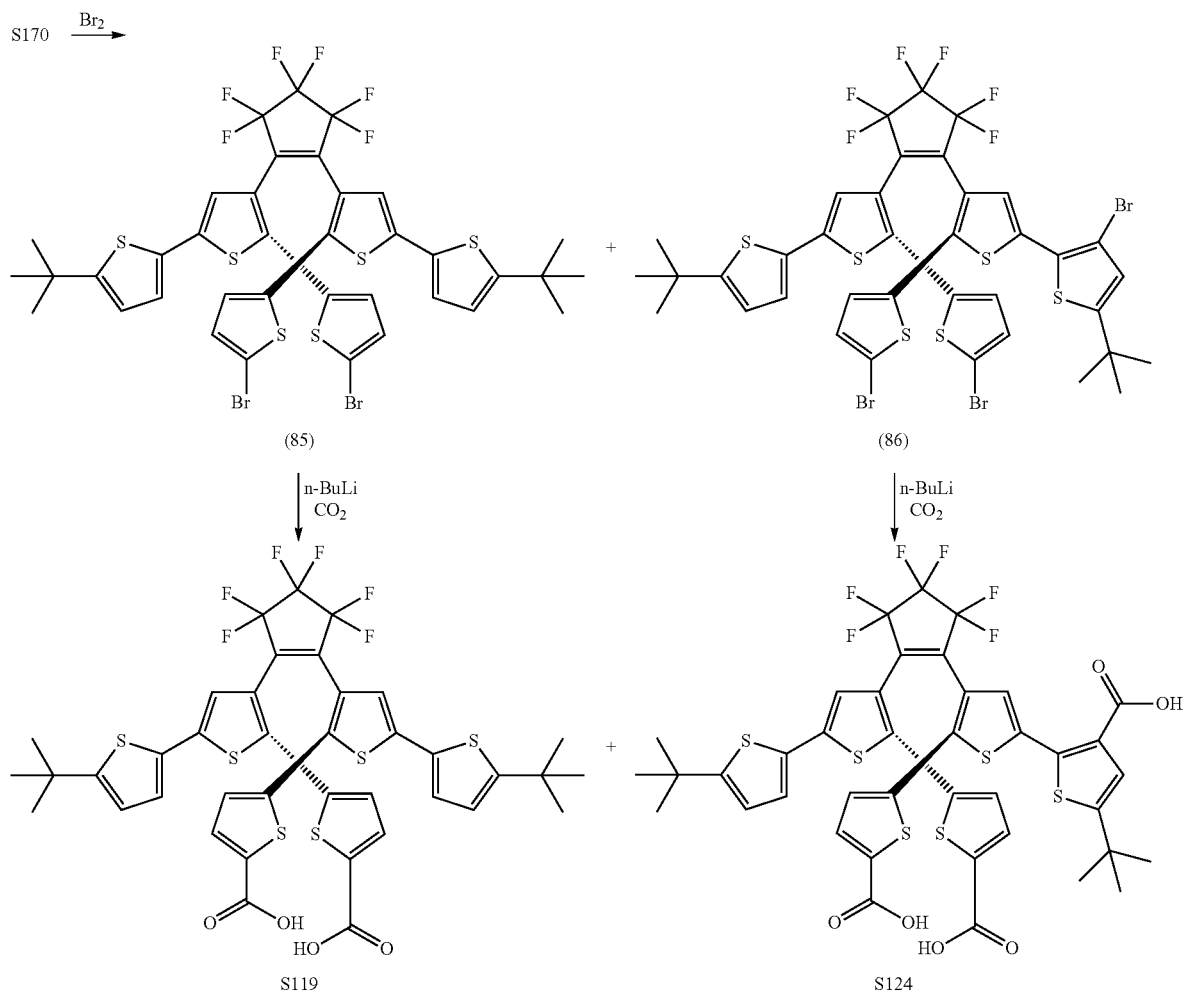

(Scheme 75)

2H), 7.43 (d, J=3.7 Hz, 2H), 7.06 (d, J=3.7 Hz, 2H), 6.85 (d, J=3.7 Hz, 2H), 6.82 (d, J=3.7 Hz, 2H), 6.40 (s, 2H), 1.38 (s, 18H). S124: $^1$H NMR (400 MHz, DMSO) δ 13.14 (s, 3H), 7.48 (d, J=3.8 Hz, 1H), 7.43 (d, J=3.8 Hz, 1H), 7.19-7.13 (m,

1H), 7.05 (d, J=3.7 Hz, 1H), 6.83 (dd, J=6.0, 3.8 Hz, 3H), 6.73 (s, 1H), 6.38 (s, 1H), 1.38 (d, J=3.8 Hz, 9H), 1.37 (s, 9H).

Example 66

Synthesis of S135

3',3''''-(perfluorocyclopent-1-ene-1,2-diyl)bis(5,5''-bis(trimethylsilyl)-2,2':5',2''-terthiophene) (Scheme 76)

Lithium diisopropylamide (LDA) was made by addition of BuLi (3.21 mL, 8.03 mmol) to a solution of diisopropylamine (1.158 mL, 8.21 mmol) in anhydrous THF (8 mL) at 0° C. and the solution stirred at this temperature for 30 min. The LDA solution was then added to a solution of S001 (1.22 g, 1.824 mmol) in THF (12 mL) at 0° C. The reaction mixture was stirred at 0° C. for 30 min then cooled to −78° C. and chlorotrimethylsilane (1.389 mL, 10.94 mmol) added. The reaction mixture was stirred with warming to RT over 2 h and stirred at RT for 18 h. The reaction was quenched by addition of water (10 mL). Organics were extracted with diethyl ether (2×30 mL), washed with brine (10 mL), dried over MgSO$_4$, filtered and concentrated under reduced pressure. The crude product was purified by column chromatography on silica gel eluting with hexanes to yield the title compound as a yellow solid (1.0 g, 57%). $^1$H NMR (400 MHz, CDCl$_3$) δ 7.11 (d, J=3.4 Hz, 1H), 7.09 (d, J=3.4 Hz, 1H), 6.86 (d, J=3.4 Hz, 1H), 6.70 (d, J=3.4 Hz, 1H), 6.37 (s, 1H), 0.34 (s, 9H), 0.15 (s, 9H).

Example 67

Synthesis of S137

3,3'-(perfluorocyclopent-1-ene-1,2-diyl)bis(2-(5-methylthiophen-2-yl)benzofuran)

(Scheme 77)

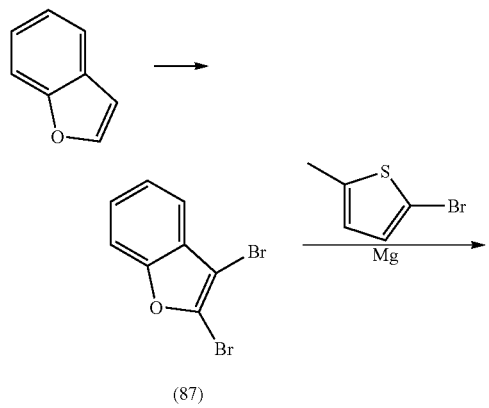

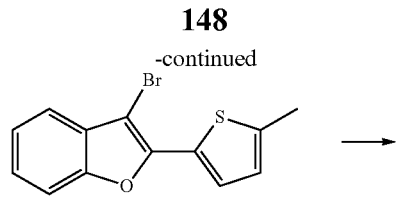

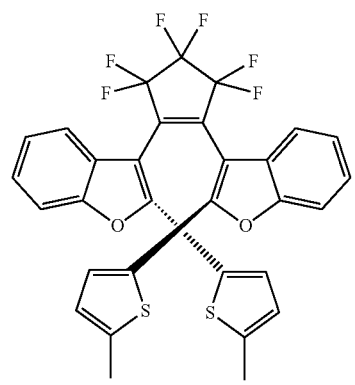

S137

Synthesis of 2,3-dibromobenzofuran (87)

To a stirred DCM solution (200 mL) containing benzofuran (24 g, 203 mmol) and potassium acetate (40 g, 408 mmol) 64.9 g of bromine (406 mmol) was slowly added at 20° C. as a solution in DCM (100 mL). The reaction mixture was stirred overnight at RT, poured into sodium thiosulfate solution and extracted with DCM. The organic layer was dried over anhydrous MgSO$_4$, and the solution was evaporated. CombiFlash chromatography (hexanes) gave 33.6 g of the target product in 60% isolated yield.

Synthesis of 3-bromo-2-(5-methylthiophen-2-yl)benzofuran (88)

(88) was prepared on 41.8 mmol scale (96% yield) according to protocol B.

Synthesis of S137

S137 was prepared on 4.6 mmol scale (33% yield) according to protocol H3. $^1$H NMR (400 MHz, CDCl$_3$) δ 7.34-7.28 (m, 4H), 7.24-7.18 (m, 2H), 7.11 (dd, J=11.2, 4.2 Hz, 2H), 6.77 (d, J=3.6 Hz, 2H), 6.25 (d, J=3.4 Hz, 2H), 2.17 (s, 6H).

Example 68

Synthesis of S138

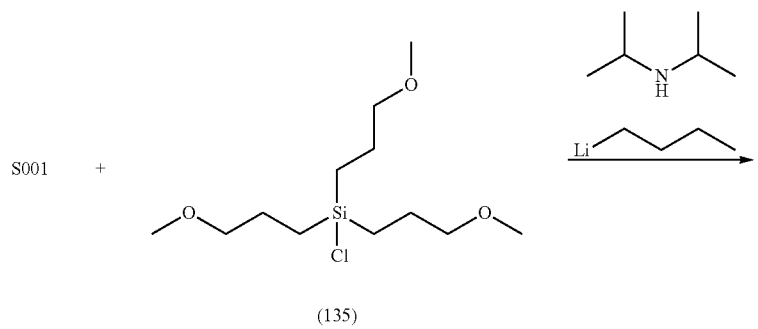

(Scheme 78)

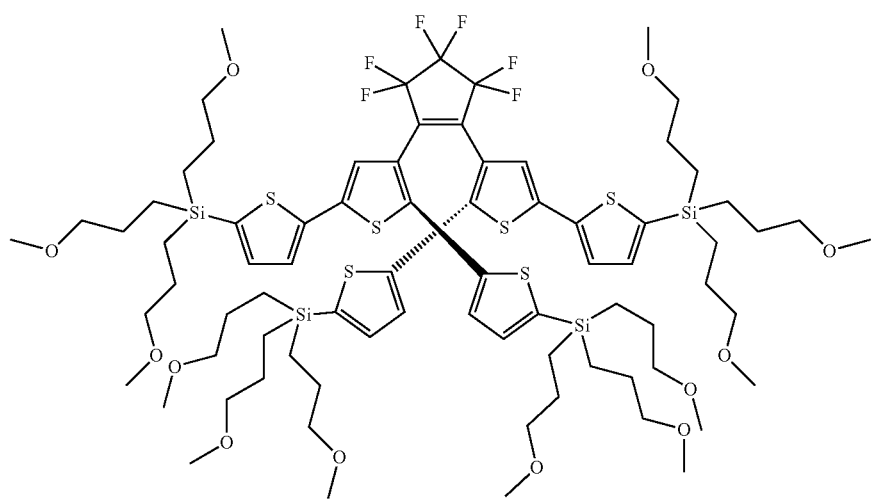

S138

3.43 g of S001 (0.75 mmol) in THF (100 mL) at −20° C. was added a solution of n-BuLi (9.4 mL, 23.3 mmol. 4.5 equiv) and stirred at −20° C. for 10 min, followed by addition of (135) (6.6 g, 23.3 mmol) in THF (50 mL). The reaction mixture was stirred for 1 h, warmed to room temperature and quenched by addition of water (30 mL). Organics were extracted with ether (2×100 mL), washed with brine (100 mL) and concentrated under reduced pressure. Flash chromatography (hexanes/ethyl acetate) afforded S138 (1.2 g, 14%). $^1$H NMR (400 MHz, CDCl$_3$) δ 7.15-7.12 (m, 2H), 7.12-7.09 (m, 2H), 6.88 (d, J=3.4 Hz, 2H), 6.70 (d, J=3.4 Hz, 2H), 6.40 (s, 2H), 3.38-3.28 (m, 60H), 1.69-1.62 (m, 12H), 1.56 (m, 12H), 0.91-0.82 (m, 12H), 0.75-0.68 (m, 12H).

Example 69

Synthesis of S139

5,5'-(((4,4''-(perfluorocyclopent-1-ene-1,2-diyl)bis(5'-(tert-butyl)-[2'',2'''-bithiophene]-5'',4-diyl))bis(4,phenylene))bis(oxy))dipentanenitrile (Scheme 79)

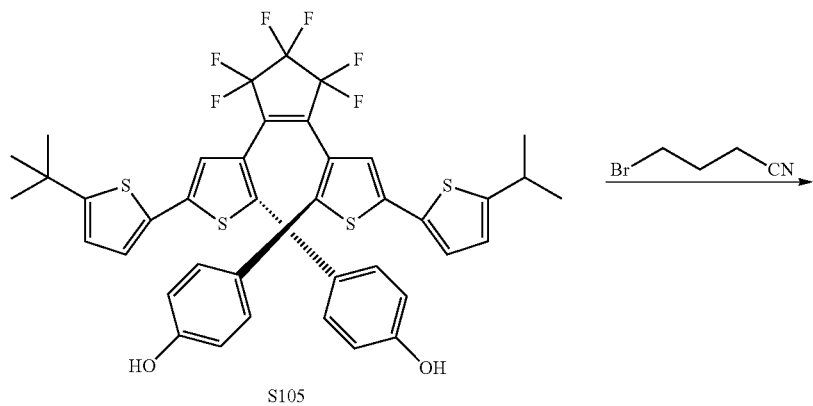

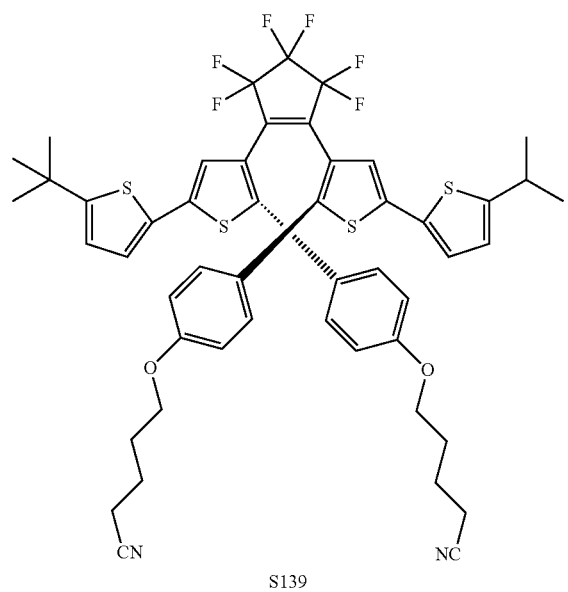

Synthesis of S139

In a 500-mL 3-neck rbf, 10 g of the S105 (12.49 mmol, 1 eq.) and 415 mg of potassium iodide (2.497 mmol, 0.2 eq.) were dissolved in 250 mL of acetonitrile at RT under argon. To this, 5-bromovaleronitrile (3.21 mL, 4.45 g, 27.5 mmol, 2.2 eq.) was added in one portion and the reaction mixture was heated to reflux. Upon dissolution of S105, potassium carbonate (6.90 g, 49.9 mmol, 4 eq.) was added and the mixture was stirred for 16 hr at reflux. The reaction mixture was allowed to cool to RT, and filtered through a fritted funnel. The product was re-dissolved in DCM and deposited on silica gel and purified by column chromatography (Combi Flash Rf (120 g gold column). $^1$H NMR (400 MHz, CDCl$_3$) δ 6.88 (d, J=8.7 Hz, 4H), 6.83 (d, J=3.6 Hz, 2H), 6.73 (d, J=3.7 Hz, 2H), 6.65 (d, J=8.7 Hz, 4H), 6.13 (s, 2H), 3.64 (m, 4H), 2.42 (t, J=6.6 Hz, 4H), 1.89-1.76 (m, 8H), 1.41 (s, 18H).

Example 70

Synthesis of S140

3,3'-(perfluorocyclopent-1-ene-1,2-diyl)bis(6-methoxy-2-(4-methoxyphenyl)benzofuran)

(Scheme 80)

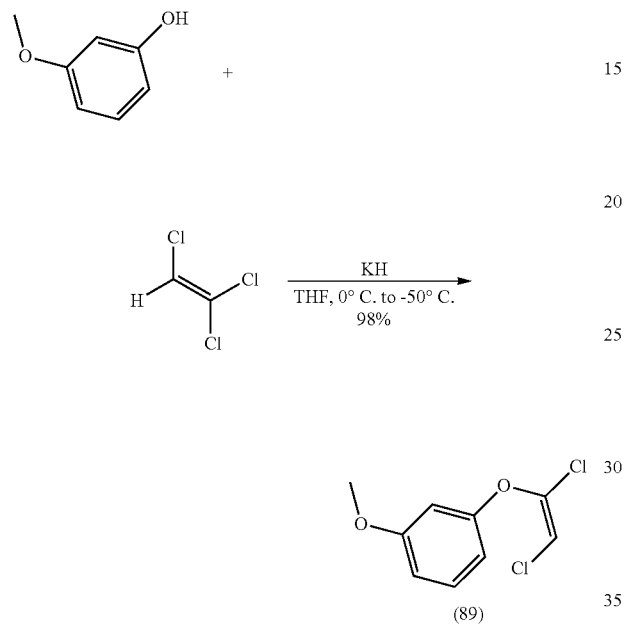

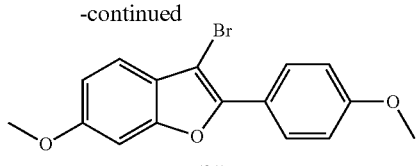

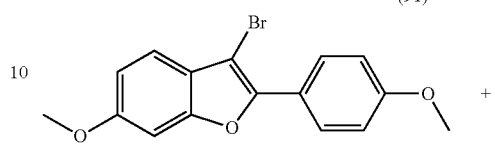

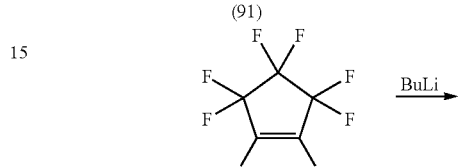

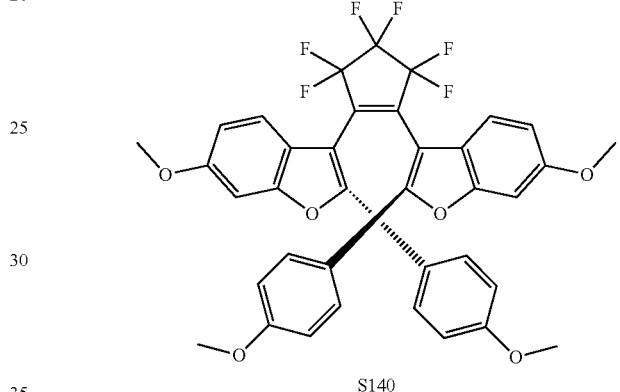

Synthesis of (E)-1-((1,2-dichlorovinyl)oxy)-3-methoxybenzene (89)

(89) was prepared on 1461 mmol scale (97%) yield according to protocol I to give (E)-1-((1,2-dichlorovinyl)oxy)-3-methoxybenzene (19.5 g, 89 mmol, 73.7% yield) as colorless oil.

Synthesis of 6-methoxy-2-(4-methoxyphenyl)benzofuran (90)

(90) was prepared on 28.4 mmol scale (62.2%) yield according to protocol J, using olefin (89) to provide 6-methoxy-2-(4-methoxyphenyl)benzofuran (7.22 g, 28.4 mmol, 62.2% yield).

Synthesis of 3-bromo-6-methoxy-2-(4-methoxyphenyl)benzofuran (91)

91) was prepared on 21 mmol scale (74%) yield according to protocol F4.

Synthesis of S140

S140 was prepared on 0.74 mmol scale (16% yield) according to protocol H2. $^1$H NMR (500 MHz, CDCl$_3$) δ 7.05

(d, J=8.7 Hz, 2H), 7.00 (d, J=8.7 Hz, 4H), 6.81 (d, J=2.2 Hz, 2H), 6.68 (dd, J=8.7, 2.3 Hz, 2H), 6.45 (d, J=8.7 Hz, 4H), 3.83 (s, 6H), 3.63 (s, 6H).

Example 71

Synthesis of S141

5,5'-(4,4'-(4,4'-(perfluorocyclopent-1-ene-1,2-diyl)bis(5'-tert-butyl-2,2'-bithiophene-5,4-diyl))bis(4,1-phenylene)bis(oxy))dipentanoic acid

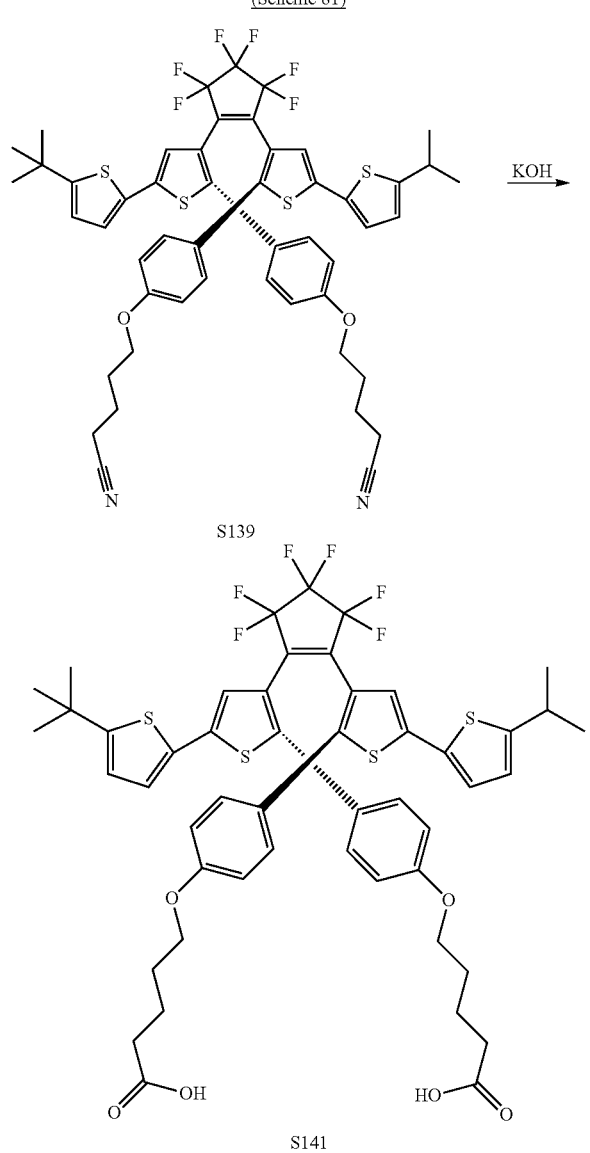

S139

S141

Synthesis of S141

A suspension of S139 (7.3 g, 7.58 mmol) and KOH (8.76 g, 152 mmol) in a water ethanol mixture (1:1; 150 mL) was heated at reflux for two weeks. The solution was allowed to cool to RT, and the mixture was concentrated under reduced pressure. The aqueous suspension was diluted with 200 mL of water, extracted with ether, and then acidified with 6 N HCl. a solid formed and was filtered off, washed with water and dried, then sonicated in ether/hexanes and filtered. The yellow solid was dried under vacuum to give 5.8 g (76%) of pure S141. $^1$H NMR (400 MHz, CDCl$_3$) δ 6.87 (d, J=8.4 Hz, 4H), 6.82 (d, J=3.4 Hz, 2H), 6.72 (d, J=3.4 Hz, 2H), 6.65 (d, J=8.4 Hz, 4H), 6.13 (s, 2H), 3.64 (s, 4H), 2.43 (d, J=6.6 Hz, 4H), 1.76 (s, 8H), 1.40 (s, 18H).

Example 72

Synthesis of S143

3,3'''-(perfluorocyclopent-1-ene-1,2-diyl)bis(5,5''-di-tert-butyl-2,2':5',2''-terthiophene)

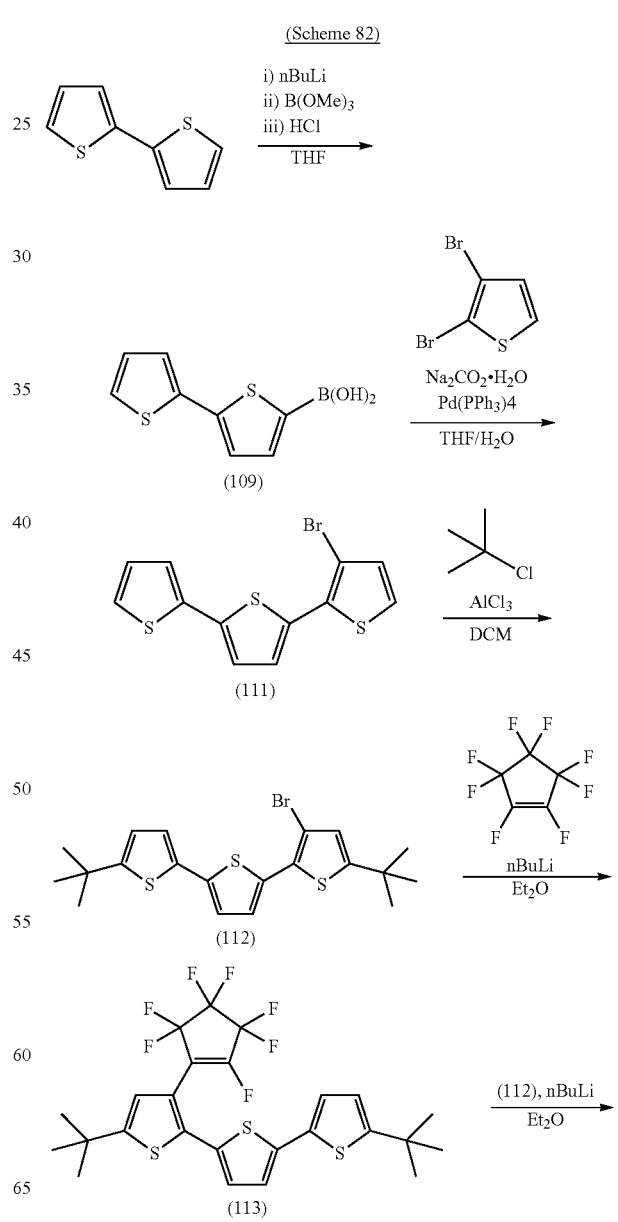

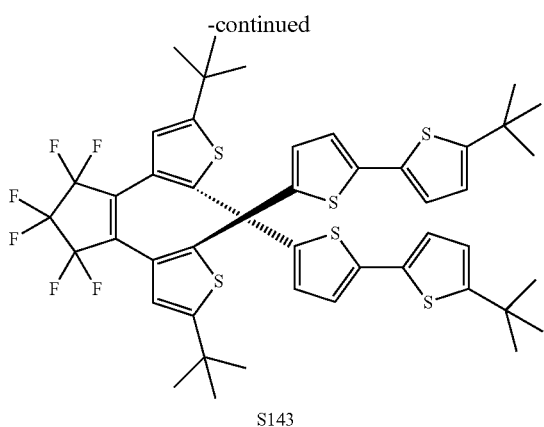

S143

Synthesis of (2,2'-bithiophen)-5-yl-boronic acid (109)

In a flame-dried, 3-neck, 250 mL rbf, 2,2'-bithiophene (5.0 g, 30.1 mmol) was dissolved in anhydrous THF (100 mL) and cooled to −78° C. (dry ice/acetone). A solution of n-BuLi in hexanes (2.5 M, 12.6 mL, 31.6 mmol) was added slowly over a period of ~5 minutes. The reaction mixture was allowed to stir at −78° C. for 15 minutes, and then trimethyl borate (10.1 mL, 90 mmol) was added dropwise over a period of 5 minutes. The reaction was allowed to stir at −78° C. for 2 hours, then warm to RT and stir for a further 1 hour. The yellow reaction mixture was quenched by pouring it into a 10% HCl solution (250 mL). The mixture was extracted with ether (2×100 mL) and the combined organic portions were washed with water (500 mL), dried over MgSO$_4$, filtered and solvent removed by rotary evaporation. The resulting yellow solid was washed with water, filtered and air dried to afford (109) (6.15 g, 97%). The material was used in the next step without further purification.

Synthesis of 3-bromo-2,2':5',2''-terthiophene (111)

(111) was prepared on 21.6 mmol scale (37% yield) according to protocol D.

Synthesis of 3-bromo-5,5''-di-t-butyl-2,2':5',2''-terthiophene (112)

(112) was prepared on 3.66 mmol scale (98% yield) according to protocol E.

Synthesis of 5,5''-di-tert-butyl-3-(perfluorocyclopent-1-en-1-yl)-2,2':5',2''-terthiophene (113)

In a flame-dried, 1 L rbf, 3-bromo-5,5''-di-t-butyl-2,2':5',2''-terthiophene (112, 4 g, 9.10 mmol) was dissolved in anhydrous diethyl ether (400 mL) and cooled to −48° C. (dry ice/acetone). n-BuLi (2.5 M in hexanes, 1.5 mL, 3.82 mmol) was added dropwise over a period of 5 minutes. The resulting yellow solution was allowed to stir for 20 minutes, then octafluorocyclopentene (0.24 mL, 1.82 mmol) was added in one portion. The reaction mixture warmed to −45° C. The reaction mixture was allowed to mix and slowly warm to 5° C., and then was poured into water (300 mL) and mixed well, then acidified with 10% HCl (100 mL). The aqueous phase was separated and extracted with EtOAc (2×100 mL). The combined organics were washed with water (500 mL), dried over MgSO$_4$, filtered and solvent removed by rotary evaporation. The resulting dark orange oil was redissolved in chloroform and dry-loaded onto silica gel. Flash chromatography (hexanes) afforded a yellow oil, which was sonicated in methanol, filtered and air dried to afford 113 as a bright yellow, powdery solid (3.62 g, 72%).

Synthesis of S143

S143 was prepared on 1.90 mmol scale (42% yield) according to protocol H1. $^1$H NMR (400 MHz, CDCl$_3$) δ 6.90 (d, J=3.7 Hz, 2H), 6.84 (d, J=3.7 Hz, 2H), 6.71 (d, J=3.7 Hz, 2H), 6.55 (d, J=3.7 Hz, 2H), 6.27 (s, 2H), 1.39 (s, 18H), 1.14 (d, J=6.1 Hz, 18H).

Example 73

Synthesis of S144

33'-(perfluorocyclopent-1-ene-1,2-diyl)bis(6-methoxy-2-(5-methylthiophen-2-yl)benzofuran)

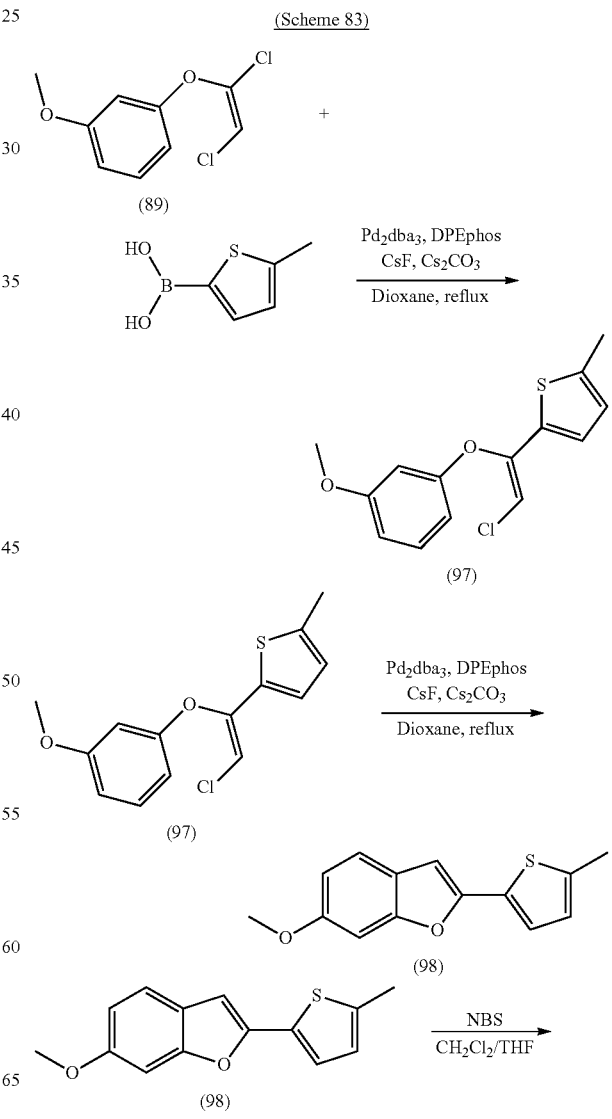

-continued

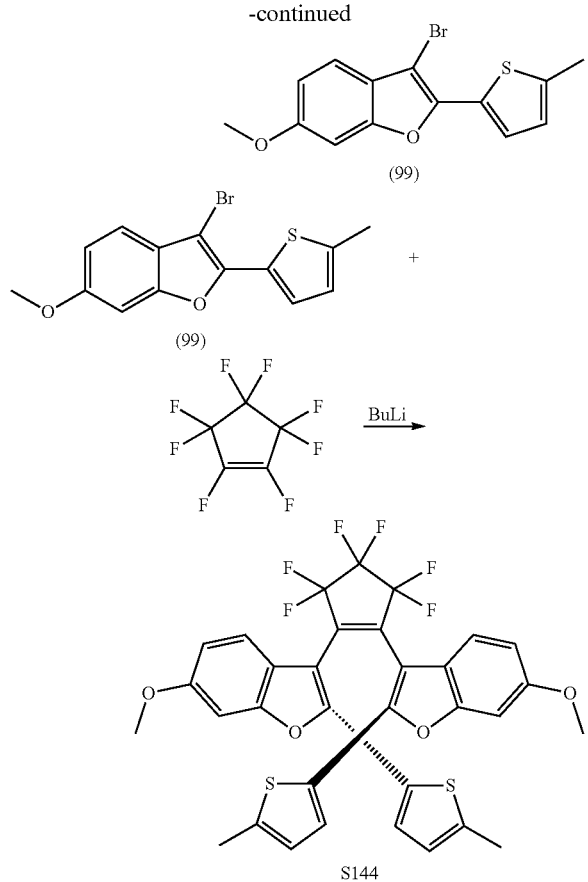

Synthesis of (Z)-2-(2-chloro-1-(3-methoxyphenoxy)vinyl)-5-methylthiophene (97)

(97) was prepared on 21.01 mmol scale (48.5%) yield according to protocol J.

Synthesis of 6-methoxy-2-(5-methylthiophen-2-yl)benzofuran (98)

(Z)-2-(2-chloro-1-(3-methoxyphenoxy)vinyl)-5-methylthiophene (97) (4.7 g, 16.74 mmol), Pd$_2$dba$_3$ (0.178 g, 0.399 mmol), (oxybis(2,1-phenylene))bis(diphenylphosphine) (0.429 g, 0.797 mmol), cesium fluoride (7.27 g, 47.8 mmol) and cesium carbonate (15.58 g, 47.8 mmol) were placed into a 250-mL three-neck rbf, sealed with a septum and purged with argon for 20-30 minutes. 100 mL dioxane was added. The solution was vigorously stirred and brought to reflux for 18 hours and cooled. The layers were separated and the aqueous layer was extracted with DCM once more. The combined organic layers were washed with brine, dried with anhydrous MgSO$_4$, filtered and concentrated. The product was purified by column to provide (98) (3.38 g, 13.83 mmol, 87% yield).

Synthesis of 3-bromo-6-methoxy-2-(5-methylthiophen-2-yl)benzofuran (99)

(99) was prepared on 13.5 mmol scale (100% yield) according to protocol F4.

Synthesis of S144

S144 was prepared on 1.3 mmol scale (19% yield) according to protocol H3. $^1$H NMR (400 MHz, CDCl$_3$) δ 7.16 (d, J=8.7 Hz, 2H), 6.85 (d, J=2.2 Hz, 2H), 6.75 (dd, J=8.8, 2.3 Hz, 2H), 6.72 (d, J=3.6 Hz, 2H), 6.27 (dd, J=3.5, 1.0 Hz, 2H), 3.83 (s, 6H), 2.19 (s, 6H).

Example 74

Synthesis of S148

4',4''''-(perfluorocyclopent-1-ene-1,2-diyl)bis(3,4,4'',5,5''-pentamethyl-2,2':5',2''-terthiophene)

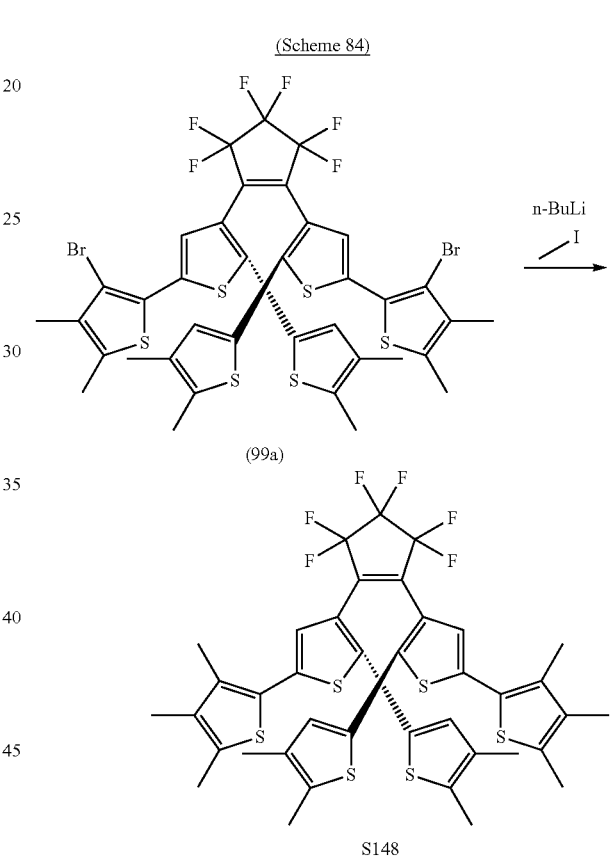

Synthesis of 4',4''''-(perfluorocyclopent-1-ene-1,2-diyl)bis(3-bromo-4,4'',5,5''-tetramethyl-2,2':5',2''-terthiophene) (99a)

To a solution of S011 (0.56 g, 0.78 mmol) in dry DCM at −20° C. was added a solution of bromine (0.23 g, 1.437 mmol). The mixture was stirred at RT for 5 h, washed with water and extracted with ether. The organic layer was separated and the solvent removed by rotary evaporation. The residue was sonicated in ether/methanol (1:5), filtered and dried to afford a yellow solid (0.51 g, 76%).

Synthesis of S148 n-BuLi (2.5 M in hexane, 0.45 mL, 1.13 mmol) was added to a solution of compound 99a (0.41 g, 0.437 mmol) in THF (35 mL) at −30° C. After 10 minutes, iodomethane (1 mL, 16.1 mmol) was added and the mixture was stirred and warmed to RT, then stirred for another 30 min. and solvents were evaporated. The residue was washed with water and extracted with hexanes, dried over MgSO$_4$, and the solvent evaporated to give S148 as a yellow solid (0.341 g, 0.421 mmol, 97% crude yield). The chromophore was purified by preparative TLC using hexanes/DCM (25%) as eluent. $^1$H NMR (400 MHz, CDCl$_3$) δ 6.42 (s, 2H), 6.41 (s, 2H), 2.37 (s, 6H), 2.23 (s, 6H), 2.10 (s, 6H), 2.06 (s, 6H), 1.91 (s, 6H).

Example 75

Synthesis of S149

3',3'''-(perfluorocyclopent-1-ene-1,2-diyl)bis(4,4''-dimethyl-2,2':5',2''-terthiophene)

(Scheme 85)

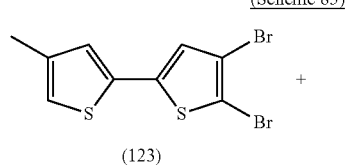

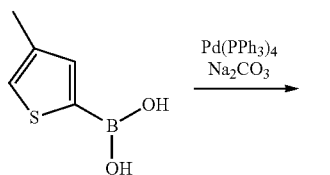

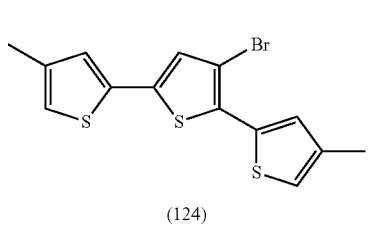

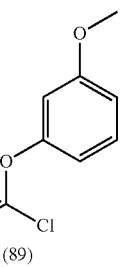

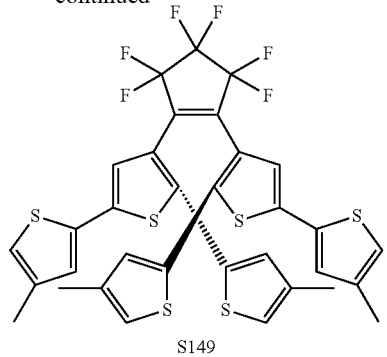

S149

Synthesis of 3'-bromo-4,4''-dimethyl-2,2':5',2''-terthiophene (124)

(124) was prepared on 29 mmol scale (66% yield) according to protocol D.

Synthesis of S149

S149 was prepared on 4.79 mmol scale (33% yield) according to protocol H1. $^1$H NMR (400 MHz, CDCl$_3$) δ 6.88 (d, J=1.3 Hz, 2H), 6.81 (s, 2H), 6.72 (s, 2H), 6.48 (d, J=1.3 Hz, 2H), 6.40 (s, 2H), 2.26 (s, 6H), 1.98 (s, 6H).

Example 76

Synthesis of S151

3,3'-(perfluorocyclopent-1-ene-1,2-diyl)bis(2-(4-(tert-butyl)phenyl)-6-methoxybenzofuran)

(Scheme 86)

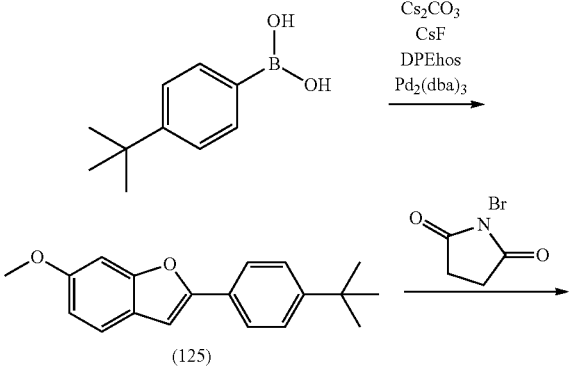

163
-continued

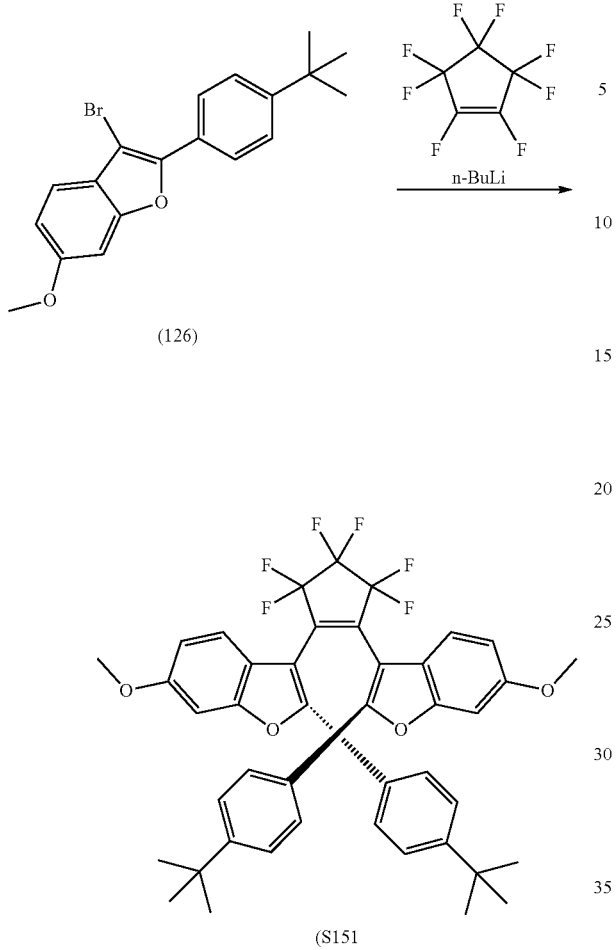

Synthesis of 2-(4-tert-butylphenyl)-6-methoxybenzofuran (125)

(125) was prepared on 13.0 mmol scale (52%) yield according to protocol J. $^1$H NMR (400 MHz, CDCl$_3$) δ 7.79-7.71 (m, 2H), 7.48-7.45 (m, 2H), 7.43 (d, J=8.5 Hz, 1H), 7.08 (d, J=2.1 Hz, 1H), 6.91 (s, 1H), 6.87 (dd, J=8.5, 2.1 Hz, 1H), 3.88 (s, 3H), 1.36 (s, 9H).

Synthesis of 3-bromo-6-methoxy-2-(5-methylthiophen-2-yl)benzofuran (126)

(126) was prepared on 12.8 mmol scale (98% yield) according to protocol F4. $^1$H NMR (400 MHz, CDCl$_3$) δ 8.11-8.02 (m, 2H), 7.54-7.48 (m, 2H), 7.40 (d, J=8.6 Hz, 1H), 7.04 (d, J=2.1 Hz, 1H), 6.94 (dd, J=8.6, 2.1 Hz, 1H), 3.88 (s, 3H), 1.37 (s, 9H).

Synthesis of S151

S151 was prepared on 0.73 mmol scale (14% yield) according to protocol H3. $^1$H NMR (400 MHz, CDCl$_3$) δ 7.16-7.03 (m, 10H), 6.77 (d, J=2.2 Hz, 2H), 6.65 (dd, J=8.8, 2.2 Hz, 2H), 3.78 (s, 6H), 1.16 (s, 18H).

164

Example 77

Synthesis of S152

3,3'-(perfluorocyclopent-1-ene-1,2-diyl)bis(2-(5'-(tert-butyl)-[2,2'-bithiophen]-5-yl)-6-methoxybenzofuran)

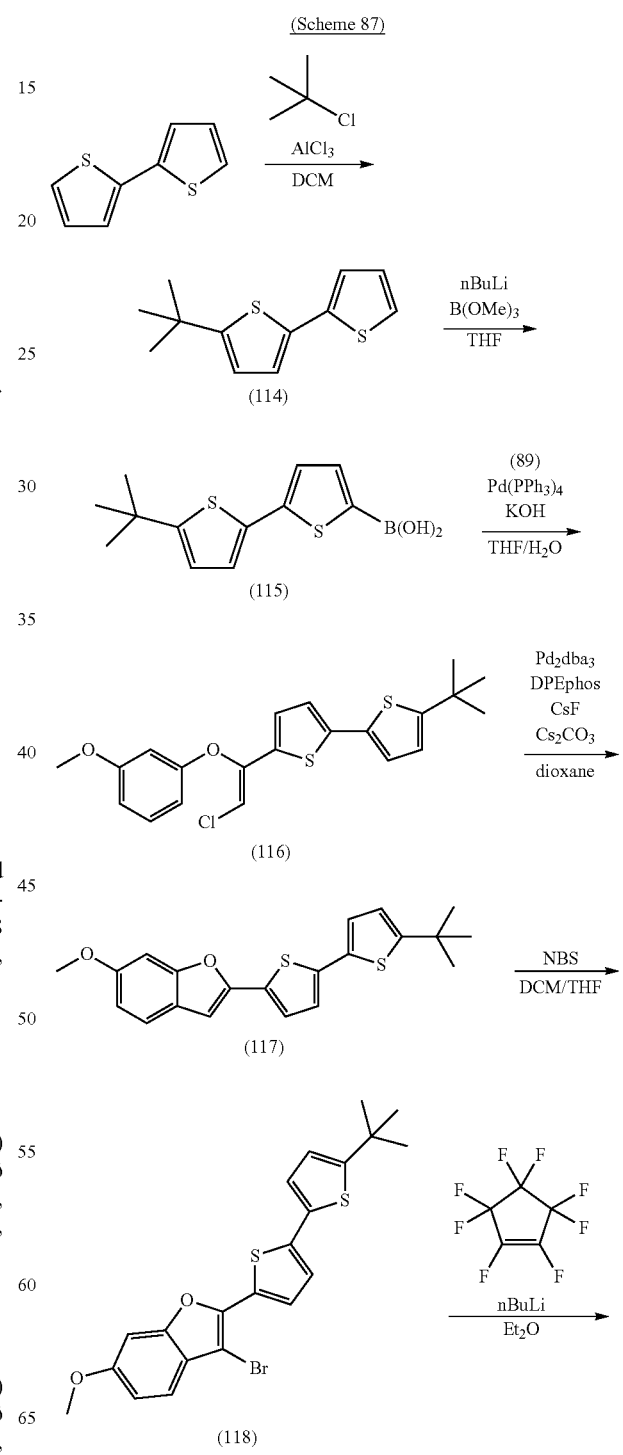

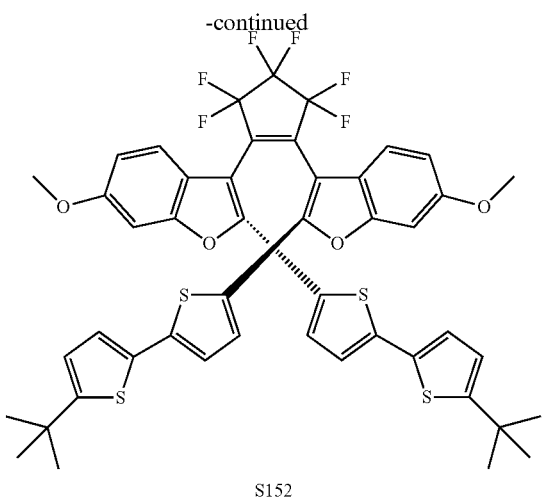

S152

Synthesis of 5-(tert-butyl)-2,2'-bithiophene (114)

2,2'-bithiophene (10 g, 60.1 mmol) was dissolved in DCM (300 mL) and 2-chloro-2-methylpropane (7.95 g, 72.2 mmol) was added. Aluminum chloride (8.82 g, 66.2 mmol) was added in one portion, and the colourless solution turned a green/brown colour immediately. The reaction mixture was stirred at room temperature for 30 minutes, then was poured into water (500 mL), mixed well and separated. The aqueous portion was extracted with DCM (200 mL) and the combined organics were washed with brine (2×400 mL), dried over MgSO$_4$, filtered and solvent removed by rotary evaporation to afford a clear, green oil (13.3 g, 99%) that was used in the next step without further purification. $^1$H NMR (400 MHz, CDCl$_3$) δ 7.17 (dd, J=5.1, 1.1 Hz, 1H), 7.10 (dd, J=3.6, 1.1 Hz, 1H), (dd, J=5.1, 3.6 Hz, 1H), 6.98 (d, J=3.6 Hz, 1H), 6.73 (d, J=3.7 Hz, 1H), 1.40 (s, 9H).

Synthesis of (5'-(tert-butyl)-[2,2'-bithiophen]-5-yl) boronic acid (115)

In a flame-dried, 500 mL round bottom flask, 5-(t-butyl)-2,2'-bithiophene (from U152-001, 13 g, 58.5 mmol) was dissolved in anhydrous THF (200 mL) and the solution was cooled to −78° C. (dry ice/acetone). n-butyl lithium (2.5 M in hexanes, 25.7 mL, 64.3 mmol) was added dropwise over a period of 10 minutes, and the resulting green solution was allowed to stir for 15 minutes. Trimethyl borate (19.6 mL, 175 mmol) was added dropwise over a period of 10 minutes, and the resulting light yellow solution was stirred for 2 hours at −78° C., then allowed to warm to room temperature and stirred for 1 hour. The reaction was quenched by pouring it into 10% HCl (500 mL). The organic phase was separated and the aqueous phase extracted with ether (250 mL). The combined organics were washed with water (500 mL), dried over MgSO$_4$, filtered and solvent removed by rotary evaporation. The resulting green solid was dried under vacuum to afford 15 g (96% yield), which was used in the next step without further purification.

Synthesis of (Z)-5-(tert-butyl)-5'-(2-chloro-1-(3-methoxyphenoxy)vinyl)-2,2'-bithiophene (116)

In a 3 neck, 1 L round bottom flask, (5'-(t-butyl)-[2,2'''-bithiophenene]-5-boronic acid (10.5 g, 39.4 mmol), (E)-1-((1,2-dichlorovinyl)oxy)-3-methoxybenzene (8.2 g, 37.6 mmol), were dissolved in THF (200 mL) and KOH (4.4 g, 79 mmol) in water (130 mL) was added. The reaction mixture was deoxygenated by bubbling argon through the solution for 1 hour. Tetrakis(triphenylphosphine)palladium (0) (2.17 g, 1.9 mmol) was added and the reaction mixture was heated to reflux for 18 hours. After cooling to room temperature, the mixture was poured into water (500 mL), mixed well and separated. The aqueous portion was extracted with ether (250 mL) and the combined organics were washed with water (500 mL), dried over MgSO$_4$, filtered and solvent removed by rotary evaporation. The resulting orange slurry was redissolved in DCM and deposited on silica. Flash chromatography (combi-flash, hexanes) afforded a yellow, powdery solid (2.97 g, 20%). $^1$H NMR (400 MHz, CDCl$_3$) δ 7.20-7.15 (m, 1H), 6.97 (d, J=3.8 Hz, 1H), 6.95 (d, J=3.7 Hz, 1H), 6.91 (d, J=3.8 Hz, 1H), 6.71 (d, J=3.7 Hz, 1H), 6.62-6.57 (m, 3H), 6.34 (s, 1H), 3.78 (s, 3H), 1.37 (s, 9H).

Synthesis of 2-(5'-(tert-butyl)-[2,2'-bithiophen]-5-yl)-6-methoxybenzofuran (117)

(Z)-5-(tert-butyl)-5'-(2-chloro-1-(3-methoxyphenoxy)vinyl)-2,2'-bithiophene (2.9 g, 7.16 mmol) and DPEphos (0.19 g, 0.36 mmol) were dissolved in anhydrous 1,4-dioxane (40 mL). Cesium carbonate (7.0 g, 21.5 mmol) and cesium fluoride (3.3 g, 21.5 mmol) were added and the reaction mixture was deoxygenated by bubbling argon through it for 1 hour. Tris(dibenzylideneacetone)dipalladium(0) (0.16 g, 0.18 mmol) was added and the reaction mixture was heated to reflux for 20 hours. After cooling to room temperature, the reaction mixture was filtered, poured into water (250 mL), mixed well and separated. The aqueous portion was extracted with ether (2×200 mL) and the combined organics were washed with water (500 mL), dried over MgSO$_4$, filtered and solvent removed by rotary evaporation. The resulting brown solid was redissolved in DCM (250 mL) and deposited onto silica gel. Flash chromatography (combi-flash, hexanes) afforded a yellow, powdery solid, 1.53 g (58%). $^1$H NMR (600 MHz, CDCl$_3$) δ 7.40 (d, J=8.5 Hz, 1H), 7.29 (d, J=3.8 Hz, 1H), 7.07 (d, J=3.8 Hz, 1H), 7.04 (d, J=1.4 Hz, 1H), 7.01 (d, J=3.6 Hz, 1H), 6.86 (dd, J=8.5, 2.2 Hz, 1H), 6.76 (s, 1H), 6.75 (d, J=3.6 Hz, 1H), 3.87 (s, 3H), 1.41 (s, 9H).

Synthesis of 3-bromo-2-(5'-(tert-butyl)-[2,2'-bithiophen]-5-yl)-6-methoxybenzofuran (118)

(118) was prepared on 3.4 mmol scale (85% yield) according to protocol F4. $^1$H NMR (600 MHz, CDCl$_3$) δ 7.64 (d, J=3.9 Hz, 1H), 7.36 (d, J=8.6 Hz, 1H), 7.13 (d, J=3.9 Hz, 1H), 7.06 (d, J=3.6 Hz, 1H), 7.01 (d, J=2.0 Hz, 1H), 6.93 (dd, J=8.6, 2.2 Hz, 1H), 6.76 (d, J=3.7 Hz, 1H), 3.88 (s, 3H), 1.41 (s, 9H).

Synthesis of S152

S152 was prepared on 9.9 μmol scale (0.6% yield) according to protocol H2. $^1$H NMR (400 MHz, CDCl$_3$) δ 7.20 (d, J=8.7 Hz, 1H), 6.80 (d, J=3.7 Hz, 1H), 6.79 (d, J=3.8 Hz, 1H), 6.75 (d, J=2.2 Hz, 1H), 6.72 (d, J=3.7 Hz, 1H), 6.64 (dd, J=8.8, 2.3 Hz, 1H), 6.55 (d, J=3.8 Hz, 1H), 3.61 (s, 3H), 1.42 (s, 9H).

Example 78

Synthesis of S154

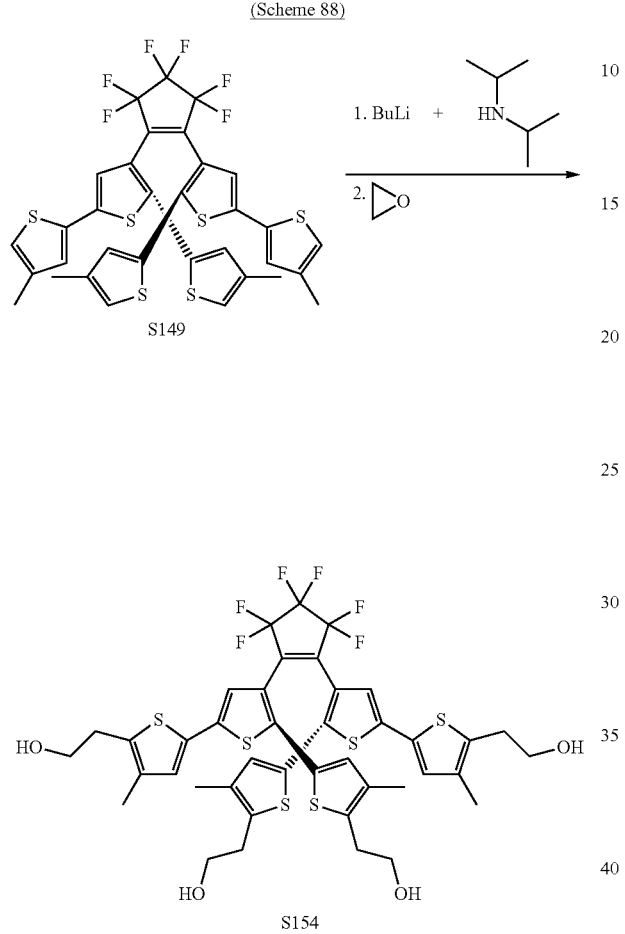

Synthesis of S154

LDA was made by addition of BuLi (0.9 mL, 2.25 mmol) to a solution of diisopropylamine (0.25 mL, 2.25 mmol) in THF (10 mL) at 0° C. with stirring for 10 min. S149 (0.365 g, 0.5 mmol) in THF (25 mL) was added with stirring at 0° C. for a further 10 min and cooled to −78° C. Oxirane (0.11 g, 2.5 mmol) was added, and stirred for 2 hr with gradual warming to RT. The reaction was quenched with water (30 mL) and 10% HCl solution. Organics were extracted with ether (2×100 mL), washed with brine (10 mL) and concentrated under reduced pressure. The crude product was purified by column chromatography eluting with hexanes/ethyl acetate, giving S154. Yield 50 mg (11%). $^1$H NMR (400 MHz, CDCl$_3$) δ 6.81 (s, 1H), 6.42 (s, 1H), 6.39 (s, 1H), 3.87 (t, J=5.8 Hz, 2H), 3.55 (t, J=7.1 Hz, 2H), 2.97 (t, J=5.8 Hz, 2H), 2.70 (t, J=7.1 Hz, 2H), 2.18 (s, 3H), 1.96 (s, 3H), 1.88 (s, 4H).

Example 79

Synthesis of S155

3,3'-(perfluorocyclopent-1-ene-1,2 diyl)bis(2-(3,4-dimethoxyphenyl)-6-methoxybenzofuran)

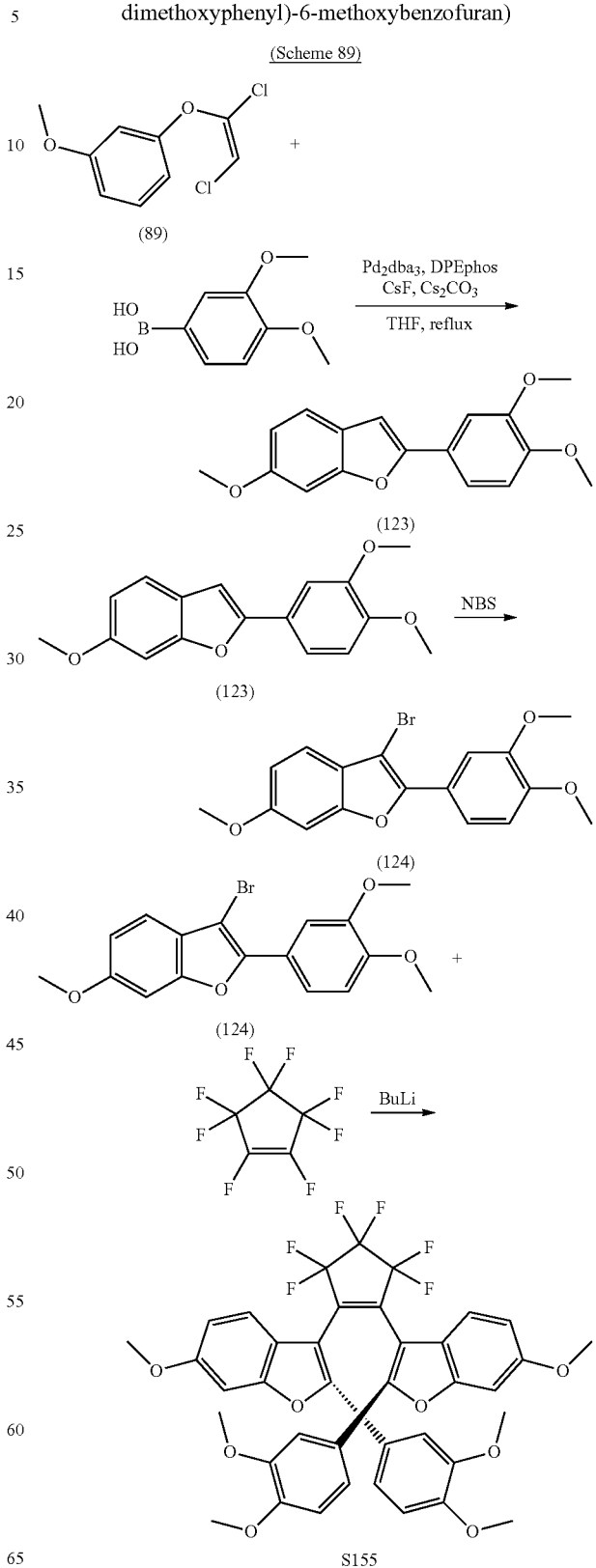

Synthesis of 2-(3,4-dimethoxyphenyl)-6-methoxybenzofuran (123)

(123) was prepared on 26.4 mmol scale (76.0%) yield according to protocol J.

Synthesis of 3-bromo-2-(3,4-dimethoxyphenyl)-6-methoxybenzofuran (124)

(124) was prepared on 24.53 mmol scale (93%) yield according to protocol F4.

Synthesis of S155

In a 100-mL round bottom flask, containing 3-bromo-2-(3,4-dimethoxyphenyl)-6-methoxybenzofuran (2 g, 5.51 mmol), a mixture of anhydrous tert-butyl methyl ether (Ratio: 2, Volume: 40 ml) and THF (Ratio: 1.000, Volume: 20.00 ml) was cooled down to −78° C. in an acetone/dry ice bath. Butyllithium (2.313 ml, 5.78 mmol) was added slowly followed by perfluorocyclopent-1-ene (0.369 ml, 2.75 mmol). The reaction mixture was stirred for 1 hour, while the temperature was increasing gradually. The reaction was stopped by the addition of brine, and the mixture was transferred to a separation funnel. The organic layer was extracted with ethyl acetate and dried over anhydrous magnesium sulfate. The product was purified by chromatography column using Combi Flash Rf eluting with pure hexanes, then crystallized from ethanol to provide 3,3'-(perfluorocyclopent-1-ene-1,2-diyl)bis(2-(3,4-dimethoxyphenyl)-6-methoxybenzofuran) (0.408 g, 0.551 mmol, 20% yield) as yellow solid. $^1$H NMR (600 MHz, CDCl$_3$) δ 6.98 (d, J=8.6 Hz, 2H), 6.83 (d, J=2.1 Hz, 2H), 6.71 (dd, J=8.7, 2.2 Hz, 2H), 6.60 (d, J=8.2 Hz, 2H), 6.59 (s, 2H), 6.32 (d, J=8.2 Hz, 2H), 3.84 (s, 6H), 3.82 (s, 6H), 3.70 (s, 6H).

Example 80

Synthesis of S158

(Scheme 90)

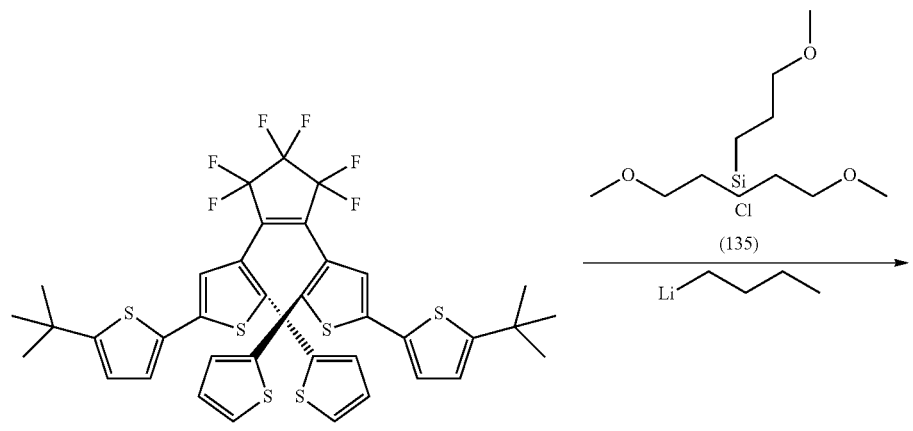

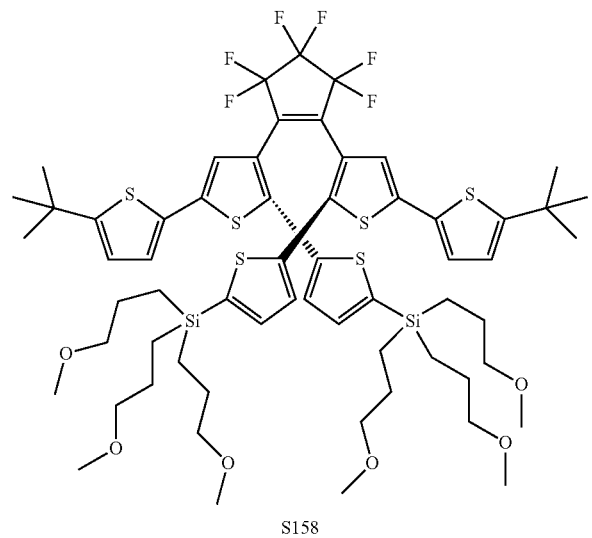

To a solution of S170 (2 g, 2.56 mmol) in THF/ether (100 mL; 1:1) at −10-15° C. was added a solution of n-BuLi (2.4 mL, 5.63 mmol). The reaction mixture turned brown, and was stirred for 15-20 min before chlorotris(3-methoxypropyl)silane (compound (135); 1.6 g, 5.66 mmol) was added. The mixture was stirred at −10-15° C. for 1 h (TLC) and quenched by methanol (6 mL) followed by water (6 mL). Saturated sodium chloride (30 mL) was then added. The mixture was extracted with ether, washed with brine and concentrated under reduced pressure. CombiFlash chromatography (eluent hexanes/ethyl acetate; gradient to 40%) provided 1.7 g (1.335 mmol; 52% yield) of S158. $^1$H NMR (400 MHz, CDCl$_3$) δ 6.91 (d, J=3.4 Hz, 2H), 6.86 (d, J=3.6 Hz, 2H), 6.72 (d, J=3.6 Hz, 2H), 6.69 (d, J=3.4 Hz, 2H), 6.30 (s, 2H), 3.33-3.29 (m, 30H), 1.63-1.53 (m, 12H), 1.41 (s, 18H), 0.77-0.69 (m, 12H).

Example 81

Synthesis of S162

3,3'-(perfluorocyclopent-1-ene-1,2-diyl)bis(2-(4-(tert-butyl)phenyl)benzofuran-6-ol)

(Scheme 91)

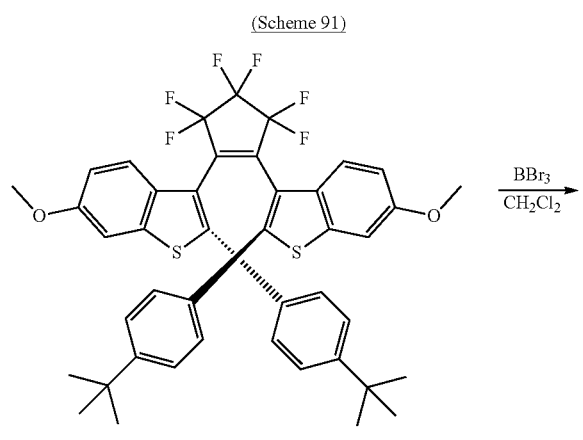

Synthesis of S162

In a one neck round bottom flask containing a solution of 3,3'-(perfluorocyclopent-1-ene-1,2-diyl)bis(2-(4-(tert-butyl)phenyl)-6-methoxybenzofuran) (1 g, 1.365 mmol) in anhydrous dichloromethane (Ratio: 1, Volume: 50 ml) at room temperature was added dropwise tribromoborane (1.8 ml, 18.68 mmol). The reaction mixture was stirred at reflux for 2 hours. The TLC after 2 hours showed that all the starting material was consumed. The reaction was quenched with methanol (vigorous reaction). The crude was washed with an aqueous solution of 10% HCl, extracted with DCM, then dried over anhydrous magnesium sulfate. The solid obtained was deposited on silica gel and purified by chromatography column using CombiFlash Rf eluting with pure DCM to obtain the product 3,3'-(perfluorocyclopent-1-ene-1,2-diyl) bis(2-(4-(tert-butyl)phenyl)benzofuran-6-ol) (0.96 g, 1.362 mmol, 100% yield) as fluffy yellow solid. $^1$H NMR (500 MHz, CDCl$_3$) δ 7.1 (AB, J=8.4 Hz, 8H), 7.06 (m, 2H), 6.73 (d, J=2.1 Hz, 2H), 6.54 (dd, J=8.6, 2.2 Hz, 2H), 4.77 (s, 2H), 1.18 (s, 18H).

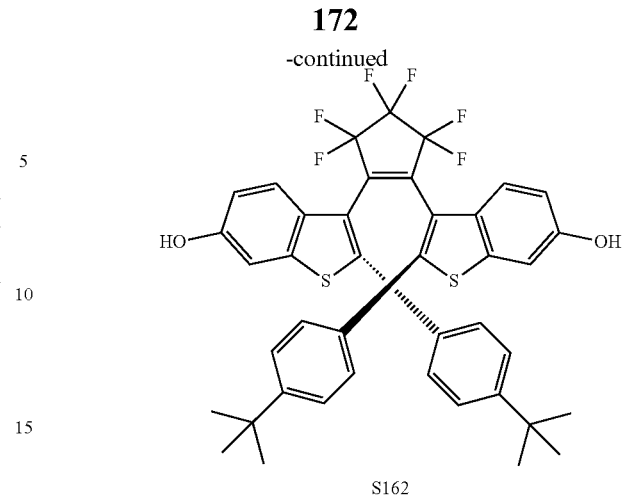

Example 82

Synthesis of S161

3,3'-(perfluorocyclopent-1-ene-1,2-diyl)bis(2-(4-(tert-butyl)phenyl)-6-(2-(2-(2-ethoxyethoxy)ethoxy)ethoxy)benzofuran)

(Scheme 92)

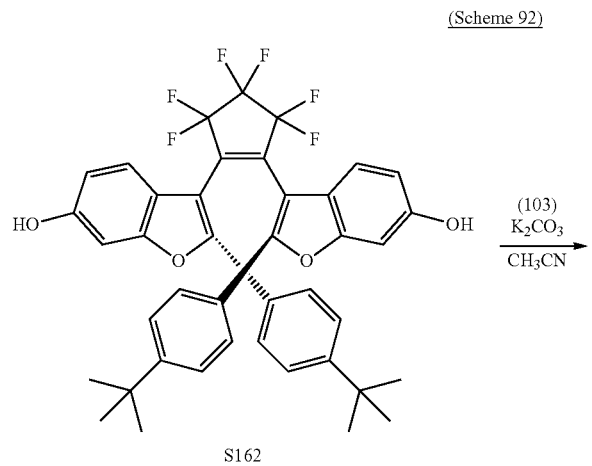

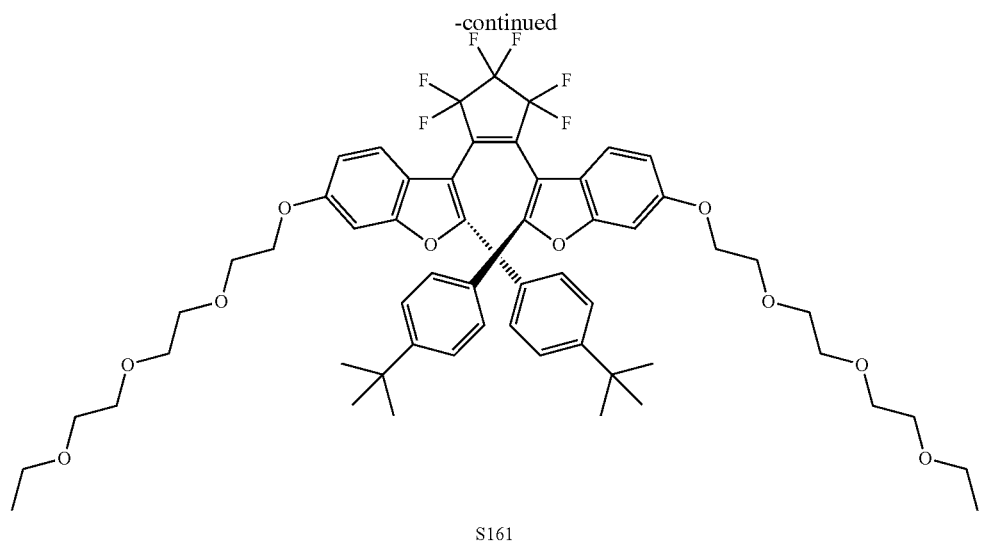

S161

Synthesis of S161

In a one neck round bottomed flask, 3,3'-(perfluorocyclopent-1-ene-1,2-diyl)bis(2-(4-(tert-butyl)phenyl)benzofuran-6-ol) (0.9 g, 1.277 mmol) was dissolved in Acetonitrile (Ratio: 1, Volume: 50 ml) at room temperature under argon, then potassium carbonate (0.706 g, 5.11 mmol) was added. To the resulting suspension was added a solution of 2-(2-(2-ethoxyethoxy)ethoxy)ethyl 4-methylbenzenesulfonate (103) (1.061 g, 3.19 mmol) in anhydrous acetonitrile in one portion and the mixture was stirred overnight at reflux. The reaction mixture was allowed to cool down to room temperature, poured into a separation funnel containing water. The organic layer was extracted with ethyl acetate and dried over magnesium sulfate. The filtrate was concentrated to provide the crude product as red/brown oil. The crude was loaded as solution into the chromatography column and purified using CombiFlash Rf (starting with 10% ethyl acetate in hexanes until 40% ethyl acetate in hexanes) to provide the product 3,3'-(perfluorocyclopent-1-ene-1,2-diyl)bis(2-(4-(tert-butyl)phenyl)-6-(2-(2-(2-ethoxyethoxy)ethoxy)ethoxy)benzofuran) (1.2 g, 1.171 mmol, 92% yield) as thick red oil (dark state). $^1$H NMR (400 MHz, CDCl$_3$) δ 7.12 (d, J=8.5 Hz, 4H), 7.07 (m, 6H), 6.78 (d, J=2.1 Hz, 2H), 6.66 (dd, J=8.8, 2.2 Hz, 2H), 4.08 (t, J=4.68 Hz, 4H), 3.85 (t, J=5.20 Hz, 4H), 3.74 (m, 4H), 3.72-3.63 (m, 8H), 3.60 (m, 4H), 3.53 (q, J=7.0 Hz, 4H), 1.21 (t, J=7.0 Hz, 6H), 1.16 (s, 18H).

Example 83

Synthesis of S163

7,7'-(perfluorocyclopent-1-ene-1,2-diyl)bis(6-(4-(tert-butyl)phenyl)-[1,3]dioxolo[4,5-f]benzofuran)

(Scheme 93)

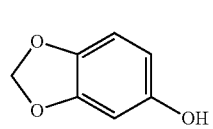

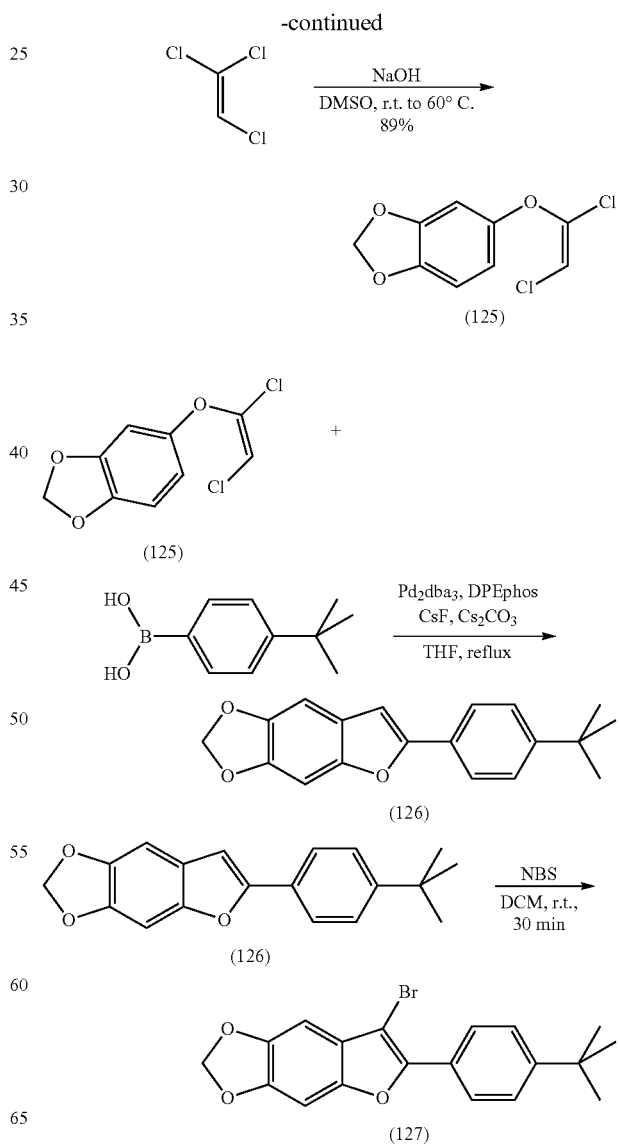

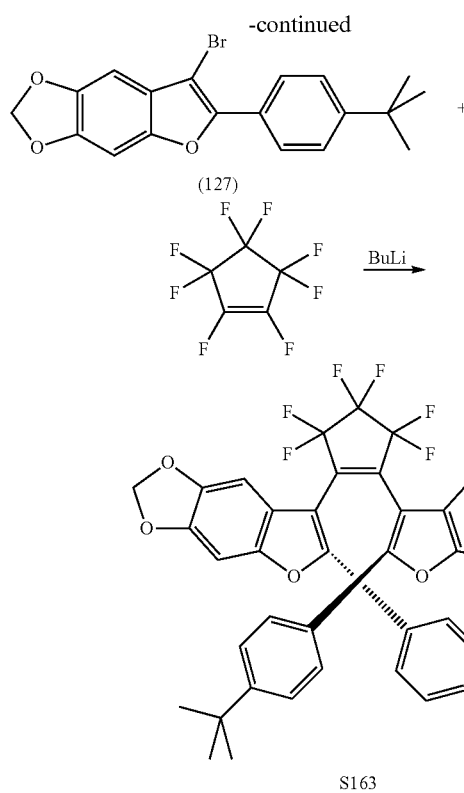

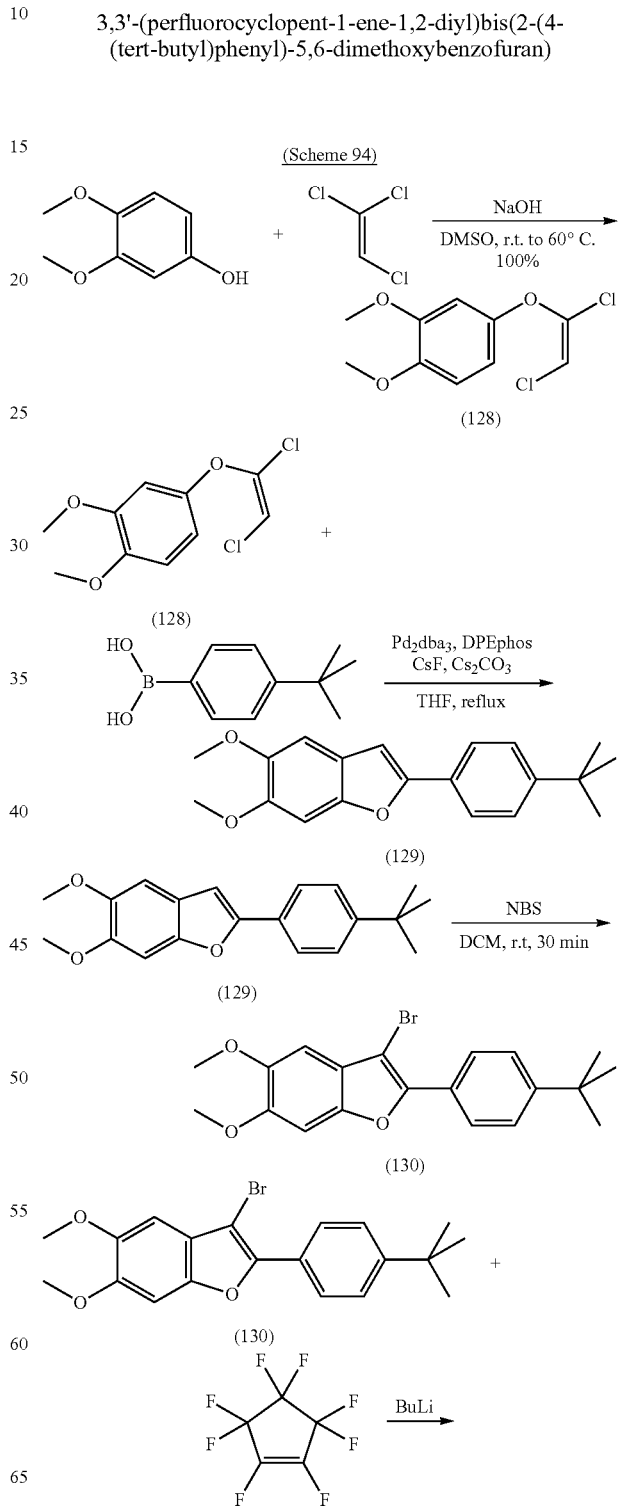

Synthesis of (E)-5-((1,2-dichlorovinyl)oxy)benzo[d][1,3]dioxole (125)

(125) was prepared on 644 mmol scale (89%) yield according to protocol I.

Synthesis of 6-(4-(tert-butyl)phenyl)-[1,3]dioxolo[4,5-f]benzofuran (126)

(126) was prepared on 43.1 mmol scale (68.2%) overall yield according to protocol J. (126) was obtained as a mixture of two isomers (41:59 ratio of product:by-product according to H NMR spectrum).

Synthesis of 7-bromo-6-(4-(tert-butyl)phenyl)-[1,3]dioxolo[4,5-f]benzofuran (127)

(127) was prepared on 38.59 mmol scale (84.0%) overall yield according to protocol F1. (127) was obtained as a mixture of two isomers (42:58 ratio) according to H NMR spectrum). The two isomers were separated by multiple chromatography column. In total, it was obtained: 8-bromo-7-(4-(tert-butyl)phenyl)-[1,3]dioxolo[4,5-e]benzofuran (8.4 g, 22.51 mmol, 49.0% yield) and 7-bromo-6-(4-(tert-butyl)phenyl)-[1,3]dioxolo[4,5-f]benzofuran (6.0 g, 16.08 mmol, 35.0% yield).

Synthesis of S163

S163 was prepared on 2.01 mmol scale (25.0%) overall yield according to protocol H3. A side product (131) was also generated (see Scheme 95 for structure). $^1$H NMR (400 MHz, CDCl$_3$) δ 7.14-7.09 (A$_2$, 8H), 6.73 (s, 2H), 6.62 (s, 2H), 5.93 (s, 4H), 1.20 (s, 18H).

Example 84

Synthesis of S164

3,3'-(perfluorocyclopent-1-ene-1,2-diyl)bis(2-(4-(tert-butyl)phenyl)-5,6-dimethoxybenzofuran)

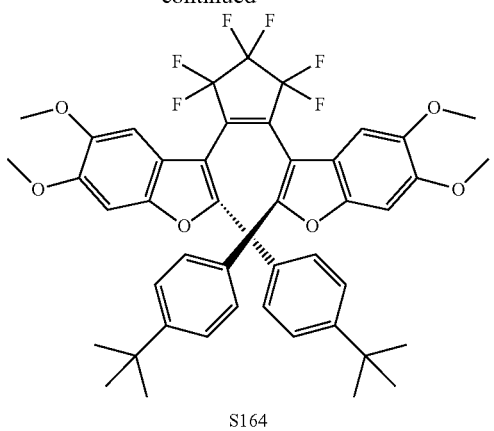

S164

Synthesis of (E)-4-((1,2-dichlorovinyl)oxy)-1,2-dimethoxybenzene (128)

(128) was prepared on 162 mmol scale (100%) yield according to protocol I.

Synthesis of 2-(4-(tert-butyl)phenyl)-5,6-dimethoxybenzofuran (129)

(129) was prepared on 19.33 mmol scale (40.1%) yield according to protocol J.

Synthesis of 3-bromo-2-(4-(tert-butyl)phenyl)-5,6-dimethoxybenzofuran (130)

(130) was prepared on 19.27 mmol scale (100%) yield according to protocol F2.

Synthesis of S164

S164 was prepared on 2.65 mmol scale (27.5%) yield according to protocol H3. A side product (139) was also generated (see Scheme 96 for structure). $^1$H NMR (400 MHz, CDCl$_3$) δ 7.13-7.05 (A$_2$, 8H), 6.81 (s, 2H), 6.75 (s, 2H), 3.86 (s, 6H), 3.76 (s, 6H), 1.12 (s, 18H).

Example 85

Other Compounds

Other compounds according to Formula I-X are illustrated in Table 8.

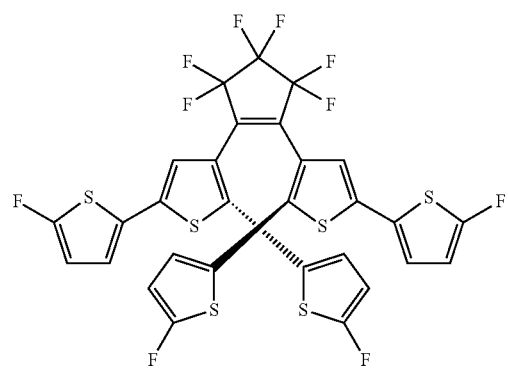

U008

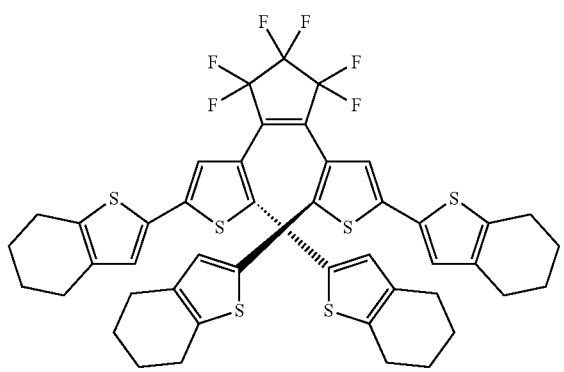

U009

-continued
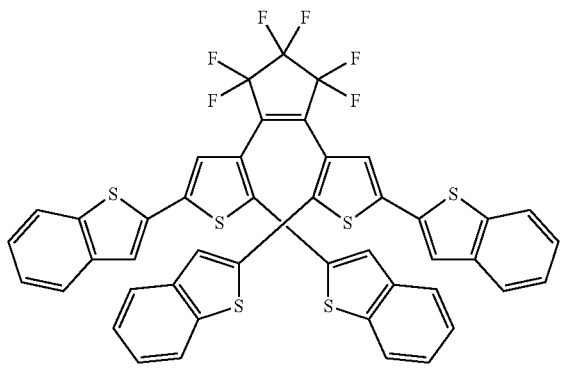 [SMILES: FC1(F)C(c2cc(-c3cc4ccccc4s3)sc2-c2cc3ccccc3s2)=C(c2cc(-c3cc4ccccc4s3)sc2-c2cc3ccccc3s2)C(F)(F)C1(F)F]
U010
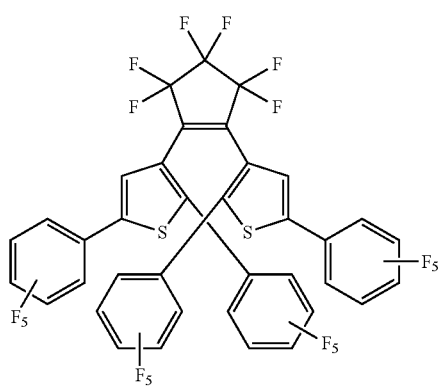
U016
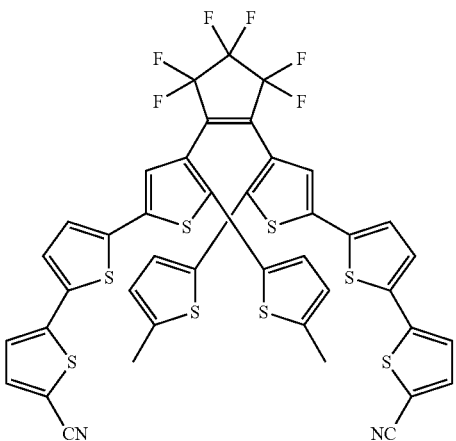 [SMILES: Cc1ccc(-c2sc(-c3ccc(-c4ccc(C#N)s4)s3)cc2C2=C(c3cc(-c4ccc(-c5ccc(C#N)s5)s4)sc3-c3ccc(C)s3)C(F)(F)C(F)(F)C2(F)F)s1]
U018

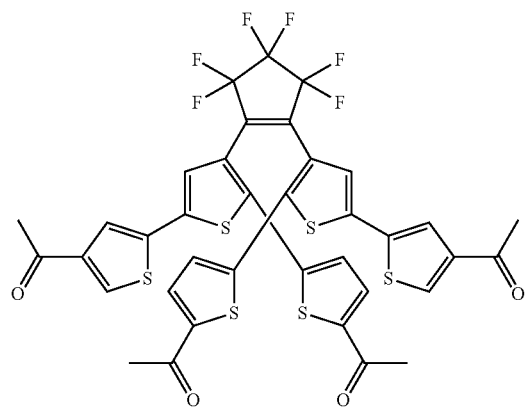 [SMILES: CC(=O)c1csc(-c2cc(C3=C(c4cc(-c5cc(C(C)=O)cs5)sc4-c4ccc(C(C)=O)s4)C(F)(F)C(F)(F)C3(F)F)c(-c3ccc(C(C)=O)s3)s2)c1]
U021
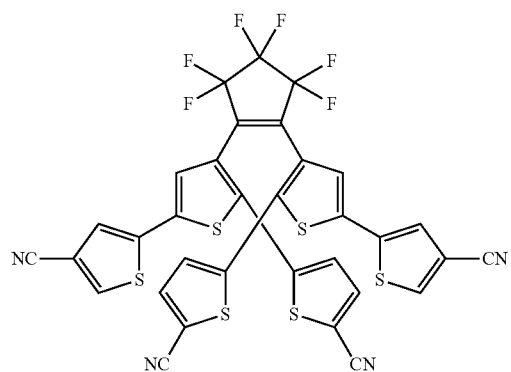 [SMILES: N#Cc1csc(-c2cc(C3=C(c4cc(-c5cc(C#N)cs5)sc4-c4ccc(C#N)s4)C(F)(F)C(F)(F)C3(F)F)c(-c3ccc(C#N)s3)s2)c1]
U022
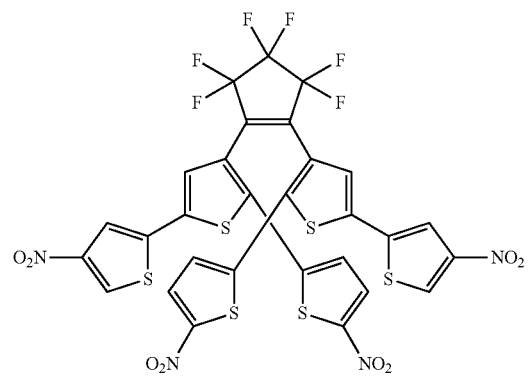 [SMILES: O=[N+]([O-])c1csc(-c2cc(C3=C(c4cc(-c5cc([N+](=O)[O-])cs5)sc4-c4ccc([N+](=O)[O-])s4)C(F)(F)C(F)(F)C3(F)F)c(-c3ccc([N+](=O)[O-])s3)s2)c1]
U023

-continued
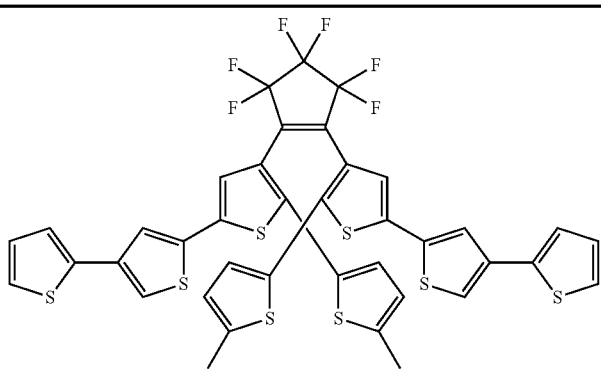
U025
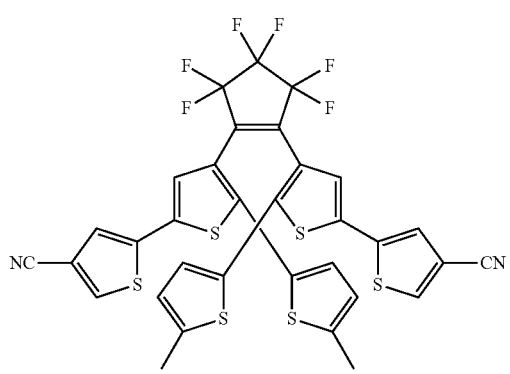 [SMILES: Cc1ccc(-c2sc(-c3cc(C#N)cs3)cc2C2=C(c3cc(-c4cc(C#N)cs4)sc3-c3ccc(C)s3)C(F)(F)C(F)(F)C2(F)F)s1]
U028
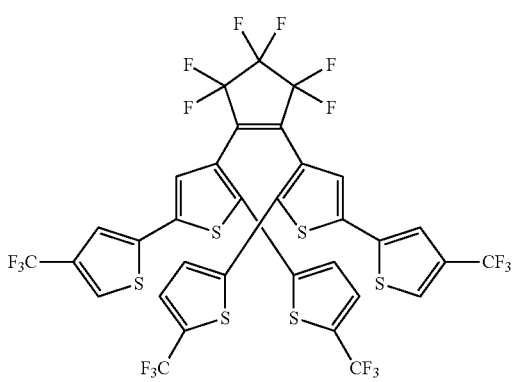 [SMILES: FC(F)(F)c1csc(-c2cc(C3=C(c4cc(-c5cc(C(F)(F)F)cs5)sc4-c4ccc(C(F)(F)F)s4)C(F)(F)C(F)(F)C3(F)F)c(-c3ccc(C(F)(F)F)s3)s2)c1]
U029
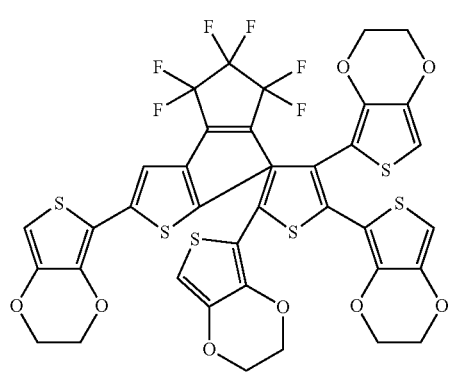
U030

-continued
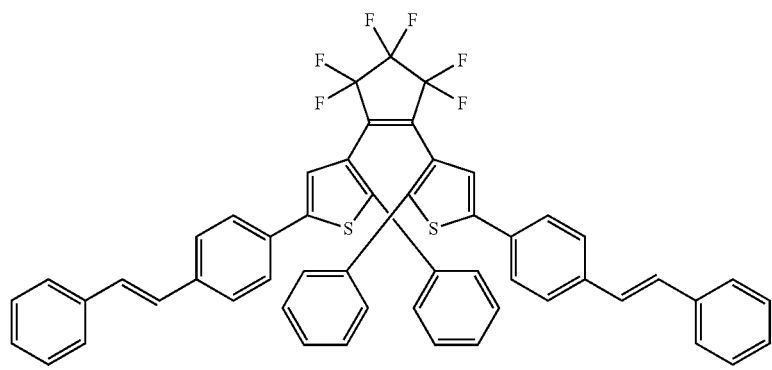 [SMILES: FC1(F)C(c2cc(-c3ccc(/C=C/c4ccccc4)cc3)sc2-c2ccccc2)=C(c2cc(-c3ccc(/C=C/c4ccccc4)cc3)sc2-c2ccccc2)C(F)(F)C1(F)F]
U031
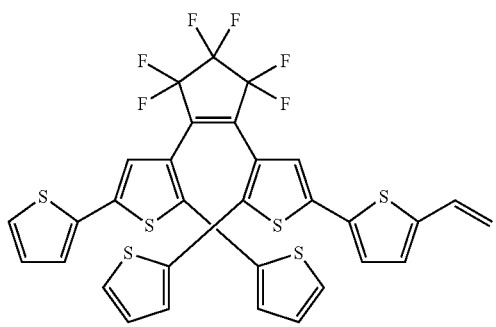 [SMILES: C=Cc1ccc(-c2cc(C3=C(c4cc(-c5cccs5)sc4-c4cccs4)C(F)(F)C(F)(F)C3(F)F)c(-c3cccs3)s2)s1]
U041
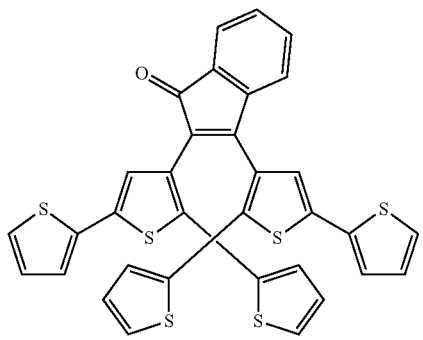 [SMILES: O=C1C(c2cc(-c3cccs3)sc2-c2cccs2)=C(c2cc(-c3cccs3)sc2-c2cccs2)c2ccccc21]
U045
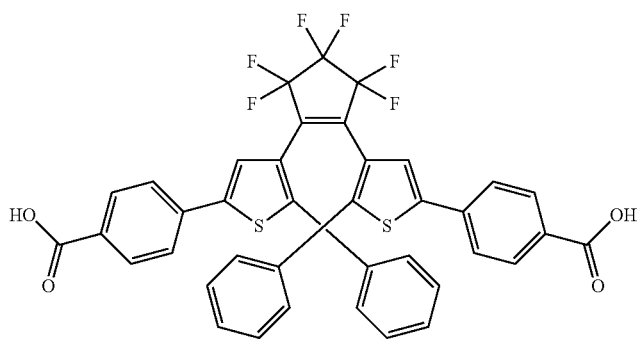 [SMILES: O=C(O)c1ccc(-c2cc(C3=C(c4cc(-c5ccc(C(=O)O)cc5)sc4-c4ccccc4)C(F)(F)C(F)(F)C3(F)F)c(-c3ccccc3)s2)cc1]
U051

-continued
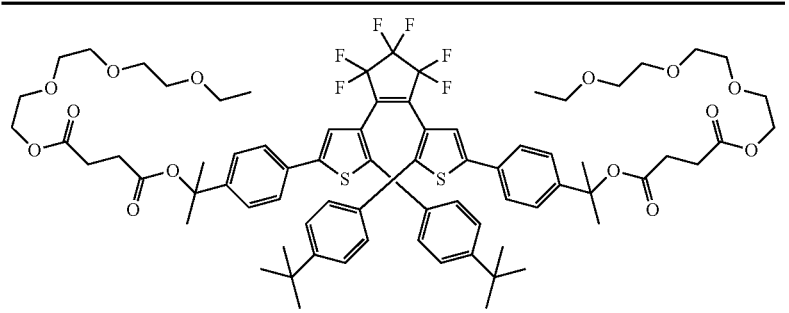
U058
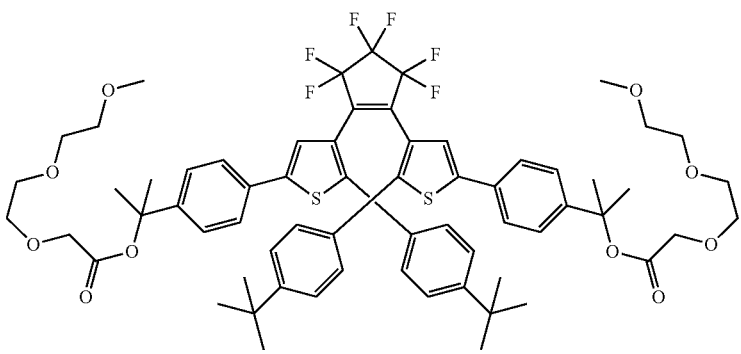 [SMILES: COCCOCCOCC(=O)OC(C)(C)c1ccc(-c2cc(C3=C(c4cc(-c5ccc(C(C)(C)OC(=O)COCCOCCOC)cc5)sc4-c4ccc(C(C)(C)C)cc4)C(F)(F)C(F)(F)C3(F)F)c(-c3ccc(C(C)(C)C)cc3)s2)cc1]
U061
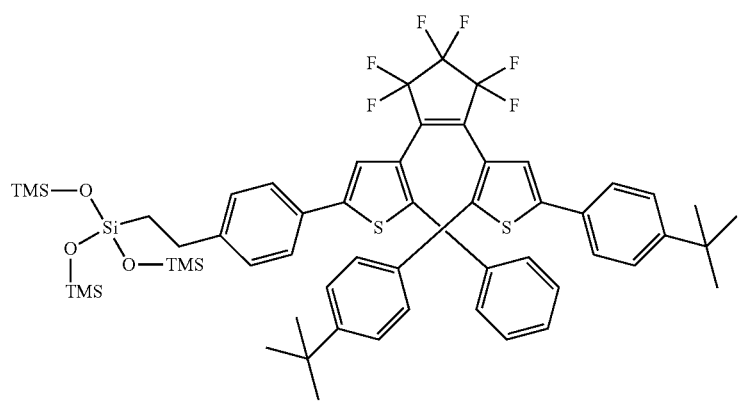 [SMILES: CC(C)(C)c1ccc(-c2cc(C3=C(c4cc(-c5ccc(CC[Si](O[Si](C)(C)C)(O[Si](C)(C)C)O[Si](C)(C)C)cc5)sc4-c4ccccc4)C(F)(F)C(F)(F)C3(F)F)c(-c3ccc(C(C)(C)C)cc3)s2)cc1]
U062
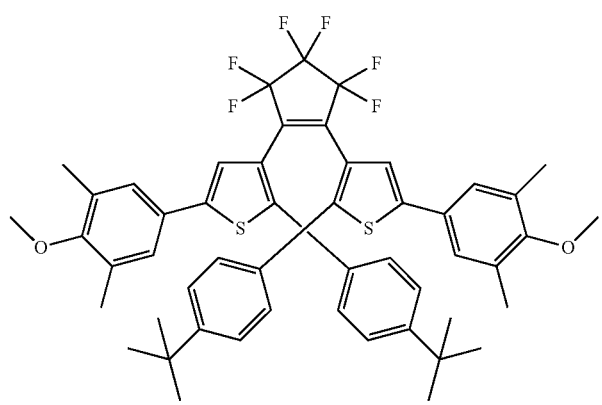
U069

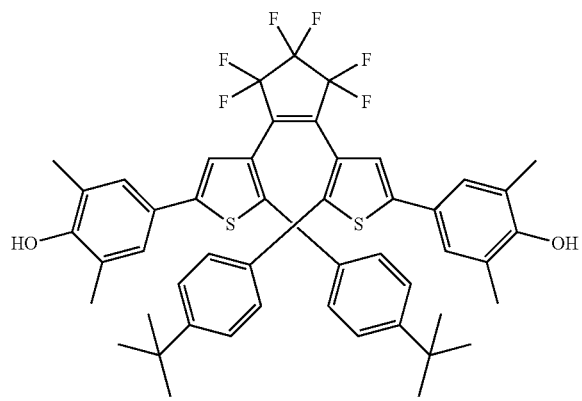 [SMILES: Cc1cc(-c2cc(C3=C(c4cc(-c5cc(C)c(O)c(C)c5)sc4-c4ccc(C(C)(C)C)cc4)C(F)(F)C(F)(F)C3(F)F)c(-c3ccc(C(C)(C)C)cc3)s2)cc(C)c1O]
U070
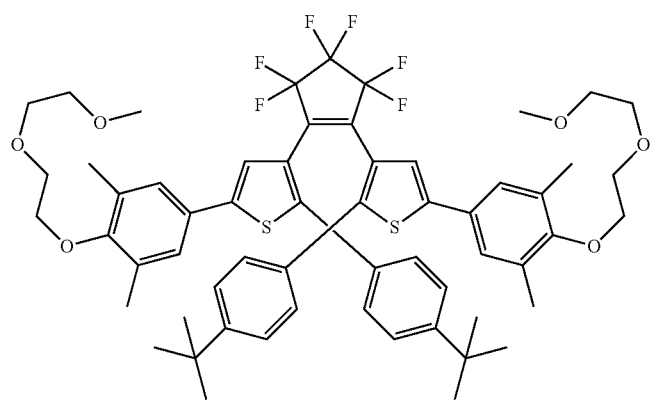 [SMILES: COCCOCCOc1c(C)cc(-c2cc(C3=C(c4cc(-c5cc(C)c(OCCOCCOC)c(C)c5)sc4-c4ccc(C(C)(C)C)cc4)C(F)(F)C(F)(F)C3(F)F)c(-c3ccc(C(C)(C)C)cc3)s2)cc1C]
U071
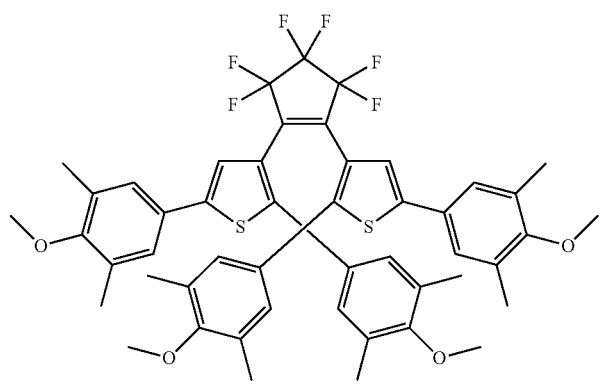
U072

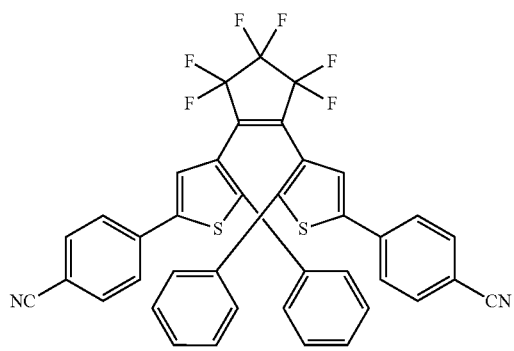 [SMILES: N#Cc1ccc(-c2cc(C3=C(c4cc(-c5ccc(C#N)cc5)sc4-c4ccccc4)C(F)(F)C(F)(F)C3(F)F)c(-c3ccccc3)s2)cc1]
U076
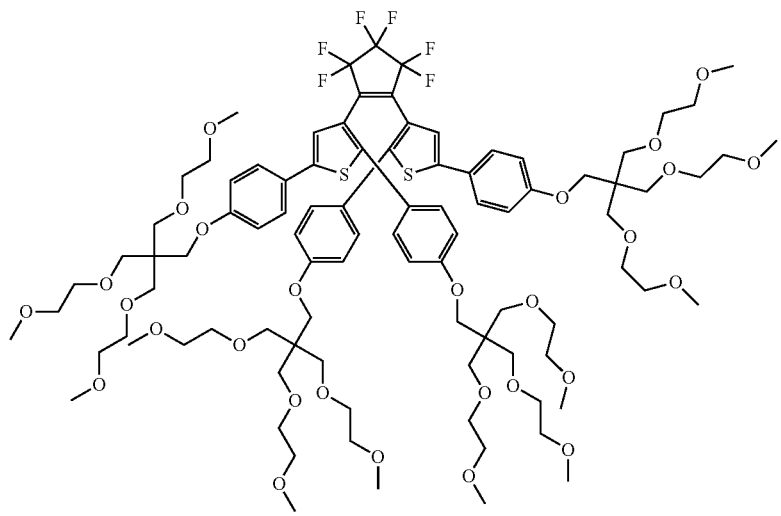
U077
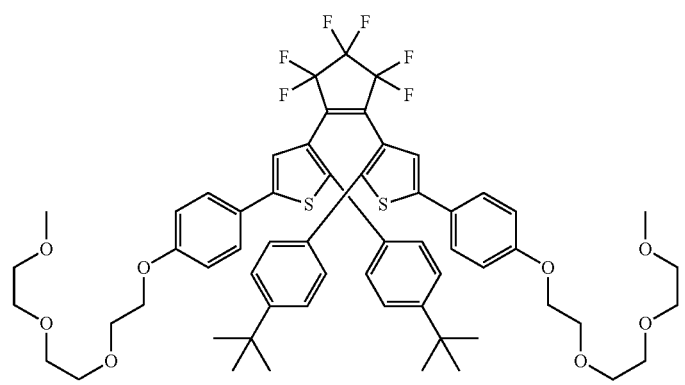 [SMILES: COCCOCCOCCOc1ccc(-c2cc(C3=C(c4cc(-c5ccc(OCCOCCOCCOC)cc5)sc4-c4ccc(C(C)(C)C)cc4)C(F)(F)C(F)(F)C3(F)F)c(-c3ccc(C(C)(C)C)cc3)s2)cc1]
U078

-continued
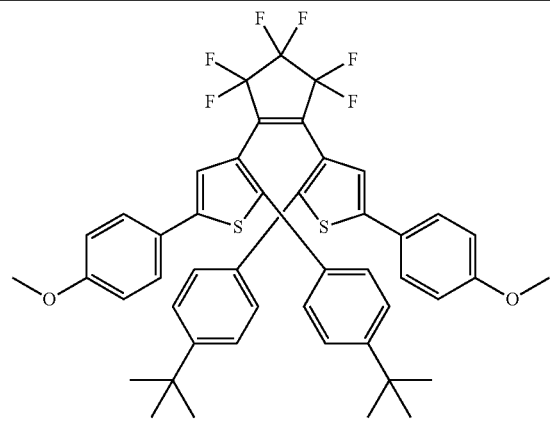
U080
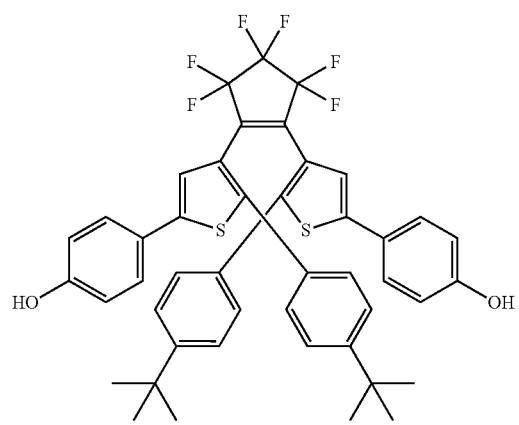 [SMILES: CC(C)(C)c1ccc(-c2sc(-c3ccc(O)cc3)cc2C2=C(c3cc(-c4ccc(O)cc4)sc3-c3ccc(C(C)(C)C)cc3)C(F)(F)C(F)(F)C2(F)F)cc1]
U081
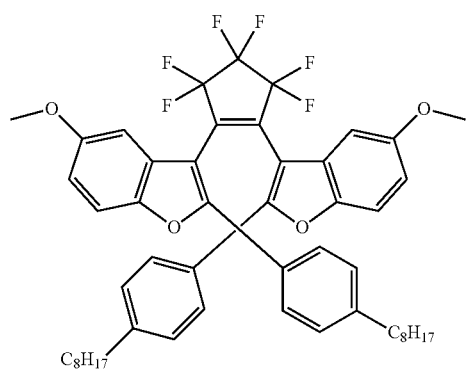
U082

-continued
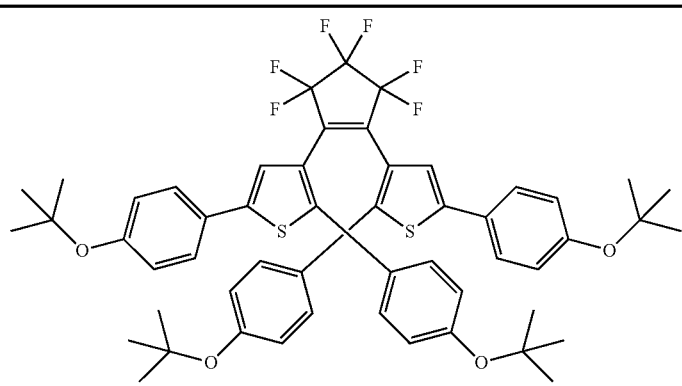
U093
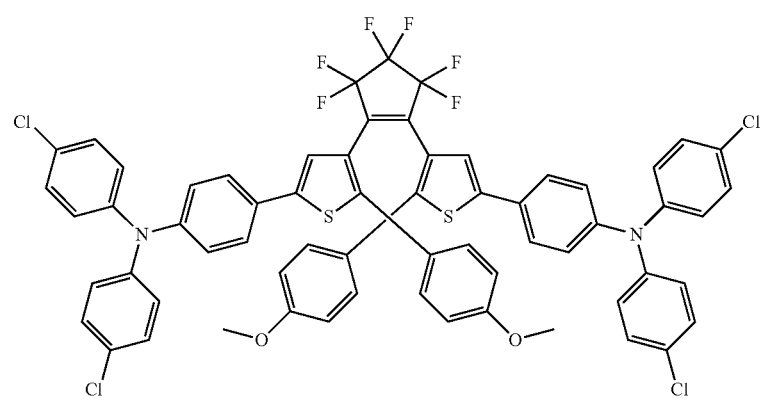 [SMILES: COc1ccc(-c2sc(-c3ccc(N(c4ccc(Cl)cc4)c4ccc(Cl)cc4)cc3)cc2C2=C(c3cc(-c4ccc(N(c5ccc(Cl)cc5)c5ccc(Cl)cc5)cc4)sc3-c3ccc(OC)cc3)C(F)(F)C(F)(F)C2(F)F)cc1]
U099
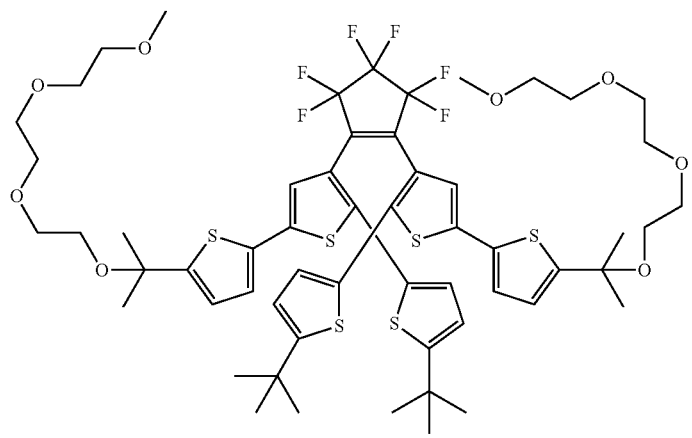 [SMILES: COCCOCCOCCOC(C)(C)c1ccc(-c2cc(C3=C(c4cc(-c5ccc(C(C)(C)OCCOCCOCCOC)s5)sc4-c4ccc(C(C)(C)C)s4)C(F)(F)C(F)(F)C3(F)F)c(-c3ccc(C(C)(C)C)s3)s2)s1]
U100

-continued
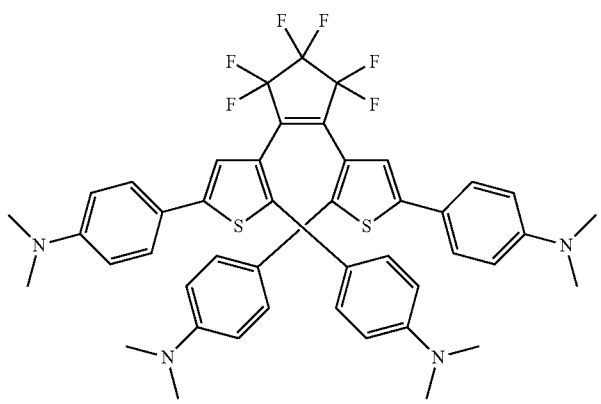
U101
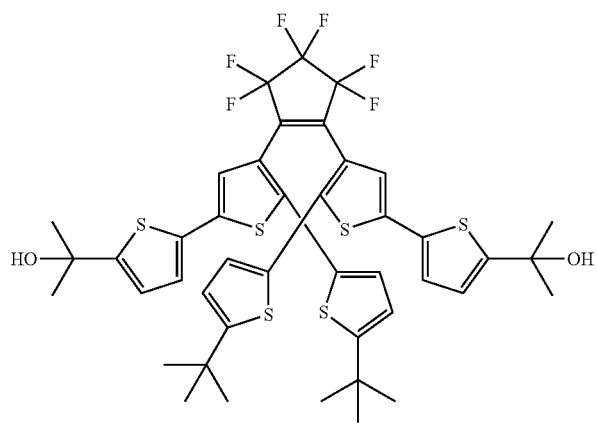 [SMILES: CC(C)(C)c1ccc(-c2sc(-c3ccc(C(C)(C)O)s3)cc2C2=C(c3cc(-c4ccc(C(C)(C)O)s4)sc3-c3ccc(C(C)(C)C)s3)C(F)(F)C(F)(F)C2(F)F)s1]
U102
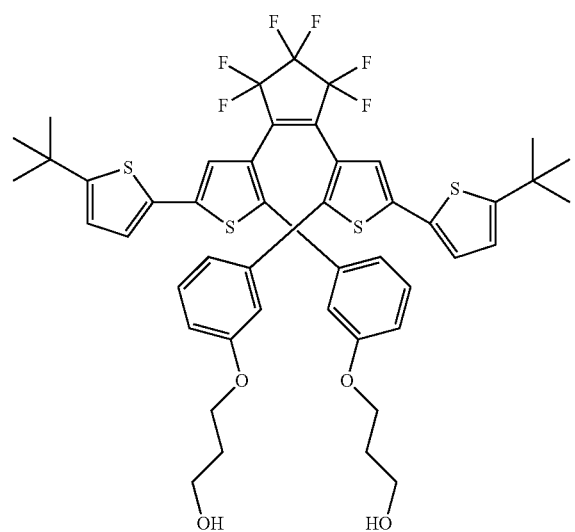 [SMILES: CC(C)(C)c1ccc(-c2cc(C3=C(c4cc(-c5ccc(C(C)(C)C)s5)sc4-c4cccc(OCCCO)c4)C(F)(F)C(F)(F)C3(F)F)c(-c3cccc(OCCCO)c3)s2)s1]
U107

-continued
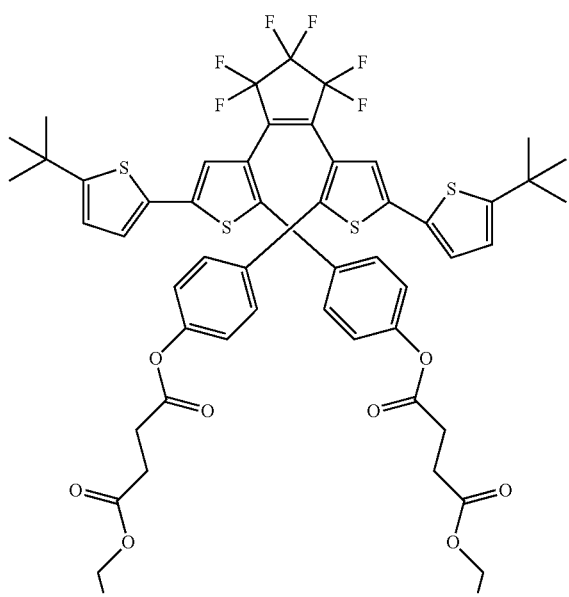
U114
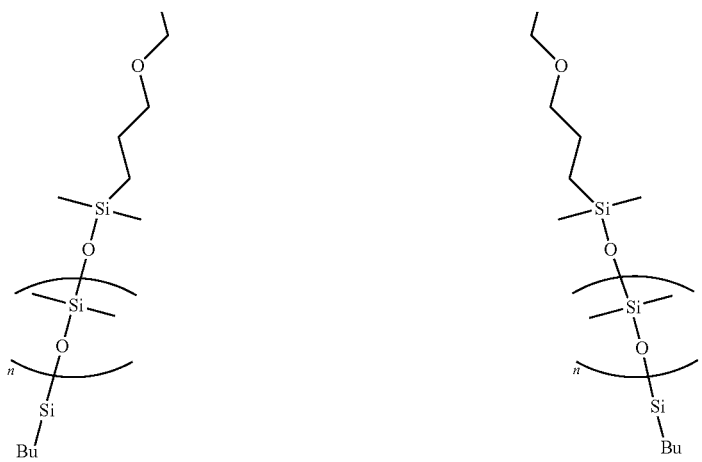
U114
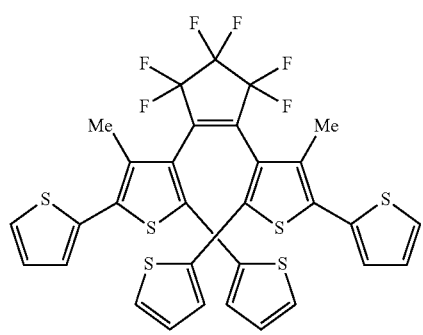 [SMILES: Cc1c(-c2cccs2)sc(-c2cccs2)c1C1=C(c2c(-c3cccs3)sc(-c3cccs3)c2C)C(F)(F)C(F)(F)C1(F)F]
U117

-continued
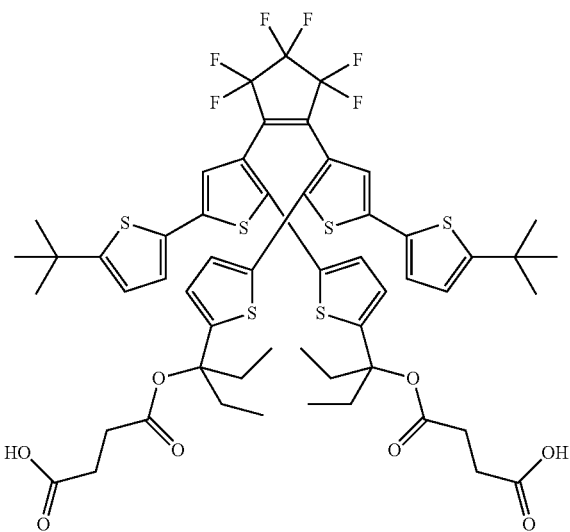 [SMILES: CCC(CC)(OC(=O)CCC(=O)O)c1ccc(-c2sc(-c3ccc(C(C)(C)C)s3)cc2C2=C(c3cc(-c4ccc(C(C)(C)C)s4)sc3-c3ccc(C(CC)(CC)OC(=O)CCC(=O)O)s3)C(F)(F)C(F)(F)C2(F)F)s1]
U120
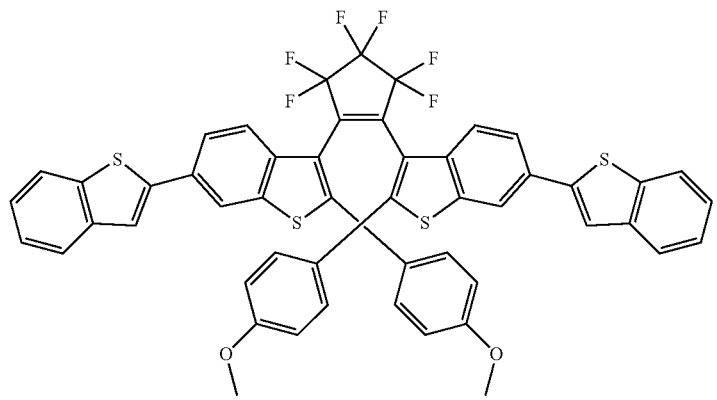 [SMILES: COc1ccc(-c2sc3cc(-c4cc5ccccc5s4)ccc3c2C2=C(c3c(-c4ccc(OC)cc4)sc4cc(-c5cc6ccccc6s5)ccc34)C(F)(F)C(F)(F)C2(F)F)cc1]
U121
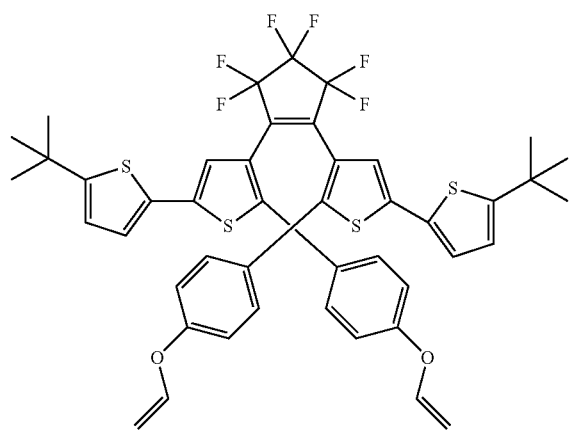 [SMILES: C=COc1ccc(-c2sc(-c3ccc(C(C)(C)C)s3)cc2C2=C(c3cc(-c4ccc(C(C)(C)C)s4)sc3-c3ccc(OC=C)cc3)C(F)(F)C(F)(F)C2(F)F)cc1]
U122

-continued
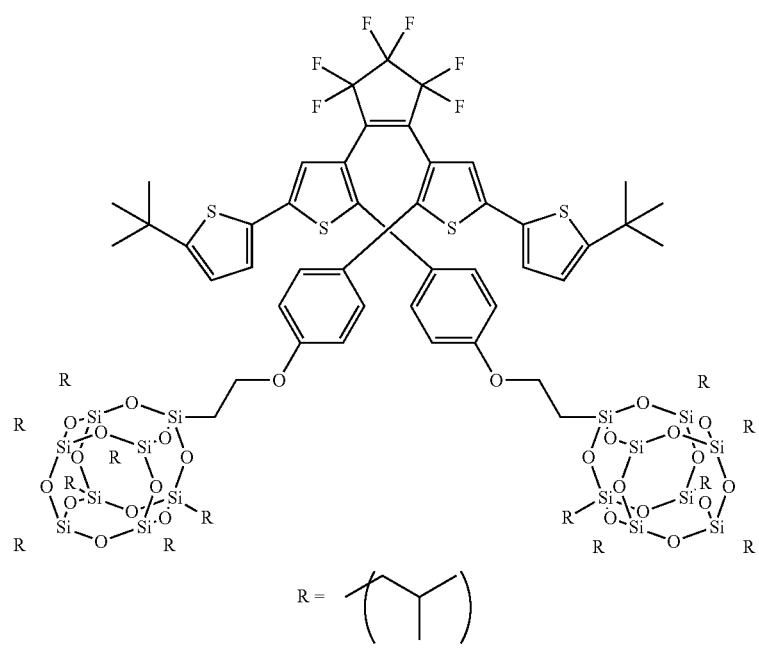
U123
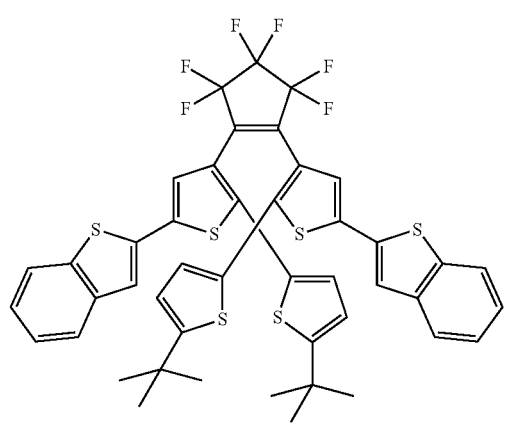 [SMILES: CC(C)(C)c1ccc(-c2sc(-c3cc4ccccc4s3)cc2C2=C(c3cc(-c4cc5ccccc5s4)sc3-c3ccc(C(C)(C)C)s3)C(F)(F)C(F)(F)C2(F)F)s1]
U125
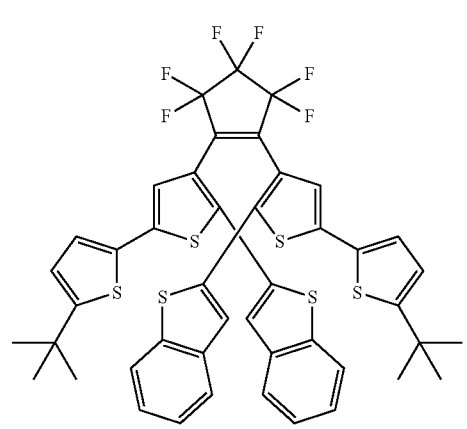 [SMILES: CC(C)(C)c1ccc(-c2cc(C3=C(c4cc(-c5ccc(C(C)(C)C)s5)sc4-c4cc5ccccc5s4)C(F)(F)C(F)(F)C3(F)F)c(-c3cc4ccccc4s3)s2)s1]
U126

-continued
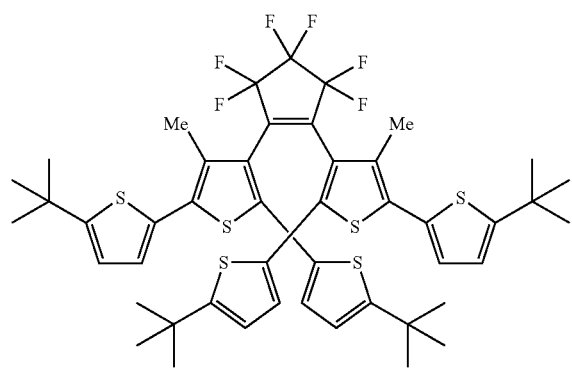 [SMILES: Cc1c(-c2ccc(C(C)(C)C)s2)sc(-c2ccc(C(C)(C)C)s2)c1C1=C(c2c(-c3ccc(C(C)(C)C)s3)sc(-c3ccc(C(C)(C)C)s3)c2C)C(F)(F)C(F)(F)C1(F)F]
U127
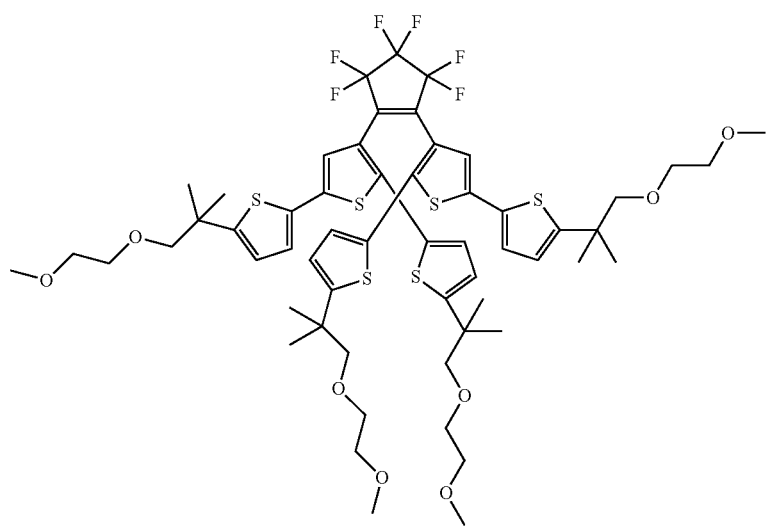
U129
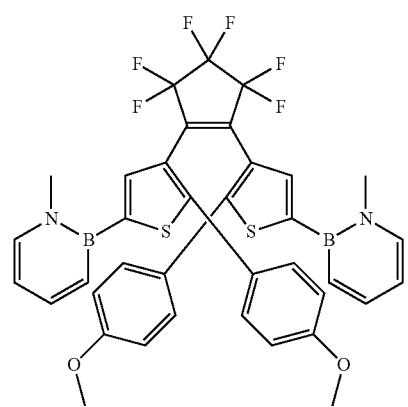 [SMILES: COc1ccc(-c2sc(B3C=CC=CN3C)cc2C2=C(c3cc(B4C=CC=CN4C)sc3-c3ccc(OC)cc3)C(F)(F)C(F)(F)C2(F)F)cc1]
U130

-continued
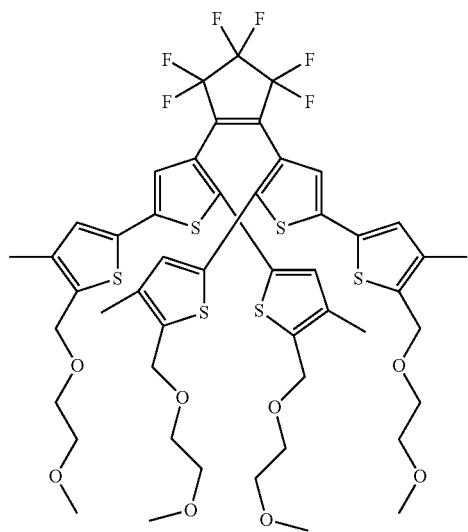
U131
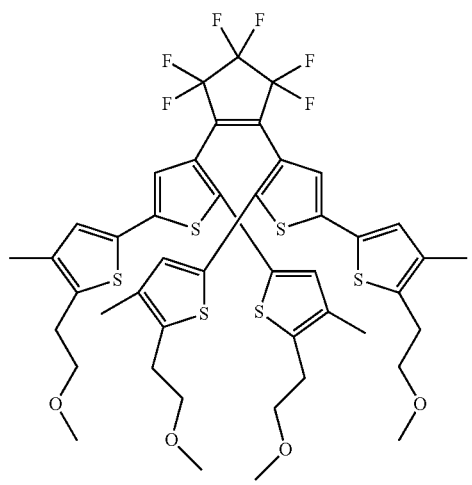
U132

-continued
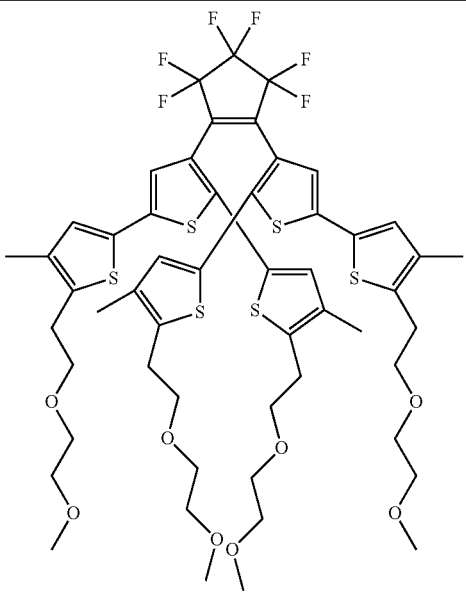
U133
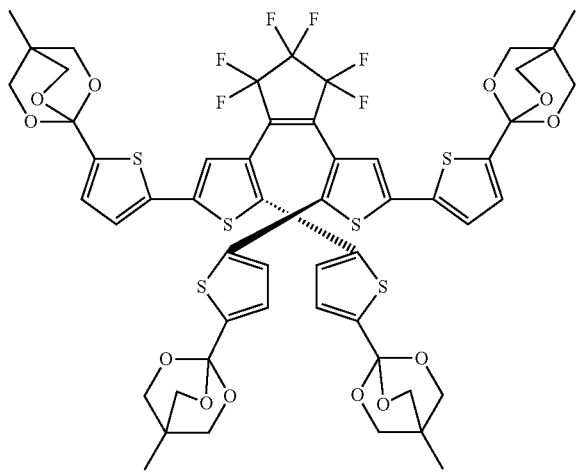
U134
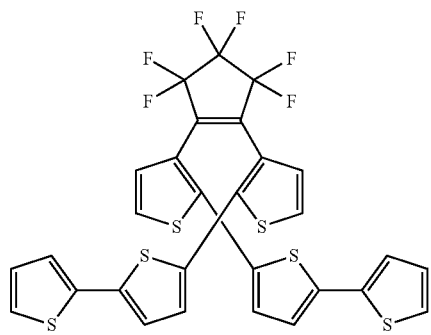 [SMILES: FC1(F)C(c2ccsc2-c2ccc(-c3cccs3)s2)=C(c2ccsc2-c2ccc(-c3cccs3)s2)C(F)(F)C1(F)F]
U136

-continued
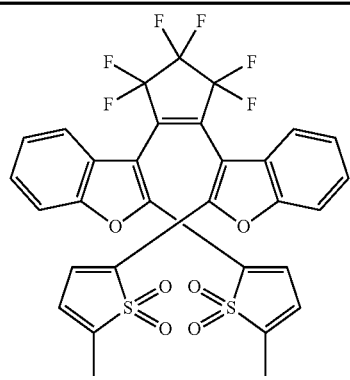
U142
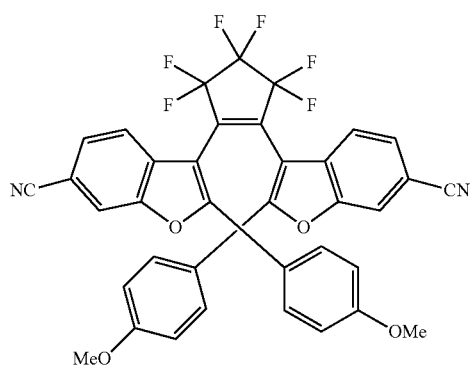 [SMILES: COc1ccc(-c2oc3cc(C#N)ccc3c2C2=C(c3c(-c4ccc(OC)cc4)oc4cc(C#N)ccc34)C(F)(F)C(F)(F)C2(F)F)cc1]
U145
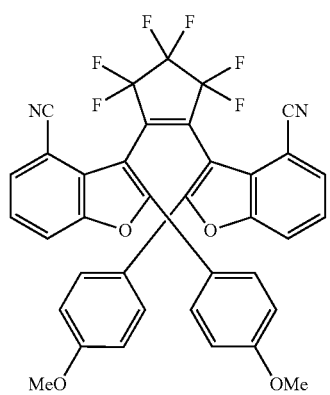 [SMILES: COc1ccc(-c2oc3cccc(C#N)c3c2C2=C(c3c(-c4ccc(OC)cc4)oc4cccc(C#N)c34)C(F)(F)C(F)(F)C2(F)F)cc1]
U146
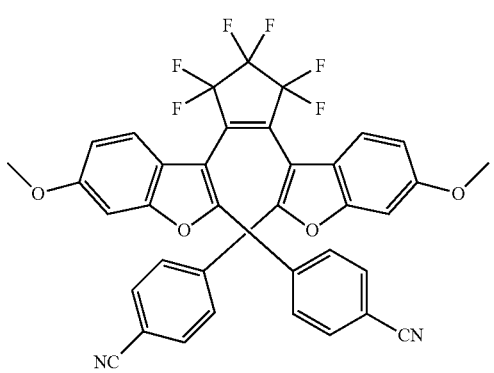
U147

-continued
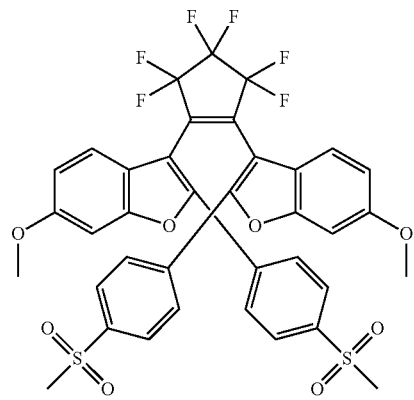 [SMILES: COc1ccc2c(C3=C(c4c(-c5ccc(S(C)(=O)=O)cc5)oc5cc(OC)ccc45)C(F)(F)C(F)(F)C3(F)F)c(-c3ccc(S(C)(=O)=O)cc3)oc2c1]
U150
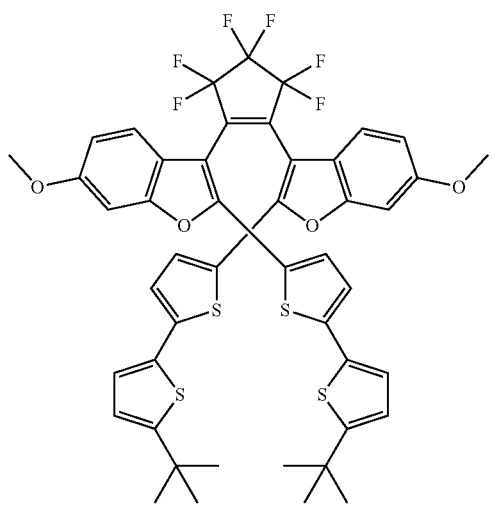
U152
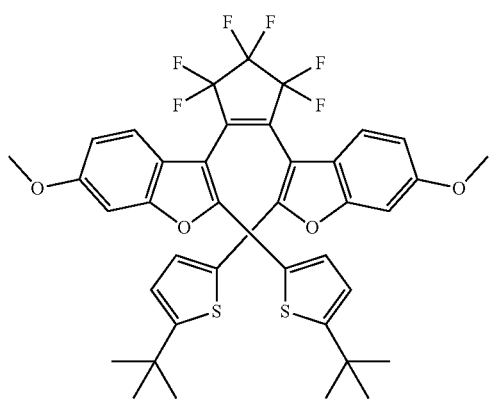
U153

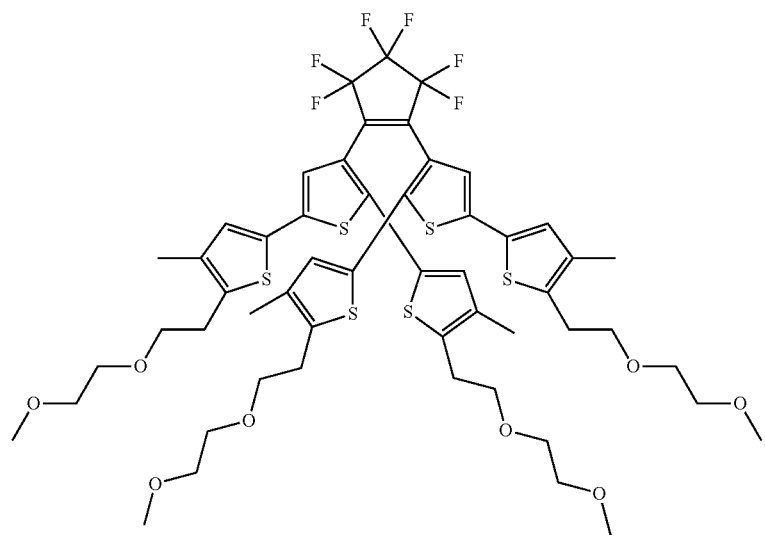
U156
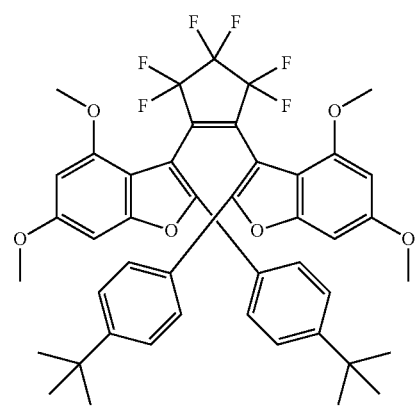 [SMILES: COc1cc(OC)c2c(C3=C(c4c(-c5ccc(C(C)(C)C)cc5)oc5cc(OC)cc(OC)c45)C(F)(F)C(F)(F)C3(F)F)c(-c3ccc(C(C)(C)C)cc3)oc2c1]
U157

-continued
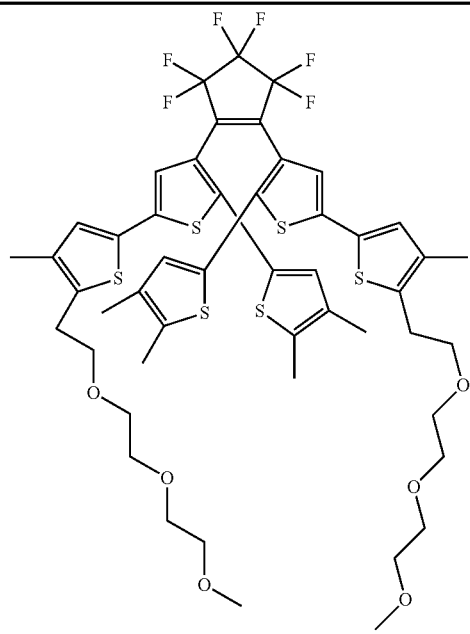
U159
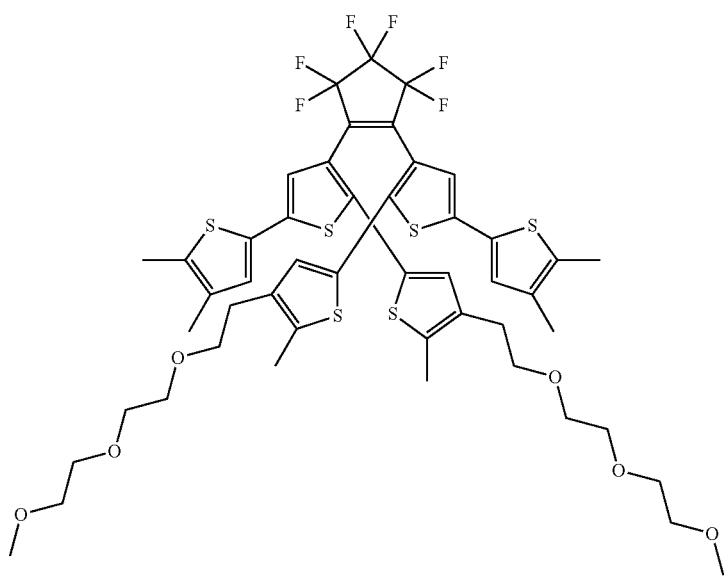
U160

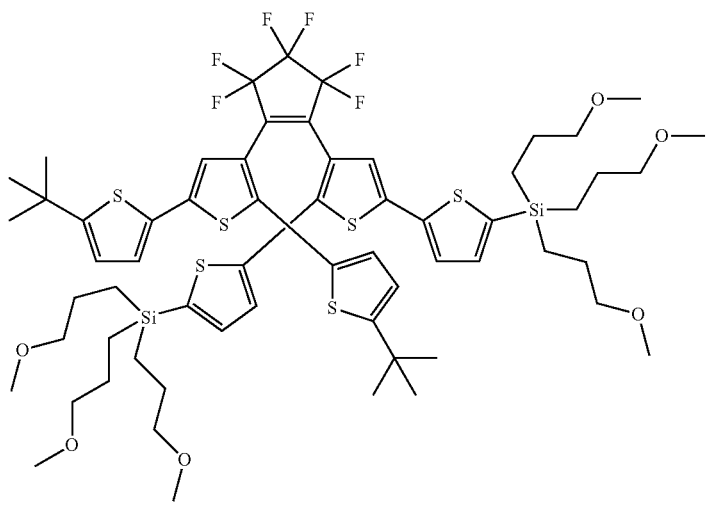 [SMILES: COCCC[Si](CCCOC)(CCCOC)c1ccc(-c2cc(C3=C(c4cc(-c5ccc(C(C)(C)C)s5)sc4-c4ccc(C(C)(C)C)s4)C(F)(F)C(F)(F)C3(F)F)c(-c3ccc([Si](CCCOC)(CCCOC)CCCOC)s3)s2)s1]
U165
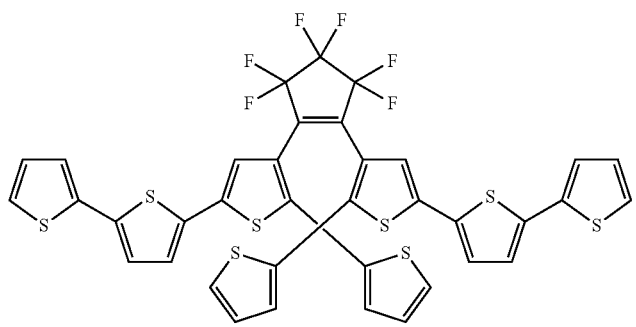 [SMILES: FC1(F)C(c2cc(-c3ccc(-c4cccs4)s3)sc2-c2cccs2)=C(c2cc(-c3ccc(-c4cccs4)s3)sc2-c2cccs2)C(F)(F)C1(F)F]
S033
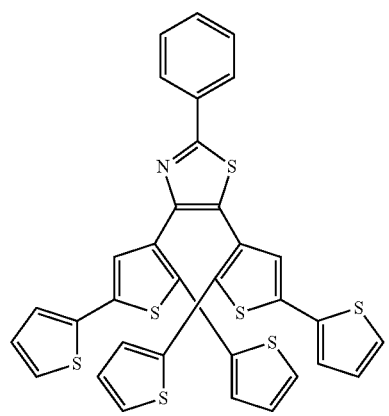 [SMILES: c1ccc(-c2nc(-c3cc(-c4cccs4)sc3-c3cccs3)c(-c3cc(-c4cccs4)sc3-c3cccs3)s2)cc1]
S075

Example 86

Synthesis of S191

(Scheme 95)

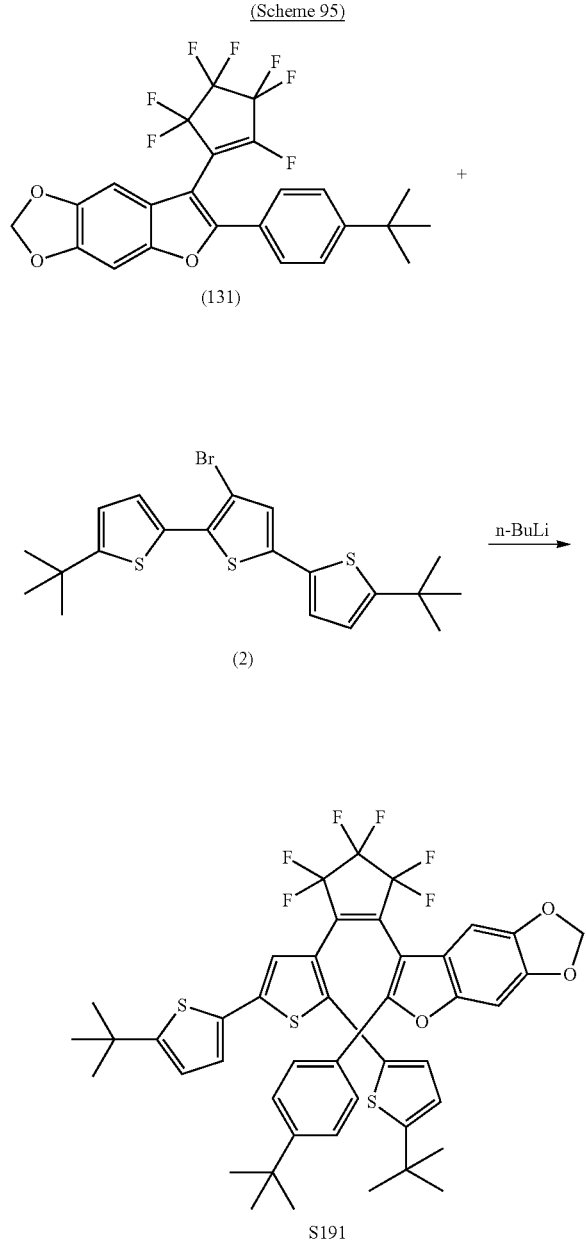

A solution of (2) (0.67 g; 1.53 mmol) in anhydrous diethyl ether (15 mL) was cooled to −78° C. n-Butyl lithium (0.67 mL; 1.66 mmol; 2.5 M in hexane) was added. The mixture was stirred at this temperature for 10 min. A solution of (139) (0.62 g; 1.28 mmol) was added as a solution in ether (10 ml) over 5 min. The reaction mixture was stirred for 10 min and allowed to warm to room temperature with stirring overnight. The reaction was quenched by addition of 10% aqueous HCl (5 mL), the organic fraction separated, and the product isolated using preparative TLC (yield: 0.14 g)

Example 87

Synthesis of S193

(Scheme 96)

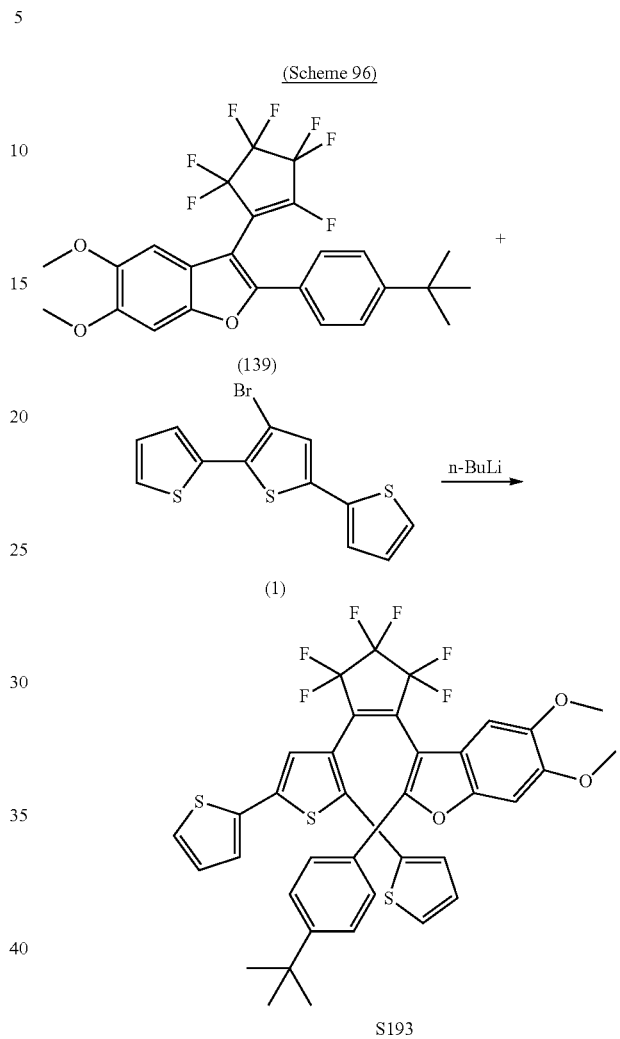

A solution of (1) (0.82 g; 2.5 mmol) in anhydrous diethyl ether (15 mL) was cooled to −78° C. n-Butyl lithium (1.05 mL; 2.63 mmol; 2.5 M in hexane) was added. The mixture was stirred for 10 min, and a solution of (139) (0.628 g; 1.25 mmol) ether (10 ml) was added over 5 min. The reaction mixture was stirred for 15 min and quenched by addition of 10% HCl (5 mL). The product was obtained by column purification. Yield 0.44 g (48.2%).

Example 88

PSS and Light Composition

The difference in PSS as a function of light source type was investigated. The light sources included direct sunlight (filtered through window glass) and interior lighting. Irradiance information and spectral profiles of light sources are provided in Table 9 and FIG. 2, respectively. Six compounds ($2\times10^{-4}$ M solutions of S096, S094, S079, S044, S042 and S035 in triglyme) were investigated and compared for performance on the basis of maximum difference in darkening ability between sunlight and interior lighting conditions. Darkening ability is indicated by the absorbance at λmax in the visible light spectrum for the ring-closed isomer of the chromophore.

TABLE 9

Description of Lighting Conditions and Intensity

| Condition | Approximate Time of Day | Temperature (° C.) | Full Spectrum Light Intensity (W/m²) |
|---|---|---|---|
| Photostationary State (FIG. 3) | | | |
| A—Interior lighting only[1] | 17:15 | 22.2 | 29 |
| B—Sunlight + Interior Lights[2] | 16:20 | 24.6 | 73 |
| C—Sunlight[3] | 15:05 | 24.7 | 114 |
| Time to Reach Photostationary State (FIG. 4) | | | |
| A—Interior lighting only[1] | 12:45 | 24.1 | 29 |
| B—Sunlight + Interior Lights[2] | 12:03 | 23.6 | 40-43 |
| C—Sunlight[3] | 12:14 | 22.4 | 32-70 |

[1]Samples were irradiated with the light from halogen bulbs (Philips Master Line 75 Watt Flood) in a lab where all window shutters were tightly closed to block out sunlight.
[2]Samples were irradiated in the same lab described above but with the shutters open to allow sunlight to enter the lab. Distance between sample and window was 300 cm.
[3]Samples were irradiated in the same lab described above but with the shutters open to allow sunlight to enter the lab. Distance between sample and window was 20 cm.

Figure 3:
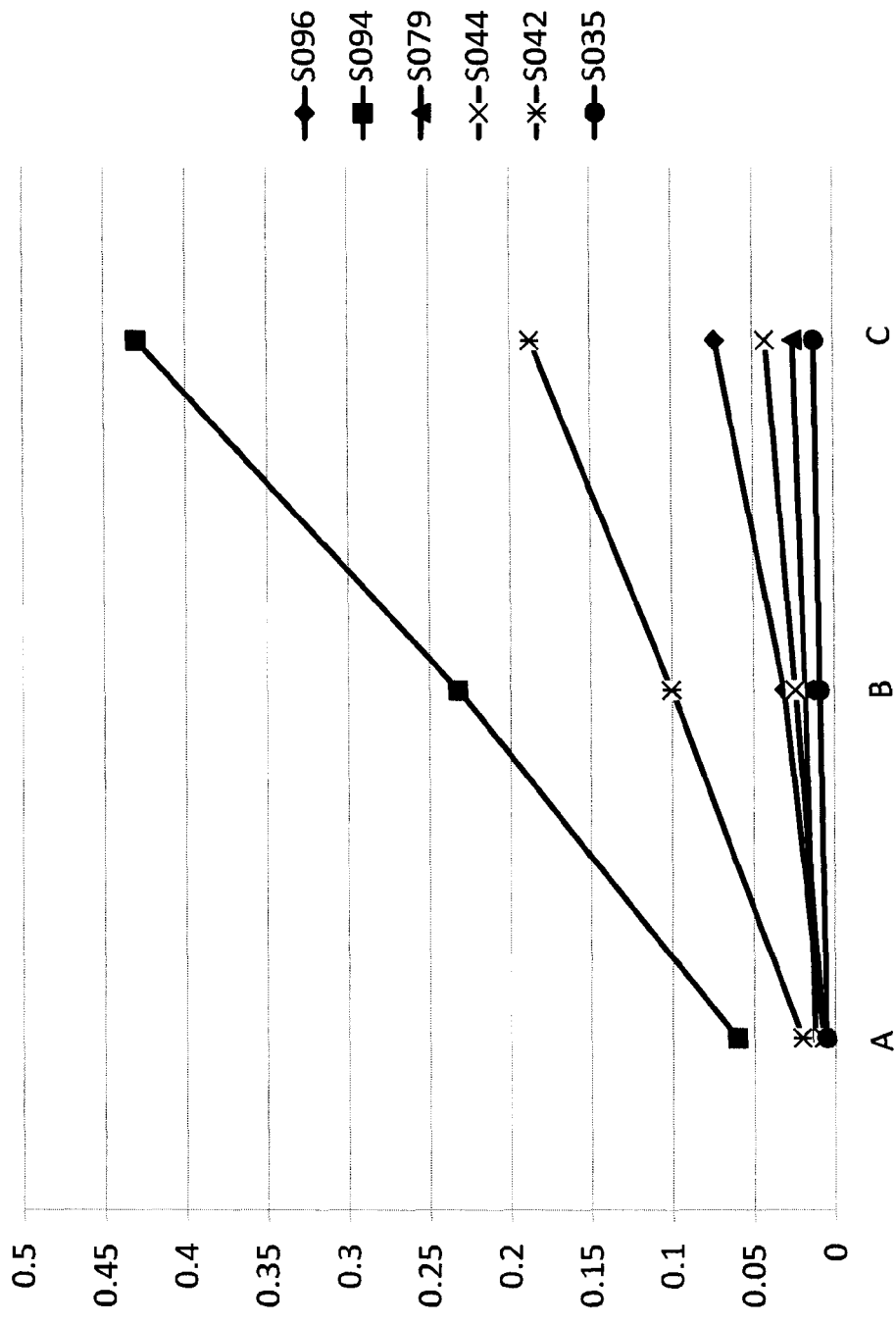
FIG. 3 shows the absorptivity of selected compounds at PSS under interior lighting (A), combined interior and sunlight lighting (B), or sunlight (C). Y-axis shows the absorbance of ring-closed isomer at λ max. S096 (solid diamond), S094 (solid square), S079 (solid triangle), S044 (cross), S042 (star) and S035 (solid circle).

Samples were first irradiated with sunlight at a distance 20 cm from the window, which resulted in the darkest colouration of the samples. Samples were then moved away from the window (300 cm from window, with interior lighting on) to alter the light composition by reducing the sunlight component. This resulted in the fading of samples due to visible-light induced photochromism (samples were thermally stable at ambient temperature and did not alter coloration over a period of several hours wen protected from light sources) as shown in FIG. 3. Finally, samples were again irradiated to the darkest state under sunlight conditions (20 cm from window) and then subjected to interior lighting conditions only (sunlight blocked out with blinds), allowing the samples to fade to a lower PSS specific to these lighting conditions as shown in FIG. 3.

Figure 2:
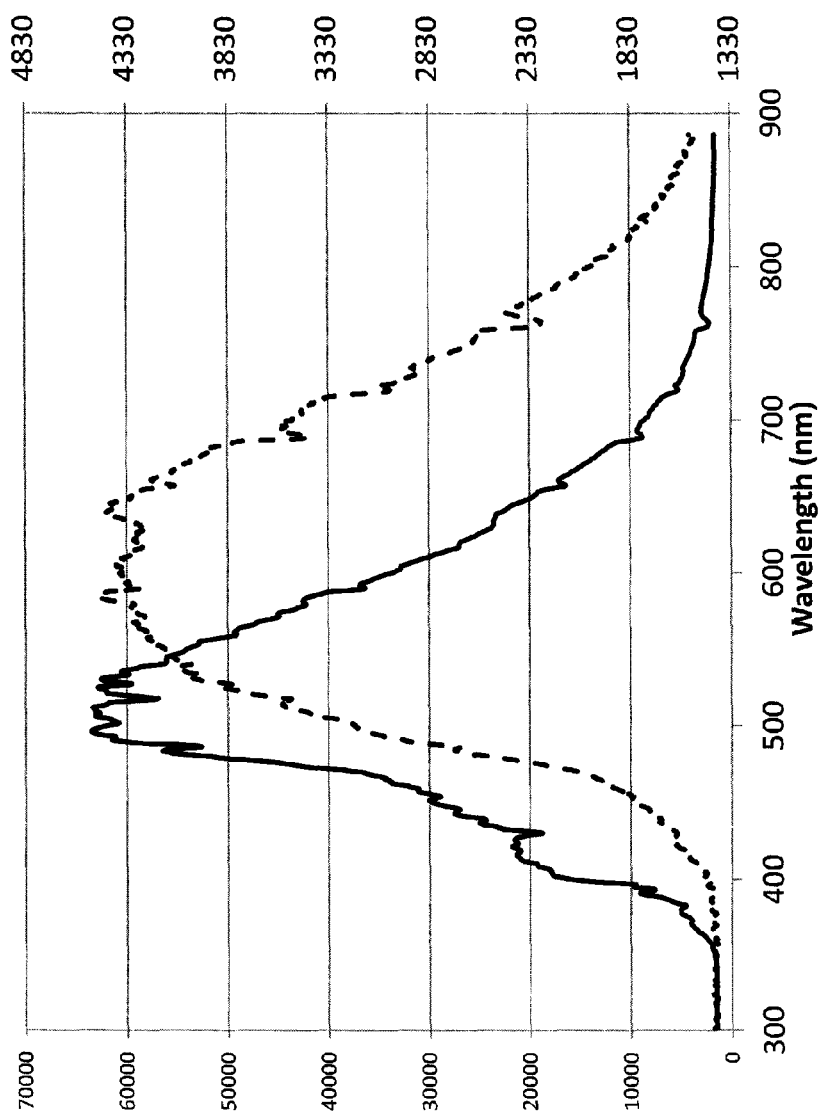
FIG. 2 shows a spectral profile for sunlight and interior halogen light sources. Spectra are plotted on separate y-axes and do not reflect relative intensities. The lighting conditions described in Table 9 reflect different weighted sums of the two light sources shown resulting in the tabulated light intensities. X-axis wavelength of light in nm; left side Y-axis—sunlight intensity (solid line); right side Y-axis—interior light intensity (dotted line).
Figure 4:
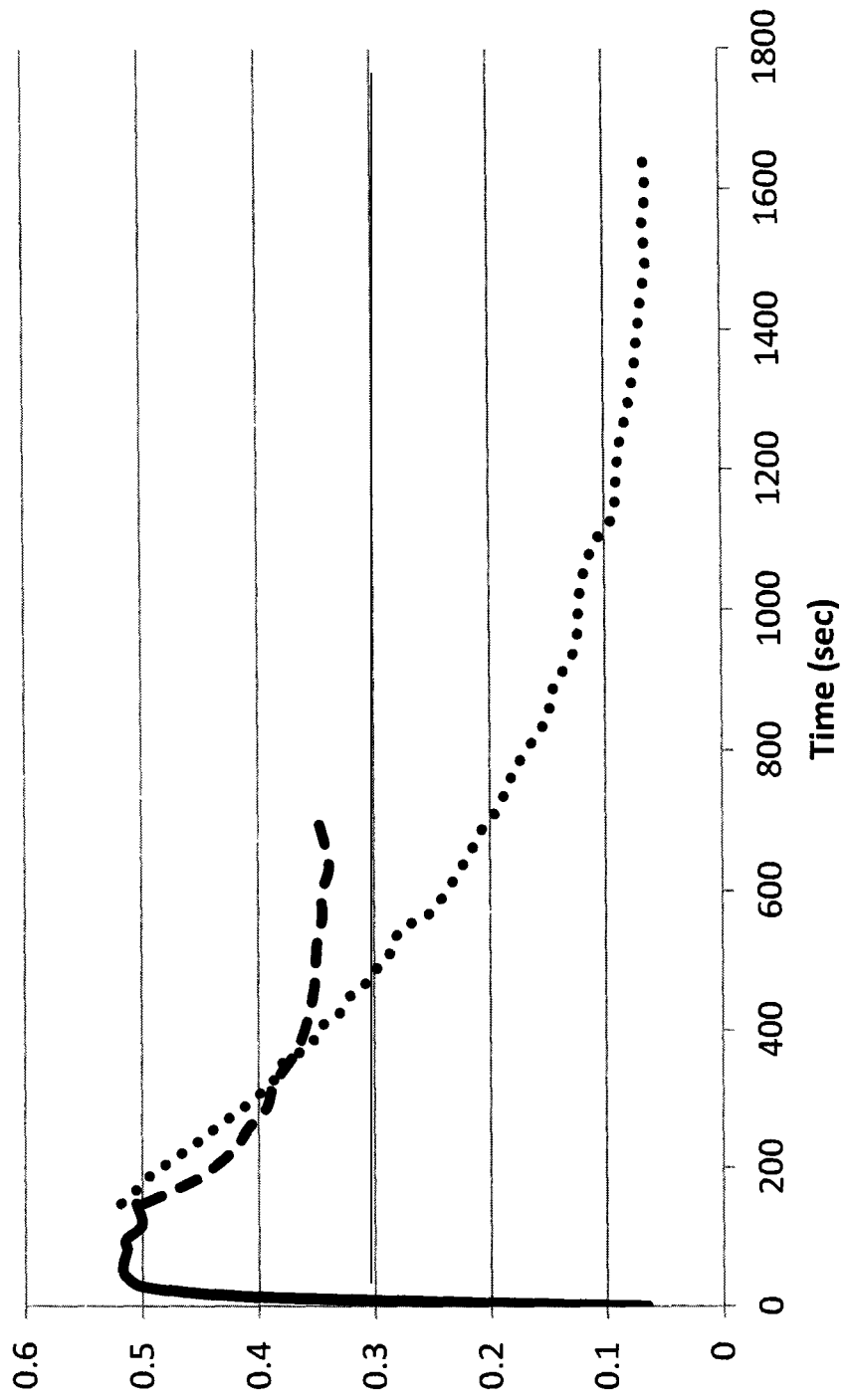
FIG. 4 shows a change in absorption of a sample of S094 exposed to different lighting conditions: solid line—sunlight (max PSS); dashed line—sunlight+interior lighting (photofaded from max dark to intermediate state); dotted line—interior lighting (photofaded from max dark to lowest absorption state). X axis—elapsed time in seconds; Y-axis—absorbance.

Compounds S094 and S042 demonstrated the greatest change in degree of coloration in response to variation in the light source. Sample darkening times were less than one minute, while sample photofading times ranged as high as 20 minutes. FIG. 4 shows the time and absorbance for sunlight+interior light, and interior light alone for S094. This experiment illustrates the differing 'sensitivity' and effect on PSS of selected compounds with respect to the composition of the light (sunlight having a UV component, which is absent in interior light, as illustrated in FIG. 2).

OTHER EMBODIMENTS

It is contemplated that any embodiment discussed in this specification can be implemented or combined with respect to any other embodiment, method, composition or aspect, and vice versa. Figures are not drawn to scale unless otherwise indicated.

The present invention has been described with regard to one or more embodiments. However, it will be apparent to persons skilled in the art that a number of variations and modifications can be made without departing from the scope of the invention as defined in the claims. Therefore, although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to," and the word "comprises" has a corresponding meaning. As used herein, the singular forms "a", "an" and "the" include plural referents unless the context clearly dictates otherwise. Citation of references herein shall not be construed as an admission that such references are prior art to the present invention, nor as any admission as to the contents or date of the references. All publications are incorporated herein by reference as if each individual publication was specifically and individually indicated to be incorporated by reference herein and as though fully set forth herein. The invention includes all embodiments and variations substantially as hereinbefore described and with reference to the examples and drawings.

Unless defined otherwise, all technical and scientific terms used herein have the same meaning as is commonly understood by one of ordinary skill in the art to which this invention belongs. If a definition set forth in this section is contrary to or otherwise inconsistent with a definition set forth in the documents that are herein incorporated by reference, the definition set forth herein prevails over the definition that is incorporated herein by reference.

What is claimed is:

1. A compound according to Formula VIIA/B, reversibly convertible under photochromic and electrochromic conditions between a ring-open isomer A and a ring-closed isomer B:

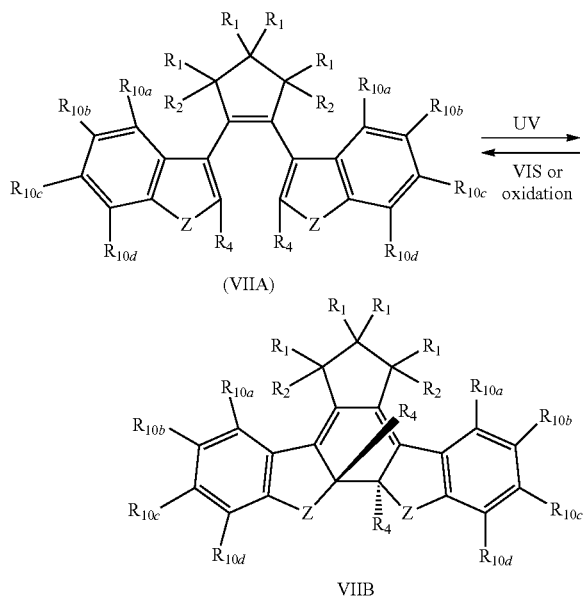

Z is O;
each $R_1$ is independently selected from the group consisting of H, or halo;
each $R_2$ is independently selected from the group consisting of H, halo, a polymer backbone, alkyl or aryl; or, when both $R_2$ together form —CH═CH— and form part of a polymer backbone;

each $R_4$ is

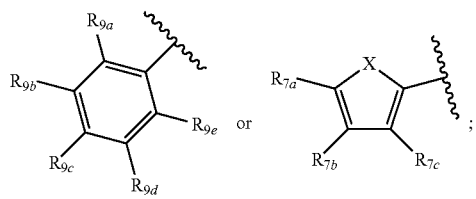

X is N, O or S; and each $R_{7a}$, $R_{7b}$, $R_{7c}$; and each $R_{9a}$, $R_{9b}$, $R_{9c}$, $R_{9d}$, $R_{9e}$ is independently selected from a group consisting of:

H, Cl, Br, F, —$CF_3$, —CN, —$NO_2$, methyl, ethyl, propyl, iso-propyl, butyl, sec-butyl, iso-butyl, tert-butyl, saturated or unsaturated alkyl that is linear or branched with 5-12 carbons, —$Si(R_{11})_3$, thiophene, substituted thiophene, benzyl, substituted benzyl, —$CH_2$—$CH_2$—, —CH=CH—, —CH=$CH_2$, —$OCH_3$, —COH, —OH, —$CO_2H$, —$COCH_3$, —$C(CH_3)_2OH$, —$Si(CH_3)_3$, —$CH_2CH_2OCH_3$, —$CH_2CH_2OH$, —$N(CH_3)_2$, —$CO_2CH_3$, —$OCH_2OCH_3$, —$SO_2CH_3$, —$OCH_2C(CH_3)_3$, —$OCH_2CH(CH_3)_2$, —$OC(CH_3)_3$, —$OCH$=$CH_2$, —$O(CH_2)_4CN$, —$O(CH_2)_4OH$, —$O(CH_2)_3OH$, —$C(CH_3)_2OH$, —$OCH_2)_2OCH_3$,

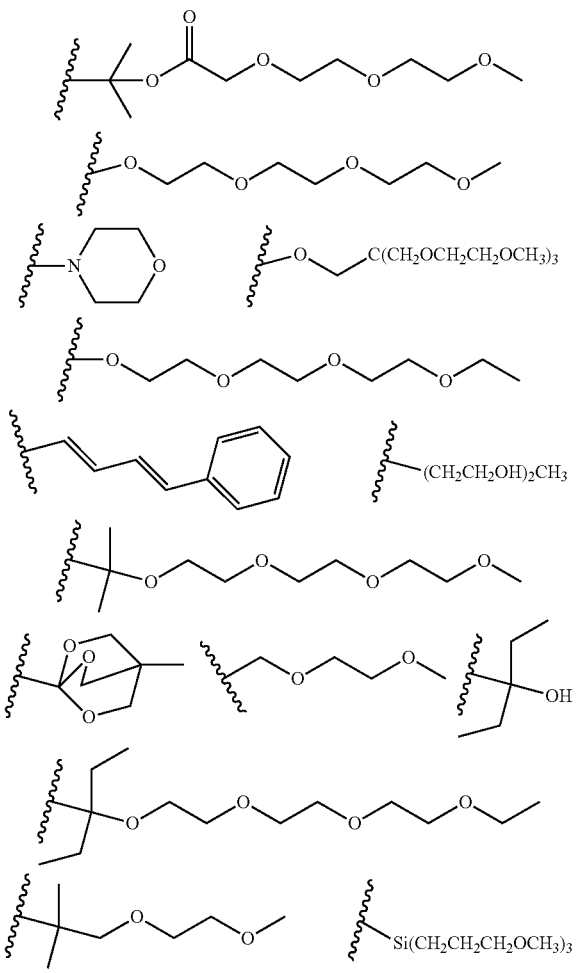

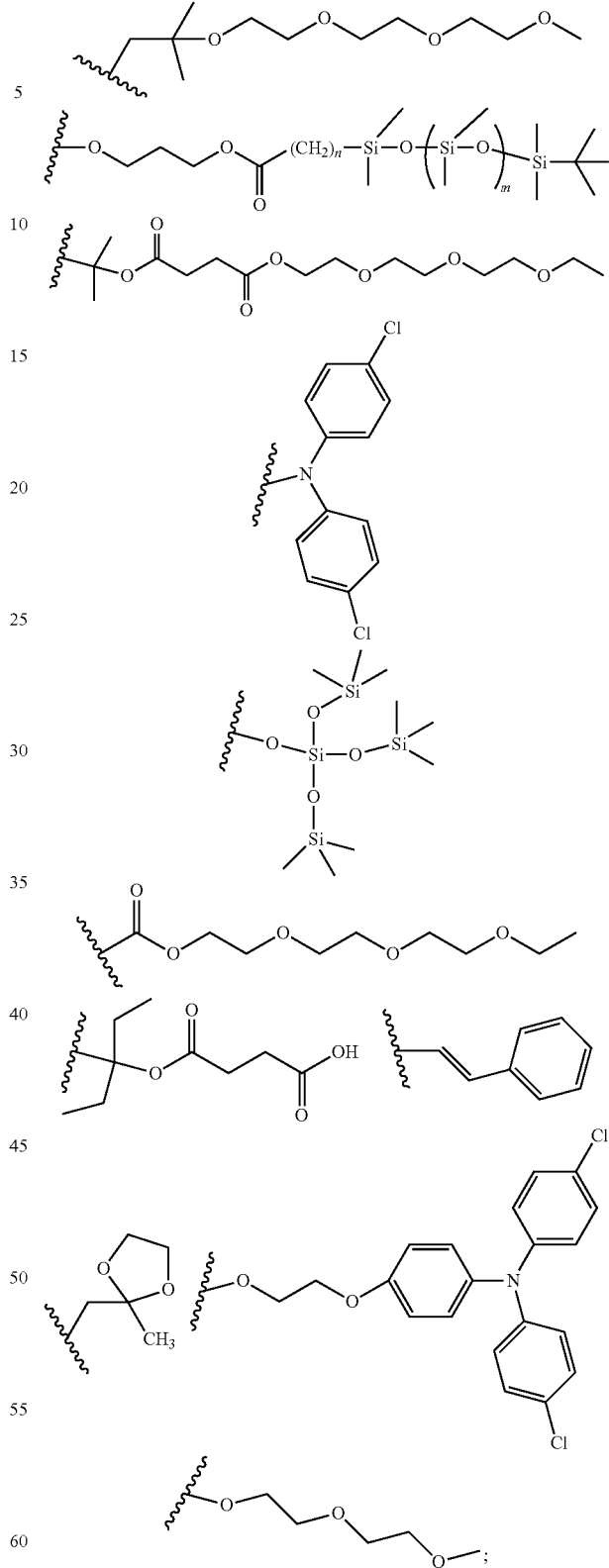

n and m are independently any integer from 0 to 20;

$R_{11}$ is independently selected from the group comprising R or —O—R, and wherein R is linear or branched, non-aromatic monocyclic or polycyclic, substituted or unsubstituted alkyl group of 1 to 20 carbons; or R is a heteroalkyl group comprising one or more of O, S, N or Si; or each R is a saturated or unsaturated alkyl that is linear or branched with 1-12 carbons; or each R is a substituted or unsubstituted methyl, ethyl, propyl, iso-propyl, butyl, sec-butyl, iso-butyl, tert-butyl, pentyl or hexyl;

$R_{10a}$ is selected from a group consisting of an electron donating group (EDG), an electron withdrawing group (EWG), —OCH$_3$, —CN, —OH, H,

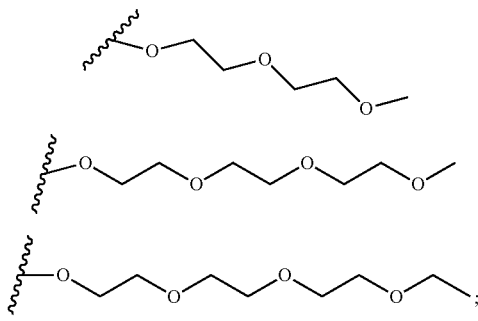

$R_{10b}$ is selected from a group consisting of an electron donating group (EDG), an electron withdrawing group (EWG), —OCH$_3$, —CN, —OH, H,

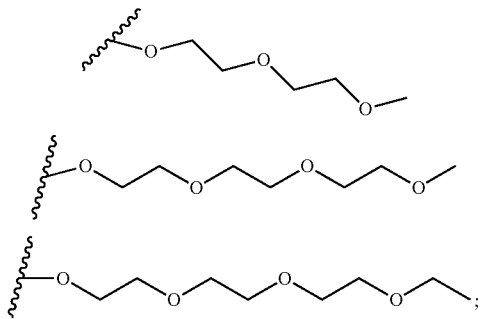

$R_{10c}$ is selected from a group consisting of an electron donating group (EDG), an electron withdrawing group (EWG), —OCH$_3$, —CN, —OH,

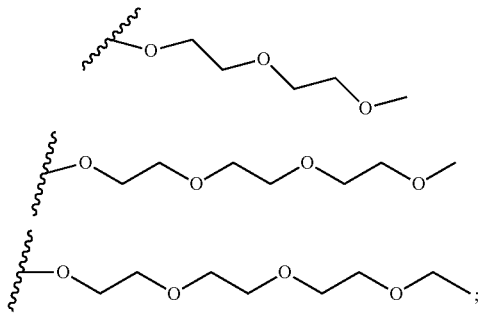

$R_{10d}$ is selected from a group consisting of, an electron donating group (EDG), an electron withdrawing group (EWG), —OCH$_3$, —CN, —OH, H,

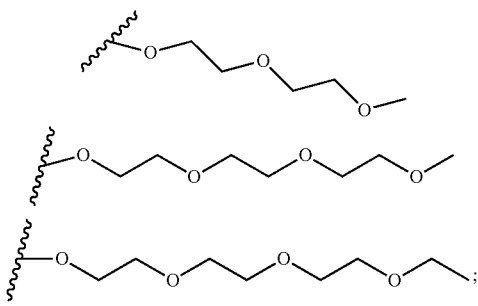

or $R_{10b}$ and $R_{10c}$ are each O and joined by —CH$_2$— to form a 5-membered ring.

2. The compound according to claim 1 wherein both $R_2$ are —CH=CH— and form part of a polymer backbone.

3. The compound according to claim 1 wherein $R_4$ is

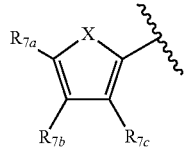

and X is S.

4. The compound according to claim 1 wherein $R_4$ is

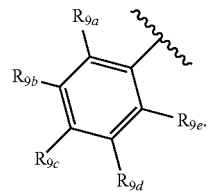

5. The compound according to claim 1 wherein:
a. the electron donating group is selected from a group consisting of —OH, OR, NH$_2$, NHR, NR$_2$, electron-rich heteroaryl groups, electron-rich substituted aryl groups, —O$^-$, amine, alcohol, ether, thioether, alkyl and carbamate; and
b. the electron withdrawing group is selected from a group consisting of halogen, electron-poor heteroaryl groups, electron-poor substituted aryl groups, —NO$_2$, —$^+$NR$_3$, —$^+$NH$_3$, —SO$_3$H, —CN, CF$_3$, aldehyde, ester, carboxylic acid, carbonyl, carbonyl chloride and amide.

6. The compound according to claim 1 wherein $R_{9a}$, $R_{9b}$, $R_{9c}$, $R_{9d}$ and $R_{9e}$ are each independently selected from a group consisting of H, Cl, Br, F, —CF$_3$, —CN, —NO$_2$, methyl, ethyl, propyl, iso-propyl, butyl, sec-butyl, iso-butyl and tert-butyl; and wherein $R_{10a}$ is selected from a group consisting of —OCH$_3$, —CN, —OH, H,

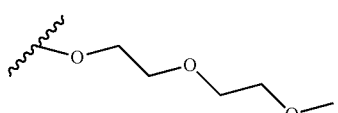

-continued

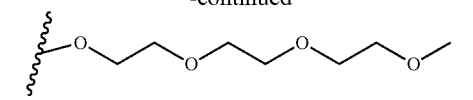

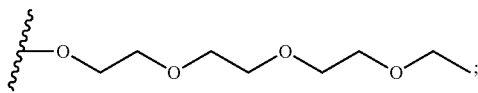

$R_{10b}$ is selected from a group consisting of —OCH$_3$, —CN, —OH, H,

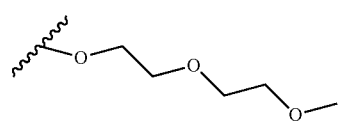

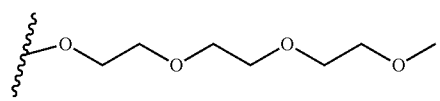

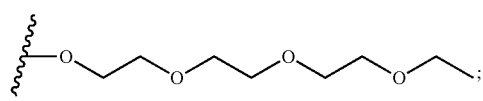

$R_{10c}$ is selected from a group consisting of —OCH$_3$, —CN, —OH,

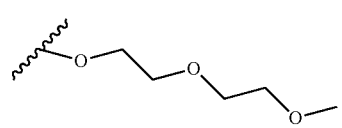

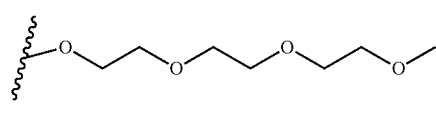

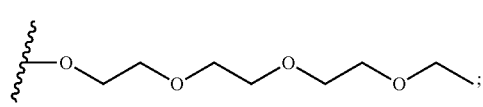

and $R_{10d}$ is selected from a group consisting of —OCH$_3$, —CN, —OH, H,

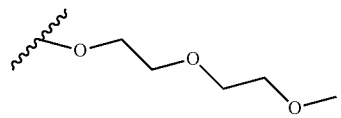

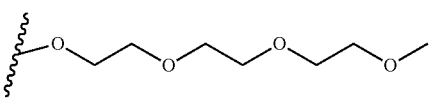

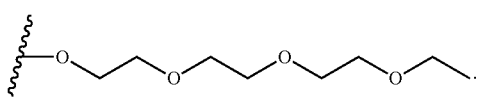

7. The compound according to claim 4 wherein $R_{9e}$ is tert-butyl.

8. The compound according to claim 1 wherein $R_{9a}$, $R_{9b}$, $R_{9d}$ and $R_{9e}$ are H.

9. The compound according to claim 1 wherein one or more of $R_{10a}$, $R_{10b}$, $R_{10c}$ and $R_{10d}$ are —OCH$_3$.

10. The compound according to claim 1 wherein $R_{10c}$ is

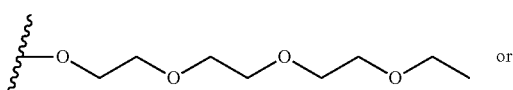 or

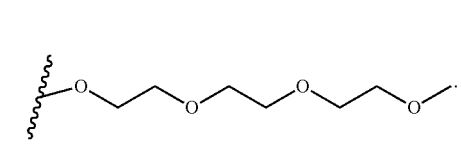

11. The compound according to claim 1 wherein R is substituted or unsubstituted methyl, ethyl, propyl, iso-propyl, butyl, sec-butyl, iso-butyl, tert-butyl, pentyl or hexyl.

12. The compound according to claim 1, selected from the group consisting of

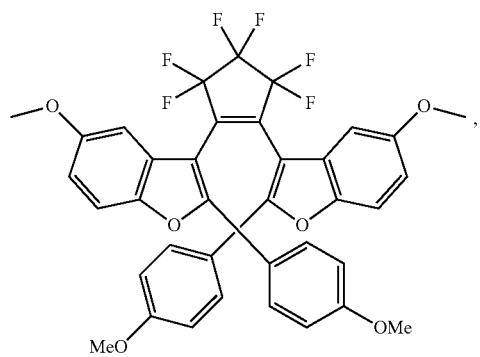

S083

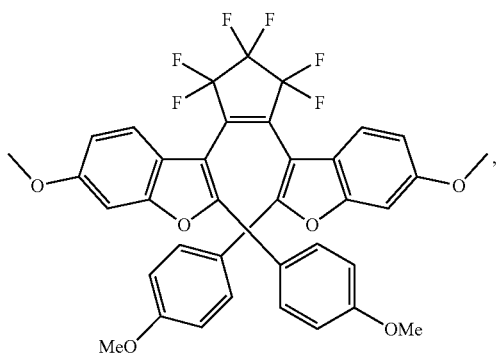

S140

-continued
S144
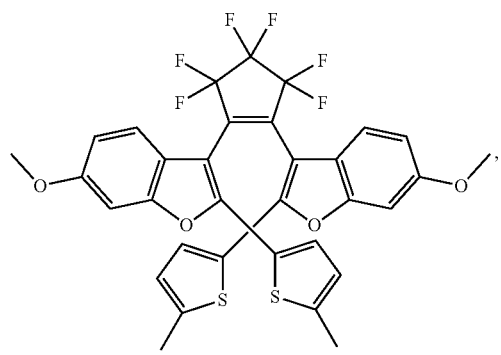
S151
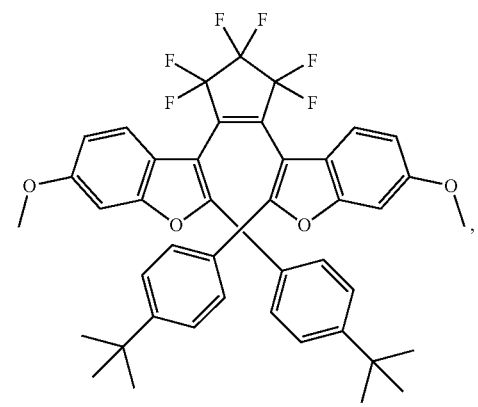
S152
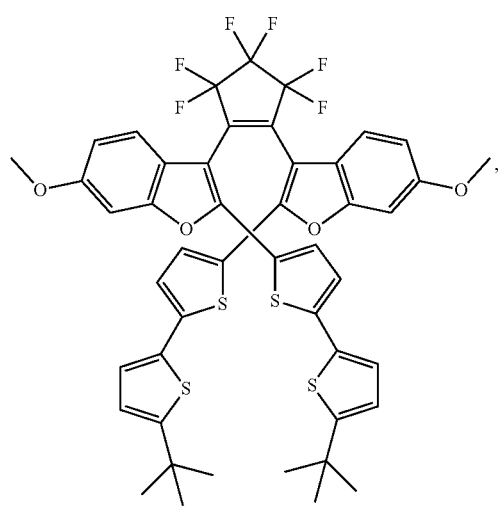
U153
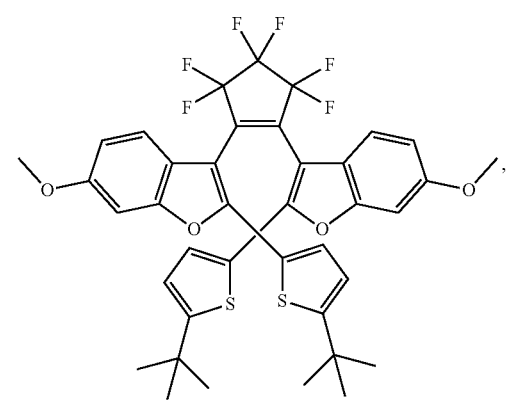
S155
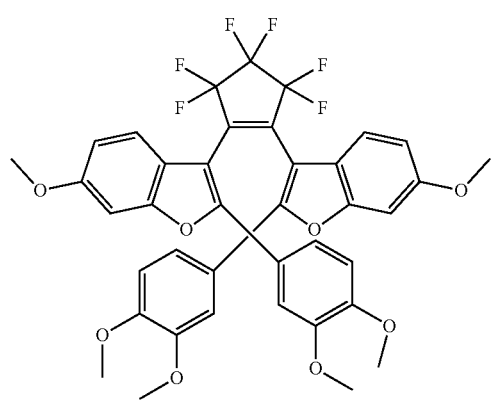

-continued
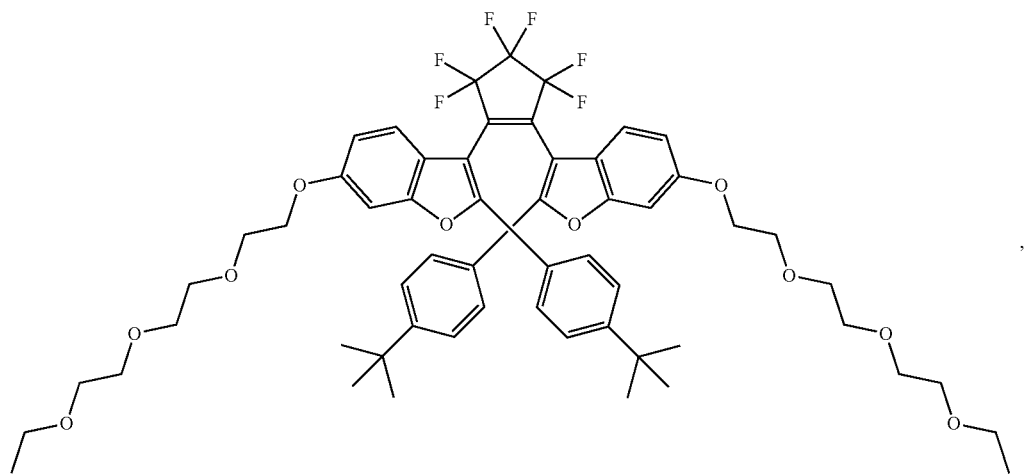
S161
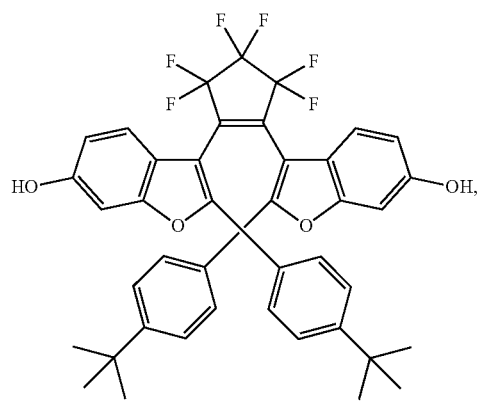
S162
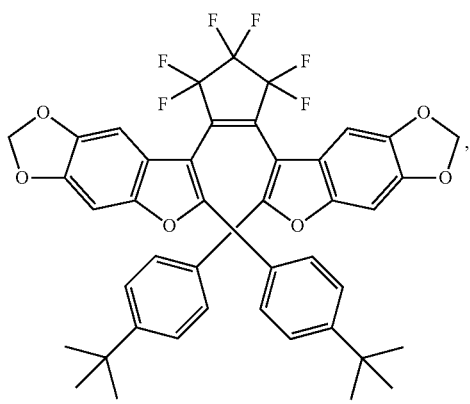
S163
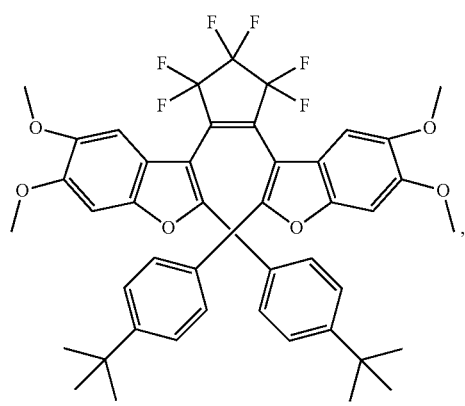
S164
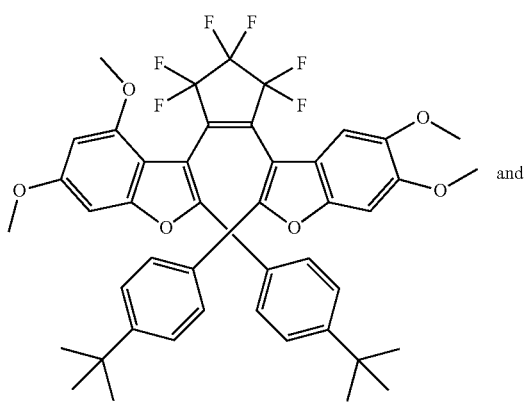
and -continued

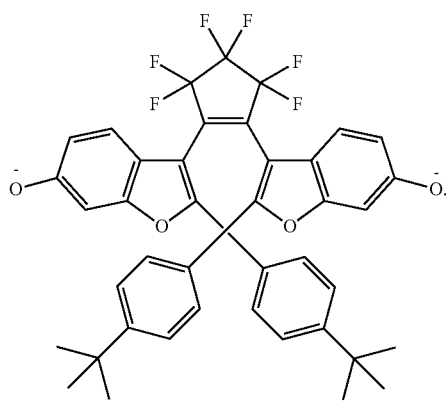

13. A compound according to Formula IA/IB, reversibly convertible under photochromic and electrochromic conditions between a ring-open isomer A and a ring-closed isomer B:

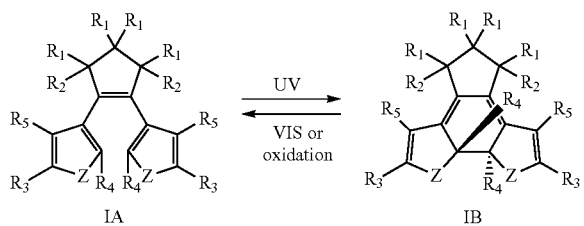

wherein

Z is N, O or S;

each $R_1$ is independently selected from the group consisting of H, or halo;

each $R_2$ is independently selected from the group consisting of H, halo, a polymer backbone, alkyl or aryl; or, when both $R_2$ together form —CH=CH— and form part of a polymer backbone;

each $R_3$ is

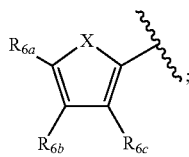

both $R_4$ are

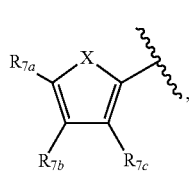

or both $R_4$ are

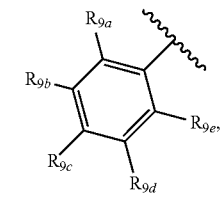

and $R_{6a}$ and $R_{7a}$ are not methyl;
X=S;
each $R_5$ is H;
each $R_{6a}$, $R_{6b}$, $R_{6c}$;
each $R_{7a}$, $R_{7b}$, $R_{7c}$; and
each $R_{9a}$, $R_{9b}$, $R_{9c}$, $R_{9d}$, $R_{9e}$
is independently selected from a group comprising:
H, Cl, Br, F, —$CF_3$, —CN, —$NO_2$, methyl, ethyl, propyl, iso-propyl, butyl, sec-butyl, iso-butyl, tert-butyl, saturated or unsaturated alkyl that is linear or branched with 5-12 carbons, —Si($R_{11}$)$_3$, thiophene, substituted thiophene, benzyl, substituted benzyl, —$CH_2$—$CH_2$—, —CH=CH—, —CH=$CH_2$, —$OCH_3$, —COH, —OH, —$CO_2$H, —$COCH_3$, —C($CH_3$)$_2$OH, —Si($CH_3$)$_3$, —$CH_2CH_2OCH_3$, —$CH_2CH_2OH$, —N($CH_3$)$_2$, —$CO_2CH_3$, —$OCH_2OCH_3$, —$SO_2CH_3$, —$OCH_2$C($CH_3$)$_3$, —$OCH_2CH(CH_3)_2$, —OC($CH_3$)$_3$, —OCH=$CH_2$, —O($CH_2$)$_4$CN, —O($CH_2$)$_4$OH, —O($CH_2$)$_3$OH, —C($CH_3$)$_2$OH, —O($CH_2$)$_2$$OCH_3$, —O($CH_2$)$_4$CN, —O($CH_2$)$_4$COOH

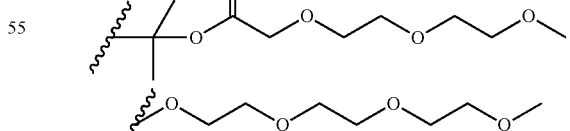

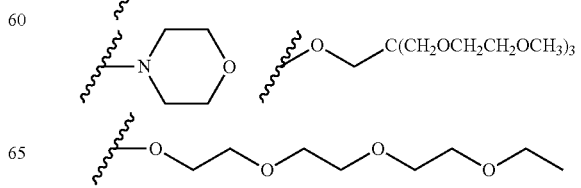

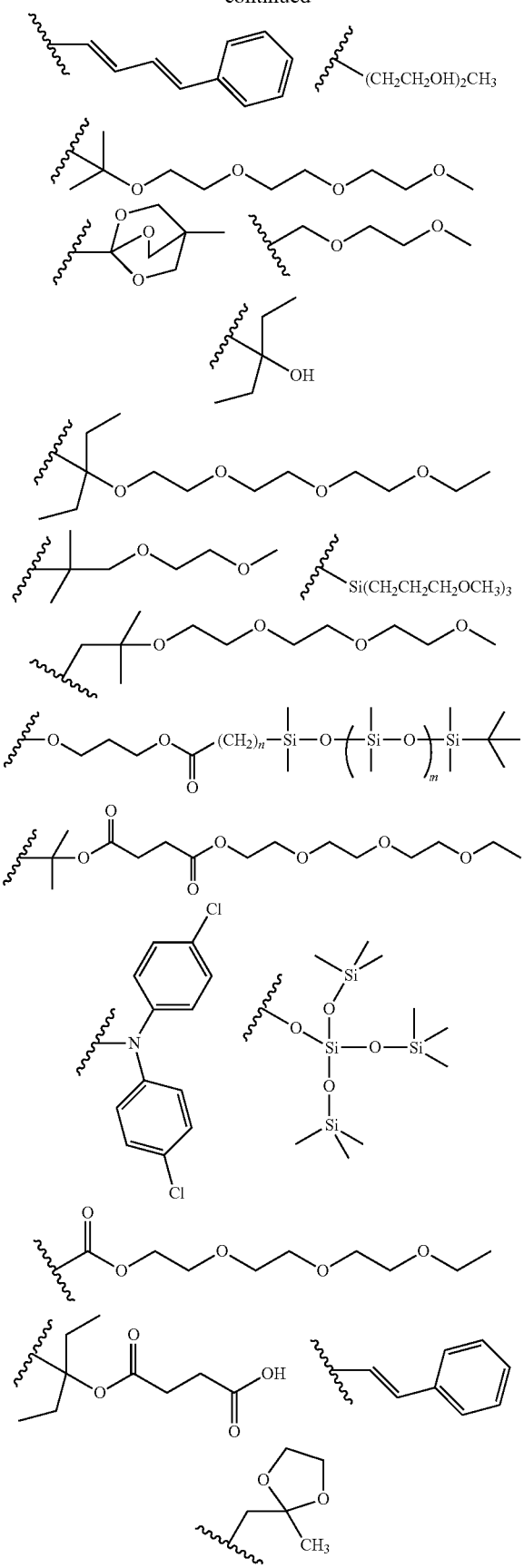
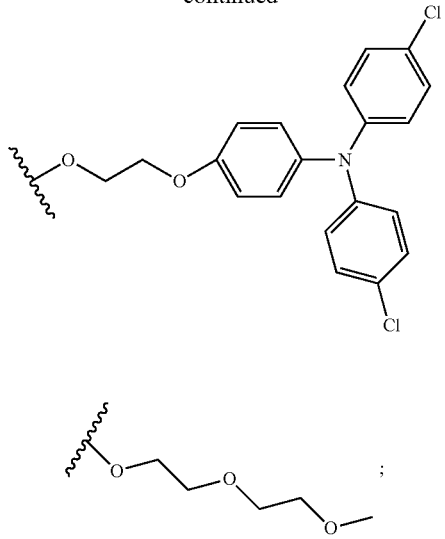

or where $R_{6a}$ and $R_{6b}$ are each —CH=CH— and joined to form an unsaturated ring;

wherein n and m are independently any integer from 0 to 20; and wherein $R_{11}$ is independently selected from the group comprising R or —O—R, and wherein R is linear or branched, non-aromatic monocyclic or polycyclic, substituted or unsubstituted alkyl group of 1 to 20 carbons; or R is a heteroalkyl group comprising one or more of O, S, N or Si; or each R is a saturated or unsaturated alkyl that is linear or branched with 1-12 carbons; or each R is a substituted or unsubstituted methyl, ethyl, propyl, iso-propyl, butyl, sec-butyl, iso-butyl, tert-butyl, pentyl or hexyl; and at least one of $R_{6a}$, $R_{6b}$, $R_{6c}$ is not H;

at least one of $R_{7a}$, $R_{7b}$, $R_{7c}$ is not H; and at least one of $R_{9a}$, $R_{9b}$, $R_{9c}$, $R_{9d}$, $R_{9e}$ is not H.

14. The compound according to claim 13 wherein both $R_2$ are —CH=CH— and form part of a polymer backbone.

15. The compound according to claim 13 wherein:

each $R_{6a}$ is independently selected from a group consisting of H, Cl, —CN, methyl, ethyl, propyl, iso-propyl, butyl, sec-butyl, iso-butyl, tert-butyl, —Si($R_{11}$)$_3$, thiophene, substituted thiophene, —CO$_2$H, —COCH$_3$, —Si(CH$_3$)$_3$;

each $R_{6b}$ is independently selected from a group consisting of H, Cl, —CN, methyl, ethyl, propyl, iso-propyl, butyl, sec-butyl, iso-butyl, tert-butyl, —Si($R_{11}$)$_3$, thiophene, substituted thiophene, —CO$_2$H, —COCH$_3$, —Si(CH$_3$)$_3$;

each $R_{6c}$ is independently selected from a group consisting of H, Cl, —CN, methyl, ethyl, propyl, iso-propyl, butyl, sec-butyl, iso-butyl, tert-butyl, —Si($R_{11}$)$_3$, thiophene, substituted thiophene, —CO$_2$H, —COCH$_3$, —Si(CH$_3$)$_3$;

$R_{11}$ is R, and R is a heteroalkyl group of from 1 to 10 carbons, comprising one or more of O, S;

and at least one of $R_{6a}$, $R_{6b}$, $R_{6c}$ is not H.

16. The compound according to claim 13 wherein the substituted thiophene of $R_{6a}$, $R_{6b}$ or $R_{6c}$ is

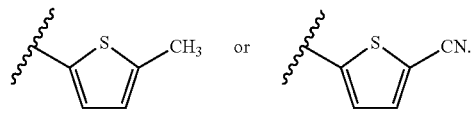

17. The compound according to claim 13 wherein
$R_{6a}$ is selected from a group consisting of Cl, —CN, methyl, ethyl, propyl, iso-propyl, butyl, sec-butyl, iso-butyl, tert-butyl, —Si($R_{11}$)$_3$, thiophene, substituted thiophene, methyl thiophene, —CO$_2$H, —COCH$_3$, —Si(CH$_3$)$_3$, and wherein $R_{11}$ is R, and R is a heteroalkyl group of from 1 to 10 carbons, comprising one or more O, S;
$R_{6b}$ is H or CH$_3$; and
$R_{6c}$ is H or CH$_3$.

18. The compound according to claim 13 wherein $R_{11}$ is —CH$_3$ or —(CH$_2$)$_{1-10}$—OCH$_3$.

19. The compound according to claim 13 wherein both $R_4$ are

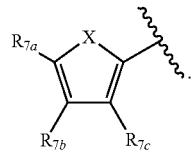

20. The compound according to claim 13 wherein both $R_4$ are

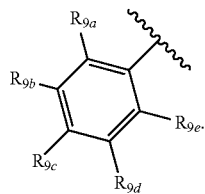

21. The compound according to claim 13 wherein $R_{9c}$ is —OCH$_3$, —OH, —O(CH$_2$)$_4$CN, —O(CH$_2$)$_4$COOH, —O(CH$_2$)$_3$OH,

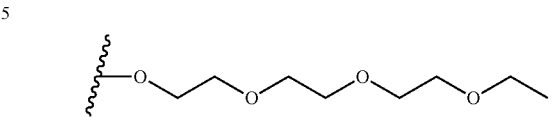

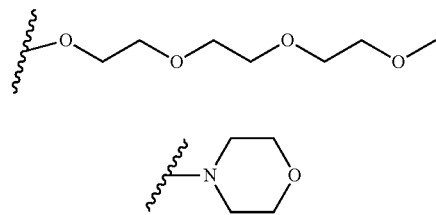

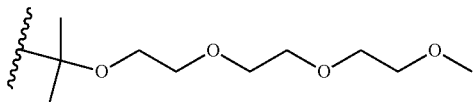

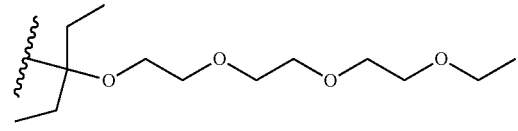

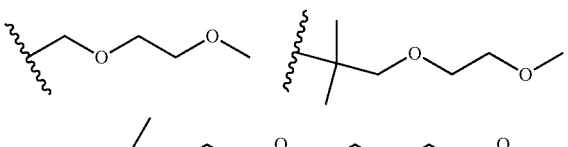

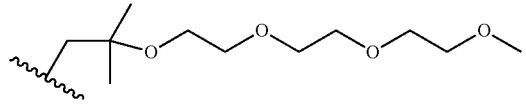

22. The compound according to claim 13 selected from the group consisting of:

S098

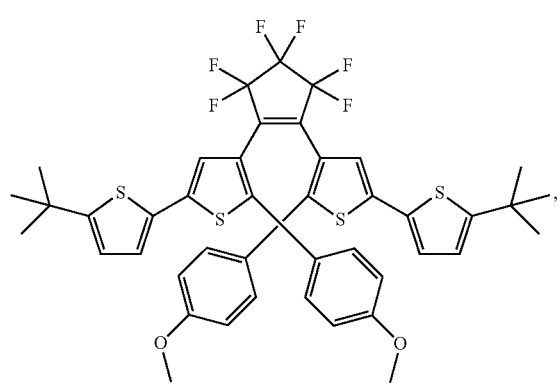

S104

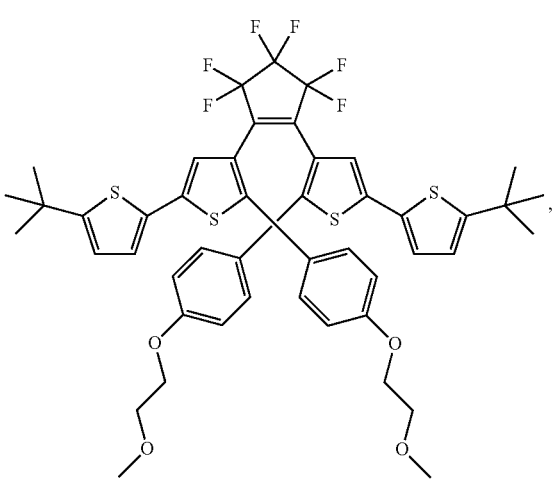

-continued
241  S105
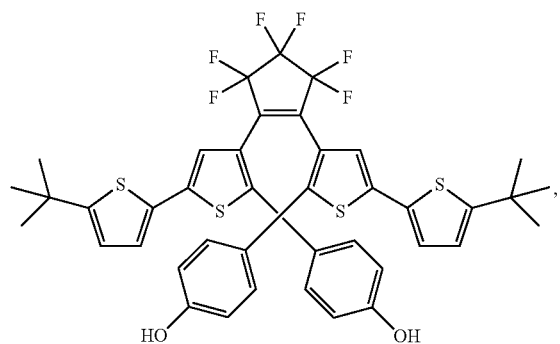
242  S108
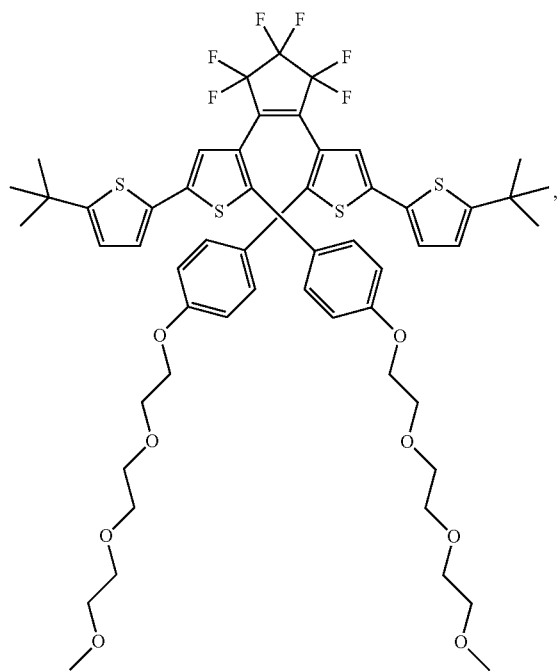
S109
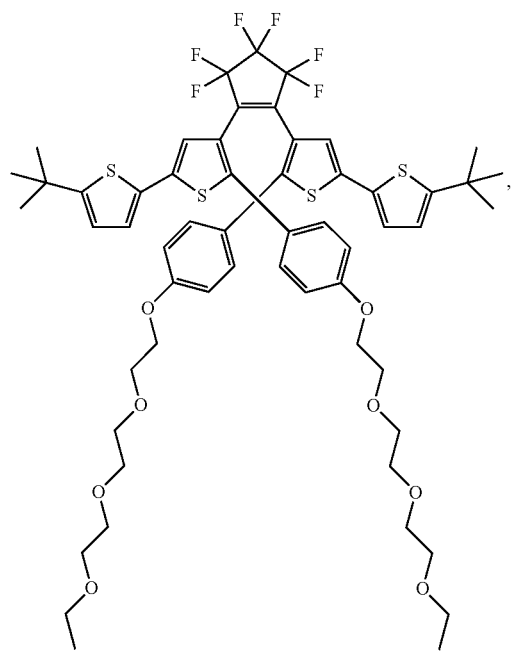
S110
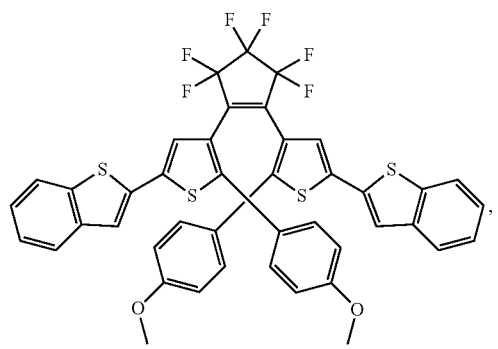

-continued
S111
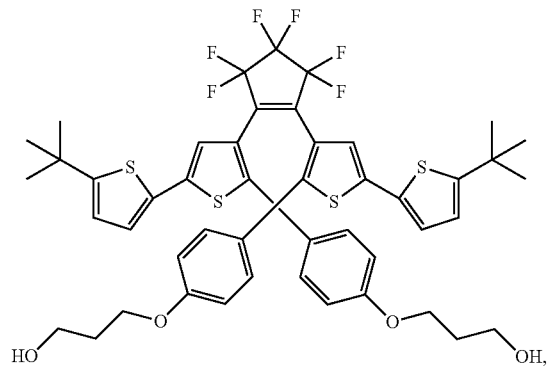
S112
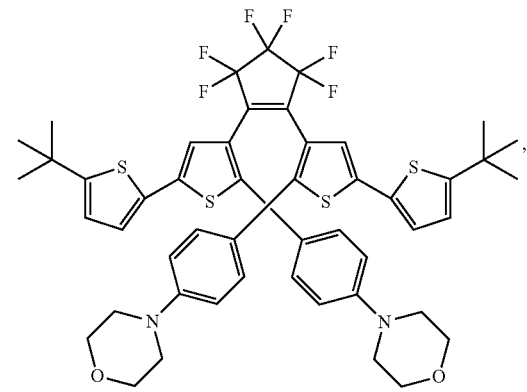
S113
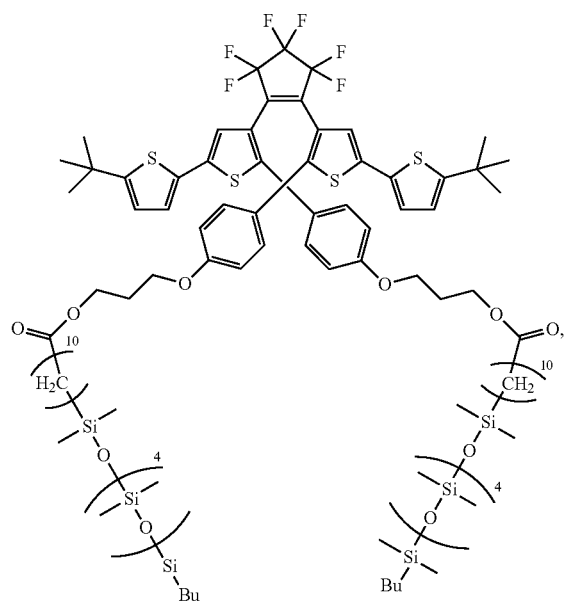
S115
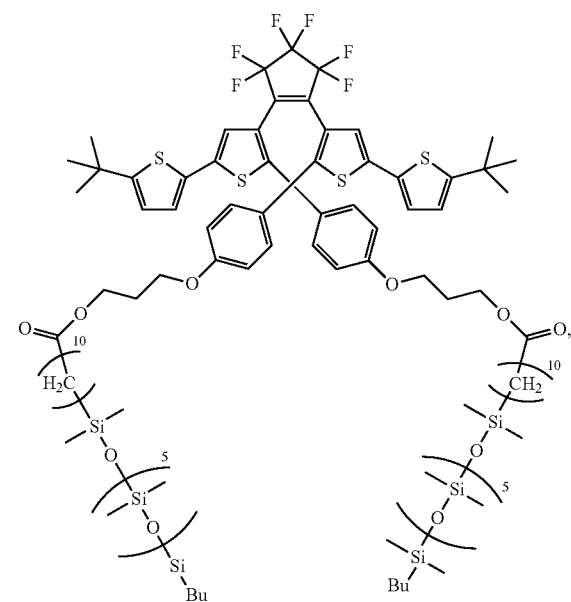
S118
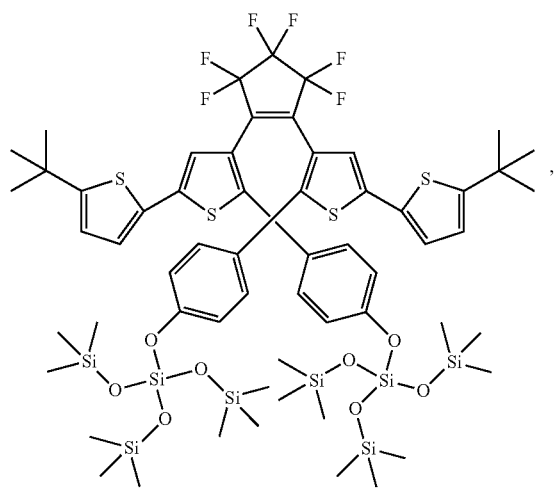
S139
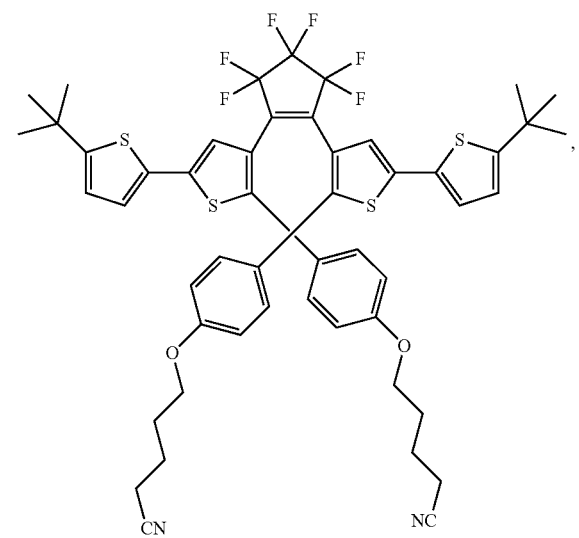

-continued
S003
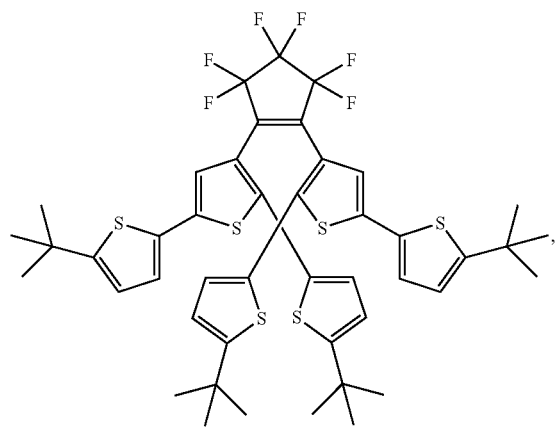
S026
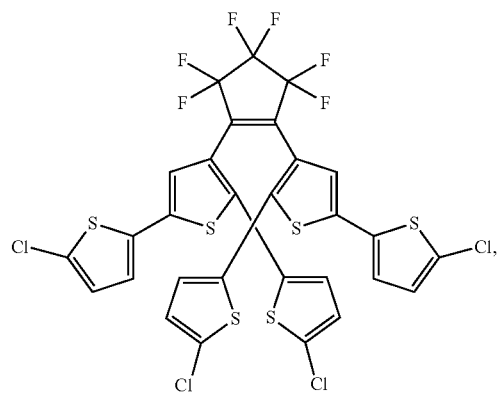
S034
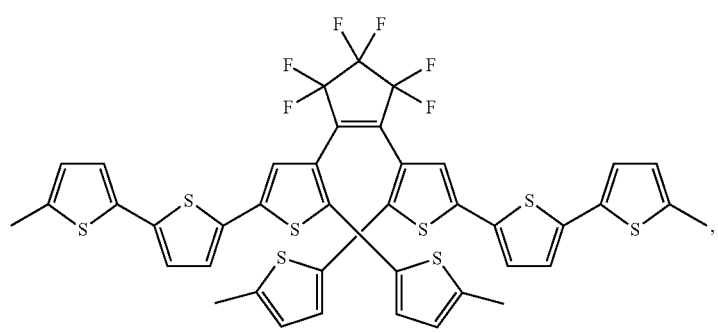
S037
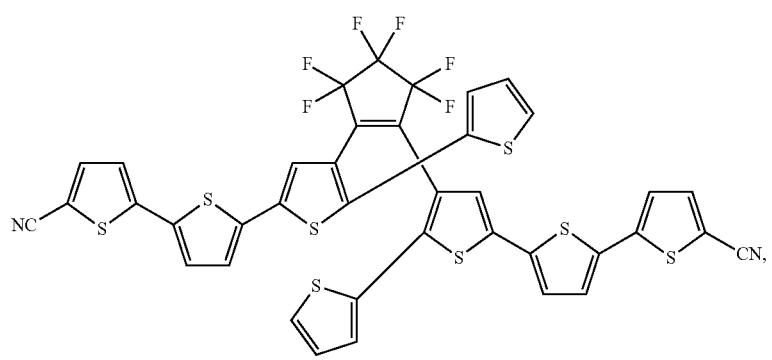
S038
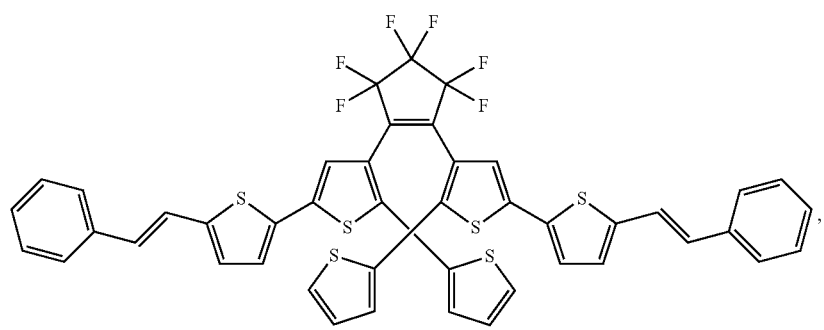

-continued
S119
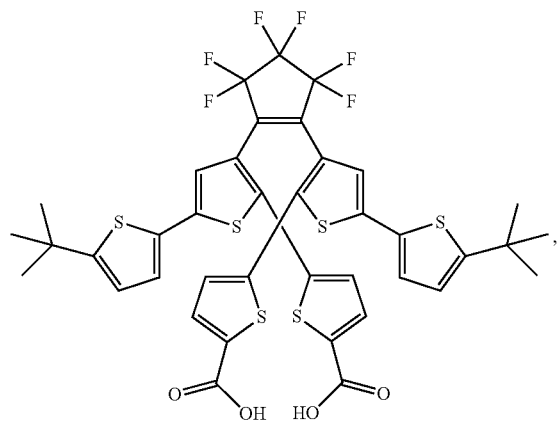
S124
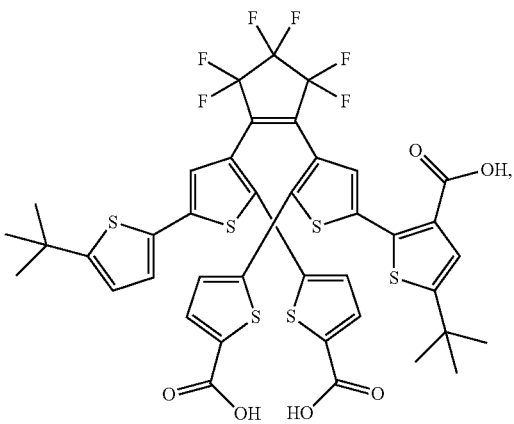
S128
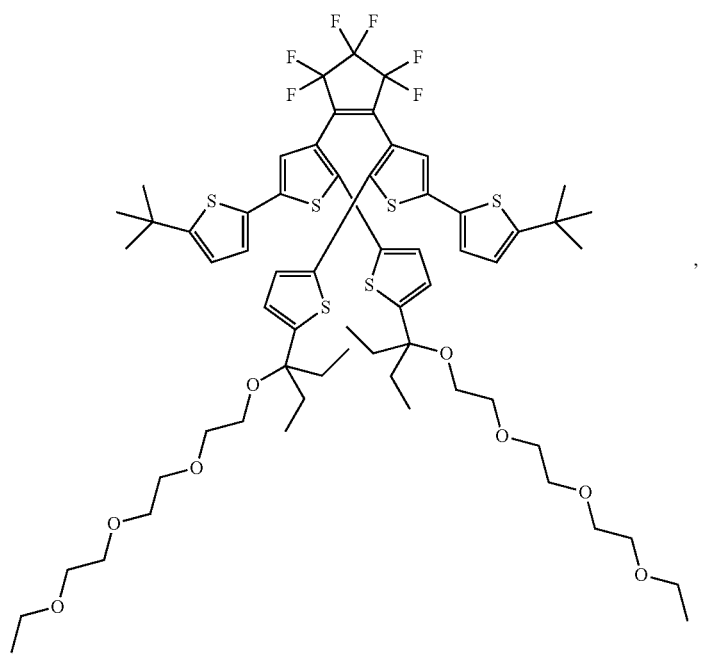
S135
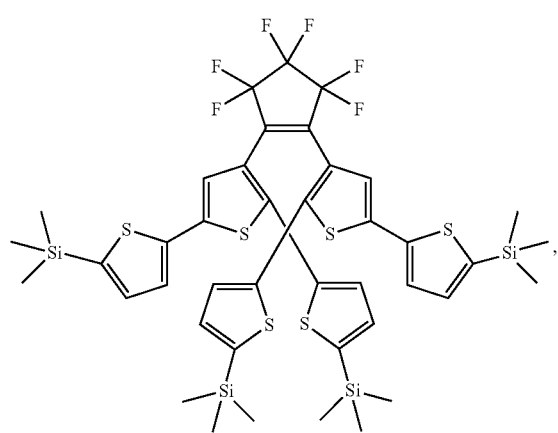

-continued
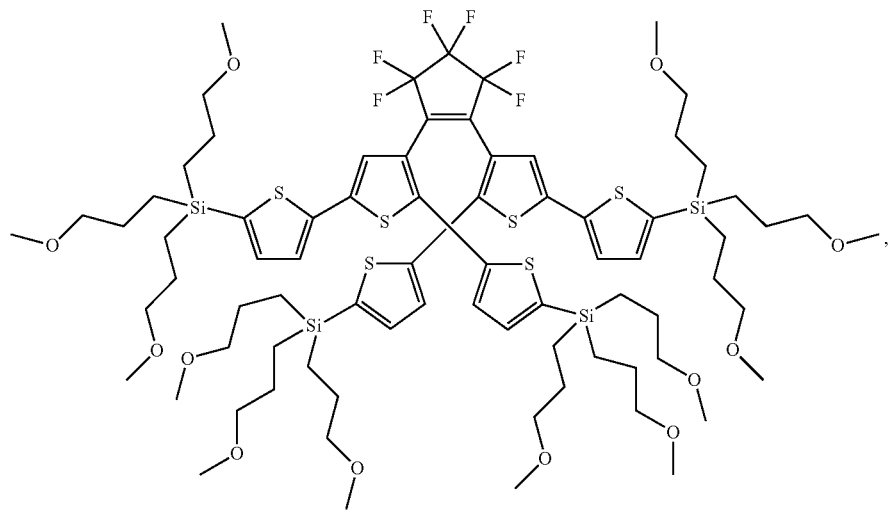
S138
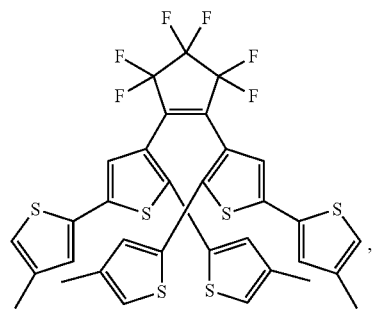
S149
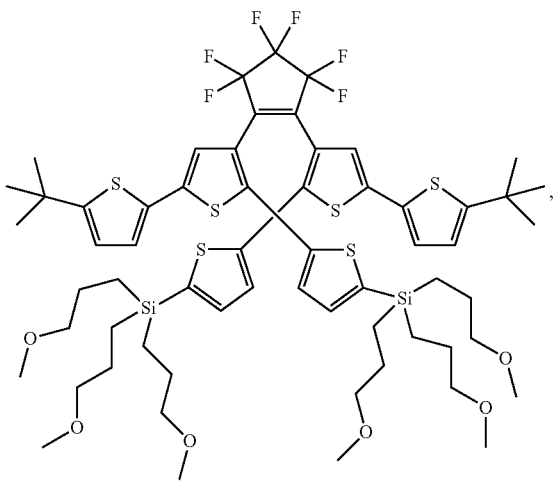
S158
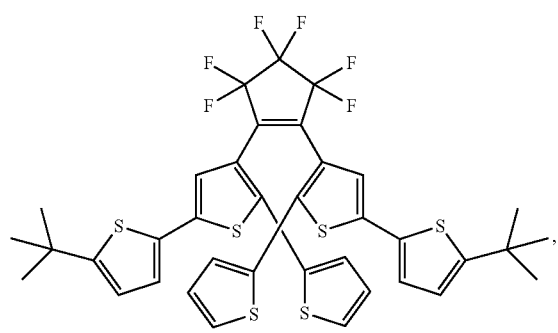
S170

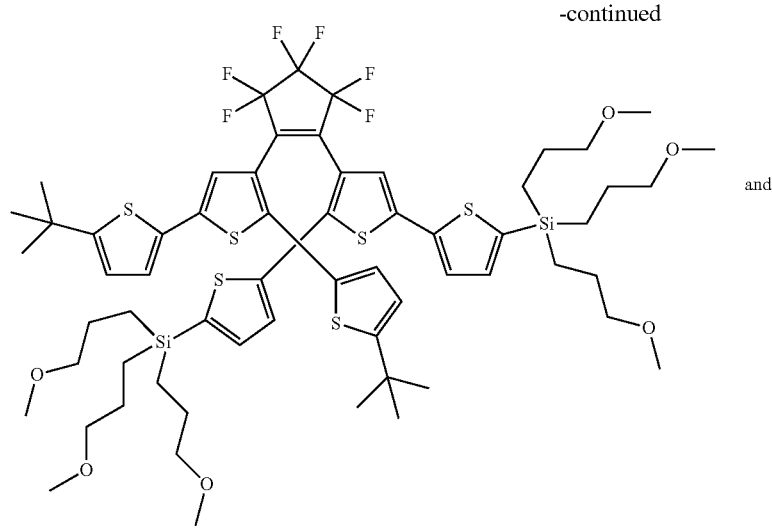

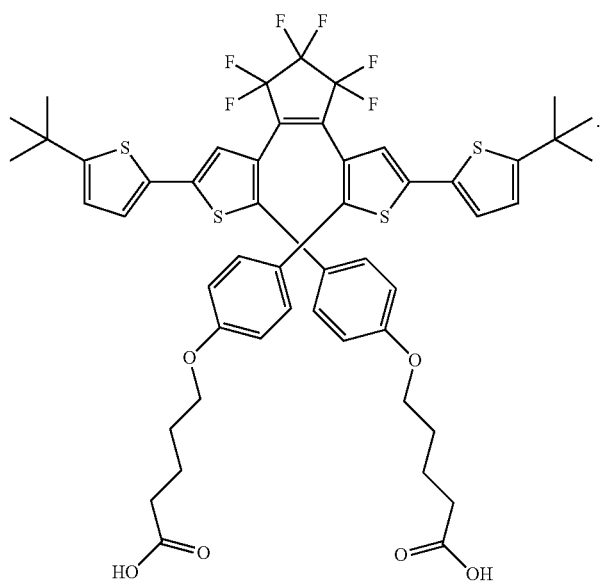

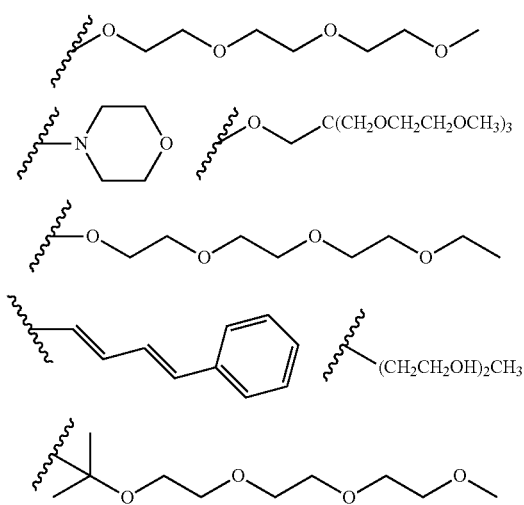

and

S141

23. The compound according to claim 13 wherein $R_{7a}$ is H, Cl, Br, F, —$CF_3$, —CN, —$NO_2$, methyl, ethyl, propyl, iso-propyl, butyl, sec-butyl, iso-butyl, tert-butyl, saturated or unsaturated alkyl that is linear or branched with 5-12 carbons, —Si($R_{11}$)$_3$, thiophene, substituted thiophene, benzyl, substituted benzyl, —$CH_2$—$CH_2$—, —CH=CH—, —CH=$CH_2$, —$OCH_3$, —COH, —OH, —$CO_2$H, —$COCH_3$, —C($CH_3$)$_2$OH, —Si($CH_3$)$_3$, —$CH_2CH_2OCH_3$, —$CH_2CH_2OH$, —N($CH_3$)$_2$, —$CO_2CH_3$, —$OCH_2OCH_3$, —$SO_2CH_3$, —$OCH_2C(CH_3)_3$, —$OCH_2CH(CH_3)_2$, —OC($CH_3$)$_3$, —OCH—$CH_2$, —O($CH_2$)$_4$CN, —O($CH_2$)$_4$OH, —O($CH_2$)$_3$OH, —C($CH_3$)$_2$OH, —O($CH_2$)$_2$$OCH_3$, —O($CH_2$)$_4$CN, —O($CH_2$)$_4$COOH,

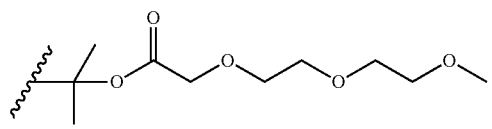

253
-continued
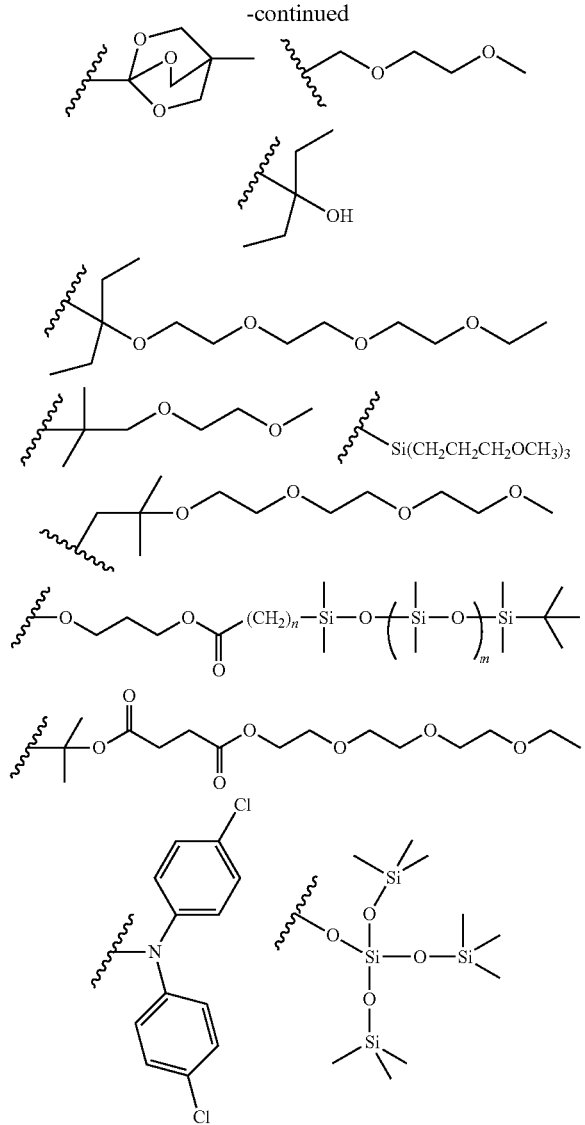
254
-continued
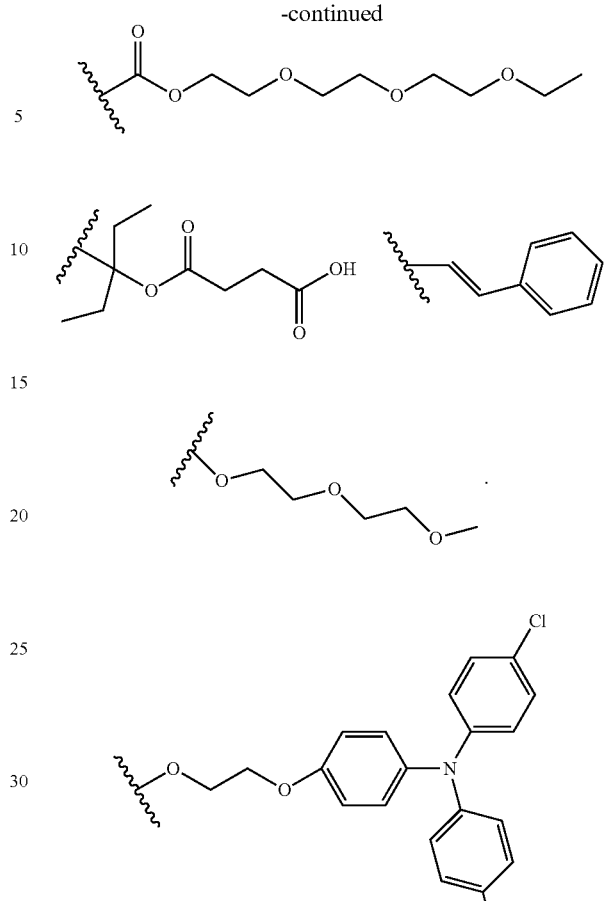
24. The compound according to claim 23 wherein $R_{11}$ is —$CH_3$ or —$(CH_2)_{1-10}$—$OCH_3$.
25. The compound according to claim 13 wherein R is substituted or unsubstituted methyl, ethyl, propyl, iso-propyl, butyl, sec-butyl, iso-butyl, tert-butyl, pentyl or hexyl.
* * * * *